United States Patent
Böhm et al.

(10) Patent No.: US 10,835,162 B2
(45) Date of Patent: Nov. 17, 2020

(54) ADVANCED ANALYTE SENSOR CALIBRATION AND ERROR DETECTION

(71) Applicant: DexCom, Inc., San Diego, CA (US)

(72) Inventors: Sebastian Böhm, San Diego, CA (US); Daiting Rong, San Diego, CA (US); Peter C. Simpson, Cardiff, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 16/586,610

(22) Filed: Sep. 27, 2019

(65) Prior Publication Data

US 2020/0037936 A1 Feb. 6, 2020

Related U.S. Application Data

(63) Continuation of application No. 16/460,943, filed on Jul. 2, 2019, now Pat. No. 10,561,354, which is a (Continued)

(51) Int. Cl.
*G08B 21/20* (2006.01)
*A61B 5/1495* (2006.01)
(Continued)

(52) U.S. Cl.
CPC .......... *A61B 5/1495* (2013.01); *A61B 5/1451* (2013.01); *A61B 5/1473* (2013.01);
(Continued)

(58) Field of Classification Search
CPC ........ A61B 2560/0276; A61B 5/14503; A61B 5/1451; A61B 5/14517; A61B 5/14532;
(Continued)

(56) References Cited

U.S. PATENT DOCUMENTS 3,581,062 A  5/1971  Aston
3,926,760 A  12/1975  Allen et al.
(Continued)

FOREIGN PATENT DOCUMENTS

EP  0098592 A2  1/1984
EP  0127958 A2  12/1984
(Continued)

OTHER PUBLICATIONS

Armour J.C., et al., "Application of Chronic Intravascular Blood Glucose Sensor in Dogs," Diabetes, Dec. 1990, vol. 39, pp. 1519-1526.
(Continued)

*Primary Examiner* — Daniel Previl
(74) *Attorney, Agent, or Firm* — Knobbe, Martens, Olson & Bear, LLP

(57) ABSTRACT

Systems and methods for processing sensor data and self-calibration are provided. In some embodiments, systems and methods are provided which are capable of calibrating a continuous analyte sensor based on an initial sensitivity, and then continuously performing self-calibration without using, or with reduced use of, reference measurements. In certain embodiments, a sensitivity of the analyte sensor is determined by applying an estimative algorithm that is a function of certain parameters. Also described herein are systems and methods for determining a property of an analyte sensor using a stimulus signal. The sensor property can be used to compensate sensor data for sensitivity drift, or determine another property associated with the sensor, such as temperature, sensor membrane damage, moisture ingress in sensor electronics, and scaling factors.

29 Claims, 56 Drawing Sheets

Related U.S. Application Data continuation of application No. 16/405,887, filed on May 7, 2019, now Pat. No. 10,682,084, which is a continuation of application No. 15/994,905, filed on May 31, 2018, now Pat. No. 10,327,688, which is a continuation of application No. 14/860,392, filed on Sep. 21, 2015, now Pat. No. 10,004,442, which is a continuation of application No. 13/446,977, filed on Apr. 13, 2012, now Pat. No. 9,149,220, which is a continuation of application No. 13/446,848, filed on Apr. 13, 2012, now Pat. No. 9,801,575.

(60) Provisional application No. 61/476,145, filed on Apr. 15, 2011.

(51) Int. Cl.

| | |
|---|---|
| *G01N 27/327* | (2006.01) |
| *A61B 5/145* | (2006.01) |
| *A61B 5/1486* | (2006.01) |
| *A61B 5/00* | (2006.01) |
| *G01D 18/00* | (2006.01) |
| *G01N 27/02* | (2006.01) |
| *G01N 33/49* | (2006.01) |
| *A61B 5/1473* | (2006.01) |

(52) U.S. Cl.
CPC ........ *A61B 5/1486* (2013.01); *A61B 5/14503* (2013.01); *A61B 5/14517* (2013.01); *A61B 5/14532* (2013.01); *A61B 5/7257* (2013.01); *A61B 5/7267* (2013.01); *G01D 18/00* (2013.01); *G01N 27/026* (2013.01); *G01N 27/3274* (2013.01); *G01N 33/49* (2013.01); *H05K 999/00* (2013.01); *H05K 999/99* (2013.01); *A61B 5/14546* (2013.01); *A61B 2560/0276* (2013.01)

(58) Field of Classification Search
CPC . A61B 5/14546; A61B 5/1473; A61B 5/1486; A61B 5/1495; A61B 5/7257; A61B 5/7267; G01D 18/00; G01N 27/026; G01N 27/3274; G01N 33/49; H05K 999/00; H05K 999/99
USPC ......... 340/604, 612, 636.11, 636.12–636.15, 340/691.6
See application file for complete search history.

(56) References Cited

U.S. PATENT DOCUMENTS

| | | |
|---|---|---|
| 3,949,388 A | 4/1976 | Fuller et al. |
| 3,960,497 A | 6/1976 | Acord |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,935,345 A | 6/1990 | Guilbeau et al. |
| 4,947,845 A | 8/1990 | Davis |
| 4,953,552 A | 9/1990 | Demarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,112,455 A | 5/1992 | Cozzette et al. |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer |
| 5,210,778 A | 5/1993 | Massart |
| 5,231,988 A | 8/1993 | Wernicke et al. |
| 5,237,123 A | 8/1993 | Miller |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,352,349 A | 10/1994 | Inamoto et al. |
| 5,356,217 A | 10/1994 | Sheffield |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk, Jr. et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,422,829 A | 6/1995 | Pollock |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |

(56) References Cited

U.S. PATENT DOCUMENTS

| | | |
|---|---|---|
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Boecker |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Carter et al. |
| 5,640,954 A | 6/1997 | Pfeiffer et al. |
| 5,645,077 A | 7/1997 | Foxlin |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,720,295 A | 2/1998 | Greenhut et al. |
| 5,733,259 A | 3/1998 | Valcke et al. |
| 5,735,285 A | 4/1998 | Albert et al. |
| 5,741,211 A | 4/1998 | Renirie et al. |
| 5,772,586 A | 6/1998 | Heinonen et al. |
| 5,785,660 A | 7/1998 | Van Lake et al. |
| 5,791,344 A | 8/1998 | Schulman et al. |
| 5,792,065 A | 8/1998 | Xue et al. |
| 5,820,551 A | 10/1998 | Hill et al. |
| 5,822,715 A | 10/1998 | Worthington et al. |
| 5,891,047 A | 4/1999 | Lander et al. |
| 5,891,048 A | 4/1999 | Nigam et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,728 A | 11/1999 | Farber et al. |
| 5,990,422 A | 11/1999 | Komori et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,134,461 A | 10/2000 | Say et al. |
| 6,143,164 A | 11/2000 | Heller et al. |
| 6,144,837 A | 11/2000 | Quy |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,224,562 B1 | 5/2001 | Lurie et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,405,066 B1 | 6/2002 | Essenpreis et al. |
| 6,413,393 B1 | 7/2002 | Van Antwerp et al. |
| 6,424,847 B1 | 7/2002 | Mastrototaro |
| 6,427,088 B1 | 7/2002 | Bowman et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,486,661 B2 | 11/2002 | Chia et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |

(56) References Cited

U.S. PATENT DOCUMENTS

| | | |
|---|---|---|
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciurczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,200 B1 | 5/2004 | Stewart et al. |
| 6,731,985 B2 | 5/2004 | Poore et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,850,790 B2 | 2/2005 | Berner et al. |
| 6,850,859 B1 | 2/2005 | Schuh |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,396 B2 | 5/2005 | Schulze et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,990,422 B2 | 1/2006 | Laletin et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,052,472 B1 | 5/2006 | Miller et al. |
| 7,052,483 B2 | 5/2006 | Wojcik |
| 7,056,302 B2 | 6/2006 | Douglas |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,253,680 B2 | 8/2007 | Laletin |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,338,639 B2 | 3/2008 | Burke et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,390,667 B2 | 6/2008 | Burke et al. |
| 7,402,153 B2 | 7/2008 | Steil et al. |
| 7,407,811 B2 | 8/2008 | Burke et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,488,601 B2 | 2/2009 | Burke et al. |
| 7,494,465 B2 | 2/2009 | Brister et al. |
| 7,494,816 B2 | 2/2009 | Burke et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,519,478 B2 | 4/2009 | Bartkowiak et al. |

(56) References Cited

U.S. PATENT DOCUMENTS

| | | | |
|---|---|---|---|
| 7,523,004 B2 | 4/2009 | Bartkowiak et al. |
| 7,524,287 B2 | 4/2009 | Bharmi |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,620,438 B2 | 11/2009 | He |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Brister et al. |
| 7,653,425 B2 | 1/2010 | Hayter et al. |
| 7,699,775 B2 | 4/2010 | Desai et al. |
| 7,699,964 B2 | 4/2010 | Feldman et al. |
| 7,711,493 B2 | 5/2010 | Bartkowiak et al. |
| 7,736,310 B2 | 6/2010 | Taub |
| 7,749,445 B2 | 7/2010 | Masters |
| 7,751,864 B2 | 7/2010 | Buck, Jr. |
| 7,766,829 B2 | 8/2010 | Sloan et al. |
| 7,771,352 B2 | 8/2010 | Shults et al. |
| 7,774,038 B2 | 8/2010 | Wang et al. |
| 7,774,145 B2 | 8/2010 | Brauker et al. |
| 7,776,559 B2 | 8/2010 | Childers et al. |
| 7,778,679 B2 | 8/2010 | Schulman et al. |
| 7,778,680 B2 | 8/2010 | Goode, Jr. et al. |
| 7,826,981 B2 | 11/2010 | Goode, Jr. et al. |
| 7,838,639 B2 | 11/2010 | Tschopp et al. |
| 7,857,760 B2 | 12/2010 | Brister et al. |
| 7,866,025 B2 | 1/2011 | James et al. |
| 7,866,026 B1 | 1/2011 | Wang et al. |
| 7,885,697 B2 | 2/2011 | Brister et al. |
| 7,885,698 B2 | 2/2011 | Feldman |
| 7,889,069 B2 | 2/2011 | Fifolt et al. |
| 7,894,870 B1 | 2/2011 | Lucisano et al. |
| 7,899,511 B2 | 3/2011 | Shults et al. |
| 7,905,833 B2 | 3/2011 | Brister et al. |
| 7,914,450 B2 | 3/2011 | Goode, Jr. et al. |
| 7,920,906 B2 | 4/2011 | Goode, Jr. et al. |
| 7,938,797 B2 | 5/2011 | Estes |
| 7,946,984 B2 | 5/2011 | Brister et al. |
| 7,974,672 B2 | 7/2011 | Shults et al. |
| 7,985,330 B2 | 7/2011 | Wang et al. |
| 7,990,828 B2 | 8/2011 | Su et al. |
| 7,996,158 B2 | 8/2011 | Hayter et al. |
| 8,000,763 B2 | 8/2011 | Mazza et al. |
| 8,026,104 B2 | 9/2011 | Wu et al. |
| 8,060,173 B2 | 11/2011 | Goode, Jr. et al. |
| 8,103,471 B2 | 1/2012 | Hayter |
| 8,112,240 B2 | 2/2012 | Fennell |
| 8,114,268 B2 | 2/2012 | Wang et al. |
| 8,116,837 B2 | 2/2012 | Huang |
| 8,140,312 B2 | 3/2012 | Hayter et al. |
| 8,149,117 B2 | 4/2012 | Fennell et al. |
| 8,160,670 B2 | 4/2012 | Ouyang et al. |
| 8,160,834 B2 | 4/2012 | Liang et al. |
| 8,160,900 B2 | 4/2012 | Taub et al. |
| 8,170,803 B2 | 5/2012 | Kamath et al. |
| 8,202,491 B2 | 6/2012 | Masters et al. |
| 8,211,016 B2 | 7/2012 | Budiman |
| 8,216,137 B2 | 7/2012 | Budiman |
| 8,216,138 B1 | 7/2012 | McGarraugh |
| 8,219,173 B2 | 7/2012 | Budiman et al. |
| 8,224,415 B2 | 7/2012 | Budiman |
| 8,239,166 B2 | 8/2012 | Hayter et al. |
| 8,249,683 B2 | 8/2012 | Wang et al. |
| 8,255,026 B1 | 8/2012 | Al-Ali |
| 8,260,558 B2 | 9/2012 | Hayter et al. |
| 8,282,549 B2 | 10/2012 | Brauker et al. |
| 8,346,335 B2 | 1/2013 | Harper et al. |
| 8,346,337 B2 | 1/2013 | Heller et al. |
| 8,348,923 B2 | 1/2013 | Kanderian, Jr. et al. |
| 8,372,351 B2 | 2/2013 | Ow-Wing |
| 8,376,945 B2 | 2/2013 | Hayter et al. |
| 8,417,312 B2 | 4/2013 | Kamath et al. |
| 8,444,560 B2 | 5/2013 | Hayter et al. |
| 8,457,703 B2 | 6/2013 | Al-Ali |
| 8,461,985 B2 | 6/2013 | Fennell et al. |
| 8,463,350 B2 | 6/2013 | Kamath et al. |
| 8,473,022 B2 | 6/2013 | Hayter et al. |
| 8,478,557 B2 | 7/2013 | Hayter et al. |
| 8,484,005 B2 | 7/2013 | Hayter et al. |
| 8,515,517 B2 | 8/2013 | Hayter et al. |
| 8,532,935 B2 | 9/2013 | Budiman |
| 8,543,354 B2 | 9/2013 | Luo et al. |
| 8,560,037 B2 | 10/2013 | Goode, Jr. et al. |
| 8,560,038 B2 | 10/2013 | Hayter et al. |
| 8,571,808 B2 | 10/2013 | Hayter |
| 8,583,205 B2 | 11/2013 | Budiman et al. |
| 8,593,109 B2 | 11/2013 | He |
| 8,600,681 B2 | 12/2013 | Hayter et al. |
| 8,612,163 B2 | 12/2013 | Hayter et al. |
| 8,657,746 B2 | 2/2014 | Roy |
| 8,663,220 B2 | 3/2014 | Wiener et al. |
| 8,665,091 B2 | 3/2014 | Fennell et al. |
| 8,682,615 B2 | 3/2014 | Hayter et al. |
| 8,718,739 B2 | 5/2014 | Harper et al. |
| 8,718,965 B2 | 5/2014 | Hayter et al. |
| 8,744,547 B2 | 6/2014 | Budiman et al. |
| 8,868,151 B2 | 10/2014 | Telson et al. |
| 8,868,161 B2 | 10/2014 | Thierman |
| 8,933,664 B2 | 1/2015 | He |
| 8,942,778 B2 | 1/2015 | Ocvirk et al. |
| 9,060,719 B2 | 6/2015 | Hayter et al. |
| 9,113,828 B2 | 8/2015 | Budiman |
| 9,125,548 B2 | 9/2015 | Hayter |
| 9,149,220 B2 * | 10/2015 | Bohm .................. A61B 5/1495 |
| 9,161,714 B2 | 10/2015 | Martini et al. |
| 9,314,196 B2 | 4/2016 | Pryor et al. |
| 9,320,462 B2 | 4/2016 | Harper et al. |
| 9,320,468 B2 | 4/2016 | Hayter et al. |
| 9,326,709 B2 | 5/2016 | Budiman |
| 9,332,934 B2 | 5/2016 | Hayter et al. |
| 9,339,217 B2 | 5/2016 | Harper et al. |
| 9,357,959 B2 | 6/2016 | Hayter et al. |
| 9,380,971 B2 | 7/2016 | He |
| 9,392,969 B2 | 7/2016 | Hayter et al. |
| 9,398,872 B2 | 7/2016 | Hayter et al. |
| 9,408,566 B2 | 8/2016 | Hayter et al. |
| 9,483,608 B2 | 11/2016 | Hayter et al. |
| 9,558,325 B2 | 1/2017 | Hayter et al. |
| 9,629,578 B2 | 4/2017 | Hayter et al. |
| 9,662,056 B2 | 5/2017 | Budiman et al. |
| 9,675,290 B2 | 6/2017 | Budiman et al. |
| 9,730,623 B2 | 8/2017 | Harper et al. |
| 9,737,249 B2 | 8/2017 | Hayter et al. |
| 9,743,863 B2 | 8/2017 | He |
| 9,770,211 B2 | 9/2017 | Hayter et al. |
| 9,797,880 B2 | 10/2017 | Hayter et al. |
| 9,801,571 B2 | 10/2017 | Hayter |
| 9,801,575 B2 * | 10/2017 | Bohm .................. A61B 5/1486 |
| 9,801,577 B2 | 10/2017 | Budiman |
| 9,804,148 B2 | 10/2017 | Hayter et al. |
| 9,804,150 B2 | 10/2017 | Hayter et al. |
| 9,808,190 B2 | 11/2017 | Böhm et al. |
| 9,814,428 B2 | 11/2017 | Budiman |
| 9,833,181 B2 | 12/2017 | Hayter et al. |
| 9,839,383 B2 | 12/2017 | Hayter et al. |
| 9,848,809 B2 | 12/2017 | Böhm et al. |
| 9,936,910 B2 | 4/2018 | Hayter et al. |
| 10,002,233 B2 | 6/2018 | Hayter et al. |
| 10,004,442 B2 * | 6/2018 | Bohm .................. G01N 27/026 |
| 10,031,002 B2 | 7/2018 | Hayter et al. |
| 10,045,720 B2 | 8/2018 | Hayter et al. |
| 10,078,380 B2 | 9/2018 | Budiman |
| 10,082,493 B2 | 9/2018 | Harper et al. |
| 10,089,446 B2 | 10/2018 | Budiman |
| 10,119,956 B2 | 11/2018 | Hayter et al. |
| 10,143,409 B2 | 12/2018 | Hayter |
| 10,188,334 B2 | 1/2019 | Budiman et al. |

(56) References Cited

U.S. PATENT DOCUMENTS

| | | | |
|---|---|---|---|
| 10,188,794 B2 | 1/2019 | Hayter et al. | |
| 10,194,868 B2 | 2/2019 | Budiman | |
| 10,261,069 B2 | 4/2019 | Hayter et al. | |
| 10,278,630 B2 | 5/2019 | Hayter et al. | |
| 10,327,688 B2 * | 6/2019 | Bohm | A61B 5/1451 |
| 10,448,873 B2 | 10/2019 | Böhm et al. | |
| 2001/0041831 A1 | 11/2001 | Starkweather et al. | |
| 2002/0016534 A1 | 2/2002 | Trepagnier et al. | |
| 2002/0019022 A1 | 2/2002 | Dunn et al. | |
| 2002/0038101 A1 | 3/2002 | Avrahami et al. | |
| 2002/0042090 A1 | 4/2002 | Heller et al. | |
| 2002/0065454 A1 | 5/2002 | Lebel et al. | |
| 2002/0068860 A1 | 6/2002 | Clark, Jr. | |
| 2002/0103499 A1 | 8/2002 | Perez et al. | |
| 2002/0106709 A1 | 8/2002 | Potts et al. | |
| 2002/0120186 A1 | 8/2002 | Keimel | |
| 2002/0128594 A1 | 9/2002 | Das et al. | |
| 2002/0143266 A1 | 10/2002 | Bock | |
| 2002/0143372 A1 | 10/2002 | Snell et al. | |
| 2002/0156355 A1 | 10/2002 | Gough | |
| 2002/0161288 A1 | 10/2002 | Shin et al. | |
| 2002/0169635 A1 | 11/2002 | Shillingburg | |
| 2002/0193679 A1 | 12/2002 | Malave et al. | |
| 2003/0004403 A1 | 1/2003 | Drinan et al. | |
| 2003/0023317 A1 | 1/2003 | Brauker et al. | |
| 2003/0023461 A1 | 1/2003 | Quintanilla et al. | |
| 2003/0032867 A1 | 2/2003 | Crothall et al. | |
| 2003/0032874 A1 | 2/2003 | Rhodes et al. | |
| 2003/0042137 A1 | 3/2003 | Mao et al. | |
| 2003/0050546 A1 | 3/2003 | Desai et al. | |
| 2003/0054428 A1 | 3/2003 | Monfre et al. | |
| 2003/0065308 A1 | 4/2003 | Lebel et al. | |
| 2003/0100821 A1 | 5/2003 | Heller et al. | |
| 2003/0125612 A1 | 7/2003 | Fox et al. | |
| 2003/0130616 A1 | 7/2003 | Steil et al. | |
| 2003/0134347 A1 | 7/2003 | Heller et al. | |
| 2003/0168338 A1 | 9/2003 | Gao et al. | |
| 2003/0175987 A1 | 9/2003 | Verdonk et al. | |
| 2003/0176933 A1 | 9/2003 | Lebel et al. | |
| 2003/0187338 A1 | 10/2003 | Say et al. | |
| 2003/0191377 A1 | 10/2003 | Robinson et al. | |
| 2003/0199744 A1 | 10/2003 | Buse et al. | |
| 2003/0199790 A1 | 10/2003 | Boecker et al. | |
| 2003/0208113 A1 | 11/2003 | Mault et al. | |
| 2003/0212317 A1 | 11/2003 | Kovatchev et al. | |
| 2003/0212379 A1 | 11/2003 | Bylund et al. | |
| 2003/0216630 A1 | 11/2003 | Jersey-Willuhn et al. | |
| 2003/0217966 A1 | 11/2003 | Tapsak et al. | |
| 2003/0235817 A1 | 12/2003 | Bartkowiak et al. | |
| 2004/0010186 A1 | 1/2004 | Kimball et al. | |
| 2004/0010207 A1 | 1/2004 | Flaherty et al. | |
| 2004/0011671 A1 | 1/2004 | Shults et al. | |
| 2004/0024553 A1 | 2/2004 | Monfre et al. | |
| 2004/0039298 A1 | 2/2004 | Abreu | |
| 2004/0040840 A1 | 3/2004 | Mao et al. | |
| 2004/0045879 A1 | 3/2004 | Shults et al. | |
| 2004/0054263 A1 | 3/2004 | Moerman et al. | |
| 2004/0064068 A1 | 4/2004 | Denuzzio et al. | |
| 2004/0077962 A1 | 4/2004 | Kroll | |
| 2004/0078065 A1 | 4/2004 | Kroll | |
| 2004/0093167 A1 | 5/2004 | Braig et al. | |
| 2004/0099529 A1 | 5/2004 | Mao et al. | |
| 2004/0106858 A1 | 6/2004 | Say et al. | |
| 2004/0108226 A1 | 6/2004 | Polychronakos et al. | |
| 2004/0122353 A1 | 6/2004 | Shahmirian et al. | |
| 2004/0133164 A1 | 7/2004 | Funderburk et al. | |
| 2004/0135684 A1 | 7/2004 | Steinthal et al. | |
| 2004/0138588 A1 | 7/2004 | Saikley et al. | |
| 2004/0138716 A1 | 7/2004 | Kon et al. | |
| 2004/0142403 A1 | 7/2004 | Hetzel et al. | |
| 2004/0146909 A1 | 7/2004 | Duong et al. | |
| 2004/0147819 A1 | 7/2004 | Caduff et al. | |
| 2004/0152622 A1 | 8/2004 | Keith et al. | |
| 2004/0158137 A1 | 8/2004 | Eppstein et al. | |
| 2004/0162678 A1 | 8/2004 | Hetzel et al. | |
| 2004/0167801 A1 | 8/2004 | Say et al. | |
| 2004/0171921 A1 | 9/2004 | Say et al. | |
| 2004/0172307 A1 | 9/2004 | Gruber | |
| 2004/0176672 A1 | 9/2004 | Silver et al. | |
| 2004/0186362 A1 | 9/2004 | Brauker et al. | |
| 2004/0186365 A1 | 9/2004 | Jin et al. | |
| 2004/0193025 A1 | 9/2004 | Steil et al. | |
| 2004/0193090 A1 | 9/2004 | Lebel et al. | |
| 2004/0197846 A1 | 10/2004 | Hockersmith et al. | |
| 2004/0199059 A1 | 10/2004 | Brauker et al. | |
| 2004/0204687 A1 | 10/2004 | Mogensen et al. | |
| 2004/0208780 A1 | 10/2004 | Faries, I et al. | |
| 2004/0225338 A1 | 11/2004 | Lebel et al. | |
| 2004/0236200 A1 | 11/2004 | Say et al. | |
| 2004/0249253 A1 | 12/2004 | Racchini et al. | |
| 2004/0249420 A1 | 12/2004 | Olson et al. | |
| 2004/0254433 A1 | 12/2004 | Bandis et al. | |
| 2004/0254434 A1 | 12/2004 | Goodnow et al. | |
| 2004/0260478 A1 | 12/2004 | Schwamm | |
| 2004/0263354 A1 | 12/2004 | Mann et al. | |
| 2004/0267300 A1 | 12/2004 | Mace | |
| 2005/0003470 A1 | 1/2005 | Nelson et al. | |
| 2005/0004439 A1 | 1/2005 | Shin et al. | |
| 2005/0004494 A1 | 1/2005 | Perez et al. | |
| 2005/0010087 A1 | 1/2005 | Banet et al. | |
| 2005/0010269 A1 | 1/2005 | Lebel et al. | |
| 2005/0016276 A1 | 1/2005 | Guan et al. | |
| 2005/0027177 A1 | 2/2005 | Shin et al. | |
| 2005/0027180 A1 | 2/2005 | Goode et al. | |
| 2005/0027181 A1 | 2/2005 | Goode et al. | |
| 2005/0027462 A1 | 2/2005 | Goode et al. | |
| 2005/0027463 A1 | 2/2005 | Goode et al. | |
| 2005/0031689 A1 | 2/2005 | Shults et al. | |
| 2005/0038332 A1 | 2/2005 | Saidara et al. | |
| 2005/0043598 A1 | 2/2005 | Goode et al. | |
| 2005/0049179 A1 | 3/2005 | Davidson et al. | |
| 2005/0049473 A1 | 3/2005 | Desai et al. | |
| 2005/0070774 A1 | 3/2005 | Addison et al. | |
| 2005/0090607 A1 | 4/2005 | Tapsak et al. | |
| 2005/0096511 A1 | 5/2005 | Fox et al. | |
| 2005/0096512 A1 | 5/2005 | Fox et al. | |
| 2005/0112169 A1 | 5/2005 | Brauker et al. | |
| 2005/0113653 A1 | 5/2005 | Fox et al. | |
| 2005/0114068 A1 | 5/2005 | Chey et al. | |
| 2005/0115832 A1 | 6/2005 | Simpson et al. | |
| 2005/0121322 A1 | 6/2005 | Say et al. | |
| 2005/0131346 A1 | 6/2005 | Douglas | |
| 2005/0143635 A1 | 6/2005 | Kamath et al. | |
| 2005/0154271 A1 | 7/2005 | Rasdal et al. | |
| 2005/0176136 A1 | 8/2005 | Burd et al. | |
| 2005/0177398 A1 | 8/2005 | Watanabe et al. | |
| 2005/0182306 A1 | 8/2005 | Sloan | |
| 2005/0187720 A1 | 8/2005 | Goode, Jr. et al. | |
| 2005/0192494 A1 | 9/2005 | Ginsberg | |
| 2005/0192557 A1 * | 9/2005 | Brauker | A61B 5/0002 604/503 |
| 2005/0195930 A1 | 9/2005 | Spital et al. | |
| 2005/0196821 A1 | 9/2005 | Monfre et al. | |
| 2005/0199494 A1 | 9/2005 | Say et al. | |
| 2005/0203360 A1 | 9/2005 | Brauker et al. | |
| 2005/0214892 A1 | 9/2005 | Kovatchev et al. | |
| 2005/0239154 A1 | 10/2005 | Feldman et al. | |
| 2005/0239156 A1 | 10/2005 | Drucker et al. | |
| 2005/0241957 A1 | 11/2005 | Mao et al. | |
| 2005/0245795 A1 | 11/2005 | Goode, Jr. et al. | |
| 2005/0245799 A1 | 11/2005 | Brauker et al. | |
| 2005/0245839 A1 | 11/2005 | Stivoric et al. | |
| 2005/0245904 A1 | 11/2005 | Estes et al. | |
| 2005/0277164 A1 | 12/2005 | Drucker et al. | |
| 2005/0277912 A1 | 12/2005 | John | |
| 2005/0287620 A1 | 12/2005 | Heller et al. | |
| 2005/0288725 A1 | 12/2005 | Hettrick et al. | |
| 2006/0001538 A1 | 1/2006 | Kraft et al. | |
| 2006/0004270 A1 | 1/2006 | Bedard et al. | |
| 2006/0010098 A1 | 1/2006 | Goodnow et al. | |
| 2006/0015020 A1 | 1/2006 | Neale et al. | |
| 2006/0015024 A1 | 1/2006 | Brister et al. | |
| 2006/0016700 A1 | 1/2006 | Brister et al. | |
| 2006/0017923 A1 | 1/2006 | Ruchti et al. | |

(56) References Cited

U.S. PATENT DOCUMENTS

| | | |
|---|---|---|
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0042353 A1 | 3/2006 | Marquis et al. |
| 2006/0091006 A1 | 5/2006 | Wang et al. |
| 2006/0142651 A1* | 6/2006 | Brister ............... A61B 5/6849 600/347 |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tivig et al. |
| 2006/0189863 A1 | 8/2006 | Peyser et al. |
| 2006/0193375 A1 | 8/2006 | Lee et al. |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1* | 11/2006 | Fennell ............... G01R 31/025 600/345 |
| 2006/0247685 A1 | 11/2006 | Bharmi |
| 2006/0247985 A1 | 11/2006 | Liamos et al. |
| 2006/0258929 A1 | 11/2006 | Goode, Jr. et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0169533 A1 | 7/2007 | Shah et al. |
| 2007/0170073 A1 | 7/2007 | Wang et al. |
| 2007/0173706 A1 | 7/2007 | Neinast et al. |
| 2007/0173709 A1 | 7/2007 | Petisce et al. |
| 2007/0173710 A1* | 7/2007 | Petisce ............... A61B 5/14532 600/345 |
| 2007/0173712 A1 | 7/2007 | Shah et al. |
| 2007/0173741 A1 | 7/2007 | Deshmukh et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0197889 A1 | 8/2007 | Brister et al. |
| 2007/0199818 A1 | 8/2007 | Petyt et al. |
| 2007/0202562 A1 | 8/2007 | Curry |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0224700 A1 | 9/2007 | Masters |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg |
| 2007/0235331 A1* | 10/2007 | Simpson ............... A61B 5/14546 204/403.01 |
| 2007/0249922 A1 | 10/2007 | Peyser et al. |
| 2007/0255321 A1 | 11/2007 | Gerber et al. |
| 2007/0299617 A1 | 12/2007 | Willis |
| 2008/0000779 A1 | 1/2008 | Wang et al. |
| 2008/0004515 A1 | 1/2008 | Jennewine |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081000 A1 | 4/2008 | MacLeod et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0115599 A1 | 5/2008 | Masters et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0156661 A1 | 7/2008 | Cooper et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |

(56) References Cited

U.S. PATENT DOCUMENTS

| | | |
|---|---|---|
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0269714 A1 | 10/2008 | Mastrototaro et al. |
| 2008/0275313 A1 | 11/2008 | Brister et al. |
| 2008/0278332 A1 | 11/2008 | Fennell et al. |
| 2008/0287761 A1 | 11/2008 | Hayter et al. |
| 2008/0287762 A1 | 11/2008 | Hayter et al. |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter et al. |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter et al. |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0012376 A1 | 1/2009 | Agus |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine |
| 2009/0054748 A1 | 2/2009 | Feldman |
| 2009/0054749 A1 | 2/2009 | He |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063402 A1 | 3/2009 | Hayter |
| 2009/0069649 A1 | 3/2009 | Budiman |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171178 A1 | 7/2009 | He et al. |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0257911 A1 | 10/2009 | Thomas et al. |
| 2009/0281407 A1 | 11/2009 | Budiman |
| 2009/0287073 A1 | 11/2009 | Boock et al. |
| 2009/0287074 A1 | 11/2009 | Shults et al. |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0023291 A1 | 1/2010 | Hayter et al. |
| 2010/0025238 A1 | 2/2010 | Gottlieb et al. |
| 2010/0045231 A1 | 2/2010 | He |
| 2010/0049015 A1 | 2/2010 | Martini et al. |

(56) References Cited

U.S. PATENT DOCUMENTS

| | | |
|---|---|---|
| 2010/0049021 A1 | 2/2010 | Jina et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0064764 A1 | 3/2010 | Hayter et al. |
| 2010/0081906 A1 | 4/2010 | Hayter et al. |
| 2010/0081909 A1 | 4/2010 | Budiman et al. |
| 2010/0081953 A1 | 4/2010 | Syeda-Mahmood et al. |
| 2010/0094111 A1 | 4/2010 | Heller et al. |
| 2010/0121167 A1 | 5/2010 | McGarraugh |
| 2010/0141656 A1 | 6/2010 | Krieftewirth |
| 2010/0145174 A1 | 6/2010 | Alferness et al. |
| 2010/0152561 A1 | 6/2010 | Goodnow et al. |
| 2010/0160759 A1 | 6/2010 | Celentano et al. |
| 2010/0160761 A1 | 6/2010 | Say et al. |
| 2010/0168538 A1 | 7/2010 | Keenan et al. |
| 2010/0168546 A1 | 7/2010 | Kamath et al. |
| 2010/0169035 A1 | 7/2010 | Liang et al. |
| 2010/0174266 A1 | 7/2010 | Estes |
| 2010/0179402 A1 | 7/2010 | Goode, Jr. et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0230285 A1 | 9/2010 | Hoss et al. |
| 2010/0234710 A1 | 9/2010 | Budiman et al. |
| 2010/0261987 A1 | 10/2010 | Kamath et al. |
| 2010/0265073 A1 | 10/2010 | Harper |
| 2010/0274107 A1 | 10/2010 | Boock et al. |
| 2010/0274515 A1 | 10/2010 | Hoss et al. |
| 2010/0277342 A1 | 11/2010 | Sicurello et al. |
| 2010/0280441 A1 | 11/2010 | Wilinska et al. |
| 2010/0280782 A1 | 11/2010 | Harper |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0029269 A1 | 2/2011 | Hayter et al. |
| 2011/0040163 A1 | 2/2011 | Telson et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman |
| 2011/0082484 A1 | 4/2011 | Saravia et al. |
| 2011/0105873 A1 | 5/2011 | Feldman et al. |
| 2011/0106126 A1 | 5/2011 | Love et al. |
| 2011/0112696 A1 | 5/2011 | Yodfat et al. |
| 2011/0148905 A1 | 6/2011 | Simmons et al. |
| 2011/0174638 A1 | 7/2011 | Katsuki |
| 2011/0184268 A1 | 7/2011 | Taub |
| 2011/0190603 A1 | 8/2011 | Stafford |
| 2011/0191044 A1 | 8/2011 | Stafford |
| 2011/0193704 A1 | 8/2011 | Harper et al. |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0224523 A1 | 9/2011 | Budiman |
| 2011/0230741 A1 | 9/2011 | Liang et al. |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0288574 A1 | 11/2011 | Curry et al. |
| 2011/0313317 A1 | 12/2011 | Callicoat et al. |
| 2011/0319729 A1 | 12/2011 | Donnay et al. |
| 2011/0319734 A1 | 12/2011 | Gottlieb et al. |
| 2011/0320130 A1 | 12/2011 | Valdes et al. |
| 2011/0320167 A1 | 12/2011 | Budiman |
| 2012/0010642 A1 | 1/2012 | Lee et al. |
| 2012/0078071 A1 | 3/2012 | Böhm et al. |
| 2012/0097554 A1 | 4/2012 | Shah et al. |
| 2012/0108931 A1 | 5/2012 | Taub et al. |
| 2012/0108934 A1 | 5/2012 | Valdes et al. |
| 2012/0123692 A1 | 5/2012 | Hayter |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0209099 A1 | 8/2012 | Ljuhs et al. |
| 2012/0215462 A1 | 8/2012 | Goode, Jr. et al. |
| 2012/0239304 A1 | 9/2012 | Hayter et al. |
| 2012/0245447 A1 | 9/2012 | Karan et al. |
| 2012/0265036 A1 | 10/2012 | Estes et al. |
| 2012/0277564 A1 | 11/2012 | Budiman et al. |
| 2012/0277565 A1 | 11/2012 | Budiman |
| 2012/0283542 A1 | 11/2012 | McGarraugh |
| 2012/0283960 A1 | 11/2012 | Budiman |
| 2012/0291516 A1 | 11/2012 | Hayter et al. |
| 2012/0330561 A1 | 12/2012 | Hayter et al. |
| 2013/0006112 A1 | 1/2013 | Vardy |
| 2013/0035575 A1 | 2/2013 | Mayou et al. |
| 2013/0060105 A1 | 3/2013 | Shah et al. |
| 2013/0060112 A1 | 3/2013 | Pryor et al. |
| 2013/0116527 A1 | 5/2013 | Harper et al. |
| 2013/0137953 A1 | 5/2013 | Harper et al. |
| 2013/0178727 A1 | 7/2013 | Hayter et al. |
| 2013/0184547 A1 | 7/2013 | Taub et al. |
| 2013/0231541 A1 | 9/2013 | Hayter et al. |
| 2013/0253846 A1 | 9/2013 | Hayter et al. |
| 2013/0281807 A1 | 10/2013 | Hayter et al. |
| 2013/0282322 A1 | 10/2013 | Hayter et al. |
| 2013/0282403 A1 | 10/2013 | Hayter et al. |
| 2013/0324823 A1 | 12/2013 | Koski et al. |
| 2013/0338454 A1 | 12/2013 | Hayter et al. |
| 2014/0005499 A1 | 1/2014 | Catt et al. |
| 2014/0005968 A1 | 1/2014 | Budiman |
| 2014/0018642 A1 | 1/2014 | Hayter |
| 2014/0041441 A1 | 2/2014 | Hayter et al. |
| 2014/0046155 A1 | 2/2014 | Hayter et al. |
| 2014/0046156 A1 | 2/2014 | Hayter et al. |
| 2014/0046157 A1 | 2/2014 | Hayter et al. |
| 2014/0046160 A1 | 2/2014 | Terashima et al. |
| 2014/0046161 A1 | 2/2014 | Hayter et al. |
| 2014/0066736 A1 | 3/2014 | Budiman |
| 2014/0088390 A1 | 3/2014 | He |
| 2014/0088392 A1 | 3/2014 | Bernstein et al. |
| 2014/0088908 A1 | 3/2014 | Hayter et al. |
| 2014/0100796 A1 | 4/2014 | Hayter et al. |
| 2014/0114156 A1 | 4/2014 | Böhm et al. |
| 2014/0121480 A1 | 5/2014 | Budiman et al. |
| 2014/0121488 A1 | 5/2014 | Budiman |
| 2014/0207400 A1 | 7/2014 | Hayter et al. |
| 2014/0221966 A1 | 8/2014 | Buckingham et al. |
| 2014/0236536 A1 | 8/2014 | Hayter et al. |
| 2014/0243638 A1 | 8/2014 | Harper et al. |
| 2014/0257059 A1 | 9/2014 | Budiman et al. |
| 2015/0005601 A1 | 1/2015 | Hoss et al. |
| 2015/0006109 A1 | 1/2015 | Fennell et al. |
| 2015/0094555 A1 | 4/2015 | He |
| 2015/0216456 A1 | 8/2015 | Budiman |
| 2015/0241407 A1 | 8/2015 | Ou et al. |
| 2015/0282742 A1 | 10/2015 | Hayter et al. |
| 2015/0366510 A1 | 12/2015 | Budiman |
| 2015/0374299 A1 | 12/2015 | Hayter |
| 2016/0022221 A1 | 1/2016 | Ou et al. |
| 2016/0073941 A1 | 3/2016 | Böhm et al. |
| 2016/0151006 A1 | 6/2016 | Harper et al. |
| 2016/0157758 A1 | 6/2016 | Böhm et al. |
| 2016/0198986 A1 | 7/2016 | Böhm et al. |
| 2016/0206233 A1 | 7/2016 | Hayter et al. |
| 2016/0220189 A1 | 8/2016 | Hayter et al. |
| 2016/0238589 A1 | 8/2016 | Harper et al. |

(56) References Cited

U.S. PATENT DOCUMENTS

| | | |
|---|---|---|
| 2016/0245791 A1 | 8/2016 | Hayter et al. |
| 2016/0270705 A1 | 9/2016 | He |
| 2016/0296697 A1 | 10/2016 | Hayter et al. |
| 2016/0317069 A1 | 11/2016 | Hayter et al. |
| 2017/0003766 A1 | 1/2017 | Budiman |
| 2017/0027484 A1 | 2/2017 | Hayter et al. |
| 2017/0042456 A1 | 2/2017 | Budiman |
| 2017/0049369 A1 | 2/2017 | Hayter et al. |
| 2017/0124287 A1 | 5/2017 | Hayter et al. |
| 2017/0188909 A1 | 7/2017 | Hayter et al. |
| 2017/0224258 A1 | 8/2017 | Hayter et al. |
| 2017/0258379 A1 | 9/2017 | Budiman et al. |
| 2017/0265790 A1 | 9/2017 | Budiman et al. |
| 2017/0340250 A1 | 11/2017 | Hayter et al. |
| 2017/0347927 A1 | 12/2017 | He |
| 2018/0000389 A1 | 1/2018 | Harper et al. |
| 2018/0008174 A1 | 1/2018 | Böhm et al. |
| 2018/0008201 A1 | 1/2018 | Hayter et al. |
| 2018/0038844 A1 | 2/2018 | Hayter et al. |
| 2018/0042530 A1 | 2/2018 | Böhm et al. |
| 2018/0042531 A1 | 2/2018 | Budiman et al. |
| 2018/0042534 A1 | 2/2018 | Hayter |
| 2018/0045707 A1 | 2/2018 | Hayter et al. |
| 2018/0059093 A1 | 3/2018 | Hayter et al. |
| 2018/0064398 A1 | 3/2018 | Budiman |
| 2018/0085037 A1 | 3/2018 | Hayter et al. |
| 2018/0098721 A1 | 4/2018 | Hayter et al. |
| 2018/0271415 A1 | 9/2018 | Böhm et al. |
| 2018/0328766 A1 | 11/2018 | Hayter et al. |
| 2018/0344220 A1 | 12/2018 | Hayter et al. |
| 2018/0364215 A1 | 12/2018 | Harper et al. |
| 2019/0035488 A1 | 1/2019 | Budiman |
| 2019/0072538 A1 | 3/2019 | Hayter et al. |
| 2019/0083012 A1 | 3/2019 | Hayter et al. |
| 2019/0083015 A1 | 3/2019 | Hayter |
| 2019/0150802 A1 | 5/2019 | Budiman et al. |
| 2019/0151542 A1 | 5/2019 | Hayter et al. |
| 2019/0159734 A1 | 5/2019 | Budiman |
| 2019/0187814 A1 | 6/2019 | Budiman |
| 2019/0192071 A1 | 6/2019 | Taub et al. |
| 2019/0254575 A1 | 8/2019 | Hayter et al. |
| 2019/0261902 A1 | 8/2019 | Böhm et al. |
| 2019/0320948 A1 | 10/2019 | Böhm et al. |
| 2019/0320949 A1 | 10/2019 | Böhm et al. |
| 2019/0336051 A1 | 11/2019 | Böhm et al. |
| 2019/0350499 A1 | 11/2019 | Böhm et al. |
| 2019/0357817 A1 | 11/2019 | Böhm et al. |
| 2019/0380627 A1 | 12/2019 | Bohm et al. |
| 2020/0022626 A1 | 1/2020 | Bohm et al. |

FOREIGN PATENT DOCUMENTS

| | | |
|---|---|---|
| EP | 0320109 A1 | 6/1989 |
| EP | 0353328 A1 | 2/1990 |
| EP | 0390390 A1 | 10/1990 |
| EP | 0396788 A1 | 11/1990 |
| EP | 0472411 A1 | 2/1992 |
| EP | 0286118 B1 | 1/1995 |
| EP | 0867146 A1 | 9/1998 |
| EP | 1048264 A1 | 11/2000 |
| EP | 1419731 A1 | 5/2004 |
| EP | 0939602 B1 | 9/2004 |
| EP | 1850909 B1 | 4/2010 |
| EP | 1677668 B1 | 7/2010 |
| EP | 2069772 B1 | 5/2014 |
| JP | 2003522558 A | 7/2003 |
| JP | 2007501028 A | 1/2007 |
| JP | 2008253482 A | 10/2008 |
| WO | WO-9625089 A1 | 8/1996 |
| WO | WO-9635370 A1 | 11/1996 |
| WO | WO-9715227 A1 | 5/1997 |
| WO | WO-9835053 A2 | 8/1998 |
| WO | WO-9907878 A1 | 2/1999 |
| WO | WO-9908485 A1 | 2/1999 |
| WO | WO-9956613 A1 | 11/1999 |
| WO | WO-0049940 A2 | 8/2000 |
| WO | WO-0059370 A1 | 10/2000 |
| WO | WO-0074753 A1 | 12/2000 |
| WO | WO-0152935 A1 | 7/2001 |
| WO | WO-0154753 A2 | 8/2001 |
| WO | WO-0216905 A2 | 2/2002 |
| WO | WO-03076893 A2 | 9/2003 |
| WO | WO-03082091 A2 | 10/2003 |
| WO | WO-2004060455 A1 | 7/2004 |
| WO | WO-2005010756 A2 | 2/2005 |
| WO | WO-2005011489 A1 | 2/2005 |
| WO | WO-2005065542 A2 | 7/2005 |
| WO | WO-2006008505 A1 | 1/2006 |
| WO | WO-2006024671 A1 | 3/2006 |
| WO | WO-2006081336 A2 | 8/2006 |
| WO | WO-2007097754 A1 | 8/2007 |
| WO | WO-2008086541 A2 | 7/2008 |
| WO | WO-2010022387 A1 | 2/2010 |
| WO | WO-2010078263 A2 | 7/2010 |
| WO | WO-2010099507 A1 | 9/2010 |

OTHER PUBLICATIONS

Arnold M.A., et al., "Selectivity Assessment of Noninvasive Glucose Measurements Based on Analysis of Multivariate Calibration Vectors," Journal of Diabetes Science and Technology, vol. 1 (4), Jul. 2007, pp. 454-462.

Bennion N., et al., "Alternate Site Glucose Testing: a Crossover Design," Diabetes Technology & Therapeutics, vol. 4 (1), 2002, pp. 25-33.

Blank T.B., et al., "Clinical Results From a Non-Invasive Blood Glucose Monitor," Optical Diagnostics and Sensing of Biological Fluids and Glucose and Cholesterol Monitoring II, Proceedings of SPIE, vol. 4624, 2002, pp. 1-10.

Boyne M.S., et al., "Timing of Changes in Interstitial and Venous Blood Glucose Measured With a Continuous Subcutaneous Glucose Sensor," Diabetes, vol. 52, Nov. 2003, pp. 2790-2794.

Bremer T.M., et al., "Benchmark Data from the Literature for Evaluation of New Glucose Sensing Technologies," Diabetes Technology & Therapeutics, vol. 3 (3), 2001, pp. 409-418.

Brooks S.L., et al., "Development of an On-line Glucose Sensor for Fermentation Monitoring," Biosensors, vol. 3, 1987/1988, pp. 45-56.

Cass A.E.G., et al., "Ferrocene-Mediated Enzyme Electrodes for Amperometric Determination of Glucose," Analytical Chemistry, vol. 56 (4), Apr. 1984, pp. 667-671.

Cheyne E.H., et al., "Performance of a Continuous Glucose Monitoring System During Controlled Hypoglycaemia in Healthy Volunteers," Diabetes Technology & Therapeutics, vol. 4 (5), 2002, pp. 607-613.

Choleau C., et al., "Calibration of a Subcutaneous Amperometric Glucose Sensor Implanted for 7 Days in Diabetic Patients Part 2. Superiority of the One-point Calibration Method," Biosensors and Bioelectronics, vol. 17 (8), 2002, pp. 647-654.

Csoregi E., et al., "Design and Optimization of a Selective Subcutaneously Implantable Glucose Electrode Based on 'Wired' Glucose Oxidase," Analytical Chemistry, vol. 67 (7), Apr. 1, 1995, pp. 1240-1244.

Eren-Oruklu M., et al., "Estimation of Future Glucose Concentrations with Subject-Specific Recursive Linear Models," Diabetes Technology & Therapeutics, vol. 11 (4), 2009, pp. 243-253.

Extended European Search Report for Application No. 13275272.6, dated Mar. 3, 2014, 8 pages.

Feldman B., et al., "A Continuous Glucose Sensor Based on Wired EnzymeTM Technology-Results from a 3-Day Trial in Patients with Type 1 Diabetes," Diabetes Technology & Therapeutics, vol. 5 (5), 2003, pp. 769-779.

Feldman B., et al., "Correlation of Glucose Concentrations in Interstitial Fluid and Venous Blood During Periods of Rapid Glucose Change," Abbott Diabetes Care, Inc. Freestyle Navigator Continuous Glucose Monitor Pamphlet, 2004, 1 page.

File History of U.S. Appl. No. 15/616,916, filed Jun. 7, 2017, 169 pages.

File History of U.S. Appl. No. 15/789,949, filed Oct. 20, 2017, 276 pages.

(56) References Cited

OTHER PUBLICATIONS

Gamry Instruments, "Basics of Electrochemical Impedance Spectroscopy," 2007, 30 pages.
Georgescu B., et al., "Real-Time Multi-Model Tracking of Myocardium in Echocardiography Using Robust Information Fusion," Medical Image Computing and Computer-Assisted Intervention, Springer-Verlag Berlin Heidelberg, 2004, pp. 777-785.
Goldman J.M., et al., "Masimo Signal Extraction Pulse Oximetry," Journal of Clinical Monitoring and Computing, vol. 16 (7), 2000, pp. 475-483.
Guerci B., et al., "Clinical Performance of CGMS in Type 1 Diabetic Patients Treated by Continuous Subcutaneous Insulin Infusion Using Insulin Analogs," Diabetes Care, vol. 26, 2003, pp. 582-589.
Hoss U., et al., "Continuous Glucose Monitoring in Subcutaneous Tissue Using Factory-Calibrated Sensors: A Pilot Study," Diabetes Technology & Therapeutics, Jul. 8, 2010, vol. 12 (8), pp. 591-597.
Hovorka R., et al., "Nonlinear Model Predictive Control of Glucose Concentration in Subjects with Type 1 Diabetes," Physiological Measurement, vol. 25, Jul. 2004, pp. 905-920.
Isermann R., "Supervision, Fault-Detection and Fault-Diagnosis Methods—An Introduction," Control Engineering Practice, vol. 5 (5), 1997, pp. 639-652.
Isermann R., et al., "Trends in the Application of Model-Based Fault Detection and Diagnosis of Technical Processes", Control Engineering Practice, vol. 5 (5), 1997, pp. 709-719.
Johnson P.C., "Peripheral Circulation," John Wiley & Sons, 1978, p. 198 (5 pages).
Jungheim K., et al., "How Rapid Does Glucose Concentration Change in Daily Life of Patients with Type 1 Diabetes?," Diabetologia, 2002, vol. 45, pp. A250-A276.
Jungheim K., et al., "Risky Delay of Hypoglycemia Detection by Glucose Monitoring at the Arm," Diabetes Care, vol. 24 (7), Jul. 2001, pp. 1303-1304.
Kaplan S.M., "Wiley Electrical and Electronics Engineering Dictionary," IEEE Press, John Wiley & Sons, Inc., 2004, pp. 141, 142, 548 & 549.
Kovatchev B.P., et al., "Evaluating the Accuracy of Continuous Glucose-Monitoring Sensors: Continuous Glucose-Error Grid Analysis Illustrated by TheraSense Freestyle Navigator Data," Diabetes Care, vol. 27 (8), Aug. 2004, pp. 1922-1928.
Kovatchev B.P., et al., "Graphical and Numerical Evaluation of Continuous Glucose Sensing Time Lag", Diabetes Technology & Therapeutics, vol. 11 (3), 2009, pp. 139-143.
Kuure-Kinsey M., et al., "A Dual-Rate Kalman Filter for Continuous Glucose Monitoring," Conf Proc IEEE Eng Med Biol Soc., 2006, vol. 1, pp. 63-66.
Lodwig V., et al., "Continuous Glucose Monitoring with Glucose Sensors: Calibration and Assessment Criteria," Diabetes Technology & Therapeutics, vol. 5 (4), 2003, pp. 572-587.
Lortz J., et al., "What is Bluetooth? We Explain the Newest Short-Range Connectivity Technology," In Smart Computing Learning Series, Wireless Computing, vol. 8 (5), 2002, pp. 72-74.
Maher R.C., "A Method for Extrapolation of Missing Digital Audio Data," Preprints of Papers Presented at the AES Convention, New York, 1993, pp. 1-19.
Maher R.C., "Audio Enhancement Using Nonlinear Time-Frequency Filtering," AES 26th International Conference, Jul. 7-9, 2005, pp. 1-9.
Malin S.F., et al., "Noninvasive Prediction of Glucose by Near-Infrared Diffuse Reflectance Spectroscopy," Clinical Chemistry, vol. 45 (9), 1999, pp. 1651-1658.
McGarraugh G., et al., "Glucose Measurements Using Blood Extracted From the Forearm and the Finger," TheraSense, Inc., 2001, pp. 1-8.
McGarraugh G., et al., "Physiological Influences on Off-Finger Glucose Testing", Diabetes Technology & Therapeutics, vol. 3 (3), 2001, pp. 367-376.
McKean B.D., et al., "A Telemetry Instrumentation System for Chronically Implanted Glucose and Oxygen Sensors," IEEE Transactions on Biomedical Engineering, vol. 35 (7), Jul. 1988, pp. 526-532.
Morbiducci U., et al., "Improved Usability of the Minimal Model of Insulin Sensitivity Based on Automated Approach and Genetic Algorithms for Parameter Estimation," Clinical Science, vol. 112 (4), 2006, pp. 257-263.
Mougiakakou S.G., et al., "A Real Time Simulation Model of Glucose-Insulin Metabolism for Type 1 Diabetes Patients," Conf Proc IEEE Eng Med Biol Soc. 2005, vol. 1, pp. 298-301.
Notice of Allowance for U.S Appl. No. 14/066,650, dated Feb. 16, 2017, 7 pages.
Notice of Allowance for U.S Appl. No. 15/796,274, dated Jul. 20, 2018, 8 pages.
Noujaim S.E., et al., "Accuracy Requirements for a Hypoglycemia Detector: An Analytical Model to Evaluate the Effects of Bias, Precision and Rate of Glucose Change" Journal of Diabetes Science & Technology, vol. 1 (5), Sep. 2007, pp. 652-668.
O'Donoghue M., et al., "Electrochemical Impedance Spectroscopy: Testing Coatings for Rapid Immersion Service," Materials Performance, Sep. 2003, pp. 36-41.
Office Action for U.S Appl. No. 14/066,650, dated Sep. 23, 2016, 6 pages.
Office Action for U.S Appl. No. 14/077,004, dated Jul. 26, 2016, 14 pages.
Panteleon A.E., et al., "The Role of the Independent Variable to Glucose Sensor Calibration," Diabetes Technology & Therapeutics, vol. 5 (3), 2003, pp. 401-410.
Park, et al., "Novel Instrumentation in Electrochemical Impedance Spectroscopy and a Full Description of an Electrochemical System," Pure Appl. Chem., 2006, vol. 78 (5), pp. 1069-1080.
Parker R.S., et al., "Robust H∞ Glucose Control in Diabetes Using a Physiological Model," AIChE Journal, vol. 46 (12), Dec. 2000, pp. 2537-2549.
Pickup J.C., et al., "Implantable Glucose Sensors: Choosing the Appropriate Sensor Strategy," Biosensors, vol. 3, (1987/1988), pp. 335-346.
Pickup J.C., et al., "In Vivo Molecular Sensing in Diabetes Mellitus: An Implantable Glucose Sensor with Direct Electron Transfer," Diabetologia, vol. 32, 1989, pp. 213-217.
Pishko M.V., et al., "Amperometric Glucose Microelectrodes Prepared Through Immobilization of Glucose Oxidase in Redox Hydrogels," Analytical Chemistry, vol. 63 (20), 1991, pp. 2268-2272.
Quinn C.P., et al., "Kinetics of Glucose Delivery to Subcutaneous Tissue in Rats Measured with 0.3-mm Amperometric Microsensors," The American Physiological Society, vol. 269, 1995, pp. E155-E161.
Roe J.N., et al., "Bloodless Glucose Measurements," Critical Reviews™ in Therapeutic Drug Carrier Systems, vol. 15 (3), 1998, pp. 199-241.
Sakakida M., et al., "Development of Ferrocene-Mediated Needle-Type Glucose Sensor as a Measure of True Subcutaneous Tissue Glucose Concentrations," Artif. Organs Today, vol. 2 (2), 1992, pp. 145-158.
Sakakida M., et al., "Ferrocene-Mediated Needle Type Glucose Sensor Covered with Newly Designed Biocompatible Membrane," Sensors and Actuators B, vol. 13-14, 1993, pp. 319-322.
Salehi C., et al., "A Telemetry-Instrumentation System for Long-Term Implantable Glucose and Oxygen Sensors," Analytical Letters, vol. 29 (13), 1996, pp. 2289-2308.
Schmidtke D.W., et al., "Measurement and Modeling of the Transient Difference Between Blood and Subcutaneous Glucose Concentrations in the Rat After Injection of Insulin," Proceedings of the National Academy of Sciences, vol. 95, Jan. 1998, pp. 294-299.
Shaw G.W., et al., "In Vitro Testing of a Simply Constructed, Highly Stable Glucose Sensor Suitable for Implantation in Diabetic Patients," Biosensors & Bioelectronics, vol. 6, 1991, pp. 401-406.
Shichiri M., et al., "Glycaemic Control in Pancreatectomized Dogs with a Wearable Artificial Endocrine Pancreas," Diabetologia, vol. 24, 1983, pp. 179-184.

(56) References Cited

OTHER PUBLICATIONS

Shichiri M., et al., "Membrane Design for Extending the Long-Life of an Implantable Glucose Sensor," Diabetes Nutrition & Metabolism, vol. 2 (4), 1989, pp. 309-313.

Shichiri M., et al., "Needle Type Glucose Sensor for Wearable Artificial Endocrine Pancreas," In Implantable Sensors for Closed-Loop Prosthetic Systems edited by KO W.H, Chapter 15, 1985, pp. 197-210.

Shichiri M., et al., "Telemetry Glucose Monitoring Device with Needle-Type Glucose Sensor: A Useful Tool for Blood Glucose Monitoring in Diabetic Individuals," Diabetes Care, vol. 9 (3), May-Jun. 1986, pp. 298-301.

Shichiri M., et al., "Wearable Artificial Endocrine Pancreas with Needle-Type Glucose Sensor," Preliminary Communication, Lancet, vol. 2, Nov. 20, 1982, pp. 1129-1131.

Shichiri, et al., "In Vivo Characteristics of Needle-Type Glucose Sensor-Measurements of Subcutaneous Glucose Concentrations in Human Volunteers," Implantable Glucose Sensors—The State of the Art, Hormone and Metabolic Research Supplement Series, 1988, vol. 20, pp. 17-20.

Shults M.C., et al., "A Telemetry-Instrumentation System for Monitoring Multiple Subcutaneously Implanted Glucose Sensors," IEEE Transactions on Biomedical Engineering, vol. 41 (10), Oct. 1994, pp. 937-942.

Steil G.M., et al., "Closed-Loop Insulin Delivery—the Path of Physiological Glucose Control," Advanced Drug Delivery Reviews, vol. 56, 2004, pp. 125-144.

Steil G.M., et al., "Determination of Plasma Glucose During Rapid Glucose Excursions with a Subcutaneous Glucose Sensor," Diabetes Technology & Therapeutics, vol. 5 (1), 2003, pp. 27-31.

Sternberg R., et al., "Study and Development of Multilayer Needle-type Enzyme Based Glucose Microsensors," Biosensors, vol. 4, 1988, pp. 27-40.

The Diabetes Control and Complications Trial Research Group, "The Effect of Intensive Treatment of Diabetes on the Development and Progression of Long-Term Complications in Insulin-Dependent Diabetes Mellitus," The New England, Journal of Medicine, vol. 329 (14), Sep. 30, 1993, pp. 977-986.

Thompson M., et al., "In Vivo Probes: Problems and Perspectives," Clinical Biochemistry, vol. 19 (5), Oct. 1986, pp. 255-261.

Turner A.P.F., et al., "Diabetes Mellitus: Biosensors for Research and Management," Biosensors, vol. 1, 1985, pp. 85-115.

Updike S.J., et al., "Principles of Long-Term Fully Implanted Sensors with Emphasis on Radiotelemetric Monitoring of Blood Glucose Form Inside a Subcutaneous Foreign Body Capsule (FBC)," Edited by Fraser D M, Biosensors in the Body: Continuous in vivo Monitoring, John Wiley & Sons Ltd., New York, 1997, Chapter 4, pp. 117-137.

Velho G., et al., "Strategies for Calibrating a Subcutaneous Glucose Sensor," Biomed Biochim Acta, vol. 48 (11/12), 1989, pp. 957-964.

Whipple G., "Low Residual Noise Speech Enhancement Utilizing Time-Frequency Filtering," Proceedings of the International Conference on Acoustics, Speech, and Signal Processing, 1994, pp. I5-I8.

Wilson G.S., et al., "Progress Toward the Development of an Implantable Sensor for Glucose," Clinical Chemistry, vol. 38 (9), 1992, pp. 1613-1617.

Wolfe P.J., et al., "Interpolation of Missing Data Values for Audio Signal Restoration Using a Gabor Regression Model," 2005 IEEE International Conference on Acoustics, Speech, and Signal Processing, vol. 5, 2005, pp. 517-520.

Yoo, et al., "An Electrochemical Impedance Measurement Technique Employing Fourier Transform," Anal. Chem. 2000, vol. 72, pp. 2035-2041.

European Extended Search Report for Application No. 19185162.5, dated Aug. 13, 2019, 7 pages.

* cited by examiner

ADVANCED ANALYTE SENSOR CALIBRATION AND ERROR DETECTION

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/460,943, filed Jul. 2, 2019, which is a continuation of U.S. application Ser. No. 16/405,887, filed May 7, 2019, which is a continuation of U.S. application Ser. No. 15/994,905, filed May 31, 2018, now U.S. Pat. No. 10,327,688, which is a continuation of U.S. application Ser. No. 14/860,392, filed Sep. 21, 2015, now U.S. Pat. No. 10,004,442, which is a continuation of U.S. application Ser. No. 13/446,977, filed Apr. 13, 2012, now U.S. Pat. No. 9,149,220, which is a continuation of U.S. application Ser. No. 13/446,848, filed Apr. 13, 2012, now U.S. Pat. No. 9,801,575, which claims the benefit of U.S. Provisional Application No. 61/476,145, filed Apr. 15, 2011. Each of the aforementioned applications is incorporated by reference herein in its entirety, and each is hereby expressly made a part of this specification.

TECHNICAL FIELD

The embodiments described herein relate generally to systems and methods for processing sensor data from continuous analyte sensors and for self-calibration.

BACKGROUND

Diabetes mellitus is a chronic disease, which occurs when the pancreas does not produce enough insulin (Type I), or when the body cannot effectively use the insulin it produces (Type II). This condition typically leads to an increased concentration of glucose in the blood (hyperglycemia), which can cause an array of physiological derangements (e.g., kidney failure, skin ulcers, or bleeding into the vitreous of the eye) associated with the deterioration of small blood vessels. Sometimes, a hypoglycemic reaction (low blood sugar) is induced by an inadvertent overdose of insulin, or after a normal dose of insulin or glucose-lowering agent accompanied by extraordinary exercise or insufficient food intake.

A variety of sensor devices have been developed for continuously measuring blood glucose concentrations. Conventionally, a diabetic person carries a self-monitoring blood glucose (SMBG) monitor, which typically involves uncomfortable finger pricking methods. Due to a lack of comfort and convenience, a diabetic will often only measure his or her glucose levels two to four times per day. Unfortunately, these measurements can be spread far apart, such that a diabetic may sometimes learn too late of a hypoglycemic or hyperglycemic event, thereby potentially incurring dangerous side effects. In fact, not only is it unlikely that a diabetic will take a timely SMBG measurement, but even if the diabetic is able to obtain a timely SMBG value, the diabetic may not know whether his or her blood glucose value is increasing or decreasing, based on the SMBG alone.

Heretofore, a variety of glucose sensors have been developed for continuously measuring glucose values. Many implantable glucose sensors suffer from complications within the body and provide only short-term and less-than-accurate sensing of blood glucose. Similarly, transdermal sensors have run into problems in accurately sensing and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts have also been made to obtain blood glucose data from transdermal devices for prospective data analysis, however similar problems have occurred.

SUMMARY OF THE INVENTION

In a first aspect, a method is provided for calibrating sensor data generated by a continuous analyte sensor, comprising: generating sensor data using a continuous analyte sensor; iteratively determining, with an electronic device, a sensitivity value of the continuous analyte sensor as a function of time by applying a priori information comprising sensor sensitivity information; and calibrating the sensor data based at least in part on the determined sensitivity value.

In an embodiment of the first aspect or any other embodiment thereof, calibrating the sensor data is performed iteratively throughout a substantially entire sensor session.

In an embodiment of the first aspect or any other embodiment thereof, iteratively determining a sensitivity value is performed at regular intervals or performed at irregular intervals, as determined by the a priori information.

In an embodiment of the first aspect or any other embodiment thereof, iteratively determining a sensitivity value is performed throughout a substantially entire sensor session.

In an embodiment of the first aspect or any other embodiment thereof, determining a sensitivity value is performed in substantially real time.

In an embodiment of the first aspect or any other embodiment thereof, the a priori information is associated with at least one predetermined sensitivity value that is associated with a predetermined time after start of a sensor session.

In an embodiment of the first aspect or any other embodiment thereof, at least one predetermined sensitivity value is associated with a correlation between a sensitivity determined from in vitro analyte concentration measurements and a sensitivity determined from in vivo analyte concentration measurements at the predetermined time.

In an embodiment of the first aspect or any other embodiment thereof, the a priori information is associated with a predetermined sensitivity function that uses time as input.

In an embodiment of the first aspect or any other embodiment thereof, time corresponds to time after start of a sensor session.

In an embodiment of the first aspect or any other embodiment thereof, time corresponds to at least one of time of manufacture or time since manufacture.

In an embodiment of the first aspect or any other embodiment thereof, the sensitivity value of the continuous analyte sensor is also a function of at least one other parameter.

In an embodiment of the first aspect or any other embodiment thereof, the at least one other parameter is selected from the group consisting of: temperature, pH, level or duration of hydration, curing condition, an analyte concentration of a fluid surrounding the continuous analyte sensor during startup of the sensor, and combinations thereof.

In an embodiment of the first aspect or any other embodiment thereof, calibrating the sensor data is performed without using reference blood glucose data.

In an embodiment of the first aspect or any other embodiment thereof, the electronic device is configured to provide a level of accuracy corresponding to a mean absolute relative difference of no more than about 10% over a sensor session of at least about 3 days, and wherein reference measurements associated with calculation of the mean absolute relative difference are determined by analysis of blood.

In an embodiment of the first aspect or any other embodiment thereof, the sensor session is at least about 4 days.

In an embodiment of the first aspect or any other embodiment thereof, the sensor session is at least about 5 days.

In an embodiment of the first aspect or any other embodiment thereof, the sensor session is at least about 6 days.

In an embodiment of the first aspect or any other embodiment thereof, the sensor session is at least about 7 days.

In an embodiment of the first aspect or any other embodiment thereof, the sensor session is at least about 10 days.

In an embodiment of the first aspect or any other embodiment thereof, the mean absolute relative difference is no more than about 7% over the sensor session.

In an embodiment of the first aspect or any other embodiment thereof, the mean absolute relative difference is no more than about 5% over the sensor session.

In an embodiment of the first aspect or any other embodiment thereof, the mean absolute relative difference is no more than about 3% over the sensor session.

In an embodiment of the first aspect or any other embodiment thereof, the a priori information is associated with a calibration code.

In an embodiment of the first aspect or any other embodiment thereof, the a priori sensitivity information is stored in the sensor electronics prior to use of the sensor.

In a second aspect, a system is provided for implementing the method of the first aspect or any embodiments thereof.

In a third aspect, a method is provided for calibrating sensor data generated by a continuous analyte sensor, the method comprising: generating sensor data using a continuous analyte sensor; determining, with an electronic device, a plurality of different sensitivity values of the continuous analyte sensor as a function of time and of sensitivity information associated with a priori information; and calibrating the sensor data based at least in part on at least one of the plurality of different sensitivity values.

In an embodiment of the third aspect or any other embodiment thereof, calibrating the continuous analyte sensor is performed iteratively throughout a substantially entire sensor session.

In an embodiment of the third aspect or any other embodiment thereof, the plurality of different sensitivity values are stored in a lookup table in computer memory.

In an embodiment of the third aspect or any other embodiment thereof, determining a plurality of different sensitivity values is performed once throughout a substantially entire sensor session.

In an embodiment of the third aspect or any other embodiment thereof, the a priori information is associated with at least one predetermined sensitivity value that is associated with a predetermined time after start of a sensor session.

In an embodiment of the third aspect or any other embodiment thereof, the at least one predetermined sensitivity value is associated with a correlation between a sensitivity determined from in vitro analyte concentration measurements and a sensitivity determined from in vivo analyte concentration measurements at the predetermined time.

In an embodiment of the third aspect or any other embodiment thereof, the a priori information is associated with a predetermined sensitivity function that uses time as input.

In an embodiment of the third aspect or any other embodiment thereof, time corresponds to time after start of a sensor session.

In an embodiment of the third aspect or any other embodiment thereof, time corresponds to time of manufacture or time since manufacture.

In an embodiment of the third aspect or any other embodiment thereof, the plurality of sensitivity values are also a function of at least one parameter other than time.

In an embodiment of the third aspect or any other embodiment thereof, the at least one other parameter is selected from the group consisting of: temperature, pH, level or duration of hydration, curing condition, an analyte concentration of a fluid surrounding the continuous analyte sensor during startup of the sensor, and combinations thereof.

In an embodiment of the third aspect or any other embodiment thereof, calibrating the continuous analyte sensor is performed without using reference blood glucose data.

In an embodiment of the third aspect or any other embodiment thereof, the electronic device is configured to provide a level of accuracy corresponding to a mean absolute relative difference of no more than about 10% over a sensor session of at least about 3 days; and wherein reference measurements associated with calculation of the mean absolute relative difference are determined by analysis of blood.

In an embodiment of the third aspect or any other embodiment thereof, the sensor session is at least about 4 days.

In an embodiment of the third aspect or any other embodiment thereof, the sensor session is at least about 5 days.

In an embodiment of the third aspect or any other embodiment thereof, the sensor session is at least about 6 days.

In an embodiment of the third aspect or any other embodiment thereof, the sensor session is at least about 7 days.

In an embodiment of the third aspect or any other embodiment thereof, the sensor session is at least about 10 days.

In an embodiment of the third aspect or any other embodiment thereof, the mean absolute relative difference is no more than about 7% over the sensor session.

In an embodiment of the third aspect or any other embodiment thereof, the mean absolute relative difference is no more than about 5% over the sensor session.

In an embodiment of the third aspect or any other embodiment thereof, the mean absolute relative difference is no more than about 3% over the sensor session.

In an embodiment of the third aspect or any other embodiment thereof, the a priori information is associated with a calibration code.

In a fourth aspect, a system is provided for implementing the method of the third aspect or any embodiments thereof.

In a fifth aspect, a method is provided for processing data from a continuous analyte sensor, the method comprising: receiving, with an electronic device, sensor data from a continuous analyte sensor, the sensor data comprising at least one sensor data point; iteratively determining a sensitivity value of the continuous analyte sensor as a function of time and of an at least one predetermined sensitivity value associated with a predetermined time after start of a sensor session; forming a conversion function based at least in part on the sensitivity value; and determining an analyte output value by applying the conversion function to the at least one sensor data point.

In an embodiment of the fifth aspect or any other embodiment thereof, the iteratively determining a sensitivity of the continuous analyte sensor is performed continuously.

In an embodiment of the fifth aspect or any other embodiment thereof, iteratively determining a sensitivity is performed in substantially real time.

In an embodiment of the fifth aspect or any other embodiment thereof, the method further comprises determining a baseline of the continuous analyte sensor, and wherein the conversion function is based at least in part on the baseline.

In an embodiment of the fifth aspect or any other embodiment thereof, determining a baseline of the continuous analyte sensor is performed continuously.

In an embodiment of the fifth aspect or any other embodiment thereof, determining a sensitivity of the continuous analyte sensor and determining a baseline of the analyte sensor are performed at substantially the same time.

In an embodiment of the fifth aspect or any other embodiment thereof, the at least one predetermined sensitivity value is set at a manufacturing facility for the continuous analyte sensor.

In an embodiment of the fifth aspect or any other embodiment thereof, the method further comprises receiving at least one calibration code; and applying the at least one calibration code to the electronic device at a predetermined time after start of the sensor session.

In an embodiment of the fifth aspect or any other embodiment thereof, iteratively determining a sensitivity is performed at regular intervals or performed at irregular intervals, as determined by the at least one calibration code.

In an embodiment of the fifth aspect or any other embodiment thereof, the at least one calibration code is associated with the at least one predetermined sensitivity.

In an embodiment of the fifth aspect or any other embodiment thereof, the at least one calibration code is associated with a predetermined sensitivity function that uses time of the function of time as input.

In an embodiment of the fifth aspect or any other embodiment thereof, time corresponds to time after start of the sensor session.

In an embodiment of the fifth aspect or any other embodiment thereof, time corresponds to time of manufacture or time since manufacture.

In an embodiment of the fifth aspect or any other embodiment thereof, the sensitivity value of the continuous analyte sensor is also a function of at least one other parameter.

In an embodiment of the fifth aspect or any other embodiment thereof, the at least one other parameter is selected from the group consisting of: temperature, pH, level or duration of hydration, curing condition, an analyte concentration of a fluid surrounding the continuous analyte sensor during startup of the sensor, and combinations thereof.

In a sixth aspect, a system is provided for implementing the method of the fifth aspect or any embodiments thereof.

In a seventh aspect, a method is provided for calibrating a continuous analyte sensor, the method comprising: receiving sensor data from a continuous analyte sensor; forming or receiving a predetermined sensitivity profile corresponding to a change in sensor sensitivity to an analyte over a substantially entire sensor session, wherein the predetermined sensitivity profile is a function of at least one predetermined sensitivity value associated with a predetermined time after start of the sensor session; and applying, with an electronic device, the sensitivity profile in real-time calibrations.

In an embodiment of the seventh aspect or any other embodiment thereof, the at least one predetermined sensitivity value, the predetermined sensitivity profile, or both are set at a manufacturing facility for the continuous analyte sensor.

In an embodiment of the seventh aspect or any other embodiment thereof, the method further comprises receiving at least one calibration code; and applying the at least one calibration code to the electronic device at a predetermined time after start of the sensor session.

In an embodiment of the seventh aspect or any other embodiment thereof, the at least one calibration code is associated with the at least one predetermined sensitivity.

In an embodiment of the seventh aspect or any other embodiment thereof, the at least one calibration code is associated with a predetermined sensitivity function that uses time as input.

In an embodiment of the seventh aspect or any other embodiment thereof, the sensitivity profile is a function of time.

In an embodiment of the seventh aspect or any other embodiment thereof, time corresponds to time after start of the sensor session.

In an embodiment of the seventh aspect or any other embodiment thereof, time corresponds to time of manufacture or time since manufacture.

In an embodiment of the seventh aspect or any other embodiment thereof, the sensitivity value is a function of time, the predetermined sensitivity value, and at least one parameter selected from the group consisting of: temperature, pH, level or duration of hydration, curing condition, an analyte concentration of a fluid surrounding the continuous analyte sensor during startup of the sensor, and combinations thereof.

In an eighth aspect, a system is provided for implementing the method of the seventh aspect or any embodiments thereof.

In a ninth aspect, a method is provided for processing data from a continuous analyte sensor, the method comprising: receiving, with an electronic device, sensor data from a continuous analyte sensor, the sensor data comprising at least one sensor data point; receiving or forming a sensitivity profile corresponding to a change in sensor sensitivity over a substantially entire sensor session; forming a conversion function based at least in part on the sensitivity profile; and determining an analyte output value by applying the conversion function to the at least one sensor data point.

In an embodiment of the ninth aspect or any other embodiment thereof, the sensitivity profile is set at a manufacturing facility for the continuous analyte sensor.

In an embodiment of the ninth aspect or any other embodiment thereof, the method comprises receiving at least one calibration code; and applying the at least one calibration code to the electronic device at a predetermined time after start of the sensor session.

In an embodiment of the ninth aspect or any other embodiment thereof, the at least one calibration code is associated with the at least one predetermined sensitivity.

In an embodiment of the ninth aspect or any other embodiment thereof, the at least one calibration code is associated with the sensitivity profile.

In an embodiment of the ninth aspect or any other embodiment thereof, the sensitivity profile is a function of time.

In an embodiment of the ninth aspect or any other embodiment thereof, time corresponds to time after start of the sensor session.

In an embodiment of the ninth aspect or any other embodiment thereof, time corresponds to time of manufacture or time since manufacture.

In an embodiment of the ninth aspect or any other embodiment thereof, the sensitivity is a function of time and at least one parameter is selected from the group consisting of: temperature, pH, level or duration of hydration, curing condition, an analyte concentration of a fluid surrounding the continuous analyte sensor during startup of the sensor, and combinations thereof.

In a tenth aspect, a system is provided for implementing the method of the ninth aspect or any embodiments thereof.

In an eleventh aspect, a system is provided for monitoring analyte concentration in a host, the system comprising: a continuous analyte sensor configured to measure analyte concentration in a host and to provide factory-calibrated sensor data, the factory-calibrated sensor data being calibrated without reference blood glucose data; wherein the system is configured to provide a level of accuracy corresponding to a mean absolute relative difference of no more than about 10% over a sensor session of at least about 3 days, wherein reference measurements associated with calculation of the mean absolute relative difference are determined by analysis of blood.

In an embodiment of the eleventh aspect or any other embodiment thereof, the sensor session is at least about 4 days.

In an embodiment of the eleventh aspect or any other embodiment thereof, the sensor session is at least about 5 days.

In an embodiment of the eleventh aspect or any other embodiment thereof, the sensor session is at least about 6 days.

In an embodiment of the eleventh aspect or any other embodiment thereof, the sensor session is at least about 7 days.

In an embodiment of the eleventh aspect or any other embodiment thereof, the sensor session is at least about 10 days.

In an embodiment of the eleventh aspect or any other embodiment thereof, the mean absolute relative difference is no more than about 7% over the sensor session.

In an embodiment of the eleventh aspect or any other embodiment thereof, the mean absolute relative difference is no more than about 5% over the sensor session.

In an embodiment of the eleventh aspect or any other embodiment thereof, the mean absolute relative difference is no more than about 3% over the sensor session.

In a twelfth aspect, a method for determining a property of a continuous analyte sensor, the method comprising: applying a bias voltage to an analyte sensor; applying a voltage step above the bias voltage to the analyte sensor; measuring, using sensor electronics, a signal response of the voltage step; determining, using the sensor electronics, a peak current of the signal response; determining, using the sensor electronics, a property of the sensor by correlating the peak current to a predetermined relationship.

In an embodiment of the twelfth aspect or any other embodiment thereof, correlating the peak current to the predetermined relationship comprises calculating an impedance of the sensor based on the peak current and correlating the sensor impedance to the predetermined relationship.

In an embodiment of the twelfth aspect or any other embodiment thereof, the property of the sensor is a sensitivity of the sensor or a temperature of the sensor.

In an embodiment of the twelfth aspect or any other embodiment thereof, the peak current is a difference between a magnitude of the response prior to the voltage step and a magnitude of the largest measured response resulting from the voltage step.

In an embodiment of the twelfth aspect or any other embodiment thereof, the predetermined relationship is an impedance-to-sensor sensitivity relationship, and wherein the property of the sensor is a sensitivity of the sensor.

In an embodiment of the twelfth aspect or any other embodiment thereof, the method further comprises compensating sensor data using the determined property of the sensor.

In an embodiment of the twelfth aspect or any other embodiment thereof, the compensating comprises correlating a predetermined relationship of the peak current to sensor sensitivity or change in sensor sensitivity and modifying a value or values of the sensor data responsive to the correlated sensor sensitivity or change in sensor sensitivity.

In an embodiment of the twelfth aspect or any other embodiment thereof, predetermined relationship is a linear relationship over time of use of the analyte sensor.

In an embodiment of the twelfth aspect or any other embodiment thereof, the predetermined relationship is a non-linear relationship over time of use of the analyte sensor.

In an embodiment of the twelfth aspect or any other embodiment thereof, wherein the predetermined relationship is determined by prior testing of sensors similar to the analyte sensor.

In an embodiment of the thirteenth aspect or any other embodiment thereof, the sensor system comprises instructions stored in computer memory, wherein the instructions, when executed by one or more processor of the sensor system, cause the sensor system to implement the method of the twelfth aspect or any embodiment thereof.

In a fourteenth aspect, a method is provided for calibrating an analyte sensor, the method comprising: applying a time-varying signal to the analyte sensor; measuring a signal response to the applied signal; determining, using sensor electronics, a sensitivity of the analyte sensor, the determining comprising correlating at least one property of the signal response to a predetermined sensor sensitivity profile; and generating, using sensor electronics, estimated analyte concentration values using the determined sensitivity and sensor data generated by the analyte sensor.

In an embodiment of the fourteenth aspect or any other embodiment thereof, the sensitivity profile comprises varying sensitivity values over time since implantation of the sensor.

In an embodiment of the fourteenth aspect or any other embodiment thereof, the predetermined sensitivity profile comprises a plurality of sensitivity values.

In an embodiment of the fourteenth aspect or any other embodiment thereof, the predetermined sensitivity profile is based on sensor sensitivity data generated from studying sensitivity changes of analyte sensors similar to the analyte sensor.

In an embodiment of the fourteenth aspect or any other embodiment thereof, the method further comprises applying a bias voltage to the sensor, wherein the time-varying signal comprises a step voltage above the bias voltage or a sine wave overlaying a voltage bias voltage.

In an embodiment of the fourteenth aspect or any other embodiment thereof, the determining further comprises calculating an impedance value based on the measured signal response and correlating the impedance value to a sensitivity value of the predetermined sensitivity profile.

In an embodiment of the fourteenth aspect or any other embodiment thereof, the method further comprises applying a DC bias voltage to the sensor to generate sensor data, wherein the estimating analyte concentration values includes generating corrected sensor data using the determined sensitivity.

In an embodiment of the fourteenth aspect or any other embodiment thereof, the method further comprises applying a conversion function to the corrected sensor data to generate the estimated analyte concentration values.

In an embodiment of the fourteenth aspect or any other embodiment thereof, the method further comprises forming a conversion function based at least in part of the determined sensitivity, and wherein the conversion function is applied to the sensor data to generate the estimated analyte concentration values.

In an embodiment of the fourteenth aspect or any other embodiment thereof, the property is a peak current value of the signal response.

In an embodiment of the fourteenth aspect or any other embodiment thereof, the determining further comprises using at least one of performing a Fast Fourier Transform on the signal response data, integrating at least a portion of a curve of the signal response, and determining a peak current of the signal response.

In an embodiment of the fourteenth aspect or any other embodiment thereof, the determining further comprises selecting the predetermined sensitivity profile based on the determined sensor property from a plurality of different predetermined sensitivity profiles.

In an embodiment of the fourteenth aspect or any other embodiment thereof, the selecting includes performing a data association analysis to determine a correlation between the determined sensor property and each of the plurality of different predetermined sensitivity profiles and wherein the selected predetermined sensitivity profile has the highest correlation.

In an embodiment of the fourteenth aspect or any other embodiment thereof, the method further comprises generating estimated analyte concentration values using the selected sensitivity profile.

In an embodiment of the fourteenth aspect or any other embodiment thereof, the method further comprises determining a second sensitivity value using the selected sensitivity profile, wherein a first set of estimated analyte concentration values is generated using the determined sensitivity value and sensor data associated with a first time period, and wherein a second set of concentration values is generated using the second sensitivity value and sensor data associated with a second time period.

In a fifteenth aspect, a sensor system is provided for implementing the method of the fourteenth aspect or any embodiments thereof.

In an embodiment of the fifteenth aspect or any other embodiment thereof, the sensor system comprises instructions stored in computer memory, wherein the instructions, when executed by one or more processors of the sensor system, cause the sensor system to implement the method of the fourteenth aspect or any embodiment thereof In a sixteenth aspect, a method is provided for determining whether an analyte sensor system is functioning properly, the method comprising: applying a stimulus signal to the analyte sensor; measuring a response to the stimulus signal; estimating a value of a sensor property based on the signal response; correlating the sensor property value with a predetermined relationship of the sensor property and a predetermined sensor sensitivity profile; and initiating an error routine if the correlation does not exceed a predetermined correlation threshold.

In an embodiment of the sixteenth aspect or any other embodiment thereof, correlating includes performing a data association analysis.

In an embodiment of the sixteenth aspect or any other embodiment thereof, the error routine comprises displaying a message to a user indicating that the analyte sensor is not functioning properly.

In an embodiment of the sixteenth aspect or any other embodiment thereof, the sensor property is an impedance of the sensor membrane.

In a seventeenth aspect, a sensor system is provided configured to implement the method of the sixteenth aspect or any embodiment thereof.

In an embodiment of the seventeenth aspect or any other embodiment thereof, the sensor system comprises instructions stored in computer memory, wherein the instructions, when executed by one or more processors of the sensor system, cause the sensor system to implement the method of the sixteenth aspect or any embodiment thereof.

In an eighteenth aspect, a method is provided for determining a temperature associated with an analyte sensor, the method comprising: applying a stimulus signal to the analyte sensor; measuring a signal response of the signal; and determining a temperature associated with of the analyte sensor, the determining comprising correlating at least one property of the signal response to a predetermined relationship of the sensor property to temperature.

In an embodiment of the eighteenth aspect or any other embodiment thereof, the method further comprises generating estimated analyte concentration values using the determined temperature and sensor data generated from the analyst sensor.

In an embodiment of the eighteenth aspect or any other embodiment thereof, the generating includes compensating the sensor data using the determined temperature and converting the compensated sensor data to the generated estimated analyte values using a conversion function.

In an embodiment of the eighteenth aspect or any other embodiment thereof, the generating includes forming or modifying a conversion function using the determined temperature and converting the sensor data to the generated estimated analyte values using the formed or modified conversion function.

In an embodiment of the eighteenth aspect or any other embodiment thereof, the method further comprises measuring a temperature using a second sensor, wherein the determining further comprises using the measured temperature to determine the temperature associated with the analyte sensor.

In an embodiment of the eighteenth aspect or any other embodiment thereof, the second sensor is a thermistor.

In a nineteenth aspect, a sensor system is provided configured to implement the methods of the eighteenth aspect or any embodiment thereof.

In an embodiment of the nineteenth aspect or any other embodiment thereof, the sensor system comprises instructions stored in computer memory, wherein the instructions, when executed by one or more processors of the sensor system, cause the sensor system to implement the method of the eighteenth aspect or any embodiment thereof.

In a twentieth aspect, a method is provided for determining moisture ingress in an electronic sensor system, comprising: applying a stimulus signal having a particular frequency or a signal comprising a spectrum of frequencies to an analyte sensor; measuring a response to the stimulus signal; calculating, using sensor electronics, an impedance based on the measured signal response; determining, using sensor electronics, whether the impedance falls within a predefined level corresponding to moisture ingress; initiating, using sensor electronics, an error routine if the impedance exceeds one or both of the respective predefined levels In an embodiment of the twentieth aspect or any other embodiment thereof, the method further comprises the error routine includes one or more of triggering an audible alarm and a visual alarm on a display screen to alert a user that the sensor system may not be functioning properly.

In an embodiment of the twentieth aspect or any other embodiment thereof, the stimulus signal has a predetermined frequency.

In an embodiment of the twentieth aspect or any other embodiment thereof, the stimulus signal comprises a spectrum of frequencies.

In an embodiment of the twentieth aspect or any other embodiment thereof, the calculated impedance comprises a magnitude value and a phase value, and wherein the determination comprises comparing the impedance magnitude value to a predefined impedance magnitude threshold and the phase value to a predefined phase threshold.

In an embodiment of the twentieth aspect or any other embodiment thereof, the calculated impedance is a complex impedance value.

In a twenty-first aspect, a sensor system is provided configured to implement the methods of the twentieth aspect or any embodiment thereof.

In an embodiment of the twenty-first aspect or any other embodiment thereof, the sensor system comprises instructions stored in computer memory, wherein the instructions, when executed by one or more processors of the sensor system, cause the sensor system to implement the method of the twentieth aspect or any embodiment thereof.

In an twenty-second aspect, a method is provided for determining membrane damage of an analyte sensor using a sensor system, comprising: applying a stimulus signal to an analyte sensor; measuring a response to the stimulus signal; calculating, using sensor electronics, an impedance based on the signal response; determining, using the sensor electronics, whether the impedance falls within a predefined level corresponding to membrane damage; and initiating, using the sensor electronics, an error routine if the impedance exceeds the predefined level.

In an embodiment of the twenty-second aspect or any other embodiment thereof, the error routine includes triggering one or more of an audible alarm and a visual alarm on a display screen.

In an embodiment of the twenty-second aspect or any other embodiment thereof, the stimulus signal has a predetermined frequency.

In an embodiment of the twenty-second aspect or any other embodiment thereof, the stimulus signal comprises a spectrum of frequencies.

In an embodiment of the twenty-second aspect or any other embodiment thereof, the calculated impedance comprises a magnitude value and a phase value, and wherein the determination comprises comparing the impedance magnitude value to a predefined impedance magnitude threshold and the phase value to a predefined phase threshold.

In an embodiment of the twenty-second aspect or any other embodiment thereof, the calculated impedance is a complex impedance value.

In a twenty-third aspect, a sensor system is provided configured to implement the methods of the twenty-second aspect or any embodiment thereof.

In an embodiment of the twenty-third aspect or any other embodiment thereof, the sensor system comprises instructions stored in computer memory, wherein the instructions, when executed by one or more processors of the sensor system, cause the sensor system to implement the method of the twenty-second aspect or any embodiment thereof.

In a twenty-fourth aspect, a method for determining reuse of an analyte sensor, comprising, applying a stimulus signal to an analyte sensor; measuring a response of the stimulus signal; calculating an impedance response based on the response; comparing the calculated impedance to a predetermined threshold; initiating a sensor reuse routine if it is determined that the impedance exceeds the threshold.

In an embodiment of the twenty-fourth aspect or any other embodiment thereof, the sensor reuse routine includes triggering an audible and/or visual alarm notifying the user of improper sensor reuse.

In an embodiment of the twenty-fourth aspect or any other embodiment thereof, the sensor reuse routing includes causing a sensor system to fully or partially shut down and/or cease display of sensor data on a user interface of the sensor system.

In a twenty-fifth aspect, a sensor system is provided configured to implement the methods of the twenty-fourth aspect or any embodiments thereof.

In an embodiment of the twenty-fifth aspect or any other embodiment thereof, the sensor system comprises instructions stored in computer memory, wherein the instructions, when executed by one or more processors of the sensor system, cause the sensor system to implement the method of the twenty-fourth aspect or any embodiments thereof.

In a twenty-sixth aspect, a system is provided for determining reuse of an analyte sensor, comprising, applying a stimulus signal to an analyte sensor; measuring a response of the stimulus signal; calculating an impedance based on the response; using a data association function to determine a correlation of the calculated impedance to one or more recorded impedance values; and initiating a sensor reuse routine if it is determined that the correlation is above a predetermined threshold.

In an embodiment of the twenty-sixth aspect or any other embodiment thereof, the sensor reuse routine includes triggering an audible and/or visual alarm notifying the user of improper sensor reuse.

In an embodiment of the twenty-sixth aspect or any other embodiment thereof, the sensor reuse routing includes causing a sensor system to fully or partially shut down and/or cease display of sensor data on a user interface of the sensor system.

In an embodiment of the twenty-sixth aspect or any other embodiment thereof, the sensor system comprises instructions stored in computer memory, wherein the instructions, when executed by one or more processors of the sensor system, cause the sensor system to implement the method of the twenty-fifth aspect.

In a twenty-seventh aspect, a method is provided for applying an overpotential to an analyte sensor, comprising, applying a stimulus signal to an analyte sensor; measuring a response of the stimulus signal; determining a sensor sensitivity or change in sensor sensitivity based on the response; and applying an over potential to the sensor based on the determined sensitivity or sensitivity change.

In an embodiment of the twenty-seventh aspect or any other embodiment thereof, the determining further comprises calculating an impedance based on the response and determining the sensitivity or sensitivity change based on the impedance.

In an embodiment of the twenty-seventh aspect or any other embodiment thereof, the determining the sensitivity or sensitivity change further comprises correlating the impedance to a predetermined impedance to sensitivity relationship.

In an embodiment of the twenty-seventh aspect or any other embodiment thereof, the applying comprises determining or modifying a length of time the over potential is applied to the sensor.

In an embodiment of the twenty-seventh aspect or any other embodiment thereof, the applying comprises determining or modifying a magnitude of the over potential applied to the sensor.

In a twenty-eighth aspect, a sensor system is provided configured to implement the methods of the twenty-seventh aspect or any embodiments thereof.

In an embodiment of the twenty-eighth aspect or any other embodiment thereof, the sensor system comprises instructions stored in computer memory, wherein the instructions, when executed by one or more processors of the sensor system, cause the sensor system to implement the method of the twenty-seventh aspect or any embodiment thereof.

In a twenty-ninth aspect, a method is provided for determining a property of a continuous analyte sensor, the method comprising: applying a stimulus signal to a first analyte sensor having a first working electrode and a first reference electrode; measuring a signal response of the stimulus signal using a second analyte sensor having a second working electrode and a second reference electrode; and determining a property of the first sensor by correlating the response to a predetermined relationship.

In an embodiment of the twenty-ninth aspect or any other embodiment thereof, the method further comprises generating sensor data by applying a bias voltage to the first working electrode and measuring a response to the bias voltage.

In an embodiment of the twenty-ninth aspect or any other embodiment thereof, the method further comprises calibrating the sensor data using the determined property.

In an embodiment of the twenty-ninth aspect or any other embodiment thereof, the determined property is one of an impedance and a temperature.

In an embodiment of the twenty-ninth aspect or any other embodiment thereof, the method further comprises determining sensor membrane damage using the determined property.

In an embodiment of the twenty-ninth aspect or any other embodiment thereof, the method further comprises determining moisture ingress in a sensor system encompassing the first and second analyte sensors using the determined property.

In a thirtieth aspect, a sensor system is provided configured to implement the methods of one of the twenty-ninth aspect or any embodiments thereof.

In an embodiment of the thirtieth aspect or any other embodiment thereof, the sensor system comprises instructions stored in computer memory, wherein the instructions, when executed by one or more processors of the sensor system, cause the sensor system to implement the method of the twenty-ninth aspect or any embodiments thereof.

In a thirty-first aspect, a method is provided for determining a scaling used in a continuous analyte sensor system, the method comprising: applying a first stimulus signal to a first working electrode of an analyte sensor; measuring a response to the first stimulus signal; applying a second stimulus signal to a second working electrode of the analyte sensor; measuring a response to the first stimulus signal; determining, using sensor electronics, a scaling factor based on the measured responses to the first and second stimulus signals; and using the scaling factor to generate estimated analyte values based on sensor data generated by the analyte sensor.

In an embodiment of the thirty-first aspect or any other embodiment thereof, the method further comprises the method is performed periodically.

In an embodiment of the thirty-first aspect or any other embodiment thereof, the determining comprises calculating a first impedance using the response to the first stimulus signal and calculating a second impedance using the response to the second stimulus signal, and wherein the scaling factor is a ratio of the first impedance and the second impedance.

In an embodiment of the thirty-first aspect or any other embodiment thereof, the first working electrode has a membrane comprising an enzyme configured to react with the analyte and the second working electrode has a membrane does not have the enzyme.

In an embodiment of the thirty-first aspect or any other embodiment thereof, determining the scaling factor comprises updating a previous scaling factor based on the measured responses to the first and second stimulus signals.

In an embodiment of the thirty-first aspect or any other embodiment thereof, scaling factor is an acetaminophen scaling factor, wherein the method further comprises updating a further scaling factor based on the acetaminophen scaling factor, and wherein the further scaling factor applied to the sensor data to generate the estimated analyte values.

In a thirty-second aspect, a sensor system is provided configured to implement the methods of the thirty-first aspect or any embodiments thereof.

In an embodiment of the thirty-second aspect or any other embodiment thereof, the sensor system comprises instructions stored in computer memory, wherein the instructions, when executed by one or more processors of the sensor system, cause the sensor system to implement the method of the thirty-first aspect or any embodiment thereof In a thirty-third aspect, a method is provided for calibrating an analyte sensor, the method comprising: applying a predetermined signal to an analyte sensor; measuring a response to the applied signal; determining, using sensor electronics, a change in impedance associated with a membrane of the analyte sensor based on the measured response; calculating a sensitivity change of the analyte sensor based on the determined impedance; calculating a corrected sensitivity based on the calculated sensitivity change and a previously used sensitivity of the analyte sensor; and generating estimated analyte values using the corrected sensitivity.

In an embodiment of the thirty-third aspect or any other embodiment thereof, calculating the sensitivity change comprises applying a non-linear compensation function.

In an embodiment of the thirty-third aspect or any other embodiment thereof, the non-linear compensation function is expressed as the equation $\Delta S=(a*\log(t)+b)*\Delta I$, where $\Delta S$ is the change in sensitivity, t is a time since calibration of the analyte sensor, $\Delta I$ is the determined change in impedance, and a and b are a predetermined coefficients.

In an embodiment of the thirty-third aspect or any other embodiment thereof, a and b are determined by prior testing of similar analyte sensors.

In a thirty-fourth aspect, a sensor system is provided configured to implement the methods of the thirty-third aspect or any embodiments thereof.

In an embodiment of the thirty-fourth aspect or any other embodiment thereof, the sensor system comprises instructions stored in computer memory, wherein the instructions, when executed by one or more processors of the sensor system, cause the sensor system to implement the method of the thirty-third aspect or any embodiments thereof.

In a thirty-fifth aspect, a method is provided for calibrating an analyte sensor, comprising: generating sensor data using a subcutaneous analyte sensor; forming or modifying a conversion function, wherein pre-implant information, internal diagnostic information, and/or external reference information are used as inputs to form or modify the conversion function; and calibrating the sensor data using the conversion function.

In an embodiment of the thirty-fifth aspect or any other embodiment thereof, the pre-implant information comprises information selected from the group consisting of: a predetermined sensitivity profile associated with the analyte sensor, a previously determined relationship between a measured sensor property and sensor sensitivity, one or more previously determined relationships between a measured sensor property and sensor temperature; sensor data obtained from previously used analyte sensors, a calibration code associated with the analyte sensor, patient specific relationships between the analyte sensor and one or more of sensitivity, baseline, drift and impedance, information indicative of a site of sensor implantation; time since manufacture of the analyte sensor, and information indicative of the analyte being exposed to temperature or humidity.

In an embodiment of the thirty-fifth aspect or any other embodiment thereof, the internal diagnostic information comprises information selected from the group consisting of: stimulus signal output; sensor data indicative of an analyte concentration measured by the sensor; temperature measurements using the sensor or a separate sensor; sensor data generated by a redundant sensor, where the redundant sensor is designed to be substantially the same as analyte sensor; sensor data generated by an auxiliary sensors, where the auxiliary sensor is having a different modality as the analyte sensor; a time since the sensor was implanted or connected to sensor electronics coupled to the sensor; data representative of a pressure on the sensor or sensor system generated by a pressure sensor; data generated by an accelerometer; a measure of moisture ingress; and a measure of noise in an analyte concentration signal.

In an embodiment of the thirty-fifth aspect or any other embodiment thereof, the reference information comprises information selected from the group consisting of: real-time and/or prior analyte concentration information obtained from a reference monitor, information relating to a type/brand of reference monitor used to provide reference data; information relating to an amount of carbohydrate consumed by a user; information received from a medicament delivery device, glucagon sensitivity information, and information gathered from population based data.

In a thirty-sixth aspect, a sensor system is provided configured to implement the methods of the thirty-fifth aspect or any embodiments thereof.

In an embodiment of the thirty-sixth aspect or any other embodiment thereof, the sensor system comprises instructions stored in computer memory, wherein the instructions, when executed by one or more processors of the sensor system, cause the sensor system to implement the method of the thirty-fifth aspect or any embodiment thereof.

BRIEF DESCRIPTION OF THE DRAWINGS

These and other features and advantages will be appreciated, as they become better understood by reference to the following detailed description when considered in connection with the accompanying drawings, wherein.

DETAILED DESCRIPTION

Definitions

Figure 1A:
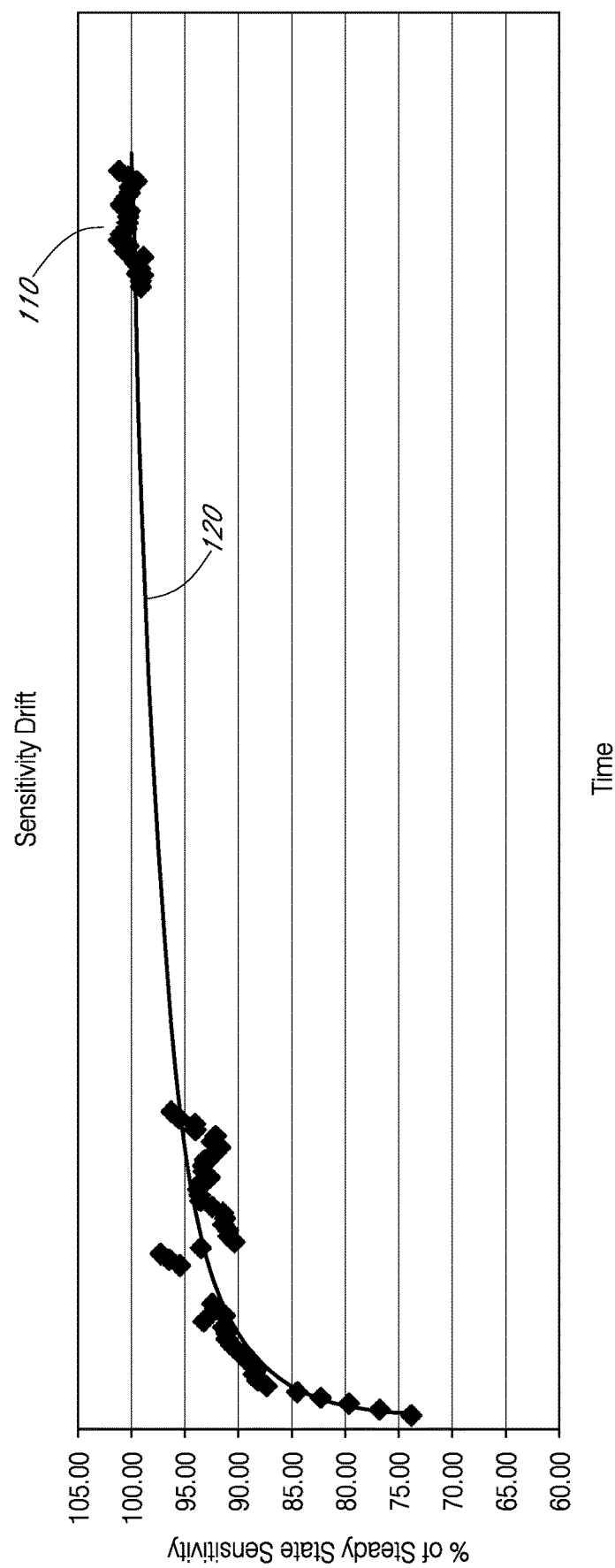
FIG. 1A illustrates a schematic diagram of sensor sensitivity as a function of time during a sensor session, in accordance with one embodiment.

In order to facilitate an understanding of the embodiments described herein, a number of terms are defined below.

The term "analyte," as used herein, is a broad term, and is to be given its ordinary and customary meaning to a person of ordinary skill in the art (and is are not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A, S, C, E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, *rickettsia* (scrub typhus), *Schistosoma mansoni, Toxoplasma gondii, Trepenoma pallidium, Trypanosoma cruzi/rangeli,* vesicular *stomatis* virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-

Dihydroxyphenylacetic acid (DOPAC), Homovanillic acid (HVA), 5-Hydroxytryptamine (5HT), and 5-Hydroxyindoleacetic acid (FHIAA).

The terms "continuous analyte sensor," and "continuous glucose sensor," as used herein, are broad terms, and are to be given their ordinary and customary meaning to a person of ordinary skill in the art (and are not to be limited to a special or customized meaning), and refer without limitation to a device that continuously or continually measures a concentration of an analyte/glucose and/or calibrates the device (e.g., by continuously or continually adjusting or determining the sensor's sensitivity and background), for example, at time intervals ranging from fractions of a second up to, for example, 1, 2, or 5 minutes, or longer.

The term "biological sample," as used herein, is a broad term, and is to be given its ordinary and customary meaning to a person of ordinary skill in the art (and is not to be limited to a special or customized meaning), and refers without limitation to sample derived from the body or tissue of a host, such as, for example, blood, interstitial fluid, spinal fluid, saliva, urine, tears, sweat, or other like fluids.

The term "host," as used herein, is a broad term, and is to be given its ordinary and customary meaning to a person of ordinary skill in the art (and is not to be limited to a special or customized meaning), and refers without limitation to animals, including humans.

The term "membrane system," as used herein, is a broad term, and is to be given its ordinary and customary meaning to a person of ordinary skill in the art (and is not to be limited to a special or customized meaning), and refers without limitation to a permeable or semi-permeable membrane that can be comprised of two or more domains and is typically constructed of materials of a few microns thickness or more, which may be permeable to oxygen and are optionally permeable to glucose. In one example, the membrane system comprises an immobilized glucose oxidase enzyme, which enables an electrochemical reaction to occur to measure a concentration of glucose.

The term "domain," as used herein, is a broad term, and is to be given its ordinary and customary meaning to a person of ordinary skill in the art (and is not to be limited to a special or customized meaning), and refers without limitation to regions of a membrane that can be layers, uniform or non-uniform gradients (for example, anisotropic), functional aspects of a material, or provided as portions of the membrane.

The term "sensing region," as used herein, is a broad term, and is to be given its ordinary and customary meaning to a person of ordinary skill in the art (and is not to be limited to a special or customized meaning), and refers without limitation to the region of a monitoring device responsible for the detection of a particular analyte. In one embodiment, the sensing region generally comprises a non-conductive body, at least one electrode, a reference electrode and a optionally a counter electrode passing through and secured within the body forming an electroactive surface at one location on the body and an electronic connection at another location on the body, and a membrane system affixed to the body and covering the electroactive surface.

The term "electroactive surface," as used herein, is a broad term, and is to be given its ordinary and customary meaning to a person of ordinary skill in the art (and is not to be limited to a special or customized meaning), and refers without limitation to the surface of an electrode where an electrochemical reaction takes place. In one embodiment, a working electrode measures hydrogen peroxide ($H_2O_2$) creating a measurable electronic current.

The term "baseline," as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation y=mx+b, the value of b represents the baseline of the signal. In certain embodiments, the value of b (i.e., the baseline) can be zero or about zero. This can be the result of a baseline-subtracting electrode or low bias potential settings, for example. As a result, for these embodiments, calibration can be defined by solving for the equation y=mx.

The term "inactive enzyme," as used herein, is a broad term, and is to be given its ordinary and customary meaning to a person of ordinary skill in the art (and is not to be limited to a special or customized meaning), and refers without limitation to an enzyme (e.g., glucose oxidase, GOx) that has been rendered inactive (e.g., by denaturing of the enzyme) and has substantially no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The term "non-enzymatic," as used herein is a broad term, and is to be given its ordinary and customary meaning to a person of ordinary skill in the art (and is not to be limited to a special or customized meaning), and refers without limitation to a lack of enzyme activity. In some embodiments, a "non-enzymatic" membrane portion contains no enzyme; while in other embodiments, the "non-enzymatic" membrane portion contains inactive enzyme. In some embodiments, an enzyme solution containing inactive enzyme or no enzyme is applied.

The term "substantially," as used herein, is a broad term, and is to be given its ordinary and customary meaning to a person of ordinary skill in the art (and is not to be limited to a special or customized meaning), and refers without limitation to being largely but not necessarily wholly that which is specified.

The term "about," as used herein, is a broad term, and is to be given its ordinary and customary meaning to a person of ordinary skill in the art (and is not to be limited to a special or customized meaning), and when associated with any numerical values or ranges, refers without limitation to the understanding that the amount or condition the terms modify can vary some beyond the stated amount so long as the function of the disclosure is realized.

The term "ROM," as used herein, is a broad term, and is to be given its ordinary and customary meaning to a person of ordinary skill in the art (and is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The term "RAM," as used herein, is a broad term, and is to be given its ordinary and customary meaning to a person of ordinary skill in the art (and is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "A/D Converter," as used herein, is a broad term, and is to be given its ordinary and customary meaning to a person of ordinary skill in the art (and is not to be limited to a special or customized meaning), and refers without limitation to hardware and/or software that converts analog electrical signals into corresponding digital signals.

The terms "raw data stream" and "data stream," as used herein, are broad terms, and are to be given their ordinary and customary meaning to a person of ordinary skill in the art (and are not to be limited to a special or customized meaning), and refer without limitation to an analog or digital signal directly related to the analyte concentration measured by the analyte sensor. In one example, the raw data stream is digital data in counts converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "counts," as used herein, is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "sensor electronics," as used herein, is a broad term, and is to be given its ordinary and customary meaning to a person of ordinary skill in the art (and is not to be limited to a special or customized meaning), and refers without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398 describe suitable electronic circuits that can be utilized with devices of certain embodiments.

The term "potentiostat," as used herein, is a broad term, and is to be given its ordinary and customary meaning to a person of ordinary skill in the art (and is not to be limited to a special or customized meaning), and refers without limitation to an electrical system that applies a potential between the working and reference electrodes of a two- or three-electrode cell at a preset value and measures the current flow through the working electrode. The potentiostat forces whatever current is necessary to flow between the working and counter electrodes to keep the desired potential, as long as the needed cell voltage and current do not exceed the compliance limits of the potentiostat.

The term "operably connected," as used herein, is a broad term, and is to be given its ordinary and customary meaning to a person of ordinary skill in the art (and is not to be limited to a special or customized meaning), and refers without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "filtering," as used herein, is a broad term, and is to be given its ordinary and customary meaning to a person of ordinary skill in the art (and is not to be limited to a special or customized meaning), and refers without limitation to modification of a set of data to make it smoother and more continuous and remove or diminish outlying points, for example, by performing a moving average of the raw data stream.

The term "algorithm," as used herein, is a broad term, and is to be given its ordinary and customary meaning to a person of ordinary skill in the art (and is not to be limited to a special or customized meaning), and refers without limitation to the computational processes (for example, programs) involved in transforming information from one state to another, for example using computer processing.

The term "calibration," as used herein, is a broad term, and is to be given its ordinary and customary meaning to a person of ordinary skill in the art (and is not to be limited to a special or customized meaning), and refers without limitation to the process of determining the graduation of a sensor giving quantitative measurements (e.g., analyte concentration). As an example, calibration may be updated or recalibrated over time to account for changes associated with the sensor, such as changes in sensor sensitivity and sensor background. In addition, calibration of the sensor can involve, automatic, self-calibration, e.g., without using reference analyte values after point of use.

The terms "sensor data," as used herein, is a broad term, and is to be given its ordinary and customary meaning to a person of ordinary skill in the art (and is not to be limited to a special or customized meaning), and refers without limitation to data received from a continuous analyte sensor, including one or more time-spaced sensor data points.

The terms "reference analyte values" and "reference data," as used herein, are broad terms, and are to be given their ordinary and customary meaning to a person of ordinary skill in the art (and are not to be limited to a special or customized meaning), and refer without limitation to reference data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or a YSI (Yellow Springs Instruments) test, for example.

The terms "interferents" and "interfering species," as used herein, are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured, producing a false positive signal.

The term "sensor session," as used herein, is a broad term, and is to be given its ordinary and customary meaning to a person of ordinary skill in the art (and is not to be limited to a special or customized meaning), and refers without limitation to the period of time the sensor is applied to (e.g. implanted in) the host or is being used to obtain sensor values. For example, in some embodiments, a sensor session extends from the time of sensor implantation (e.g. including insertion of the sensor into subcutaneous tissue and placing the sensor into fluid communication with a host's circulatory system) to the time when the sensor is removed.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (e.g., $H_2O_2$) associated with the measured analyte (e.g., glucose). For example, in one embodiment, a sensor has a sensitivity of from about 1 to about 300 picoAmps of current for every 1 mg/dL of glucose analyte.

The term "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time Overview Conventional in vivo continuous analyte sensing technology has typically relied on reference measurements performed during a sensor session for calibration of the continuous analyte sensor. The reference measurements are matched with substantially time corresponding sensor data to create matched data pairs. Regression is then performed on the matched data pairs (e.g., by using least squares regression) to generate a conversion function that defines a relationship between a sensor signal and an estimated glucose concentration.

In critical care settings, calibration of continuous analyte sensors is often performed by using, as reference, a calibration solution with a known concentration of the analyte. This calibration procedure can be cumbersome, as a calibration bag, separate from (and an addition to) an IV (intravenous) bag, is typically used. In the ambulatory setting, calibration of continuous analyte sensors has traditionally been performed by capillary blood glucose measurements (e.g., a finger stick glucose test), through which reference data is obtained and input into the continuous analyte sensor system. This calibration procedure typically involves frequent finger stick measurements, which can be inconvenient and painful.

Heretofore, systems and methods for in vitro calibration of a continuous analyte sensor by the manufacturer (e.g., factory calibration), without reliance on periodic recalibration, have for the most part been inadequate with respect to high levels of sensor accuracy. Part of this can be attributed to changes in sensor properties (e.g., sensor sensitivity) that can occur during sensor use. Thus, calibration of continuous analyte sensors has typically involved periodic inputs of reference data, whether they are associated with a calibration solution or with a finger stick measurement. This can be very burdensome to the patient in the ambulatory setting or the hospital staff in the critical care setting.

Described herein are continuous analyte sensors that are capable of continuous, automatic self-calibration during a sensor session and capable of achieving high levels of accuracy, without (or with reduced) reliance on reference data from a reference analyte monitor (e.g., from a blood glucose meter). In some embodiments, the continuous analyte sensor is an invasive, minimally invasive, or non-invasive device. The continuous analyte sensor can be a subcutaneous, transdermal, or intravascular device. In certain embodiments, one or more of these devices may form a continuous analyte sensor system. For instance, the continuous analyte sensor system may be comprised of a combination of a subcutaneous device and a transdermal device, a combination of a subcutaneous device and an intravascular device, a combination of a transdermal device and an intravascular device, or a combination of a subcutaneous device, a transdermal device, and an intravascular device. In some embodiments, the continuous analyte sensor can analyze a plurality of intermittent biological samples (e.g., blood samples). The continuous analyte sensor can use any glucose-measurement method, including methods involving enzymatic, chemical, physical, electrochemical, spectrophotometric, polarimetric, calorimetric, iontophoretic, and radiometric mechanisms, and the like.

In certain embodiments, the continuous analyte sensor includes one or more working electrodes and one or more reference electrode, which operate together to measure a signal associated with a concentration of the analyte in the host. The output signal from the working electrode is typically a raw data stream that is calibrated, processed, and used to generate an estimated analyte (e.g., glucose) concentration. In certain embodiments, the continuous analyte sensor may measure an additional signal associated with the baseline and/or sensitivity of the sensor, thereby enabling monitoring of baseline and/or additional monitoring of sensitivity changes or drift that may occur in a continuous analyte sensor over time.

In some embodiments, the sensor extends through a housing, which maintains the sensor on the skin and provides for electrical connection of the sensor to sensor electronics. In one embodiment, the sensor is formed from a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments the smallest dimension of the elongated conductive body is less than about 0.1 inches, 0.075 inches, 0.05 inches, 0.025 inches, 0.01 inches, 0.004 inches, or 0.002 inches. Other embodiments of the elongated conductive body are disclosed in U.S. Patent Application Publication No. 2011/0027127, which is incorporated herein by reference in its entirety. Preferably, a membrane system is deposited over at least a portion of electroactive surfaces of the sensor 102 (including a working electrode and optionally a reference electrode) and provides protection of the exposed electrode surface from the biological environment, diffusion resistance (limitation) of the analyte if needed, a catalyst for enabling an enzymatic reaction, limitation or blocking of interferants, and/or hydrophilicity at the electrochemically reactive surfaces of the sensor interface. Disclosures regarding the different membrane systems that may be used with the embodiments described herein are described in U.S. Patent Publication No. US-2009-0247856-A1, which is incorporated herein by reference in its entirety.

Calibrating sensor data from continuous analyte sensors generally involves defining a relationship between sensor-generated measurements (e.g., in units of nA or digital counts after A/D conversion) and one or more reference measurement (e.g., in units of mg/dL or mmol/L). In certain embodiments, one or more reference measurements obtained shortly after the analyte sensor is manufactured, and before sensor use, are used for calibration. The reference measurement may be obtained in many forms. For example, in certain embodiments, the reference measurement may be determined from a ratio or correlation between the sensitivity of a sensor (e.g., from a certain sensor lot) with respect to in vivo analyte concentration measurements and the sensitivity of another sensor (e.g., from the same lot made in substantially the same way under substantially same conditions) with respect to in vitro analyte concentration measurements at a certain time period. By providing a continuous analyte sensor with a predetermined in vivo to in vitro ratio and a predetermined sensitivity profile (as described in more detail elsewhere herein), self-calibration of the sensor can be achieved in conjunction with high levels of sensor accuracy.

With self-calibration, the need for recalibration, by using reference data during a sensor session, may be eliminated, or else lessened, such that recalibration may be called for only in certain limited circumstances, such as when sensor failure is detected. Additionally or alternatively, in some embodiments, the continuous analyte sensor may be configured to request and accept one or more reference measurements (e.g., from a finger stick glucose measurement or a calibration solution) at the start of the sensor session. In some embodiments, use of a reference measurement at the start of the sensor session in conjunction with a predetermined sensor sensitivity profile can eliminate or substantially reduce the need for further reference measurements.

With certain implantable enzyme-based electrochemical glucose sensors, the sensing mechanism depends on certain phenomena that have a generally linear relationship with glucose concentration, for example: (1) diffusion of an analyte through a membrane system situated between an implantation site (e.g., subcutaneous space) and an electroactive surface, (2) rate of an enzyme-catalyzed reaction of the analyte to produce a measured species within the membrane system (e.g., the rate of a glucose oxidase-catalyzed reaction of glucose with $O_2$ which produces gluconic acid and $H_2O_2$), and (3) diffusion of the measured species (e.g., $H_2O_2$) to the electroactive surface. Because of this generally linear relationship, calibration of the sensor is obtained by solving the equation:

$$y=mx+b$$

wherein y represents the sensor signal (counts), x represents the estimated glucose concentration (mg/dL), m represents the sensor sensitivity to analyte concentration (counts/mg/dL), and b represents the baseline signal (counts). As described elsewhere herein, in certain embodiments, the value b (i.e., the baseline) can be zero or about zero. As a result, for these embodiments, calibration can be defined by solving for the equation $y=mx$.

In some embodiments, the continuous analyte sensor system is configured to estimate changes or drift in sensitivity of the sensor for an entire sensor session as a function of time (e.g., elapsed time since start of the sensor session). As described elsewhere herein, this sensitivity function plotted against time may resemble a curve. Additionally or alternatively, the system can also be configured to determine sensor sensitivity changes or drift as a function of time and one or more other parameters that can also affect sensor sensitivity or provide additional information about sensor sensitivity. These parameters can affect sensor sensitivity or provide additional information about sensor sensitivity prior to the sensor session, such as parameters associated with the sensor fabrication (e.g., materials used to fabricate sensor membrane, the thickness of the sensor membrane, the temperature at which the sensor membrane was cured, the length of time the sensor was dipped in a particular coating solution, etc.). In certain embodiments, some of the parameters involve information, obtained prior to the sensor session, which can be accounted for in a calibration code that is associated with a particular sensor lot. Other parameters can be associated with conditions surrounding the sensor after its manufacture, but before the sensor session, such as, for example, the level of exposure of the sensor to certain levels of humidity or temperature while the sensor is in a package in transit from the manufacturing facility to the patient. Yet other parameters (e.g., sensor membrane permeability, temperature at the sample site, pH at the sample site, oxygen level at the sample site, etc.) can affect sensor sensitivity or provide additional information about sensor sensitivity during the sensor session.

Determination of sensor sensitivity at different times of a sensor session based on the predetermined sensor sensitivity profile can be performed prior to the sensor session or at the start of the sensor session. Additionally, in certain embodiments, determination of sensor sensitivity, based on the sensor sensitivity profile, can be continuously adjusted to account for parameters that affect sensor sensitivity or provide additional information about sensor sensitivity during the sensor session. These determinations of sensor sensitivity change or drift can be used to provide self-calibration, update calibration, supplement calibration based on measurements (e.g., from a reference analyte monitor), and/or validate or reject reference analyte measurements from a reference analyte monitor. In some embodiments, validation or rejection of reference analyte measurements can be based on whether the reference analyte measurements are within a range of values associated with the predetermined sensor sensitivity profile.

Some of the continuous analyte sensors described herein may be configured to measure a signal associated with a non-analyte constant in the host. Preferably, the non-analyte constant signal is measured beneath the membrane system on the sensor. In one example of a continuous glucose sensor, a non-glucose constant that can be measured is oxygen. In some embodiments, a change in oxygen transport, which can be indicative of a change or drift in the sensitivity of the glucose signal, can be measured by switching the bias potential of the working electrode, an auxiliary oxygen-measuring electrode, an oxygen sensor, or the like.

Additionally, some of the continuous analyte sensors described herein may be configured to measure changes in the amount of background noise in the signal. Detection of changes which exceed a certain threshold can provide the basis for triggering calibration, updating calibration, and/or validating or rejecting inaccurate reference analyte values from a reference analyte monitor. In one example of a continuous glucose sensor, the background noise is composed substantially of signal contribution from factors other than glucose (for example, interfering species, non-reaction-related hydrogen peroxide, or other electroactive species with an oxidation potential that overlaps with hydrogen peroxide). Namely, the continuous glucose sensor is configured to measure a signal associated with the baseline (which includes substantially all non-glucose related current generated), as measured by the sensor in the host. In some embodiments, an auxiliary electrode located beneath a non-enzymatic portion of the membrane system is used to measure the baseline signal. The baseline signal can be subtracted from the glucose+baseline signal to obtain a signal associated entirely or substantially entirely with glucose concentration. Subtraction may be accomplished electronically in the sensor using a differential amplifier, digitally in the receiver, and/or otherwise in the hardware or software of the sensor or receiver as described in more detail elsewhere herein.

Together, by determining sensor sensitivity based on a sensitivity profile and by measuring a baseline signal, the continuous analyte sensor can be continuously self-calibrated during a sensor session without (or with reduced) reliance on reference measurements from a reference analyte monitor or calibration solution.

Determination of Sensor Sensitivity

As described elsewhere herein, in certain embodiments, self-calibration of the analyte sensor system can be performed by determining sensor sensitivity based on a sensitivity profile (and a measured or estimated baseline), so that the following equation can be solved:

$$y=mx+b$$

wherein y represents the sensor signal (counts), x represents the estimated glucose concentration (mg/dL), m represents the sensor sensitivity to the analyte (counts/mg/dL), and b represents the baseline signal (counts). From this equation, a conversion function can be formed, whereby a sensor signal is converted into an estimated glucose concentration.

Figure 1B:
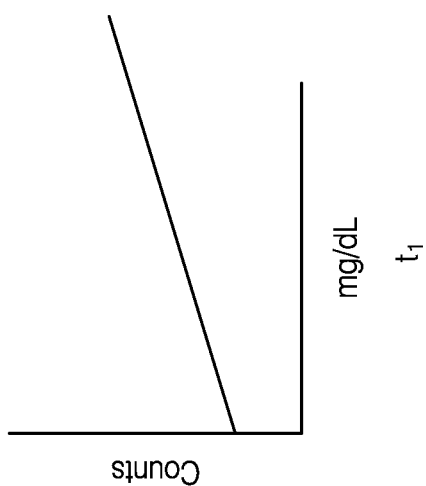
FIG. 1B illustrates schematic diagrams of conversion functions at different time periods of a sensor session, in accordance with the embodiment of FIG. 1A.
Figure 1B:
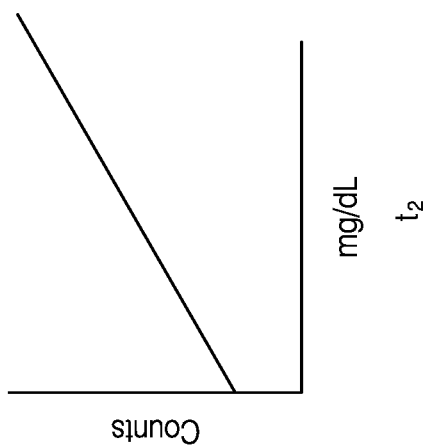
Figure 1B:
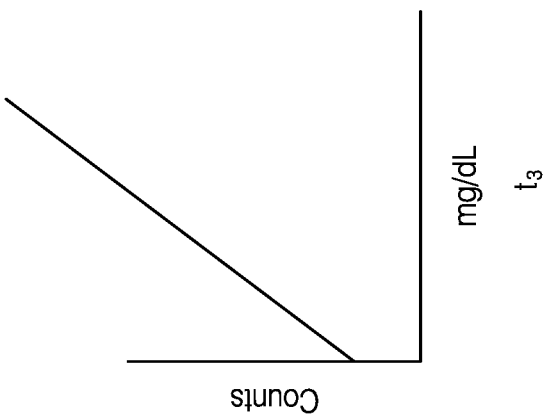

It has been found that a sensor's sensitivity to analyte concentration during a sensor session will often change or drift as a function of time. FIG. 1A illustrates this phenomenon and provides a plot of sensor sensitivities 110 of a group of continuous glucose sensors as a function of time during a sensor session. FIG. 1B provides three plots of conversion functions at three different time periods of a sensor session. As shown in FIG. 1B, the three conversion functions have different slopes, each of which correspond to a different sensor sensitivity. Accordingly, the differences in slopes over time illustrate that changes or drift in sensor sensitivity occur over a sensor session.

Referring back to the study associated with FIG. 1A, the sensors were made in substantially the same way under substantially the same conditions. The sensor sensitivities associated with the y-axis of the plot are expressed as a percentage of a substantially steady state sensitivity that was reached about three days after start of the sensor session. In addition, these sensor sensitivities correspond to measurements obtained from YSI tests. As shown in the plot, the sensitivities (expressed as a percentage of a steady state sensitivity) of each sensor, as measured, are very close to sensitivities of other sensors in the group at any given time of the sensor session. While not wishing to be bound by theory, it is believed that the observed upward trend in sensitivity (over time), which is particularly pronounced in the early part of the sensor session, can be attributed to conditioning and hydration of sensing regions of the working electrode. It is also believed that the glucose concentration of the fluid surrounding the continuous glucose sensor during startup of the sensor can also affect the sensitivity drift.

With the sensors tested in this study, the change in sensor sensitivity (expressed as a percentage of a substantially steady state sensitivity), over a time defined by a sensor session, resembled a logarithmic growth curve. It should be understood that other continuous analyte sensors fabricated with different techniques, with different specifications (e.g., different membrane thickness or composition), or under different manufacturing conditions, may exhibit a different sensor sensitivity profile (e.g., one associated with a linear function). Nonetheless, with improved control over operating conditions of the sensor fabrication process, high levels of reproducibility have been achieved, such that sensitivity profiles exhibited by individual sensors of a sensor population (e.g., a sensor lot) are substantially similar and sometimes nearly identical.

It has been discovered that the change or drift in sensitivity over a sensor session is not only substantially consistent among sensors manufactured in substantially the same way under substantially same conditions, but also that modeling can be performed through mathematical functions that can accurately estimate this change or drift. As illustrated in FIG. 1A, an estimative algorithm function 120 can be used to define the relationship between time during the sensor session and sensor sensitivity. The estimative algorithm function may be generated by testing a sample set (comprising one or more sensors) from a sensor lot under in vivo and/or in vitro conditions. Alternatively, the estimative algorithm function may be generated by testing each sensor under in vivo and/or in vitro conditions.

In some embodiments, a sensor may undergo an in vitro sensor sensitivity drift test, in which the sensor is exposed to changing conditions (e.g., step changes of glucose concentrations in a solution), and an in vitro sensitivity profile of the sensor is generated over a certain time period. The time period of the test may substantially match an entire sensor session of a corresponding in vivo sensor, or it may encompass a portion of the sensor session (e.g., the first day, the first two days, or the first three days of the sensor session, etc.). It is contemplated that the above-described test may be performed on each individual sensor, or alternatively on one or more sample sensors of a sensor lot. From this test, an in vitro sensitivity profile may be created, from which an in vivo sensitivity profile may be modeled and/or formed.

From the in vivo or in vitro testing, one or more data sets, each comprising data points associating sensitivity with time, may be generated and plotted. A sensitivity profile or curve can then be fitted to the data points. If the curve fit is determined to be satisfactory (e.g., if the standard deviation of the generated data points is less a certain threshold), then the sensor sensitivity profile or curve may be judged to have passed a quality control and suitable for release. From there, the sensor sensitivity profile can be transformed into an estimative algorithm function or alternatively into a look-up table. The algorithm function or look-up table can be stored in a computer-readable memory, for example, and accessed by a computer processor.

The estimative algorithm function may be formed by applying curve fitting techniques that regressively fit a curve to data points by adjusting the function (e.g., by adjusting constants of the function) until an optimal fit to the available data points is obtained. Simply put, a "curve" (i.e., a function sometimes referred to as a "model") is fitted and generated that relates one data value to one or more other data values and selecting parameters of the curve such that the curve estimates the relationship between the data values. By way of example, selection of the parameters of the curve may involve selection of coefficients of a polynomial function. In some embodiments, the curve fitting process may involve evaluating how closely the curve determined in the curve fitting process estimates the relationship between the data values, to determine the optimal fit. The term "curve," as used herein, is a broad term, and is to be given its ordinary and customary meaning to a person of ordinary skill in the art (and is not to be limited to a special or customized meaning), and refers to a function or a graph of a function, which can involve a rounded curve or a straight curve, i.e., a line.

The curve may be formed by any of a variety of curve fitting techniques, such as, for example, the linear least squares fitting method, the non-linear least squares fitting method, the Nelder-Mead Simplex method, the Levenberg-Marquardt method, and variations thereof. In addition, the curve may be fitted using any of a variety of functions, including, but not limited to, a linear function (including a constant function), logarithmic function, quadratic function, cubic function, square root function, power function, polynomial function, rational function, exponential function, sinusoidal function, and variations and combinations thereof. For example, in some embodiments, the estimative algorithm comprises a linear function component which is accorded a first weight w1, a logarithmic function component which is accorded a second weight w2, and an exponential function component which is accorded a third weight w3. In further embodiments, the weights associated with each component can vary as a function of time and/or other parameters, but in alternative embodiment, one or more of these weights are constant as a function of time.

In certain embodiments, the estimative algorithm function's correlation (e.g., R2 value), which is a measure of the quality of the fit of the curve to the data points, with respect to data obtained from the sample sensors, may be one metric used to determine whether a function is optimal. In certain embodiments, the estimative algorithm function formed from the curve fitting analysis may be adjusted to account for other parameters, e.g., other parameters that may affect sensor sensitivity or provide additional information about sensor sensitivity. For example, the estimative algorithm function may be adjusted to account for the sensitivity of the sensor to hydrogen peroxide or other chemical species.

Estimative algorithms formed and used to accurately estimate an individual sensor's sensitivity, at any time during a sensor session, can be based on factory calibration and/or based on a single early reference measurement (e.g., using a single point blood glucose monitor). In some embodiments, sensors across a population of continuous analyte sensors manufactured in substantially the same way under substantially same conditions exhibit a substantially fixed in vivo to in vitro sensitivity relationship. For example, in one embodiment, the in vivo sensitivity of a sensor at a certain time after start of sensor use (e.g., at t=about 5, 10, 15, 30, 60, 120, or 180 minutes after sensor use) is consistently equal to a measured in vitro sensitivity of the sensor or of an equivalent sensor. From this relationship, an initial value of in vivo sensitivity can be generated, from which an algorithmic function corresponding to the sensor sensitivity profile can be formed. Put another way, from this initial value (which represents one point in the sensor sensitivity profile), the rest of the entire sensor sensitivity profile can be determined and plotted. The initial value of in vivo sensitivity can be associated with any portion of the sensor sensitivity profile. In certain embodiments, multiple initial values of in vivo sensitivities, which are time-spaced apart, and which correspond to multiple in vitro sensitivities, can be calculated and combined together to generate the sensor sensitivity profile.

Figure 2A:
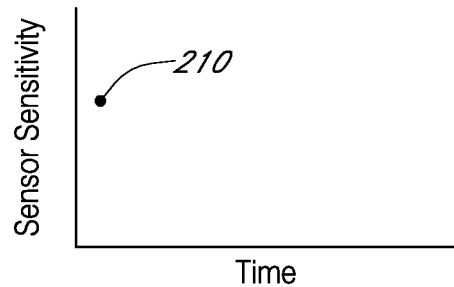
FIGS. 2A-2B and FIGS. 2C-2D collectively illustrate different embodiments of processes for generating a sensor sensitivity profile.
Figure 2B:
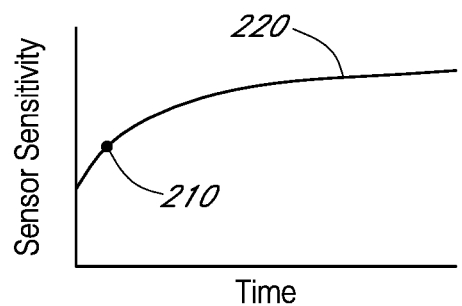
Figure 2C:
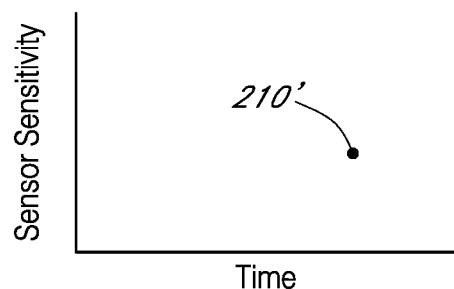
Figure 2D:
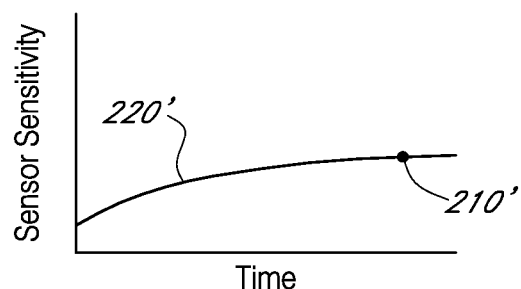

In some embodiments, as illustrated in FIG. 2A, the initial value 210 of in vivo sensitivity is associated with a time corresponding to the start (near the start) of the sensor session. As illustrated in FIG. 2B, based on this initial value 210, the rest of the sensor sensitivity profile 220 is plotted (i.e., plotted forward and backward across the x-axis corresponding to time). However, as illustrated in FIG. 2C, in some embodiments, the initial value 210' may be associated with any other time of the sensor session. For example, as illustrated in FIG. 2C, in one embodiment, the in initial value 210' of in vivo sensitivity is associated with a time (e.g., at about day 3) when the sensitivity has substantially reached steady state. From the initial value 210', the rest of the sensor sensitivity profile 220' is plotted, as illustrated in FIG. 2D.

With other embodiments, although the in vivo to in vitro sensitivity relationship was not equal, the relationship nonetheless involved a consistently fixed ratio. By having a substantially fixed in vivo to in vitro sensitivity relationship, some of the sensors described herein can be factory calibrated by evaluating the in vitro sensitivity characteristic (e.g., one or more sensitivity values measured at certain time periods) of a sensor from a particular sensor lot at a manufacturing facility, defining the in vivo sensitivity characteristic of other sensors in the same sensor lot based on its relationship with the measured in vitro sensitivity characteristic, and storing this calculated in vivo sensitivity characteristic onto electronics associated with the sensors (e.g., in computer memory of a sensor electronics, discussed more elsewhere herein, configured to be operably coupled to the sensor during sensor use).

Accordingly, with information obtained prior to the sensor session relating to an in vivo to in vitro sensor sensitivity relationship and a predetermined sensor sensitivity profile, factory calibration is achieved in conjunction with high levels of sensor accuracy. For example, in some embodiments, the sensor was capable of achieving an accuracy corresponding to a mean absolute relative difference of no more than about 10% over a sensor session of at least about 3 days, and sometimes at least about 4, 5, 6, 7, or 10 days. In some embodiments, the sensor was capable of achieving an accuracy, over a over a sensor session of at least about 3 days, corresponding to a mean absolute relative difference of no more than about 7%, 5%, or 3%. With factory calibration, the need for recalibration may be eliminated, or else required only in certain circumstances, such as in response to detection of sensor failure.

With reference back to the study associated with FIG. 1A, the sensors were built with a working electrode configured to measure a glucose+baseline signal and a corresponding auxiliary electrode configured to measure only the baseline signal. Sensor electronics in the sensor system subtracted the baseline signal from the glucose+baseline signal to obtain a signal associated entirely or substantially entirely to glucose concentration. In addition, an algorithmic function was generated and stored in sensor electronics associated with the sensors to estimate the sensitivity of these sensors during their lives. This algorithmic function is plotted in FIG. 1A and shown closely overlying the measured sensor sensitivities of the sensors. With the determination of baseline and sensitivity at any given time during the life of a sensor, a conversion function is formed, whereby a sensor signal is converted into an estimated glucose concentration.

Figure 3A:
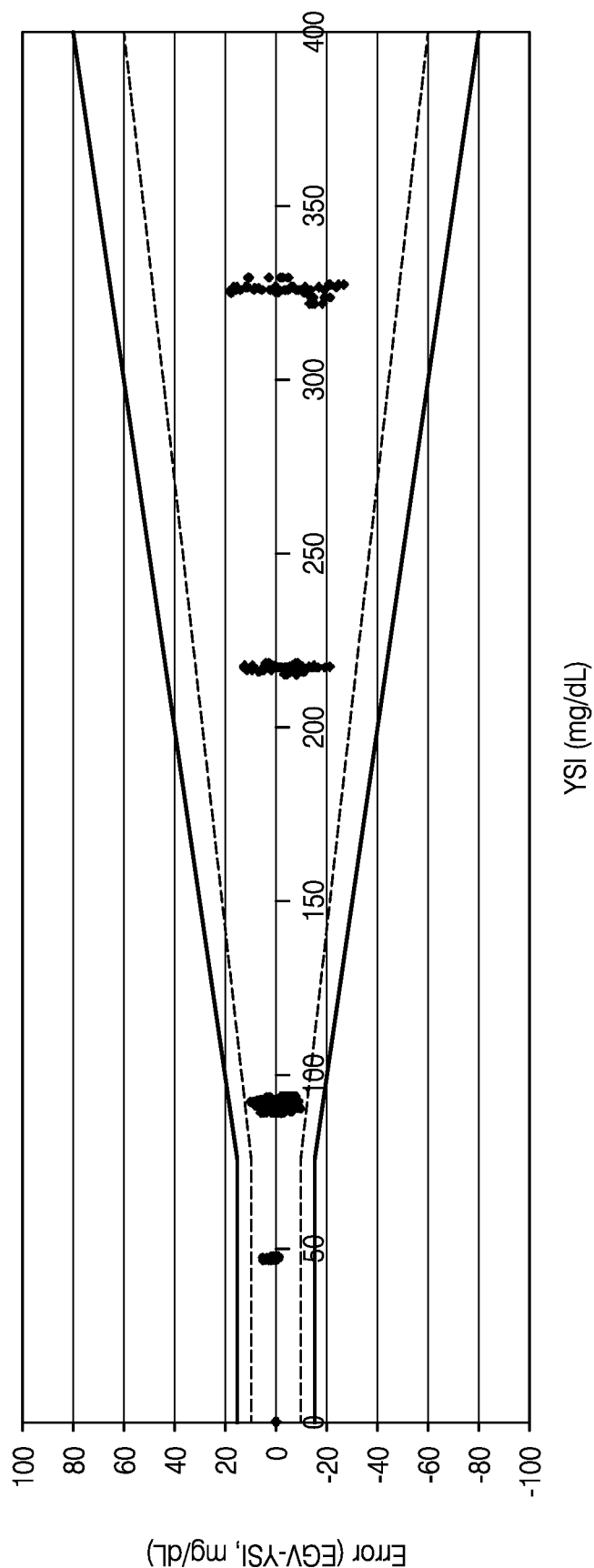
FIG. 3A is a Bland-Altman plot illustrating differences between YSI reference measurements and certain in vivo continuous analyte sensors that were factory calibrated, in accordance with one embodiment.

As illustrated in FIG. 3A, which is a Bland-Altman plot showing differences between YSI reference measurements and certain in vivo continuous analyte sensors that were factory calibrated, the measurements from these sensors exhibited very high accuracy. The lines in FIG. 3A represent accuracy standards corresponding to a deviation from actual measured values (using YSI tests) of less than ±10 mg/dL at glucose concentrations between about 40 and 75 mg/dL, and less than ±15% at glucose concentrations between about 75 mg/dL and 400 mg/dL. Indeed, the difference between estimated glucose concentration values, which are calculated using a predetermined sensor sensitivity profile, and actual measured values (using YSI tests) over a sensor life, differed by no more than about 10 mg/dL at glucose concentrations between about 40 and 75 mg/dL, and no more than 15% at glucose concentrations between about 75 mg/dL and 400 mg/dL. Furthermore, at glucose concentrations between about 40 mg/dL and 75 mg/dL, about 97% of the estimated glucose concentrations values were within ±5 mg/dL of corresponding YSI measured values, and at glucose concentrations between about 70 mg/dL and 400 mg/dL, about 99% of the estimated glucose concentrations were within ±10% of corresponding YSI measured values.

Figure 3B:
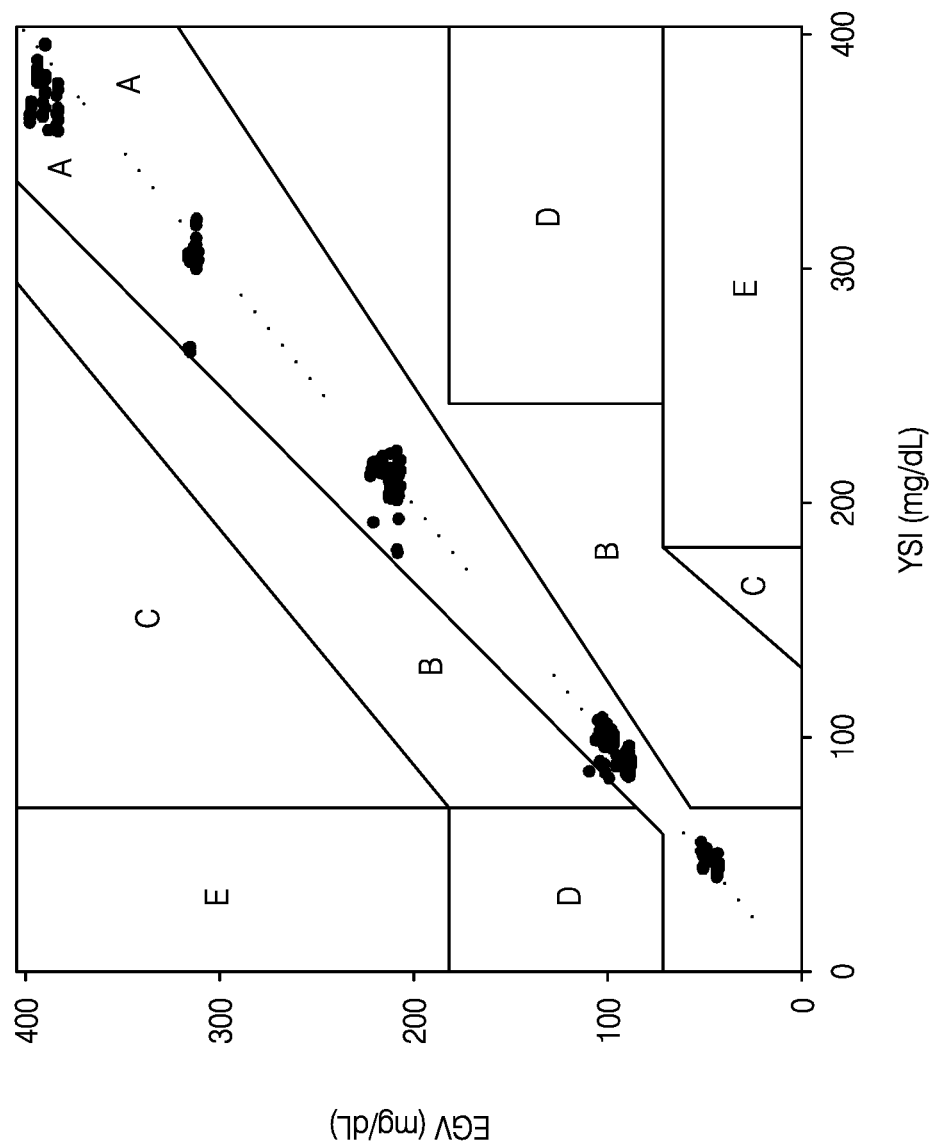
FIG. 3B is a Clarke error grid associated with data from the continuous analyte sensors associated with FIG. 3A.

FIG. 3B illustrates a Clarke error grid associated with the factory calibration study associated with FIG. 3A. The Clarke error grid of FIG. 3B is a Clarke error grid is based on a correlation plot of the performance of the above-described factory calibration method with respect to a reference method in the form of YSI measurements. If the correlation was perfect, all points would fall on a 45° line. The area surrounding this line is divided into zones that predict the clinical consequences in terms of action taken by the patient, depending on where the measurements by the factory calibration method fall off the line. Zone A corresponds to a clinically accurate decision (e.g., take insulin, take glucose, or do nothing), zone B a clinically acceptable decision, and zone D corresponds to a clinically erroneous decision. As shown in FIG. 3B, all of data points from the factory calibration study fell within either zone A or zone B. In fact, almost all of the data points fell within Zone A, thus establishing that the above-described factory calibration study provided very accurate glucose concentration measurements.

While individual sensors of a sensor group manufactured under substantially identical conditions have been found to generally exhibit a substantially similar or a nearly identical sensor sensitivity profile and have a substantially similar or a nearly identical in vivo to in vitro sensor sensitivity relationship, it has been found that at times the actual sensor sensitivity (i.e., sensitivity expressed as an actual sensitivity value, and not as a percentage of a substantially steady state sensitivity) can vary between sensors. For example, even though individual sensors may have been manufactured under substantially identical conditions, they can have different sensitivity characteristics during use if they are exposed to different environment conditions (e.g., exposure to radiation, extreme temperature, abnormal dehydration conditions, or any environment that can damage the enzyme in the sensor membrane or other parts of the sensor, etc.) during the time period between sensor fabrication and sensor use.

Accordingly, to compensate for potential effects resulting from these conditions, in certain embodiments, the continuous analyte sensors are configured to request and accept one or more reference measurements (e.g., from a finger stick glucose measurement or from a calibration solution) at the start of the sensor session. For example, the request for one or more reference measurements can be made at about 15 minutes, 30 minutes, 45 minutes, 1 hour, 2 hours, 3 hours, etc., after activation of the sensor. In some embodiments, sensor electronics are configured to process and use the reference data to generate (or adjust) a sensor sensitivity profile in response to the input of one or more reference measurements into the sensor. For example, if a reference measurement of glucose concentration is taken and input into the sensor at time=x, an algorithmic function of sensor sensitivity can be generated by matching the sensor sensitivity profile at time=x with the reference measurement. Use of the one of the one or more reference measurements at the start of the sensor in conjunction with a predetermined sensor sensitivity profile permits self-calibration of the sensor without or with a reduced need for further reference measurements.

Figure 4:
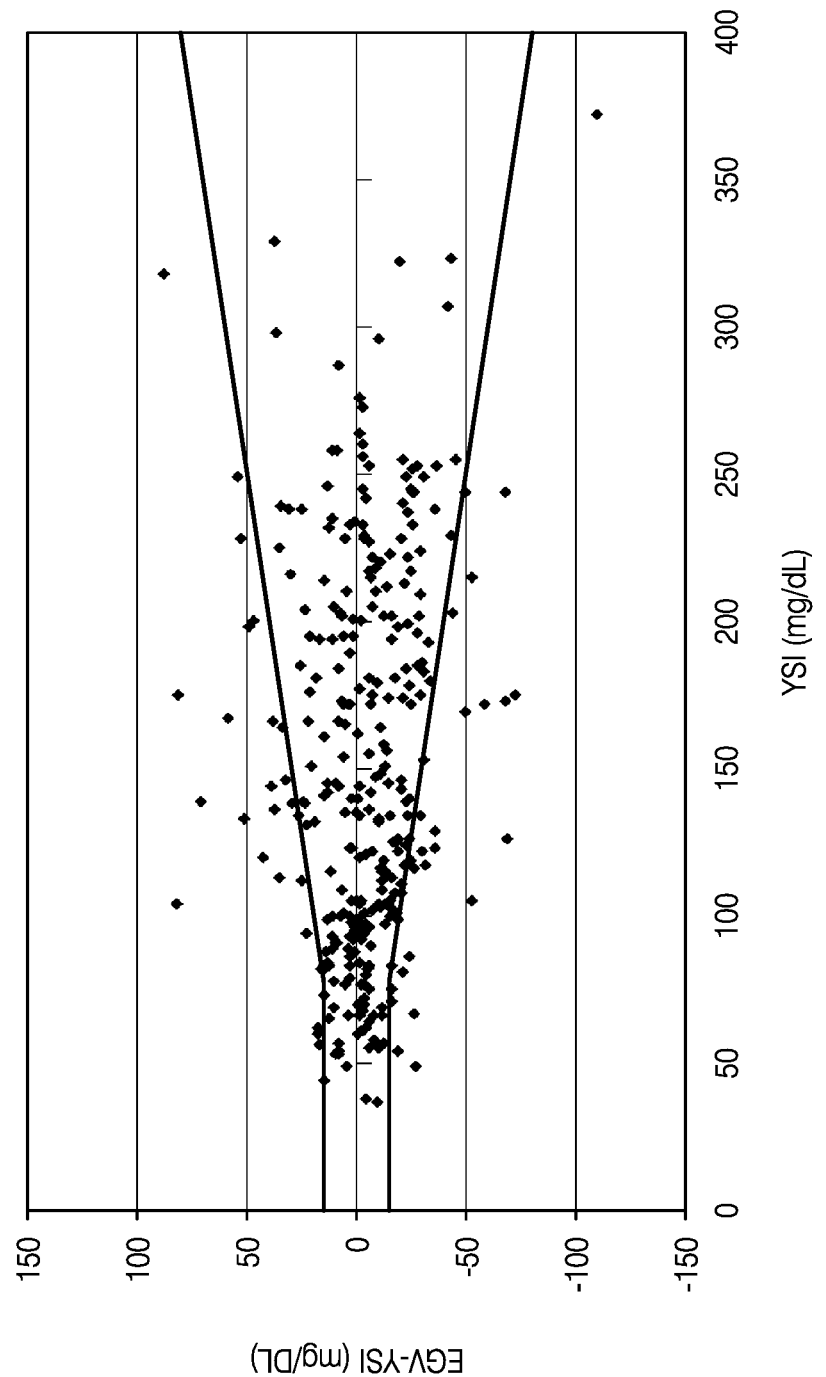
FIG. 4 illustrates data from one study that examined the accuracy level of continuous analyte sensors that accepted one reference measurement about one hour after insertion into patients, in accordance with one embodiment.

FIG. 4 illustrates a Bland-Altman plot showing differences between YSI reference measurements and in vivo continuous analyte sensors that accepted one reference measurement about one hour after insertion into patients. The lines in FIG. 4 represent accuracy standards corresponding to a deviation from actual measured values (using YSI tests) of less than about ±20 mg/dL at glucose concentrations between about 40 mg/dL and 75 mg/dL, and less than about ±20% at glucose concentrations between about 75 mg/dL and 400 mg/dL. From this reference measurement, an initial value of in vivo sensor sensitivity was generated, which in turned allow for the formation of an algorithmic function corresponding to the sensitivity profile for the rest of the sensor session. The sensors were built with a working electrode and an auxiliary electrode used to measure a baseline signal, which was subtracted from the glucose+baseline signal obtained by the working electrode. As shown, about 85% of the estimated glucose concentrations were within the range 410, defined as ±20 mg/dL from corresponding YSI measured values for glucose concentrations between about 40 mg/dL and 75 mg/dL and ±20% from corresponding YSI measured values for glucose concentrations between about 75 mg/dL and 400 mg/dL. Additionally, at glucose concentrations between about 40 mg/dL and 75 mg/dL, about 95% of the estimated glucose concentrations values were within ±20 mg/dL of corresponding YSI measured values. The sensors in this study obtained an overall accuracy level corresponding to a Mean Absolute Relative Difference of about 12% over a sensor session of at least seven days, and a first-day accuracy level corresponding to a Mean Absolute Relative Difference of about 11%. The Median Absolute Relative Difference obtained were about 10% for both overall and first-day accuracy levels.

Figure 5:
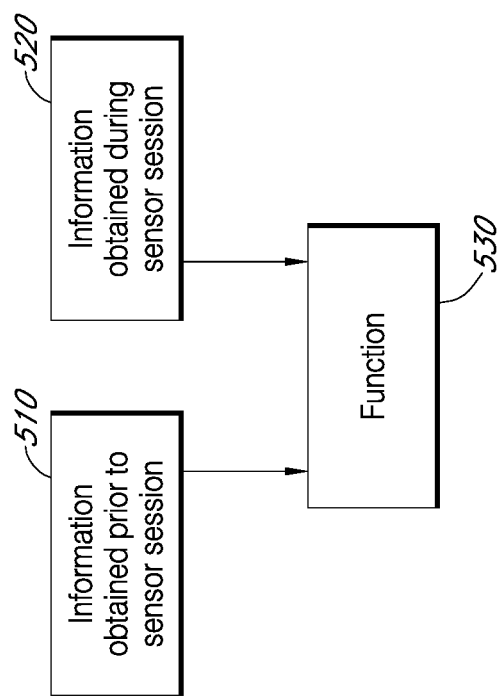
FIG. 5 illustrates a diagram showing different types of information that can be input into the sensor system to define the sensor sensitivity profile over time

FIG. 5 is a diagram illustrating different types of information that can be input into the sensor system to define the sensor sensitivity profile over time, in one embodiment. Input information can include information obtained prior to the sensor session 510 and information obtained during the sensor session 520. In the embodiment depicted in FIG. 5, both information obtained prior to the sensor session 510 and information obtained during the sensor session 520 are used to generate, adjust, or update a function 530 associated with the sensor sensitivity profile, but in another embodiment, the sensor system may be configured to use only information obtained prior to the sensor session. In certain embodiments, formation of an initial sensor sensitivity profile can occur prior to the sensor session, at the start of the sensor session, or shortly after the start of the sensor session. Additionally, in certain embodiments, the sensor sensitivity profile can be continuously adjusted, regenerated, or updated to account for parameters that may affect sensor sensitivity or provide additional information about sensor sensitivity during the sensor session. Information obtained prior to the sensor session can include, for example, the sensor sensitivity profile that is generated before or at the start of the sensor session, as previously described. It can also include a sensitivity value associated with a substantially fixed in vivo to in vitro sensor sensitivity relationship, as previously described.

Alternatively, instead of a fixed sensitivity value, the in vivo to in vitro sensor sensitivity relationship may be defined as a function of time between completion of sensor fabrication (or the time calibration check was performed on sensors from the same lot) and the start of the sensor session.

Figure 6:
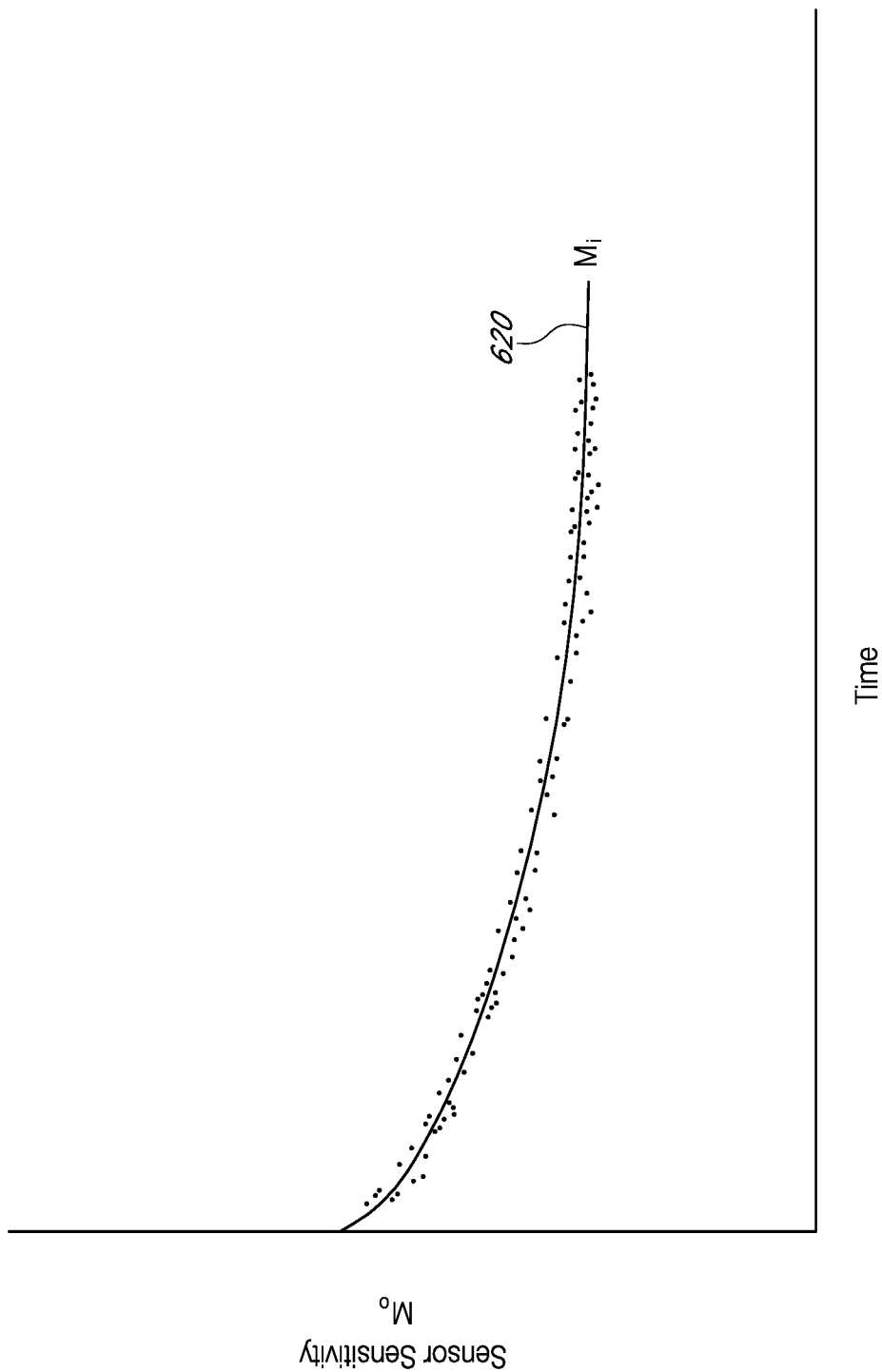
FIG. 6 illustrates a schematic diagram of sensor sensitivity as a function of time between completion of sensor fabrication and the start of the sensor session, in accordance with one embodiment.

As shown in FIG. 6, it has been discovered that a sensor's sensitivity to analyte concentration can change as a function of time between completion of sensor fabrication and the start of the sensor session. FIG. 6 illustrates this phenomenon through a plot, which resembles a downward trend in sensitivity over time between completion of sensor fabrication and the start of the sensor session. Similar to the discovered change or drift in sensitivity over time of a sensor session, this change or drift in sensitivity over time between completion of sensor fabrication and the start of the sensor session is generally consistent among sensors that have not only been manufactured in substantially the same way under substantially same conditions, but that also have avoided exposure to certain conditions (e.g., exposure to radiation, extreme temperature, abnormal dehydration conditions, or any environment that can damage the enzyme in the sensor membrane or other parts of the sensor, etc.) Accordingly, the change or drift in sensitivity over time between completion of sensor fabrication and the start of the sensor session can also be modeled through a mathematical function 620 that accurately estimates this change or drift. The estimative algorithm function 620 may be any of a variety of functions, such as, for example, a linear function (including a constant function), logarithmic function, quadratic function, cubic function, square root function, power function, polynomial function, rational function, exponential function, sinusoidal function, and combinations thereof.

Information obtained prior to the sensor session can also include information relating to certain sensor characteristics or properties. By way of example and not to be limiting, information obtained prior to the sensor session may include the particular materials used to fabricate the sensor (e.g., materials used to form the sensor membrane), the thickness of the sensor membrane, the membrane's permeability to glucose or other chemical species, the in vivo or in vitro sensor sensitivity profile of another sensor made in substantially the same way under substantially same conditions, etc. In certain embodiments, information obtained prior to the sensor session can include information relating to the process conditions under which the sensor is fabricated. This information can include, for example, the temperature at which the sensor membrane was cured, the length of time the sensor was dipped in a particular coating solution, etc. In other embodiments, information obtained prior to the sensor session can relate to patient physiological information. For example, the patient's age, body mass index, gender, and/or historic patient sensitivity profiles, can be used as parameters to form the sensor sensitivity profile. Other information obtained prior to the sensor session that may also be used includes information relating to sensor insertion, such as, for example, location (e.g., abdomen vs. back) or depth of sensor insertion.

In general, the sensor sensitivity functions can be created by theoretical or empirical methods, or both, and stored as functions or as look-up-tables, thereby allowing for sensor self-calibration that eliminates (or substantially reduces) the need for reference measurements. The sensor sensitivity functions can be generated at the manufacturing facility and shipped with the system or generated by the system shortly prior to (or during) use. The term "self-calibration," as used herein, is a broad term, and is to be given its ordinary and customary meaning to a person of ordinary skill in the art (and is not to be limited to a special or customized meaning), and refers without limitation to calibration of a sensor or device which is performed by a control system manufacturer or installer, the sensor manufacturer, or anyone other than the user of the sensor. The sensor calibration can be performed on the individual sensor on which the control system is installed, or it can be performed on a reference sensor, for example one from the same sensor lot, and the calibration functions can be transferred from one control system to another. In some embodiments, systems may be shipped with some self-calibration functions and then have others added by the sensor user. Also, sensor systems may be shipped with self-calibration functions and only need adjustments or touch-up calibrations during use.

In certain embodiments, the sensor sensitivity profile may be adjusted during sensor use to account for, in real-time, certain parameters that may affect sensor sensitivity or provide additional information about sensor sensitivity. These parameters may include, but are not limited to, parameters associated with sensor properties, such as, for example, sensor membrane permeability or the level of sensor hydration, or parameters associated with patient physiological information, such as, for example, patient temperature (e.g., temperature at the sample site or skin temperature), pH at the sample site, hematocrit level, or oxygen level at the sample site. In some embodiments, the continuous analyte sensor may be fitted with a thermistor on an ex vivo portion of the sensor and a thermal conductive line that extends from the thermistor to the sample site.

In some embodiments, calibration methods can be improved by algorithmically quantifying each unique sensor/user environment. Quantification can be achieved by generation or adjustment of the sensitivity profile, which may involve an inference engine involving a causal probabilistic network such as a Bayesian network. A Bayesian network includes a conditional probability-based network that relies on the Bayes theorem to characterize the likelihood of different outcomes based on known prior probabilities (e.g., prevalence of observed in vivo sensitivities under certain parameter conditions) and newly acquired information (e.g., occurrence or nonoccurrence of the aforementioned conditions).

In certain embodiments, quantification is achieved through the application of an analytical Bayesian framework to data already existing within the system algorithm. Quantification can involve: (1) wedge (e.g., maximum or minimum) values for parameters related to sensitivity and baseline; (2) sensitivity values calculated during a sensor session; and (3) baselines calculated during the sensor session. In some embodiments, the first set of wedge values are based on parameter distributions of "prior" data (e.g., data collected from previous clinical studies). By using a Bayesian network, a system can learn from data collected during the sensor session, and adapt the wedge values (or other algorithm parameters and/or constraints) to a particular sensor/user environment. In turn, the system's calibration method can be improved to have better accuracy, reliability, and overall performance.

In one embodiment, the Bayesian framework used involves using known prior information to establish a framework and then accounting for gathered new information to make inferences from their combination (i.e., combination of prior and new information), to generate posterior information. When the prior information and the new information are mathematically related and combined to form posterior information that can be represented functionally, the relationship is defined as conjugate. The Bayesian framework of one embodiment employs conjugate distributional relationships that result in the posterior distributional parameters (e.g., mean, variance) being directly available. This can be advantageous under a computationally restrictive space where both time and resources are constrained.

In some embodiments, under the Bayesian framework, in which the wedge parameters follow a prior substantially normal distribution for each parameter, and in which the algorithmically calculated sensitivity and baseline values follow their own substantially normal distribution representing the new information, an independent posterior distribution for sensitivity and/or baseline can be generated. These two posterior distributions are then used in parallel to construct glucose threshold values used for accepting, rejecting, or modifying a user's manual calibration entry (e.g., entry from a fingerstick measurement). In certain embodiments, the posterior distributions of sensitivity and baseline can also be used for semi-self-calibration, thereby reducing the number of fingerstick measurements required for manual calibration.

In one exemplary embodiment, from prior information, the wedge min/max values for a sensor's sensitivity to glucose are known to be A and B at the 95% confidence interval in a substantially normal distribution. Using algorithmically calculated sensitivity values as new information, the previous three, four, five, six, seven, or more sensitivity values calculated through manual calibration can be used as new information to generate a posterior distribution, which will typically have reduced variability than the distribution based on prior information, and which is a direct quantification of a unique sensor/user environment. Because of reduced variability, the posterior distribution generated will typically have wedge values, which should be closer together than the difference between A and B, i.e., the wedge values of the distribution generated from prior information. This tightening of the difference between the wedge values between the prior distribution and the posterior distribution allow the system to more reliably reject manual calibration entries that are clearly erroneous, such as, for example, a calibration entry of 60 mg/dL that was intended by the user to be an entry of 160 mg/dL.

Figure 7A:
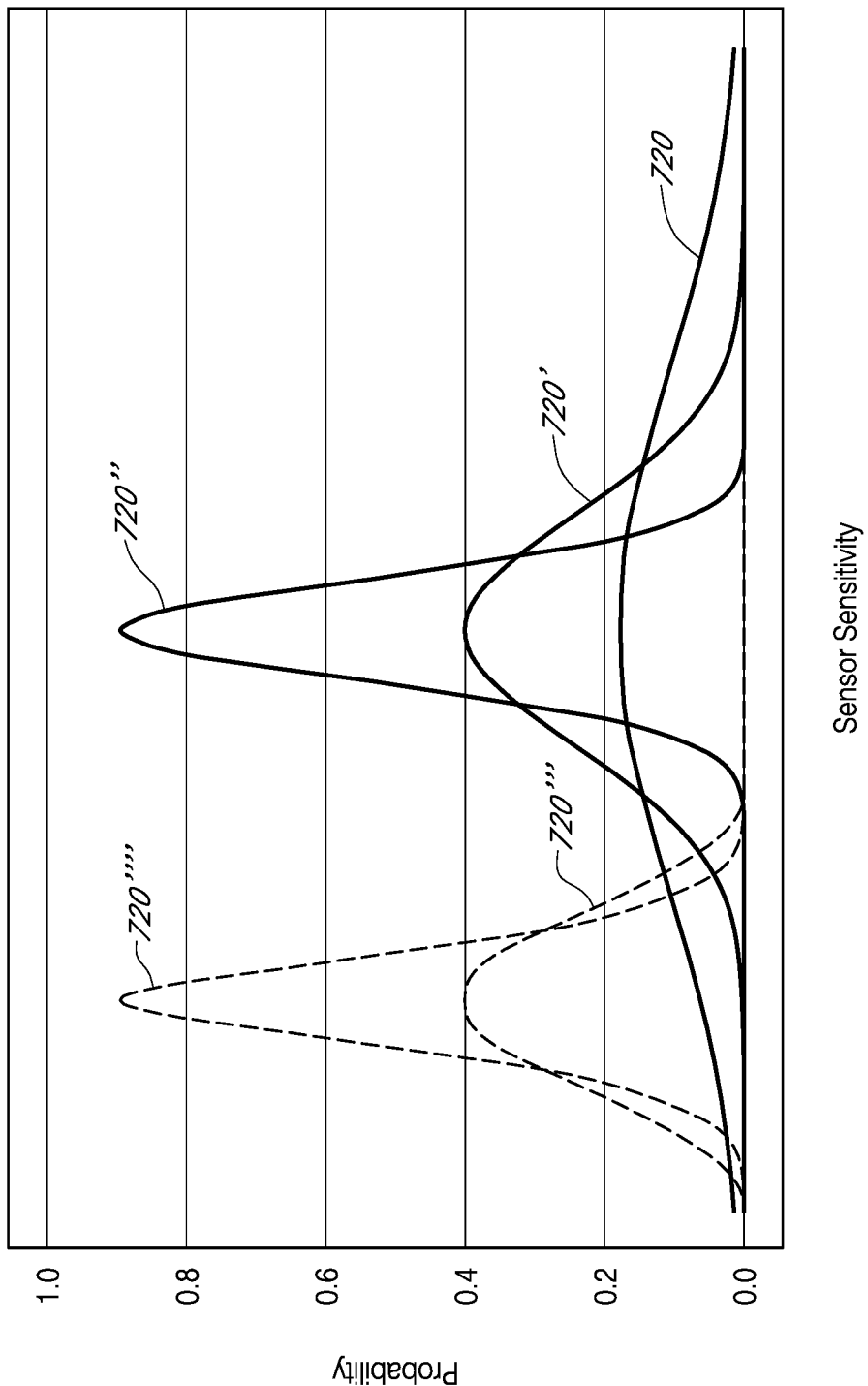
FIG. 7A is a schematic diagram depicting distribution curves of sensor sensitivity corresponding to the Bayesian learning process, in accordance with one embodiment.
Figure 7B:
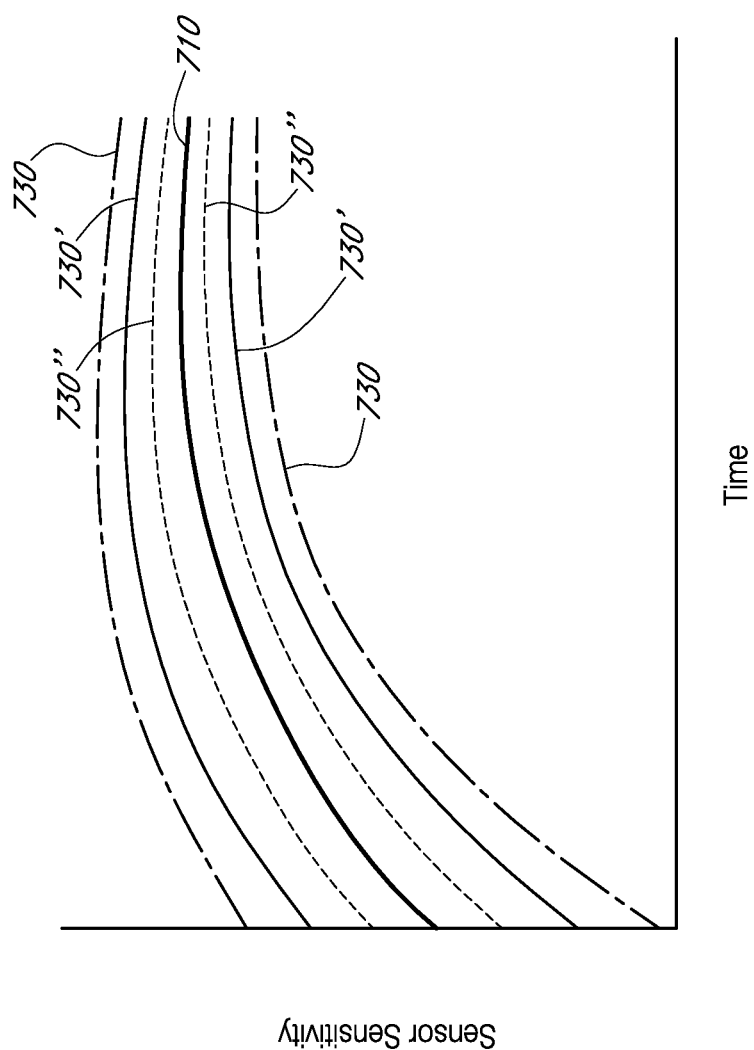
FIG. 7B is a schematic diagram depicting confidence levels, associated with the sensor sensitivity profile, that correspond with the distribution curves shown in FIG. 7A.

Bayesian networks use causal knowledge and model probabilistic dependence and independence relationships between different events. FIG. 7A depicts distribution curves of sensor sensitivity corresponding to the Bayesian learning process, in accordance with one embodiment. FIG. 7B depicts confidence levels, associated with the sensor sensitivity profile, that correspond with the distribution curves shown in FIG. 7A. Distribution curve 720 and confidence level 730 (e.g., 25%, 33%, 50%, 75%, 95%, or 99% confidence level) are associated with a lack of initial knowledge about certain parameters that affect sensor sensitivity or provide additional information about sensor sensitivity. For example, distribution curve 720 can be associated with factory information. As information regarding a certain parameter is acquired, the distribution curve 720' becomes steeper and the confidence interval 730' becomes narrower, as certainty of sensor sensitivity profile 710 is increased. Examples of information that may be used to change the distribution curves can include a reference analyte value, a cal-check of the sensor at the factory, patient history information, and any other information described elsewhere herein that can affect sensor sensitivity or provide information about sensor sensitivity. As information regarding still another parameter is acquired, the distribution curve 720" becomes even steeper and the confidence interval 730" becomes even narrower, as certainty of sensor sensitivity profile 710 is further increased.

During sensor use, the confidence interval curves 730, 730', and/or 730" may be used to form the sensitivity profile 710, which provides an estimated sensitivity value at a given time. In turn the estimated sensitivity value may be used to calibrate the sensor, which allows for processing of sensor data to generate a glucose concentration value that is displayed to the user. In some embodiments, a first estimated sensitivity profile 710, formed from the confidence interval curves 730, 730', and/or 730", may be used to monitor and display glucose concentrations. In addition, one or more of the confidence interval curves 730, 730', 730", or combinations thereof, can be used to form a second estimated sensitivity profile that, while possibly not as accurate as the first estimated sensitivity profile, is nonetheless more likely to result in the detection of a hypoglycemic or hyperglycemic range than the first estimated sensitivity profile 710.

Determination of Baseline

A variety of types of noise can occur when a sensor is implanted in a host. Some implantable sensors measure a signal (e.g., counts) that comprises two components, the baseline signal and the analyte signal. The baseline signal is substantially comprised of a signal contribution from factors other than the measure analyte (e.g., interfering species, non-reaction-related hydrogen peroxide, or other electroactive species with an oxidation potential that overlaps with the analyte or co-analyte). The analyte signal (e.g., glucose signal) is substantially comprised of a signal contribution from the analyte. Consequently, because the signal includes these two components, calibration can be performed to determine the analyte (e.g., glucose) concentration by solving for the equation $y=mx+b$, wherein the value of b represents the baseline of the signal. In some circumstances, the baseline is comprised of constant and non-constant non-analyte factors. Generally, it is desirable to reduce or remove the background signal, to provide a more accurate analyte concentration to the patient or health care professional.

In certain embodiments, an analyte sensor (e.g., glucose sensor) is configured for insertion into a host for measuring an analyte in the host. The sensor includes a working electrode disposed beneath an active enzymatic portion of a membrane on the sensor, an auxiliary electrode disposed beneath an inactive- or non-enzymatic portion of the membrane on the sensor, and sensor electronics operably connected to the working and auxiliary electrodes. The sensor electronics are configured to process signals from the electrodes to generate an analyte (e.g., glucose) concentration estimate that substantially excludes signal contribution from non-glucose related noise artifacts.

In some embodiments, the working electrode is configured to generate via sensor electronics a first signal associated with both the analyte and non-analyte related electroactive compounds that have a oxidation potential less than or similar to a first oxidation potential. The auxiliary electrode is configured to generate a second signal associated with the non-analyte related electroactive compounds. Non-analyte related electroactive compounds can be any compound, present in the sensor's local environment, which has an oxidation potential less than or similar to the oxidation potential of the measured species (e.g., $H_2O_2$). While not wishing to be bound by theory, it is believed that with a glucose-measuring electrode, both the signal directly related to the enzyme-catalyzed reaction of glucose (which produces $H_2O_2$ that is oxidized at the first working electrode) and signals from unknown compounds that are in the extracellular milieu surrounding the sensor can be measured. These unknown compounds can be constant or non-constant (e.g., intermittent or transient) in concentration and/or effect. In some circumstances, it is believed that some of these unknown compounds can be related to the host's disease state. For example, it is known that blood chemistry can change dramatically during/after a heart attack (e.g., pH changes, changes in the concentration of various blood components/protein, and the like). As another example, the transcutaneous insertion of a needle-type sensor can initiate a cascade of events that includes the release of various reactive molecules by macrophages. Other compounds that can contribute to the non-glucose related signal are compounds associated with the wound healing process, which can be initiated by implantation/insertion of the sensor into the host, as described in more detail with reference to U.S. Patent Publication No. US-2007-0027370-A1.

As described above, the auxiliary electrode is configured to generate a second signal associated with the non-analyte related electroactive compounds that have an oxidation potential less than or similar to the first oxidation potential. Non-analyte related electroactive species can include interfering species, non-reaction-related species (e.g., $H_2O_2$) that correspond to the measured species, and other electroactive species. Interfering species includes any compound that is not directly related to the electrochemical signal generated by the enzyme-catalyzed reaction of the analyte, such as, electroactive species in the local environment produced by other bodily processes (e.g., cellular metabolism, wound healing, a disease process, and the like). Non-reaction-related species includes any compound from sources other than the enzyme-catalyzed reaction, such as, $H_2O_2$ released by nearby cells during the course of the cells' metabolism, $H_2O_2$ produced by other enzymatic reactions (e.g., extracellular enzymes around the sensor or such as can be released during the death of nearby cells or such as can be released by activated macrophages), and the like. Other electroactive species includes any compound that has an oxidation potential less than or similar to the oxidation potential of $H_2O_2$.

The non-analyte signal produced by compounds other than the analyte (e.g., glucose) is considered as background noise and can obscure the signal related to the analyte, thereby contributing to sensor inaccuracy. As described in greater detail elsewhere herein, background noise can include both constant and non-constant components and can be removed to accurately calculate the analyte concentration.

In certain embodiments, the analyte sensor system is configured in a way (e.g., with a certain symmetry, coaxial design, and/or integral formation) such that the working and auxiliary electrodes are influenced by substantially the same external/environmental factors, thereby enabling substantially equivalent measurement of both the constant and non-constant species/noise. This allows for the substantial elimination of noise on the sensor signal by using sensor electronics described elsewhere herein. In turn, the substantial reduction or elimination of signal effects associated with noise, including non-constant noise (e.g., transient, unpredictable biologically related noise) increases accuracy of continuous sensor signals.

In some embodiments, sensor electronics are operably connected to the working and auxiliary electrodes. The sensor electronics may be configured to measure the current (or voltage) to generate the first and second signals. Collectively, the first and second signals can be used to produce glucose concentration data without substantial signal contribution from non-glucose-related noise. This can be performed, for example, by subtraction of the second signal from the first signal to produce a signal associated with analyte concentration and without substantial noise contribution, or by alternative data analysis techniques.

In other embodiments, the sensor electronics are operably connected to one or more working electrodes only, as an auxiliary electrode is not needed. For example, the sensor membrane in some embodiments may comprise polymers that contain mediators and enzymes that chemically attach to the polymers. The mediator used may oxidize at lower potentials than hydrogen peroxide, and thus fewer oxidizable interferents are oxidized at these low potentials. Accordingly, in some embodiments, a very low baseline (i.e., a baseline that approaches a zero baseline and that does not receive substantial signal contribution from non-glucose-related noise) may be achieved, thereby potentially eliminating (or reducing) the need for an auxiliary electrode that measures signal contribution from non-glucose-related noise.

The sensor electronics can be comprised of a potentiostat, A/D converter, RAM, ROM, transceiver, processor, and/or the like. The potentiostat may be used to provide a bias to the electrodes and to convert the raw data (e.g., raw counts) collected from the sensor to an analyte concentration value (e.g., a glucose concentration value expressed in units of mg/dL). The transmitter may be used to transmit the first and second signals to a receiver, where additional data analysis and/or calibration of analyte concentration can be processed. In certain embodiments, the sensor electronics may perform additional operations, such as, for example, data filtering and noise analysis.

In certain embodiments, the sensor electronics may be configured to analyze an analyte equivalent baseline or normalized baseline, instead of the baseline. The normalized baseline is calculated as the b/m or y-intercept divided by slope (from the equation $y=mx+b$). The unit for analyte equivalent baseline may be expressed as the analyte concentration unit (mg/dL), which correlates with the output of the continuous analyte sensor. By using the analyte equivalent baseline (normalized baseline), the influence of glucose sensitivity on the baseline may be eliminated, thereby making it possible to evaluate the baselines of different sensors (e.g., from the same sensor lot or from different sensor lots) with different glucose sensitivities.

Figure 8:
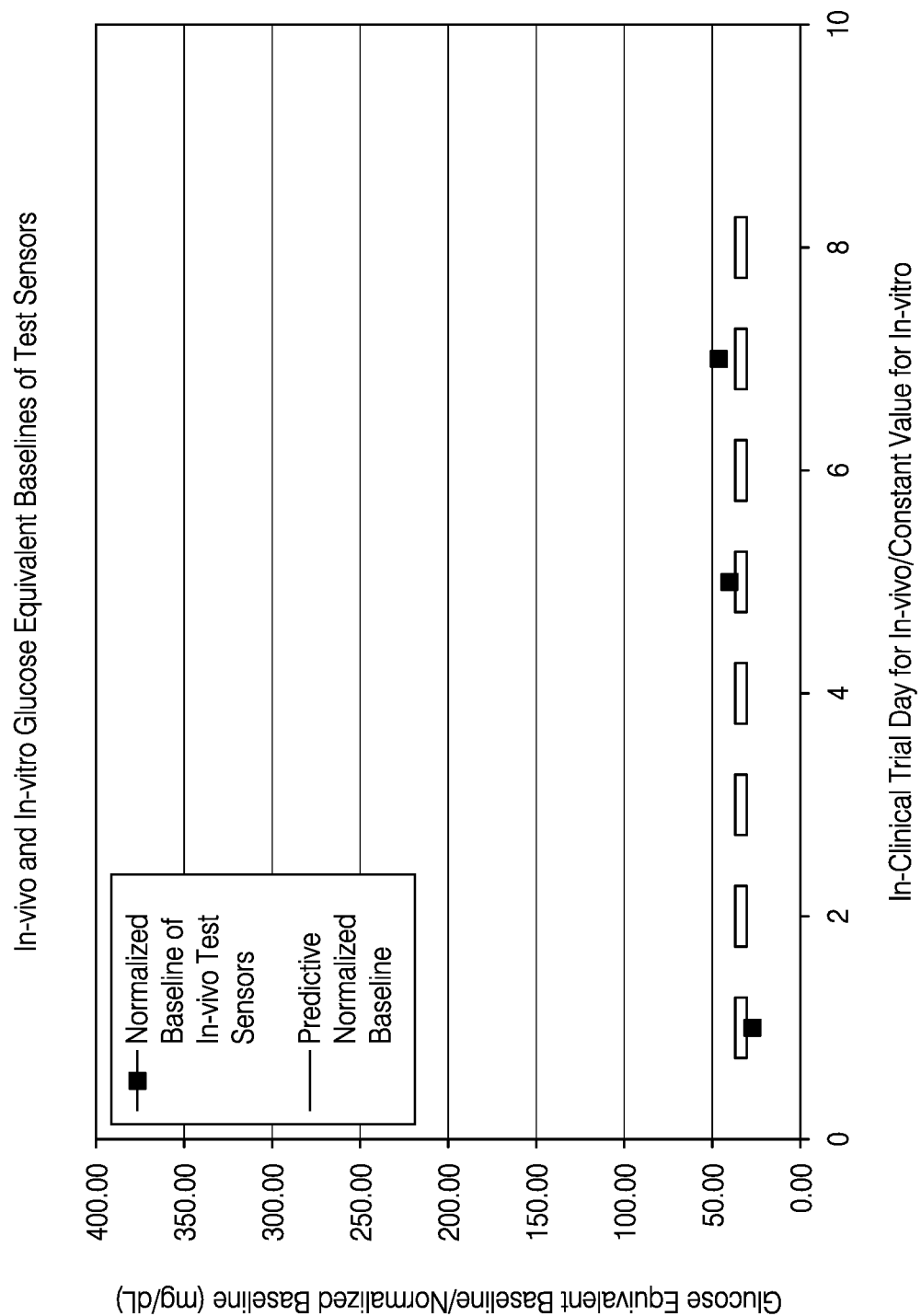
FIG. 8 illustrates a graph that provides a comparison between an estimated glucose equivalent baseline and detected glucose equivalent baseline, in accordance with one study.

Although some embodiments have been described herein which employ an auxiliary electrode to allow for the subtraction of a baseline signal from a glucose+baseline signal, it should be understood that the use of this electrode is optional and may not be used in other embodiments. For example, in certain embodiments, the membrane system covering the working electrode is capable of substantially blocking interferents, and substantially reducing the baseline to a level that is negligible, such that the baseline can be estimated. Estimation of the baseline can be based on an assumption of the sensor's baseline at physiological conditions associated with a typical patient. For example, baseline estimation can be modeled after in vivo or in vitro measurements of baseline in accordance with certain physiological levels of interferents that are inherent in the body. FIG. 8 is a graph that provides a comparison between an estimated glucose equivalent baseline and detected glucose equivalent baseline, in accordance with one study. The estimated glucose equivalent baseline was formed by conducting in vitro measurements of the baseline of glucose sensors in a solution that mimicked physiological levels of interferents in a human. The interferents included uric acid with a concentration of about 4 mg/dL and ascorbic acid, with a concentration of about 1 mg/dL of ascorbic acid. As shown in FIG. 8, it was found in this study that the estimated baseline closely resembled the detected baseline. Accordingly, with the possibility of accurate estimation of baseline and/or with a baseline that is negligible, a single working electrode alone (i.e., without use of an ancillary electrode), together with a predetermined sensor sensitivity profile, may be sufficient to provide a sensor system with self-calibration.

With some embodiments, it has been found that not only does the sensor's sensitivity tend to drift over time, but that the sensor's baseline also drifts over time. Accordingly, in certain embodiments, the concepts behind the methods and systems used to predict sensitivity drift can also be applied to create a model that predicts baseline drift over time. Although not wishing to be bound by theory, it is believed that the total signal received by the sensor electrode is comprised of a glucose signal component, an interference signal component, and a electrode-related baseline signal component that is a function of the electrode and that is substantially independent of the environment (e.g., extracellular matrix) surrounding the electrode. As noted above, the term "baseline," as used herein, refers without limitation to the component of an analyte sensor signal that is not related to the analyte concentration. Accordingly, the baseline, as the term is defined herein, is comprised of the interference signal component and the electrode-related baseline signal component. While not wishing to be bound by theory, it is believed that increased membrane permeability typically not only results in an increased rate of glucose diffusion across the sensor membrane, but also to an increased rate of diffusion of interferents across the sensor membrane. Accordingly, changes in sensor membrane permeability over time which causes sensor sensitivity drift, will similarly also likely cause the interference signal component of the baseline to drift. Simply put, the interference signal component of the baseline is not static, and is typically changing as a function of time, which, in turn, causes the baseline to also drift over time. By analyzing how each of the aforementioned components of the baseline reacts to changing conditions and to time (e.g., as a function of time, temperature), a predictive model can be developed to predict how the baseline of a sensor will drift during a sensor session. By being able to prospectively predict both sensitivity and baseline of the sensor, it is believed that a self-calibrating continuous analyte sensor can be achieved, i.e., a sensor that does not require use of reference measurements (e.g., a fingerstick measurement) for calibration.

Calibration Code

The process of manufacturing continuous analyte sensors may sometimes be subjected to a degree of variability between sensor lots. To compensate for this variability, one or more calibration codes may be assigned to each sensor or sensor set to define parameters that can affect sensor sensitivity or provide additional information about the sensitivity profile. The calibration codes can reduce variability in the different sensors, ensuring that the results obtained from using sensors from different sensors lots will be generally equal and consistent by applying an algorithm that adjusts for the differences. In one embodiment, the analyte sensor system may be configured such that one or more calibration codes are to be manually entered into the system by a user. In other embodiments, the calibration codes may be part of a calibration encoded label that is adhered to (or inserted into) a package of multiple sensors. The calibration encoded label itself may be read or interrogated by any of a variety of techniques, including, but not limited to, optical techniques, RFID (Radio-frequency identification), or the like, and combinations thereof. These techniques for transferring the code to the sensor system may be more automatic, accurate, and convenient for the patient, and less prone to error, as compared to manual entry. Manual entry, for instance, possesses the inherent risk of an error caused by a patient or hospital staff entering the wrong code, which can lead to an incorrect calibration, and thus inaccurate glucose concentration readings. In turn, this may result in a patient or hospital staff taking an inappropriate action (e.g., injecting insulin while in a hypoglycemic state).

In some embodiments, calibration codes assigned to a sensor may include a first calibration code associated with a predetermined logarithmic function corresponding to a sensitivity profile, a second calibration code associated with an initial in vivo sensitivity value, and other calibration codes, with each code defining parameter that affects sensor sensitivity or provides information about sensor sensitivity. The other calibration codes may be associated with any priori information or parameter described elsewhere herein and/or any parameter that helps define a mathematical relationship between the measured signal and analyte concentration.

In some embodiments, the package used to store and transport a continuous analyte sensor (or sensor set) may include detectors configured to measure certain parameters that may affect sensor sensitivity or provide additional information about sensor sensitivity or other sensor characteristics. For example, in one embodiment, the sensor package may include a temperature detector configured to provide calibration information relating to whether the sensor has been exposed to a temperature state greater than (and or less than) one or more predetermined temperature values. In some embodiments, the one or more predetermined temperature value may be greater than about 75° F., greater than about 80° F., greater than about 85° F., greater than about 90° F., greater than about 95° F., greater than about 100° F., greater than about 105° F., and/or greater than about 110° F. Additionally or alternatively, the one or more predetermined temperature value may be less than about 75° F., less than about 70° F., less than about 60° F., less than about 55° F., less than about 40° F., less than about 32° F., less than about 10° F., and/or less than about 0° F. In certain embodiments, the sensor package may include a humidity exposure indicator configured to provide calibration information relating to whether the sensor has been exposed to humidity levels greater than or less than one or more predetermined humidity values. In some embodiments, the one or more predetermined humidity value may be greater than about 60% relative humidity, greater than about 70% relative humidity, greater than about 80% relative humidity, and/or greater than about 90% relative humidity. Alternatively or additionally, the one or more predetermined humidity value may be less than about 30% relative humidity, less than about 20% relative humidity, and/or less than about 10% relative humidity.

Upon detection of exposure of the sensor to certain levels of temperature and/or humidity, a corresponding calibration code may be changed to account for possible effects of this exposure on sensor sensitivity or other sensor characteristics. This calibration code change may be automatically performed by a control system associated with the sensor package. Alternatively, in other embodiments, an indicator (e.g., a color indicator) that is adapted to undergo a change (e.g., a change in color) upon exposure to certain environments may be used. By way of example and not to be limiting, the sensor package may include an indicator that irreversibly changes color from a blue color to a red color, upon exposure of the package to a temperature greater than about 85° F., and also include instructions to the user to enter a certain calibration code when the indicator has a red color. Although exposure to temperature and humidity are described herein as examples of conditions that may be detected by the sensor package, and used to activate a change in calibration code information, it should be understood that other conditions may also be detected and used to activate a change in calibration code information.

In certain embodiments, the continuous analyte system may comprise a library of stored sensor sensitivity functions or calibration functions associated with one or more calibration codes. Each sensitivity function or calibration function results in calibrating the system for a different set of conditions. Different conditions during sensor use may be associated with temperature, body mass index, and any of a variety of conditions or parameters that may affect sensor sensitivity or provide additional information about sensor sensitivity. The library can also include sensitivity profiles or calibrations for different types of sensors or different sensor lots. For example, a single sensitivity profile library can include sub-libraries of sensitivity profiles for different sensors made from different sensor lots and/or made with different design configurations (e.g., different design configurations customized for patients with different body mass index).

Determining Sensor Properties and Calibrating Sensor Data Using One or More Stimulus Signals Some embodiments apply one or more stimulus signals to a sensor to determine properties of a sensor and/or calibrate sensor data. The term "stimulus signal," as used herein, is a broad term, and is to be given its ordinary and customary meaning to a person of ordinary skill in the art (and are not to be limited to a special or customized meaning), and refers without limitation to a signal (e.g., any time-varying or spatial-varying quantity, such as an electric voltage, current or field strength) applied to a system being used (e.g., an analyte sensor) to cause or elicit a response.

Non-limiting examples of stimulus signals that can be used in the embodiments described herein can be a waveform including one or more of: a step increase in voltage of a first magnitude, a step decrease in voltage of a second magnitude (where the first and second magnitudes can be the same or different), an increase in voltage over time at first rate, a gradual decrease in voltage over time having a second rate (where the first rate and the second rate can be different or the same), one or more sine waves overlayed on the input signal having the same or different frequencies and/or amplitudes and the like. A response to the stimulus signal can then be measured and analyzed (the response is also referred to herein as the "signal response"). The analysis can include one or more of calculating impedance values, capacitance values, and correlating the signal response to one or more predetermined relationships. As used herein, the term "impendence value" can mean a value for expressing an electrical impedance, including but not limited to, a value that only represents a magnitude of impedance or a value that express both magnitude and phase of impendence, should impendence be represented in a polar form, or expresses a real impendence only or both a real and complex impendence, should impedance be represented in a Cartesian form. Based on the calculated impedance values, capacitance values and/or predetermined relationships, various sensor properties can be determined and/or characterized, such as one or more of the sensor properties discussed herein.

The sensor information can then be used to determine if the analyte sensor is functioning properly or not, and/or to calibrate the sensor. For example, the techniques described herein can be used to generate calibration information (e.g., one or more of baseline, sensor sensitivity, and temperature information) that can in turn be used to form or modify a conversion function, or calibration factor, used to convert sensor data (e.g., in units of electrical current) into blood glucose data (e.g., glucose concentration values in units of mg/dL or mmol/L), as described in more detail elsewhere herein. The sensor information can alternatively or additionally be used to first correct uncalibrated sensor data (e.g., raw sensor data) and then apply a conversion function to convert the corrected, uncalibrated data to calibrated sensor data (e.g., glucose concentration values in units of glucose concentration).

For example, one technique that can be used to determine properties of a system being used (e.g., an analyte sensor) is Electrochemical Impedance Spectroscopy (EIS). EIS is an electrochemical technique based on the measurement of electrical impedance of the system being used over a range of different frequencies. Changes in the system being used can reflect changes in the frequency spectrum. As an example, a reduction in impedance may be observed at a particular frequency over a time period if the system being used has a sensitivity change over that period of time. Other techniques can also be used to determine properties of a system being used as discussed further below.

As one illustrative example of how a stimulus signal can be used to determine sensor properties, reference will now be made to a schematic diagram of an equivalent sensor circuit model 900 illustrated in FIG. 9. Sensor circuit model 900 can represent electrical properties of an analyte sensor, such as an embodiment of a continuous glucose sensor. Circuit 900 includes working electrode 904 and reference electrode 902. Operatively connected in serial to reference electrode is Rsolution, representative of a resistance of bulk between the working and reference electrodes. The bulk can be a liquid or other medium in which the sensor is placed, such as a buffer solution in the example of a bench laboratory study, or, in the example of the use as a subcutaneously placed sensor, the bulk can be representative of the resistance of the subcutaneous tissue between the working and reference electrodes. Operatively connected to Rsolution is Cmembrane, representative of a capacitance of the sensor membrane, and Rmembrane, representative of a resistance of the sensor membrane. A parallel network of Cdouble layer and Rpolarization are operatively connected to Rmembrane. The parallel network of Cdouble layer and Rpolarization is representative of the reactions occurring at the surface of a platinum interface of the working electrode. In particular, Cdouble layer is representative of the charge that is built up when a platinum electrode is in the bulk and Rpolarization is the polarization resistance of the electrochemical reactions that occur at the platinum interface.

Figure 9:
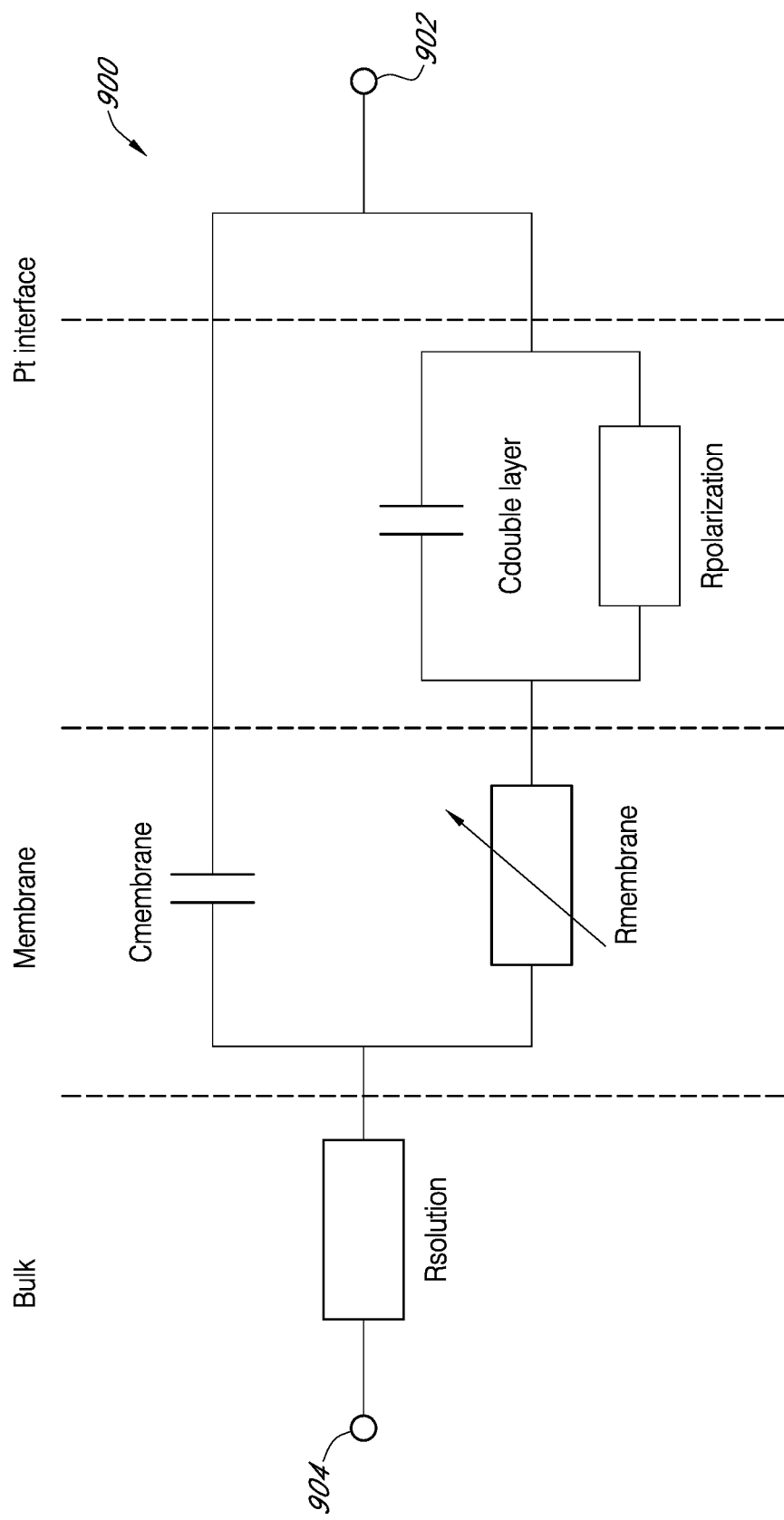
FIG. 9 is a schematic of a model sensor circuit in accordance with one embodiment.
Figure 10:
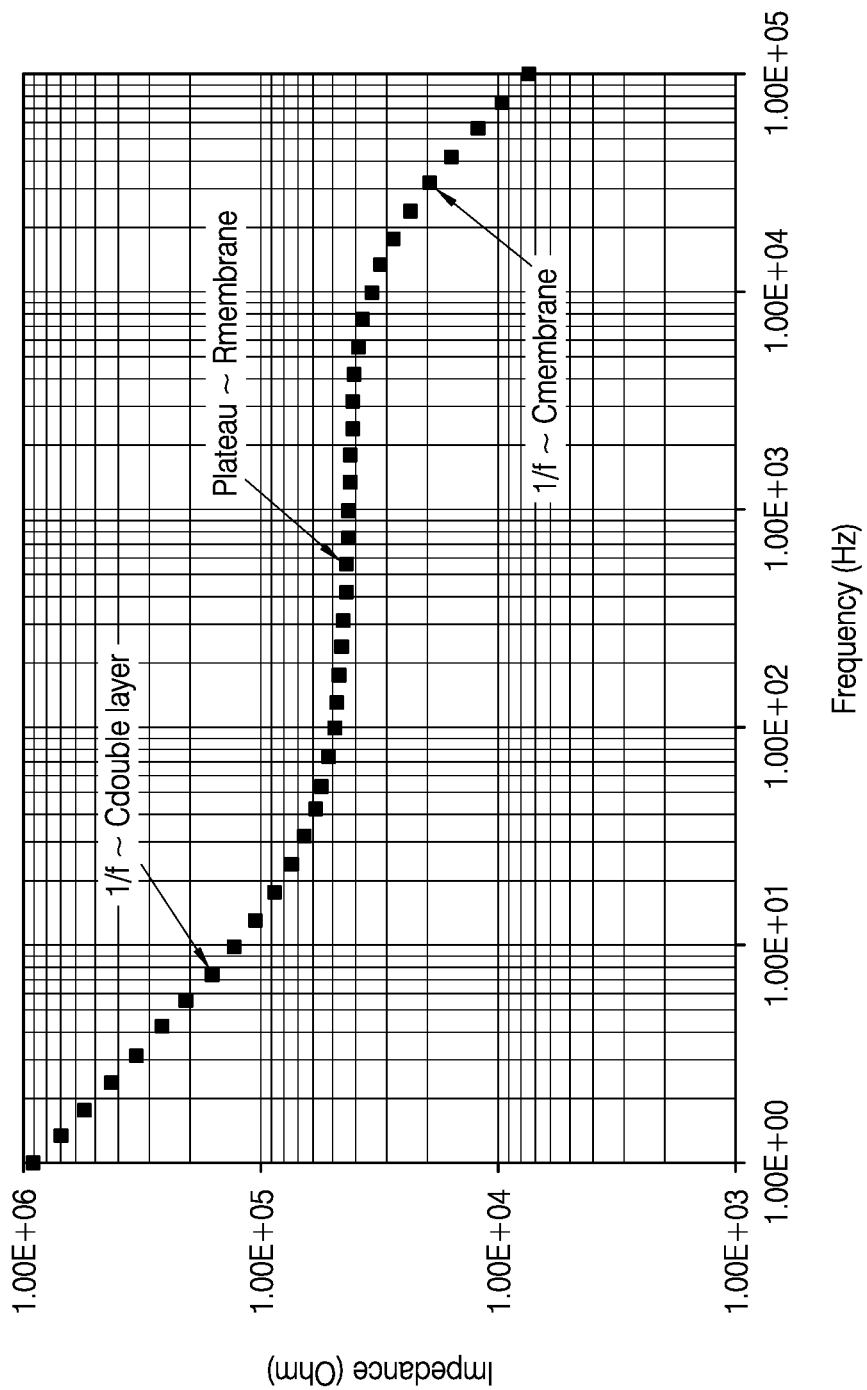
FIG. 10 is a Bode plot of an analyte sensor in accordance with one embodiment.

FIG. 10 is a Bode plot (i.e. $|Z_{real}|$ vs. log w, wherein $Z_{real}$ is real impedance, $w=2\pi f$ and f is frequency) of an analyte sensor in accordance with one embodiment. The analyte sensor can have properties of sensor circuit model 900 of FIG. 9. Referring back to the Bode plot of FIG. 10, the x-axis is the frequency of a stimulus signal applied to the analyte sensor and the y-axis is the impedance derived from a response signal of the analyte sensor. Although not wishing to be bound by theory, it is believed that different frequencies can be used to measure or determine different material properties of the sensor. For example, in the plot of FIG. 10, the impedance value derived from the measured response to an input signal having a frequency of about 7 Hz can be indicative of Cdouble layer, a frequency of about 1 kHz can be indicative of Rmembrane, and a frequency in the range of about 10-20 kHz can indicative of Cmembrane.

Based on this information, one can determine a state of particular properties of the sensor by applying a stimulus signal of a particular frequency or comprising a plurality of frequencies to the sensor and determining a sensor impedance based on the signal response. For instance, a capacitance of a sensor having the characteristics of the Bode plot of FIG. 10 can be determined using a stimulus signal having a frequency in the range of about 1 Hz to 100 Hz, for example 10 Hz or greater than 10 kHz. In addition, a resistance of a sensor can be determined using a stimulus signal having a frequency in the range of about 100 Hz to 10 kHz, for example 1 kHz.

Figure 11:
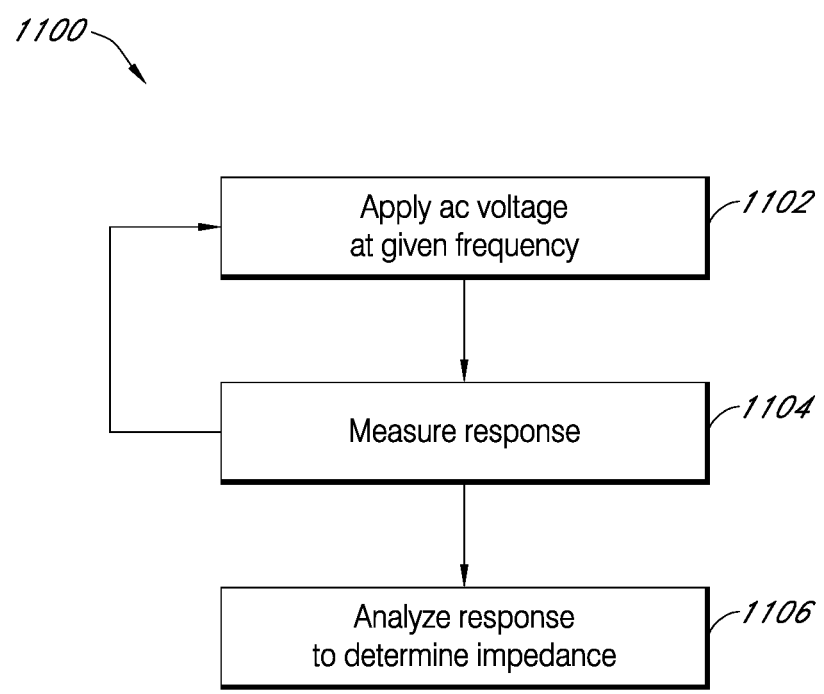
FIG. 11 is a flowchart describing a process for determining an impedance of a sensor in accordance with one embodiment.

FIG. 11 is a flowchart illustrating a process 1100 for determining an impedance of a sensor in accordance with one embodiment. At step 1102, a stimulus signal in the form of an active current (ac) voltage at a given frequency is applied to a working electrode of the sensor being studied. The ac voltage can be overlayed on a bias potential and can be relatively small as compared to the bias potential, such as a voltage that is in the range of about 1% to 10% of the bias voltage. In one embodiment, the ac voltage is a sine wave having an amplitude in the range of 10-50 mV and a frequency in the range of between about 100-1 kHz. The sine wave can be overlayed on a 600 mV bias voltage. The response signal (e.g., in units of current) can then be measured in step 1104 and analyzed in step 1106 to determine an impedance at the given frequency. Should the impedance of the sensor at a range of frequencies be of interest, process 1100 can be repeated by applying an ac voltage at each frequency of interest and analyzing a corresponding output response.

Figure 12:
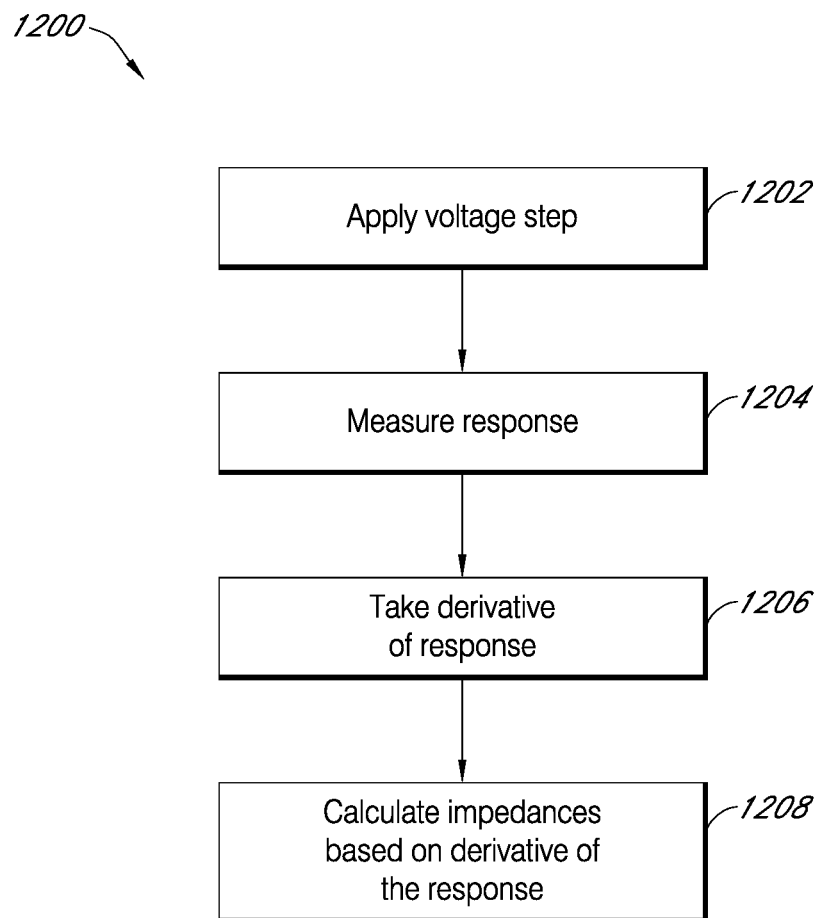
FIG. 12 is a flowchart describing a process for determining an impedance of a sensor based on a derivative response in accordance with one embodiment.

Reference will now be made to FIG. 12, which describes a process for determining an impedance or plurality of impedances of a sensor being studied by applying one or more stimulus signals and converting the response signal or signals to a frequency domain in accordance with one embodiment. The data can be converted to the frequency domain using a Fourier transform technique, such as a fast Fourier transform (FFT), discrete time Fourier transform (DTFT) or the like. At step 1202, a stimulus signal in the form of a voltage step can be applied to a bias voltage of the sensor. The voltage step can be in the range of 10-50 mV, for example 10 mV, and the bias voltage can be 600 mV. The signal response can then be measured and recorded (e.g., an output current) at step 1204, and a derivative of the response can be taken at step 1206. At step 1208, a Fourier transform of the derivative of the response can then be calculated to yield ac currents in the frequency domain. One or more impedances of the sensor over a wide spectrum of frequencies can then be calculated based on the ac currents at step 1210.

Figure 13:
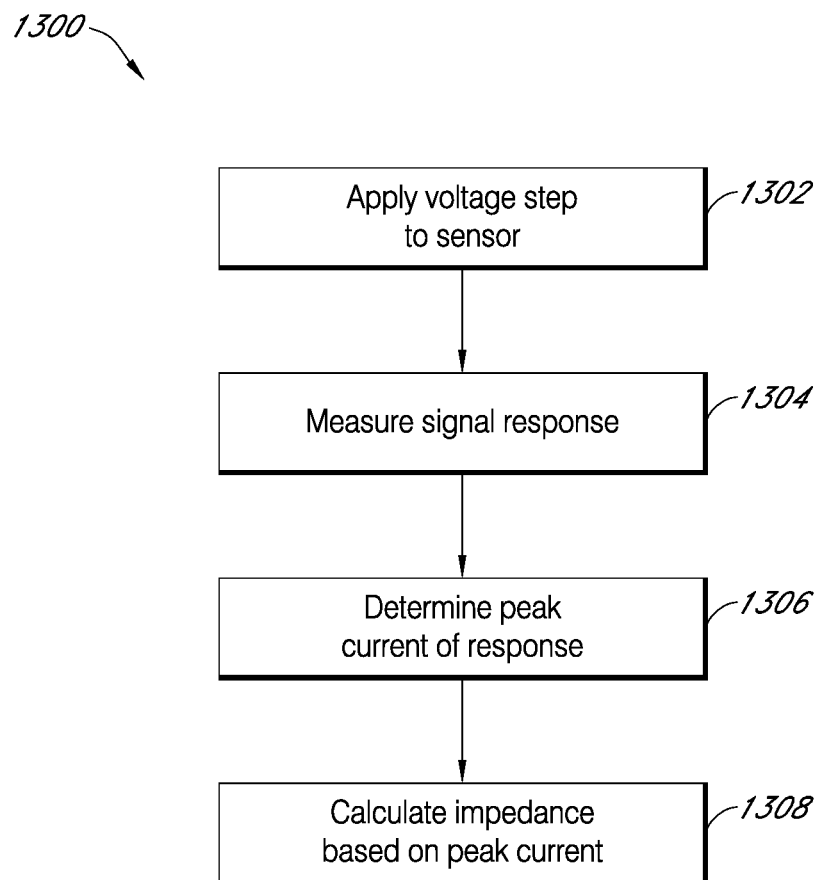
FIG. 13 is a flowchart describing a process for determining an impedance of a sensor based on a peak current response in accordance with one embodiment.

FIG. 13 is a flowchart of process 1300 for determining an impedance of a sensor being studied, such as the impedance of the sensor's membrane, in accordance with one embodiment. At step 1302, a stimulus signal in the form of a voltage step above a bias voltage is applied to the sensor. The signal response is measured at step 1304, and, at step 1306, a peak current of the response is determined. Next, at step 1308, one or more impedance characteristics (e.g., resistance) of the sensor membrane (e.g., Rmembrane) is calculated based on the peak current. The one or more impedance characteristics can then be correlated to a property of the sensor.

In an alternative embodiment, instead of calculating a sensor impedance based on the peak current, the peak current can be correlated to one or more predetermined sensor relationships to determine a property of the sensor, such as the sensor's sensitivity. That is, in the alternative embodiment, the step of calculating the one or more impendence characteristics is omitted.

The relationship between a signal response resulting from a stimulus signal in the form of a voltage step and a sensor membrane resistance of embodiments of analyte sensors will now be discussed further with reference to FIGS. 14A, 14B and FIG. 9.

Figure 14A:
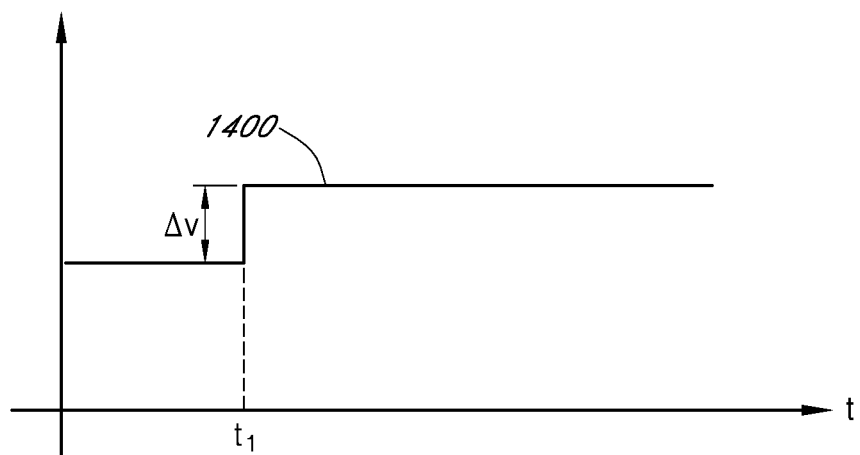
FIG. 14A illustrates a step voltage applied to a sensor and FIG. 14B illustrates a response to the step voltage in accordance with one embodiment.

FIG. 14A is a graph of an input voltage 1400 applied to an analyte sensor over time in accordance with one embodiment. The input voltage 1400 applied to the analyte sensor initially corresponds to the bias voltage, which in one embodiment is about 600 mV. A stimulus signal in the form of a voltage step is then applied to the input voltage at time t1. The magnitude of the voltage step, $\Delta v$, can be in the range of 10-50 mV, for example 10 mV.

Figure 14B:
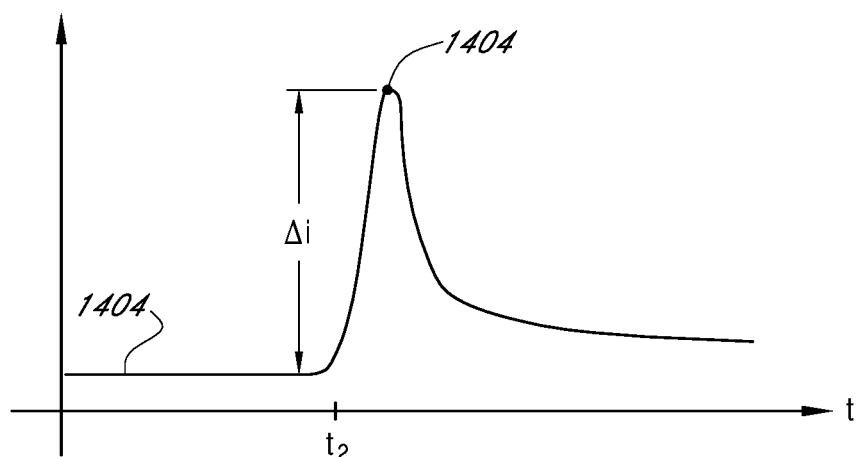

FIG. 14B is a graph of a current response 1402 of the analyte sensor to the input voltage 1400 of FIG. 14A. As illustrated in FIG. 14B, the current response 1402 can include a sharp spike in current starting at time t2, which corresponds to the time in which the voltage step begins to impact the response. The current response 1402 includes a peak current at point 1404 and then the current response 1402 gradually decreases and levels off to a slightly higher level due to the increase in input voltage 1400 as compared to before the voltage step.

In one embodiment, a change in current, $\Delta i$, measured as the difference between the magnitude of the current response 1402 prior to the voltage step and the peak current 1404 resulting from the voltage step, can then be used to estimate the sensor membrane resistance, such as Rmembrane in FIG. 9. In one embodiment, an estimated sensor membrane resistance can be calculated in accordance with Ohms Law, where $$R\text{membrane} = \Delta v / \Delta i$$

As discussed above, $\Delta v$ is the step voltage increase and $\Delta i$ is the change in current response due to the step voltage increase.

Although not wishing to be bound by theory, it is believed that certain embodiments of sensors provide a direct relationship between a change in current in response to a voltage step to the sensor's membrane impendence characteristics (e.g., resistance).

As a non-limiting example of such a relationship, the following description refers back to sensor circuit model 900 of FIG. 9. In some embodiments, the capacitance, Cmembrane, is much smaller than the capacitance, Cdouble layer. For example, Cmembrane can have a value that is about 1/1000 smaller than Cdouble layer. The bulk resistance, Rsolution, of sensor circuit 900 is typically much smaller than the resistance Rmembrane, and the resistance, Rpolarization, can be quite large, such as around 3 MOhms. Due to such sensor properties, a voltage step, $\Delta v$, applied to circuit 900 can cause the current to flow substantially through circuit 900 along a path from lead 902, through Rsolution, Rmembrane, Cdouble layer and finally to lead 904. Specifically, because capacitive resistance is inversely proportional to the capacitance and the frequency, the capacitive resistance of Cmembrane is initially very large due to the voltage step, as the voltage step is, theoretically, an extremely high frequency. Substantially all of the current flows through Rmembrane, rather than through Cmembrane because of the high capacitive resistance of Cmembrane. Further, the current substantially flows through Cdouble layer instead of Rpolarization because the capacitive resistance of Cdouble is initially small due to the voltage step (high capacitive value of Cdouble layer results in low capacitive resistance at high frequencies, e.g., at the time of a voltage step) and the relatively large resistance of Rpolarization. Consequently, the initial total resistance through which substantially all of the current flows through circuit 900 when the step voltage is applied to circuit 900 can be summed up as the series resistance of Rsolution plus Rmembrane. However, because Rsolution is much smaller than Rmembrane in this example, the total resistance can be estimated as the membrane resistance, Rmembrane.

Thus, because the membrane resistance, Rmembrane, is essentially the resistance of the circuit 900 at the time of the voltage step, it has been found that the value of Rmembrane can be estimated using Ohms Law using the known value of the step increase, $\Delta v$, and the measured change in current response, $\Delta i$, due to the voltage step.

a. Sensitivity

As discussed herein, a sensor's sensitivity to analyte concentration during a sensor session can often change as a function of time. This change in sensitivity can manifest itself as an increase in current for a particular level of sensitivity. In some embodiments, the sensitivity increases during the first 24-48 hours with a relative change in tens of percents. In order to provide an accurate analyte concentration reading to a user, system calibrations using reference meters (e.g., strip-based blood glucose measurements) may be needed. Typically, the rate of calibrations can be 1, 2 or more calibrations a day.

As discussed further below, a relationship between sensitivity and impedance has been observed in embodiments of analyte sensors. Although not wishing to be bound by theory, embodiments of analyte sensors are believed to have a relationship between an impedance of a sensor's membrane and the diffusivity of the membrane. For example, a change in impedance of an analyte sensor can indicate a proportional change in diffusivity of the analyte sensor's membrane. Further, an increase in diffusivity can yield an increased transport of the analyte being measured (e.g., glucose) through the membrane, resulting in an increased sensor output current. That is, a change in diffusivity can result in a proportional change in sensor sensitivity. It is noted that other factors may also contribute to changes in sensitivity apart from just changes in diffusivity of the sensor membrane, depending upon the characteristics of sensor and the environment in which the sensor is used.

A relationship between sensitivity and impedance can be used to estimate a sensor sensitivity value and/or correct for sensitivity changes of the sensor over time, resulting in increased accuracy, a reduction in required calibrations or both. In addition to detection of sensitivity, some embodiments can detect other characteristics of an analyte sensor system based on measurements of electrical impedance over one or more frequencies. These characteristics include, but are not limited to, temperature, moisture ingress into sensor electronics components and sensor membrane damage.

In some exemplary embodiments, a relationship between a sensor's impedance and the sensor's sensitivity can be used to calculate and compensate for sensitivity changes of an analyte sensor. For example, a change in impedance of an analyte sensor can correspond to a proportional change in sensitivity of the sensor. In addition, an absolute value of an impedance of an analyte sensor can correspond to an absolute value of the analyte sensor's sensitivity and the corresponding sensitivity value can be determined based on a predetermined relationship determined from prior studies of similar sensors. Sensor data can then be compensated for changes in sensitivity based on an impedance-to-sensitivity relationship.

Figure 15:
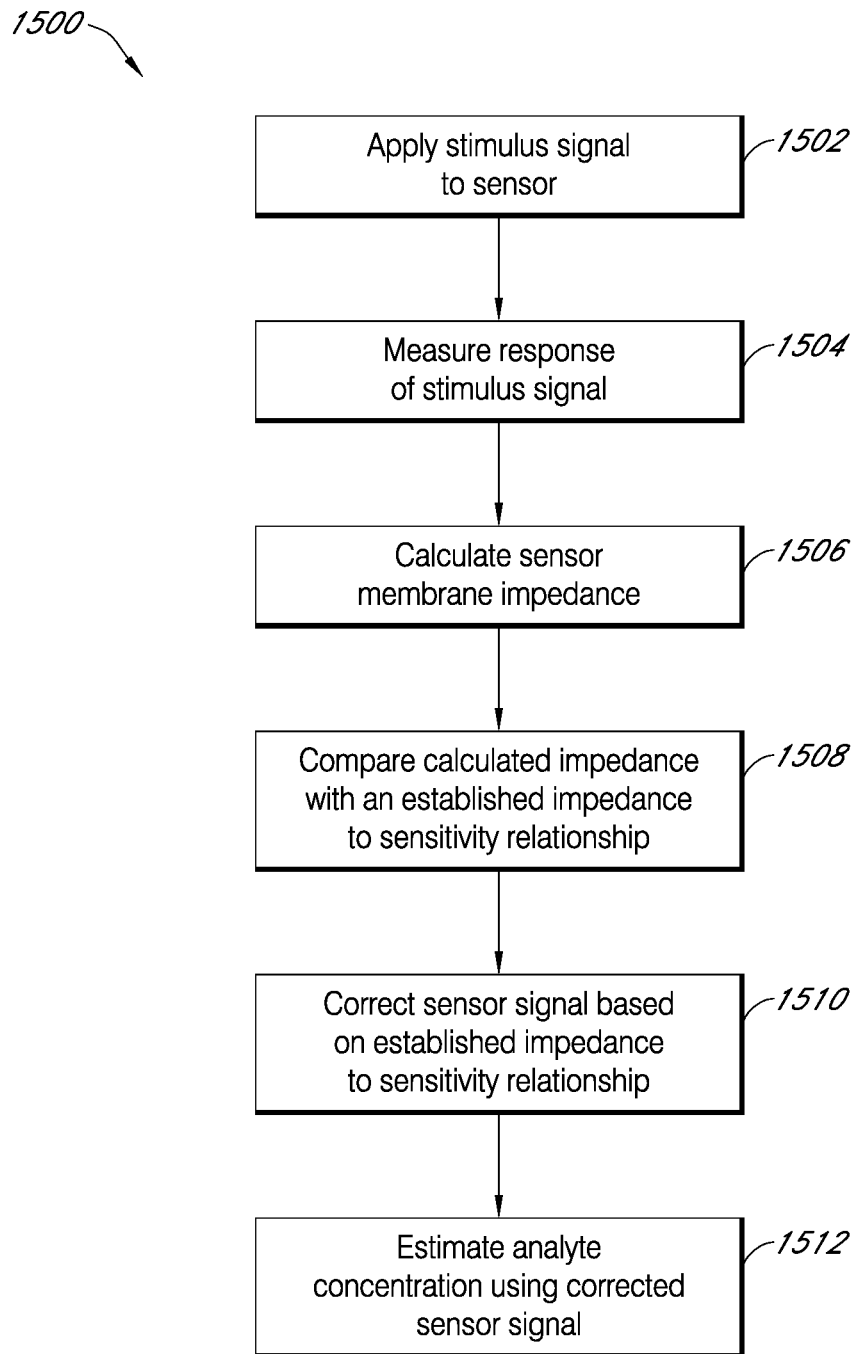
FIG. 15 is a flowchart describing a process for estimating analyte concentration values using a corrected signal based on an impedance measurement in accordance with one embodiment.

FIG. 15 is a flowchart of an exemplary process 1500 for compensating sensor data for changes in sensitivity in accordance with one embodiment. At step 1502, a stimulus signal can be applied to the sensor that can be used to determine an impedance of the sensor's membrane, such as a signal having a given frequency, as discussed with respect to FIG. 11, or a voltage step, as discussed with respect to FIGS. 12-14. A response to the applied signal is then measured at step 1504 and an impedance of the sensor's membrane is determined based on the response at step 1506. Next, at step 1508, the determined impedance is compared to an established impedance-to-sensor sensitivity relationship. The established relationship can be determined from prior studies of analyte sensors that exhibit similar sensitivity-to-impedance relationships as the analyte sensor currently being used; for example, sensors that were made in substantially the same way under substantially the same conditions as the sensor currently being used. At step 1510, a sensor signal (e.g., in units of electrical current or counts) of the sensor currently being used is corrected using the impedance to sensitivity relationship. An estimated analyte concentration value or values is then calculated based on the corrected sensor signal at step 1512 using, for example, a conversion function. The estimated analyte concentration values can then be used for further processing and/or outputting, such as triggering alerts, displaying information representative of the estimated values on a user device and/or outputting the information to an external device.

It should be understood that process 1500 is but one example of using an impedance of a sensor to compensate for changes in sensor sensitivity, and that various modifications can be made to process 1500 that fall within the scope of the embodiments For example, an established impedance-to-sensitivity relationship can be used to determine a sensitivity value of the sensor being used, and the sensitivity value can then be used to modify or form a conversion function used to convert a sensor signal of the sensor being used into one or more estimated glucose concentration values. In addition, instead of calculating an impedance based on the stimulus signal response, one or more properties of the stimulus signal response (e.g., peak current value, counts, etc.) can be directly correlated to a sensitivity based on a predetermined relationship between the stimulus signal property and the sensitivity.

Some embodiments use one or more impedance values of the sensor to form, modify or select a sensitivity profile of an analyte sensor. As discussed above, a sensor can have a sensitivity profile that indicates the sensor's change in sensitivity over time. Although sensors made in substantially the same way under substantially the same conditions can exhibit similar sensitivity profiles, the profiles can still vary. For example, the environment in which a particular sensor is used can cause the sensor's sensitivity profile to differ from other, similar sensors. Accordingly, some embodiments can, for example, select a sensitivity profile out of a plurality of predetermined sensitivity profiles based on a correlation of the calculated one or more impedance values to the selected sensitivity profile. Further, some embodiments modify a sensor sensitivity profile already associated with the analyte sensor being used to more closely predict the sensor's sensitivity profile, where the modification is based on the one or more impedance values.

Figure 16:
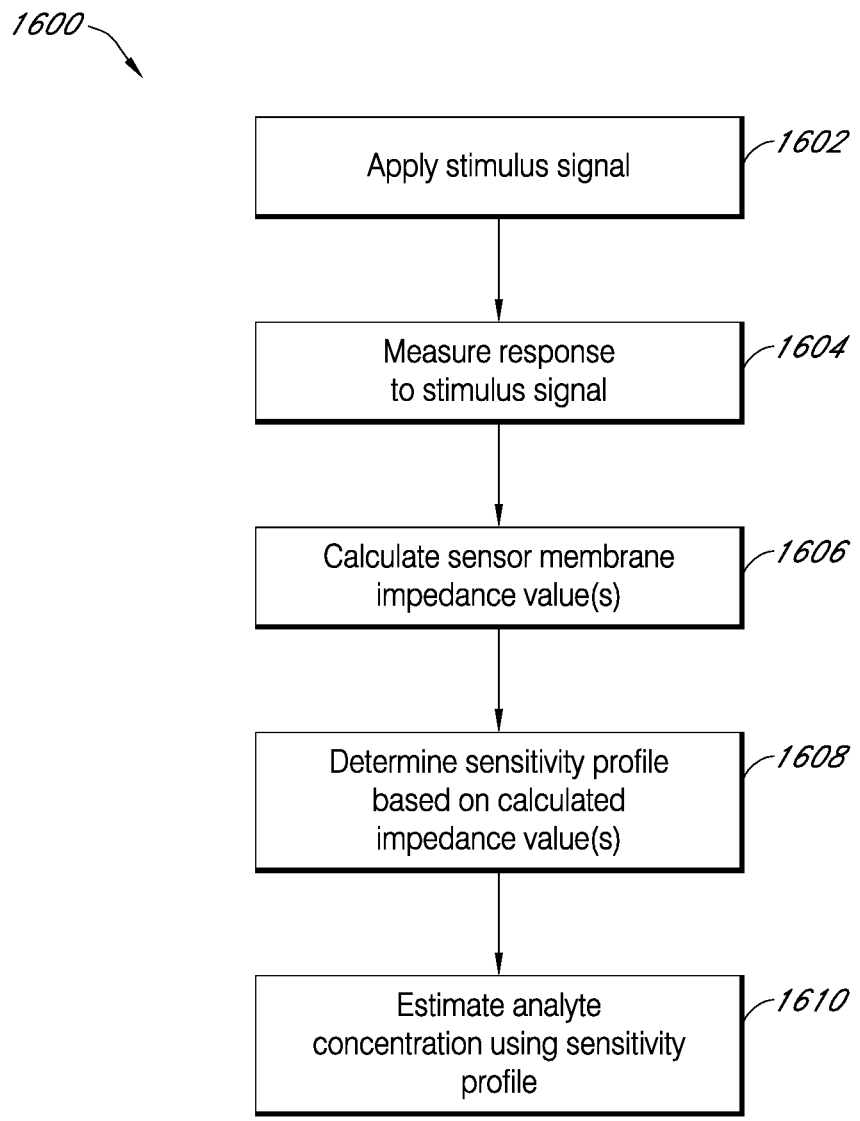
FIG. 16 is a flowchart describing a process for estimating analyte concentration values using a predetermined sensitivity profile selected based on an impedance measurement in accordance with one embodiment.

FIG. 16 is a flowchart of an exemplary process 1600 for determining a predicted sensitivity profile using one or more sensor membrane impedance measurements in accordance with one embodiment. At step 1602, a stimulus signal is applied to an analyte sensor being used and a response is measured at step 1604. Next, one or more sensor membrane impedance values are calculated based on the response at step 1606. Various techniques for calculating sensor membrane impedance values based on the response that can be used in process 1600 are described elsewhere herein, such as one or more of the techniques discussed with reference to FIGS. 11-14. A sensitivity profile is then determined based on the one or more calculated impedance values in step 1608. Process 1600 then calculates (which can include retrospectively correcting and/or prospectively calculating) estimated analyte concentration values using the determined sensitivity profile. The estimated analyte concentration values can then be used for further processing and outputting, such as displaying information representative of the estimated values on a user device and/or outputting the information to an external computing device.

Further to step 1608, various techniques can be used to determine the sensitivity profile. One exemplary technique can compare the one or more calculated impedance values to a plurality of different predicted sensitivity profiles and select a predicted sensitivity profile that best fits the one or more calculated impedance values. The plurality of different predicted sensitivity profiles can be predetermined and stored in computer memory of sensor electronics, for example. Another technique that can be used includes using an estimative algorithm to predict or determine a sensitivity profile based on the one or more calculated impedance values. A further technique includes determining a sensitivity profile by modifying a sensitivity profile associated with the sensor being used (e.g., a sensor profile previously used to generate estimated glucose values using the sensor). Modifying the sensitivity profile can include using an estimative algorithm to modify the sensitivity profile to more closely track the sensitivity profile of the sensor being used based on the one or more calculated impedance values.

Some embodiments compare one or more impedance values of an analyte sensor being used to a predetermined or predicted sensitivity profile associated with the sensor to determine if the sensor is functioning properly. As discussed above, a sensor can be predicted to have a particular sensitivity profile based on, for example, a study of sensitivity changes over time of sensors made in substantially the same way and used under substantially the same conditions. However, it can be determined that a sensor is functioning improperly—due to, for example, improper sensor insertion, damage to the sensor during shipping, manufacturing defects and the like—if the sensor is found not to be sufficiently tracking its predicted sensitivity profile based on sensitivities derived from impedance measurements of the sensor. Put another way, it can be determined that a sensor is not functioning properly if one or more impedance values of a sensor's membrane do not sufficiently correspond to a predicted sensitivity profile (e.g., because the impedance of a sensor membrane can indicate a sensitivity of the sensor) of the sensor.

Figure 17:
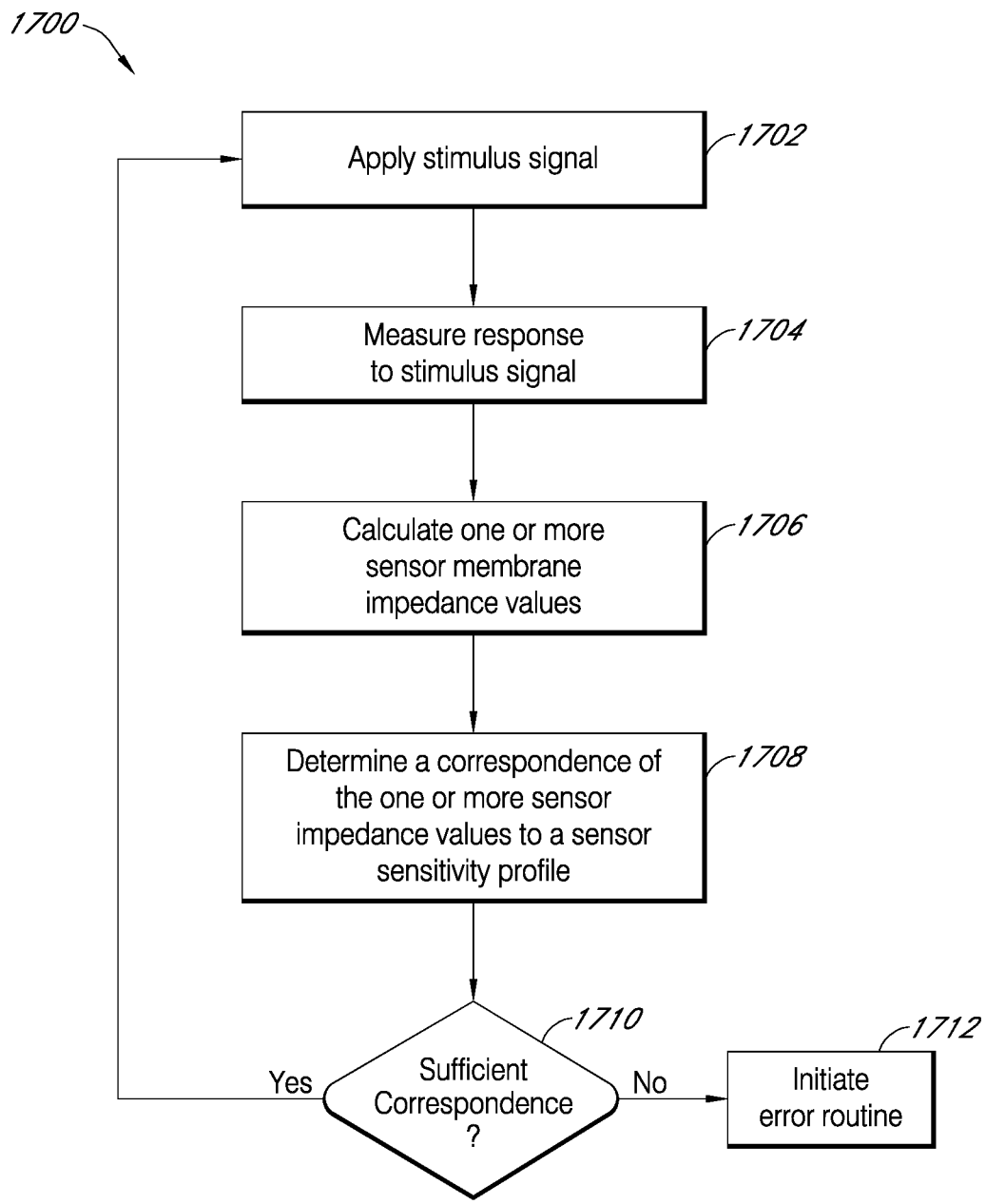
FIG. 17 is a flowchart describing a process for determining an error based whether a sensitivity determined using an impedance measurement sufficiently corresponds to a predetermined sensitivity in accordance with one embodiment.

FIG. 17 is a flowchart of an exemplary process 1700 for determining whether an analyte sensor being used is functioning properly based on a predicted sensitivity profile and one or more impedance measurements. At step 1702, a stimulus signal is applied to an analyte sensor being used and a response is measured at step 1704. Next, one or more sensor membrane impedance values are calculated based on the signal response at step 1706. Various stimulus signals and techniques for calculating sensor membrane impedance values based on the signal response that can be used in process 1700 are described elsewhere herein, such as with any one of the techniques discussed with reference to FIGS. 11-14. Process 1700 then determines a correspondence of the one or more calculated impedance values to a sensitivity profile in step 1708. Next, in decision step 1710, process 1700 queries whether the one or more calculated impedance values sufficiently correspond to the predicted sensitivity profile. If it is determined that the one or more calculated impedance values sufficiently correspond to the predicted sensitivity profile, then process 1700 confirms proper operation of the analyte sensor being used. If confirmed to be proper in step 1710, process 1700 may then be repeated after a predetermined time delay ranging from about 1 minute to 1 day, for example about 10 minutes, 1 hour, 12 hours, or 1 day. However, process 1700 initiates an error routine 1712 if it is determined that the one or more calculated impedance values do not sufficiently correspond to the predicted sensitivity profile. Error routine 1712 can include one or more of triggering and audible alarm, displaying an error message on a user display, discontinuing display of sensor data on a user display, sending a message to a remote communication device over a communication network, such as a mobile phone over a cellular network or remote computer over the internet, and the like. The error routine can also include modifying the predicted sensitivity profile—based on the one or more impedance measurements, for example—or selecting a new predicted sensitivity profile based on the one or more impedance measurements. The modified predicted sensitivity profile or new predicted sensitivity profile can be a sensitivity profile that more closely corresponds to changes in sensitivity of the sensor being used based on the one or more impedance measurements as compared to the unmodified or previously used predicted sensitivity profile.

Further to step 1708 of process 1700, various statistical analysis techniques can be used to determine a correspondence of the one or more impedance values to the predicted sensitivity profile. As one example, correspondence can be determined based on whether a sensitivity value derived from the calculated impedance value (e.g., derived from a predetermined relationship of impedance and sensitivity) differs by no less than a predetermined threshold amount from a predicted sensitivity value as determined from the predicted sensitivity profile. The predetermined threshold amount can be in terms of an absolute value or a percentage. As another example, correspondence can be determined based on a data association function. The term "data association function," as used herein, is a broad term and is used in its ordinary sense, including, without limitation, a statistical analysis of data and particularly its correlation to, or deviation from, from a particular curve. A data association function can be used to show data association. For example, sensor sensitivity data derived from impedance measurements described herein may be analyzed mathematically to determine its correlation to, or deviation from, a curve (e.g., line or set of lines) that defines a sensor sensitivity profile; this correlation or deviation is the data association. Examples of a data association function that can be used includes, but is not limited to, linear regression, non-linear mapping/regression, rank (e.g., non-parametric) correlation, least mean square fit, mean absolute deviation (MAD), and mean absolute relative difference. In one such example, the correlation coefficient of linear regression is indicative of the amount of data association of sensitivity data derived from impedance measurements from a sensitivity profile, and thus the quality of the data and/or sensitivity profile. Of course, other statistical analysis methods that determine a correlation of one or more points to a curve can be used in process 1700 in addition to those described herein.

As discussed above, processes 1600 and 1700 can use one or more impedance values. When more than one impedance value is used, each impedance value can be time-spaced from the other impedance value(s). In other words, one impedance value can be taken at a first point in time t1

(indicative of a sensor impedance at time t1), a second impedance value can be taken at a second, later point in time t2 (indicative of a sensor impedance at time t2), and third impedance value taken at a third, even later point in time t3 (indicative of a sensor impedance at time t3), and so on. Further, the time between t1 and t2 can be a first amount of time and the time between t2 and t3 can be a second amount of time that is either the same or different than the first amount of time. The time-spaced impedance values can then be used separately or combined using a statistical algorithm (e.g., calculating an average or median value of the time-spaced values). The separate values or combined value can then be used to determine a sensitivity value and/or sensitivity profile in step 1608 of process 1600 or determine a correspondence with a sensitivity profile in step 1708 of process 1700, for example. Additionally or alternatively, more than one of the impedance values can be taken at substantially the same time, but each derived using a different measurement technique, such as using two of the measurement techniques described herein. For example, a first impedance can be calculated using a step voltage technique as described in the process of FIG. 13, and a second impedance can be calculated using a sine wave overlay technique as described in the process of FIG. 11. The impedance values derived from different measurement techniques can then be applied to a statistical algorithm (e.g., calculating an average or median value) to determine a processed impedance value. The processed impedance value can then be used to determine a sensitivity value and/or sensitivity profile in step 1608 of process 1600 or determine a correspondence with a sensitivity profile in step 1708 of process 1700, for example.

b. Temperature

Some embodiments can use signal processing techniques to determine a temperature of the sensor. For example, a stimulus signal can be applied to a sensor and a signal response measured and, based on the signal response, a temperature of the sensor can be derived.

An impedance of a sensor membrane, as determined using one of the techniques described with reference to FIGS. 11-14, for example, can be used to estimate a temperature of the sensor in accordance with one embodiment. Although not wishing to be bound by theory, it is believed that sensitivity of a sensor is affected by temperature, where a higher temperature can result in a higher sensitivity and a lower temperature can result in a lower sensitivity. Similarly, because an impedance of a sensor membrane can have a direct relationship to the sensor's sensitivity, it is believed that a higher temperature can result in lower impedance and a lower temperature can result in higher impedance. That is, sensitivity and impedance can have a direct relationship to the sensor's temperature. Accordingly, using a known relationship between impedance and temperature—based on previously conducted studies of substantially similar sensors, for example—one can estimate a sensor's temperature based on a sensor impedance measurement.

Figure 18:
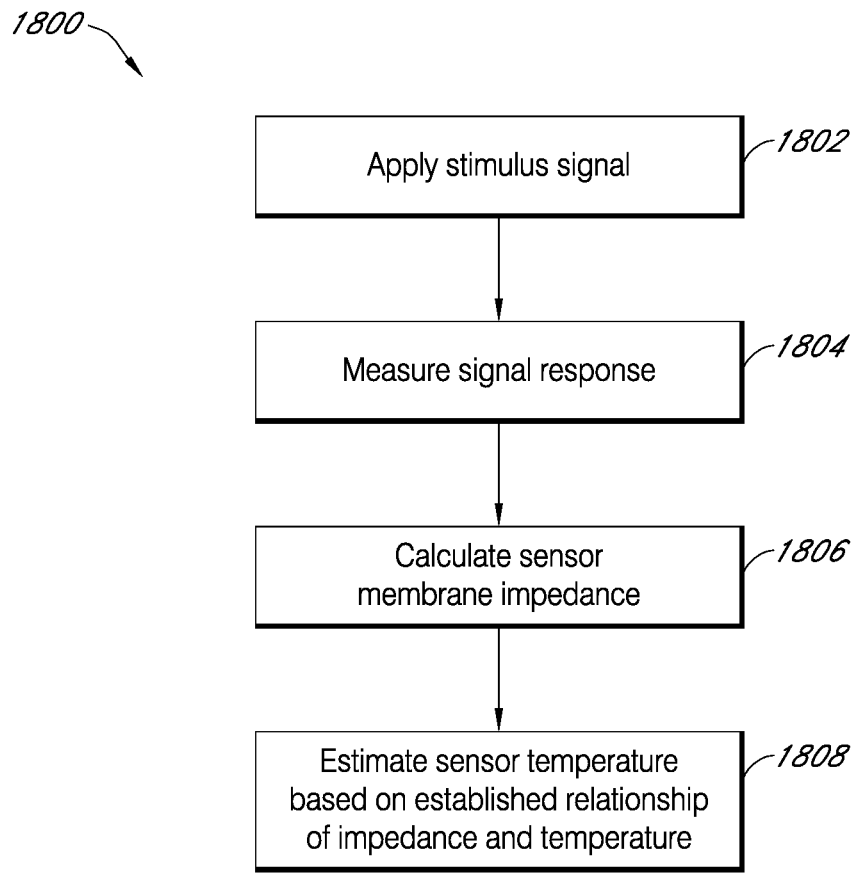
FIG. 18 is a flowchart describing a process for determining a temperature associated with a sensor by correlating an impedance measurement to a predetermined temperature-to-impedance relationship in accordance with one embodiment.

FIG. 18 is a flowchart of an exemplary process 1800 for determining a sensor temperature in accordance with one embodiment. At step 1802, a stimulus signal is applied to an analyte sensor being used, and a response is measured and recorded at step 1804. Impedance is calculated based on the signal response at step 1806. The impedance can be calculated using, for example, any of the techniques described herein such as those described with reference to FIGS. 11-14. A temperature of the sensor is then estimated based on a predetermined relationship between impedance and temperature at step 1808. The temperature can then be used to estimate analyte concentration values (e.g., glucose concentration) using sensor data or otherwise used for further processing and/or outputting. For example, the temperature can be used to compensate for temperature effects on sensor sensitivity, more accurate analyte concentration values can be estimated based on the sensitivity compensation, and the more accurate analyte concentrations can be outputted to a display or used to trigger an alert using a glucose monitoring system.

A relationship between sensor sensitivity and different temperatures can be mathematically modeled (e.g., by fitting a mathematical curve to data using one of the modeling techniques described herein), and the mathematical model can then be used to compensate for temperature effects on the sensor sensitivity. That is, a sensitivity of a sensor (which is affected by the sensor's temperature) can be determined based on associating a measured impedance of the sensor to the mathematical curve. The predetermined relationship between impedance and temperature can be determined by studying impedances of similar sensors over a range of temperatures. Sensor data can then be converted to estimated analyte concentration values based on the determined sensor sensitivity.

As a non-limiting example, some embodiments of analyte sensors can have an essentially linear relationship of impedance to temperature after a sensor run-in period (e.g., a period of time after sensor implantation in which the sensor stabilizes, which can last one to five hours in some embodiments). The slope of the linear relationship can be established by studying sensors made in substantially the same way as the sensor being used over a range of temperatures. Thus, a sensor temperature can be estimated by measuring an impedance value of the sensor's membrane and applying the impedance value to the established linear relationship. Other embodiments can have a non-linear relationship of impedance to temperature and with these other embodiments the relationship can be characterized using an established non-linear relationship.

Some embodiments can compare a first sensor temperature, where the first temperature is derived from an impedance measurement of an analyte sensor, with a second sensor temperature, where the second sensor temperature is derived independent from the impedance measurement. The second estimated temperature can be measured using a thermistor, for example. In the example of using a thermistor, the thermistor can be configured to measure an in vivo or ex vivo temperature, and can be located on the analyte sensor or separate from the analyte sensor. As non-limiting examples, the thermistor can be integral with the analyte sensor, positioned on the surface of the skin of a host adjacent to an insertion site in which the analyte sensor is implanted, positioned on the skin of the host at a location away from the insertion site or spaced apart from the host entirely, such as on a handheld device carried by the host. Factors contributing to a change in sensor sensitivity or a change in other sensor properties can then be determined or confirmed based, at least in part, on the comparison of the first and second temperatures.

c. Moisture Ingress

In some embodiments, moisture ingress into sensor electronics can be determined based on measuring an impedance of the sensor at a particular frequency or range of frequencies. Should the measured impedance not correspond sufficiently with predetermined impedance value(s), then a sensor system operatively connected to the sensor can initiate a moisture ingress error routine. Correspondence can be determined using one or more threshold, a data association function, and the like. Further, it should be noted that it has been found that impedance phase information can provide beneficial information in determining moisture egress. Accordingly, in some embodiments, the impedance measurement can be broken into separate impendence magnitude and phase components, and one or both impendence components can be compared to predetermined values to determine the correspondence.

Figure 19:
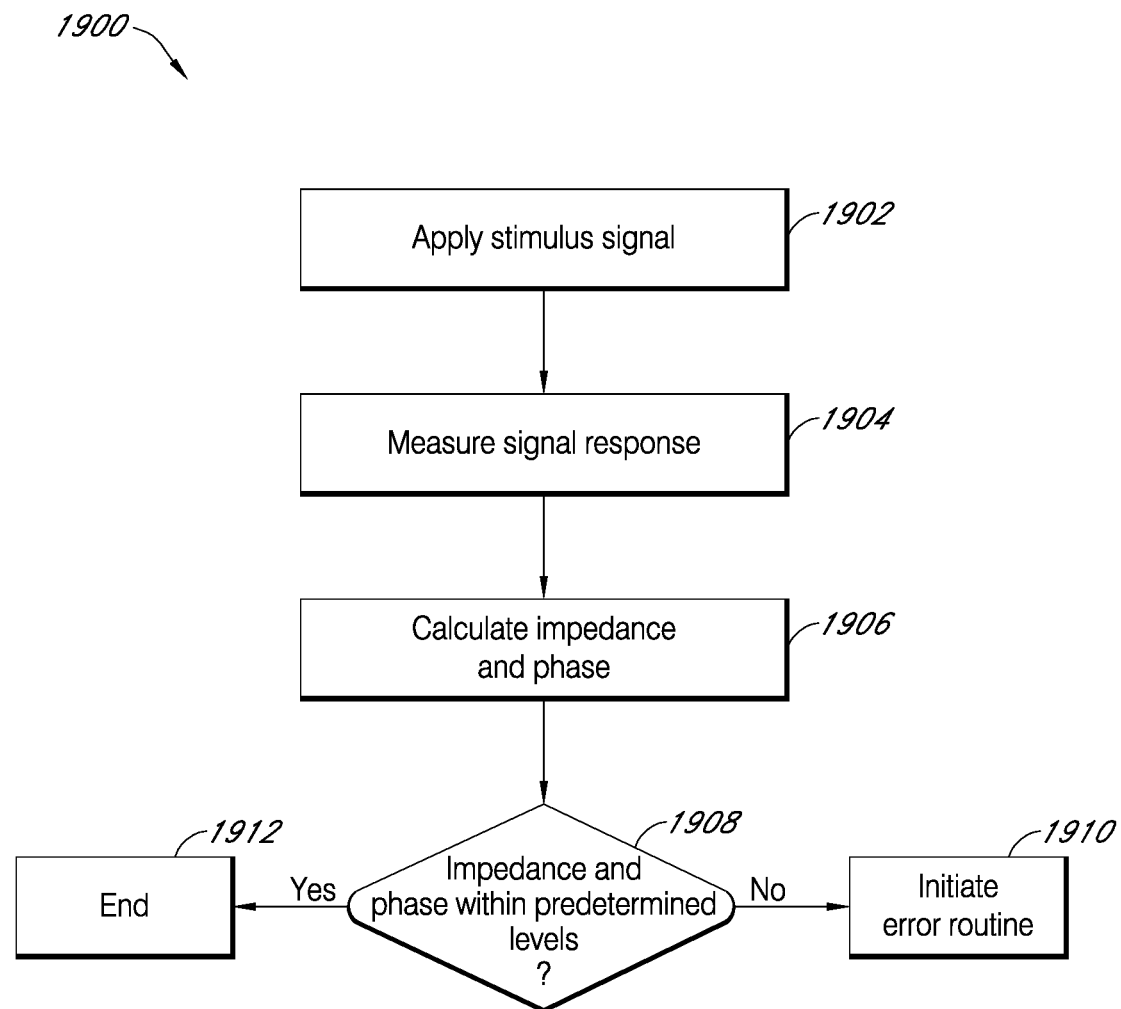
FIG. 19 is a flowchart describing a process for determining moisture egress in sensor electronics associates with an analyte sensor accordance with one embodiment.

FIG. 19 is a flowchart of an exemplary process 1900 for determining moisture ingress. At step 1902, a stimulus signal having a particular frequency or a signal comprising a spectrum of frequencies (e.g., a voltage step) is applied to an analyte sensor being used, and a signal response is measured and recorded at step 1904. Impedance magnitude and phase is calculated based on the signal response at step 1906. Process 1900 then determines whether the impedance magnitude and phase values fall within respective predefined levels at decision step 1908. If the impedance magnitude and phase values exceed one or both of the respective predefined levels, then process 1900 initiates an error routine at step 1910. The error routine can include one or more of triggering an audible alarm and/or visual alarm on a display screen to alert a user that the sensor system may not be functioning properly. The alarm can notify a user that the current sensor system is defective, for example. If, on the other hand, one or both of the impedance and phase values fall within the respective predefined levels, then process 1900 ends.

Although the above description describes calculating separate impedance and phase values, it is understood that the above process 1900 can determine a complex impedance value and determine a correspondence of the determined complex impedance value to one or more predetermined complex impedance value(s), such as by using a data association function or comparing the determined complex impedance to a threshold or range of predetermined complex impendence values. The error routine can then be initiated responsive to the correspondence.

d. Membrane Damage

In some embodiments, membrane damage can be detected based on measuring an impedance at a particular frequency or range of frequencies. Should the measured impedance not correspond sufficiently with predetermined one or more impedance values, then a sensor system operatively connected to the sensor can initiate a membrane damage error routine. Correspondence can be determined using a data association function.

Figure 20:
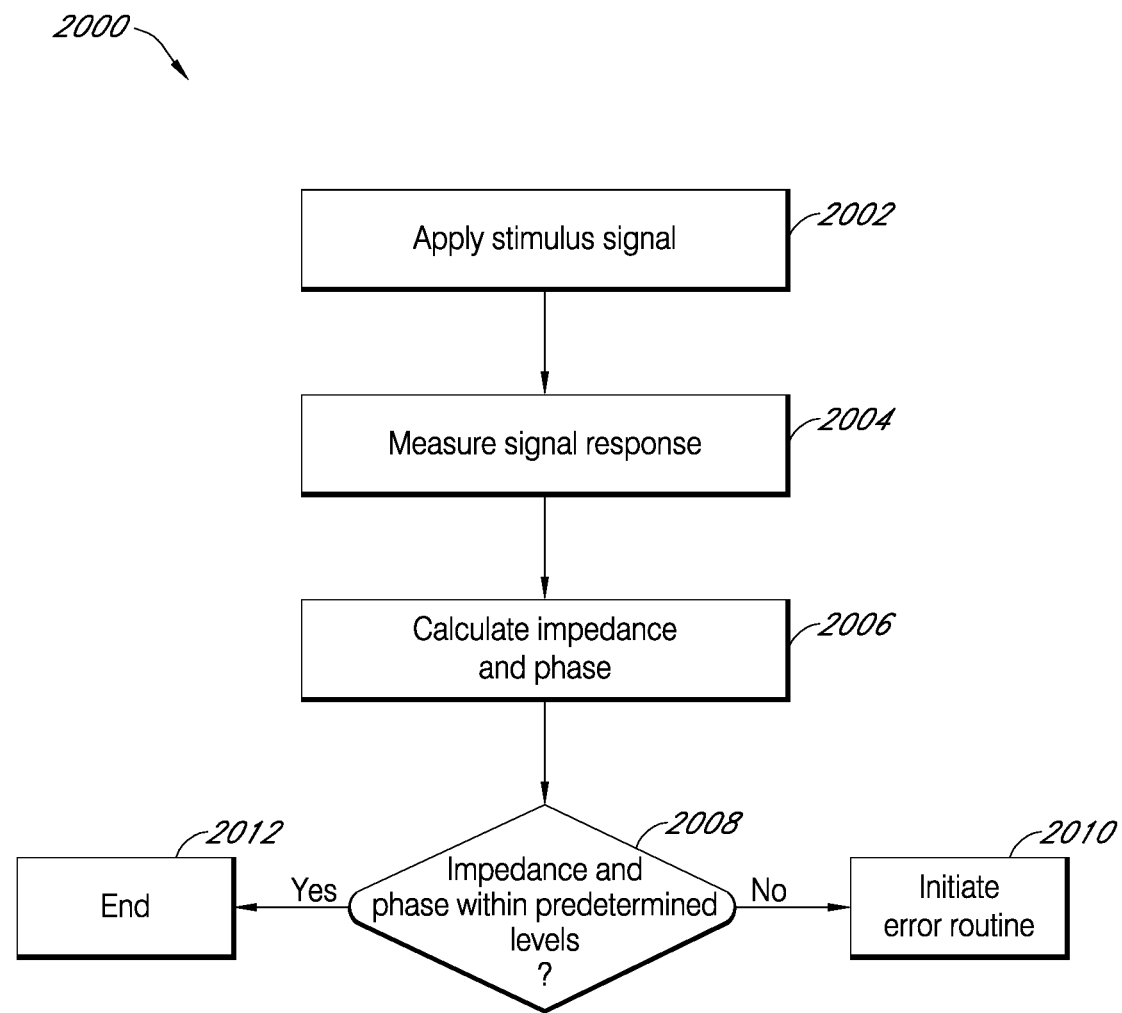
FIG. 20 is a flowchart describing a process for determining membrane damage associated with an analyte sensor in accordance with one embodiment.

FIG. 20 is a flowchart of an exemplary process 2000 for determining membrane damage. At step 2002, a stimulus signal having a particular frequency, multiple signals having different frequencies and/or a signal comprising a spectrum of frequencies is applied to an analyte sensor being used, and the signal response(s) is/are measured and recorded at step 2004. Both impedance magnitude and phase is calculated based on the signal response(s) at step 2006. Process 2000 then determines whether the impedance magnitude and phase value(s) fall within respective predefined levels at decision step 2008. If the impedance magnitude and phase values exceed one or both of the respective predefined levels, then process 2000 initiates an error routine at step 2010. The error routine can include one or more of triggering an audible alarm and/or visual alarm on a display screen to alert a user that the sensor system is not functioning properly. The alarm can notify a user that the currently used sensor is damaged and needs to be replaced, for example. If, on the other hand, one or both of the impedance magnitude and phase values fall within the respective predefined levels, then process 2000 ends.

Although the above description describes using separate impedance magnitude and phase values, it is understood that the above process 2000 can use a complex impedance value and determine a correspondence of the complex impedance value to a predetermined values or levels. The error routine can be initiated responsive to the determined correspondence.

e. Sensor Reuse

In some embodiments, sensor reuse can be detected. Embodiments of glucose sensors described herein may have a defined life in which a sensor can provide reliable sensor data. After the defined life, the sensor may no longer be reliable, providing inaccurate sensor data. To prevent use beyond the predefined life, some embodiments notify a user to change the sensor after it has been determined that the sensor should no longer be used. Various methods can be used to determine whether a sensor should no longer be used, such as a predetermined amount of time transpiring since the sensor was first used (e.g., when first implanted into a user or when first electrically connected to a sensor electronics module) or a determination that the sensor is defective (e.g., due to membrane rupture, unstable sensitivity and the like). Once it is determined that the sensor should no longer be used, the sensor system can notify a user that a new sensor should be used by audibly and/or visually prompting a user to use a new sensor and/or shutting down a display or ceasing to display sensor data on the display, for example. However, a user may try to reuse the same sensor instead of using a new sensor. This can be dangerous to the user because the sensor may provide inaccurate data upon which the user may rely.

Accordingly, some embodiments can be configured determine sensor reuse based at least in part on one or more measurements of the impedance of the sensor. As discussed in more detail elsewhere herein, the impedance that relates to the membrane resistance of a sensor is typically initially high and then gradually decreases as the sensor is run-in. Thus, in one embodiment, sensor re-use can be detected if an impedance measured soon after sensor implantation is greater than what a sensor should typically have when a sensor is initially implanted, as this can indicate that the sensor had already been used.

Figure 21:
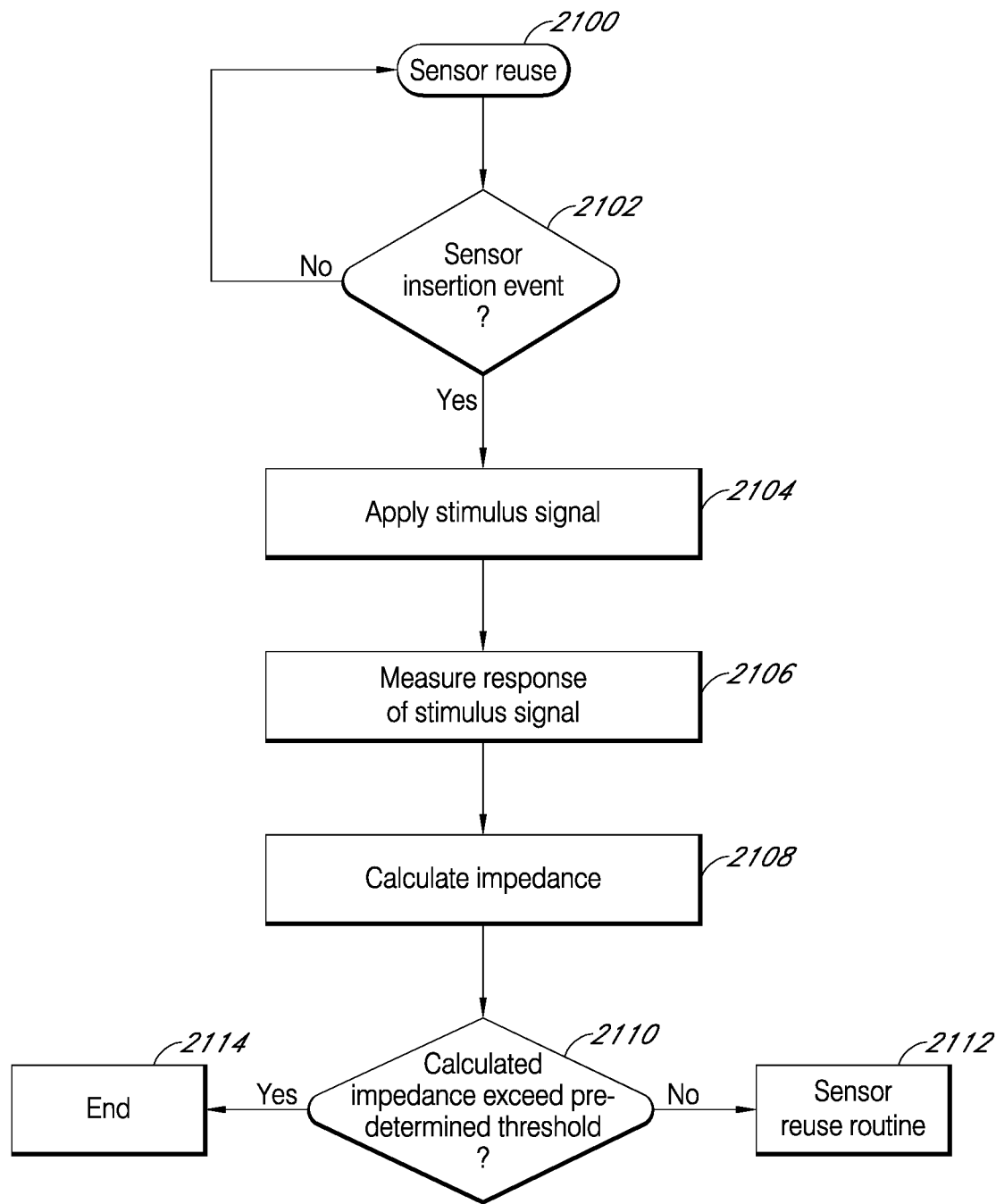
FIG. 21 is a flowchart describing a first process for determining sensor reuse associated in accordance with one embodiment.

FIG. 21 is a flowchart of an exemplary process 2100 for determining sensor reuse in accordance with one embodiment. At step 2102, a sensor insertion event is triggered. An insertion event can be one of any number of possible events that indicate a new sensor has been implanted, such as a user providing input to a sensor system that a new sensor has been implanted, the sensor system detecting electrical connection to a sensor, a predetermined amount of time transpiring since the system prompted a user to use a new sensor, and the like. Next, at step 2104, a stimulus signal is applied to an analyte sensor being used, and a response is measured and recorded at step 2106. Impedance is calculated based on the signal response at step 2108. The stimulus signal and technique for calculating impedance in steps 2106 and 2108 can be any of the signals and techniques described herein such as those described with reference to FIGS. 11-14. Then, at decision step 2110, the calculated impedance is compared to a predetermined threshold. Should it be determined that the impedance exceeds the threshold, then a sensor reuse routine is initiated at step 2112. If it is determined in decision step 2110 that the impedance does not exceed the threshold, then the process 2100 ends at step 2114.

The sensor reuse routine of step 2112 can include triggering an audible and/or visual alarm notifying the user of improper sensor reuse. The alarm can also inform the user why sensor reuse may be undesirable, such as potentially providing inaccurate and unreliable sensor readings. The sensor reuse routine 2112 can alternatively or additionally cause the sensor system to fully or partially shut down and/or cease display of sensor data on a user interface of the sensor system.

In an embodiment, recent impedance measurement information (e.g., one or more recent impedance measurement values) of a previously-used sensor (such as the sensor used immediately prior to the newly implanted sensor) or a predetermined sensor profile can be stored in computer memory and compared to impedance measurement information of a newly implanted sensor (e.g., what is supposed to be a newly used sensor). It can then be determined that the sensor is being reused should the comparison indicate that the impedances of the previously used sensor at a time close to when the use of the prior sensor was discontinued (e.g., removed) and the newly inserted sensor are too similar using, for example, a data association function, as a new sensor should have a significantly different impedance soon after initial implantation than the impedance of the previously used sensor substantially prior to its discontinuation of use. If it is determined that the sensor is being reused, then the sensor system can trigger an error routine, which can include notifying the user via audible and/or visual alarms using a user interface of the sensor system of improper sensor reuse and prompting the user to use a new sensor, as discussed above with respect to step 2112.

Figure 22:
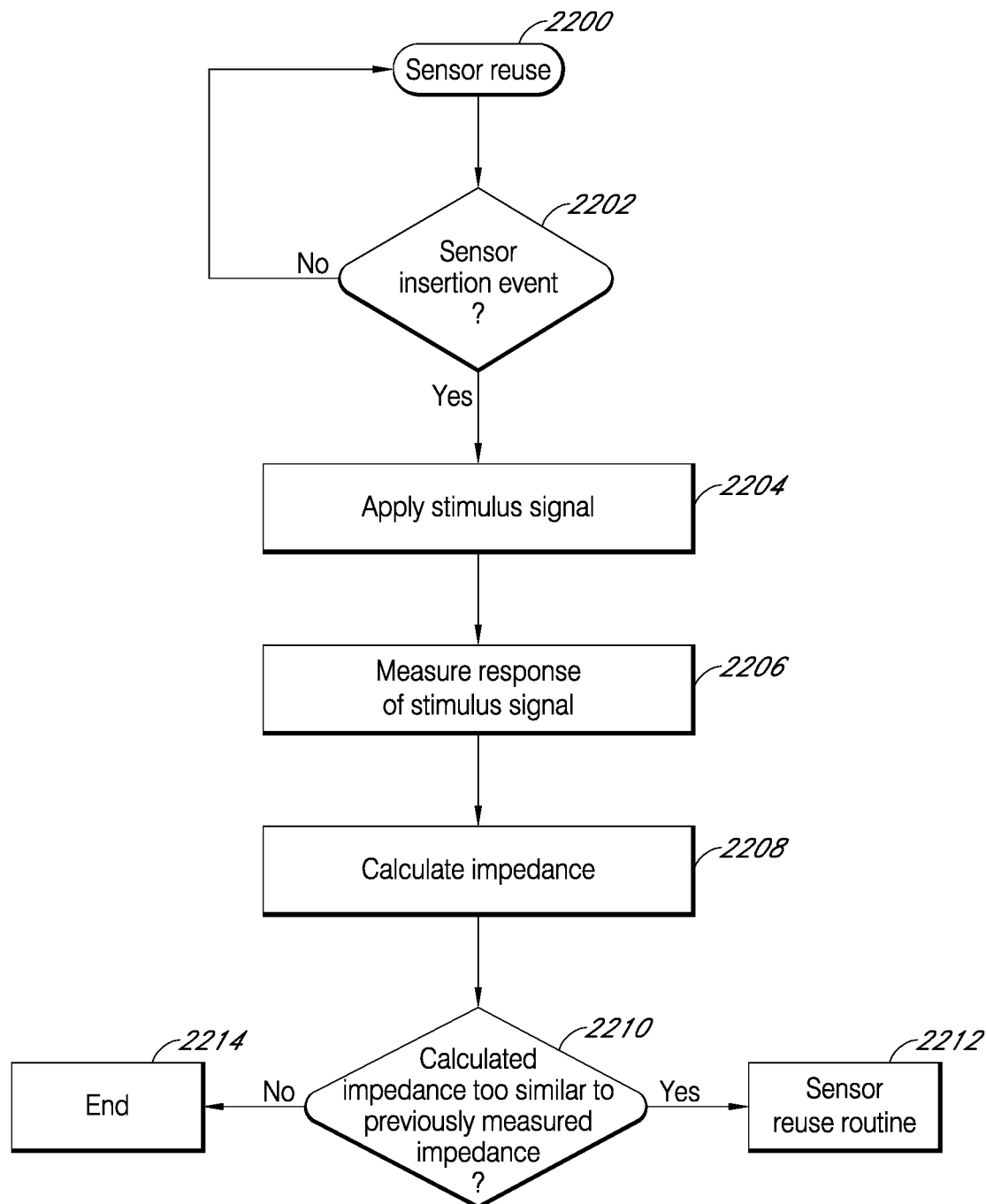
FIG. 22 is a flowchart describing a second process for determining sensor reuse associated in accordance with one embodiment.

FIG. 22 is a flowchart of another exemplary process 2200 for determining sensor reuse in accordance with one embodiment. At step 2202, a sensor insertion event is triggered. A an insertion event can be one of any number of possible events that indicate a new sensor has been implanted, such as a user providing input to a sensor system that a new sensor has been implanted, the sensor system detecting electrical connection to a sensor, a predetermined amount of time transpiring since the system prompted a user to use a new sensor, and the like. Next, at step 2204, a stimulus signal is applied to an analyte sensor being used, and a response is measured and recorded at step 2206. Impedance is calculated based on the signal response at step 2208. The stimulus signal and technique for calculating impedance in steps 2206 and 2208 can be any of the signals and techniques described herein such as those described with reference to FIGS. 11-14. Then, at decision step 2210, the calculated impedance is compared to one or more previously measured impedance values measured using one or more previously implanted sensors (at what at least should have been a previously implanted sensor according to the sensor system). Should it be determined that the calculated impedance correlates within a predetermined amount with the one or more previously measured impedance measurements, then a sensor reuse routine is initiated at step 2112. Correlation can be determined using a data association function, such as one of the data association functions described herein. If it is determined in decision step 2110 that the impedance does not correlate within the predetermined amount to previously measured impedance values, then the process 2100 ends at step 2114, wherein the system continues to use the sensor to measure glucose concentrations of the host.

The sensor reuse routine of step 2212 can include triggering an audible and/or visual alarm notifying the user of improper sensor reuse. The alarm can also inform the user why sensor reuse may be undesirable, such as potentially providing inaccurate and unreliable sensor readings. The sensor reuse routine 2212 can alternatively or additionally cause the sensor system to fully or partially shut down and/or cease display of sensor data on a display of the sensor system.

f. Sensor Overpotential

Some embodiments apply an overpotential routine based on one or more measured impedances of the sensor membrane. It has been found that applying an overpotential (e.g., a voltage potential greater than the bias potential applied to the sensor when used for continuous analyte sensing) to some embodiments of analyte sensors can aid in stabilizing the analyte sensor, thereby reducing a run-in period of the sensor. The overpotential may need to be discontinued once the sensor has sufficiently stabilized, otherwise damage to the sensor can occur. Accordingly, one or more impedance measurements of the sensor can be used to determine a sensitivity or change in sensitivity of the sensor. Any of the techniques described herein, such as those described with reference to FIGS. 11-14, can be used to measure an impendence of the sensor. The determined sensitivity or sensitivity change can be, in turn, used to indicate whether or not the sensor has stabilized or will stabilize within a determined amount of time by, for example, determining a correspondence of the measured impedance to predetermined sensitivity-to-impedance relationships. Upon determining that the sensor has stabilized or will stabilize within a determined amount of time, application of the overpotential can be discontinued or reduced. In addition, a magnitude of an overpotential and/or length of time in which the overpotential is to be applied to the sensor can be determined or modified based on one or more impedance measurements taken prior to application of the overpotential or during application of the overpotential. That is, an overpotential routine can be modified or discontinued according to one or more impedance measurements in accordance with some embodiments.

g. Multi-Electrode or Multi-Sensor Configuration

Some embodiments of sensor systems comprise a plurality of sensor electrodes. For example, as discussed above, in addition to an analyte sensing electrode, some embodiments can include an auxiliary electrode to allow for the subtraction of a baseline signal from an analyte+baseline signal. Some embodiments can also include one or more redundant analyte sensors.

In accordance with one embodiment, a first stimulus signal can be applied to a first sensor and a second stimulus signal can be applied to a second sensor. The first sensor can be configured to sense an analyte concentration (e.g., glucose) and, in this regard, can generate an analyte+baseline signal. The second sensor can be an auxiliary sensor configured to measure a baseline signal that can be subtracted from the signal of the first sensor. In addition, the first stimulus signal can have the same waveform or different waveform than the second stimulus signal. A response to the first stimulus signal and a response to the second stimulus signal can each be measured and recorded. The first response and the second response can be processed, and sensor characteristics can be determined based on the processing, such as impedance values associated with each sensor. The processing can include a comparison (e.g., using a data association function described herein) of the first and second response signals to one another and/or compare each of the first and second response signals to established relationships. The sensor characteristics can include any of the sensor characteristics described herein, including a sensitivity value or sensitivity change of the first and/or second electrodes, a temperature of the first and/or second electrodes, magnitude of detected membrane damage of the first electrode, and the like. Further, sensor data can be compensated for changes in sensor characteristics, such as changes in sensor sensitivity, based on the processing of the first and second response signals.

Figure 23:
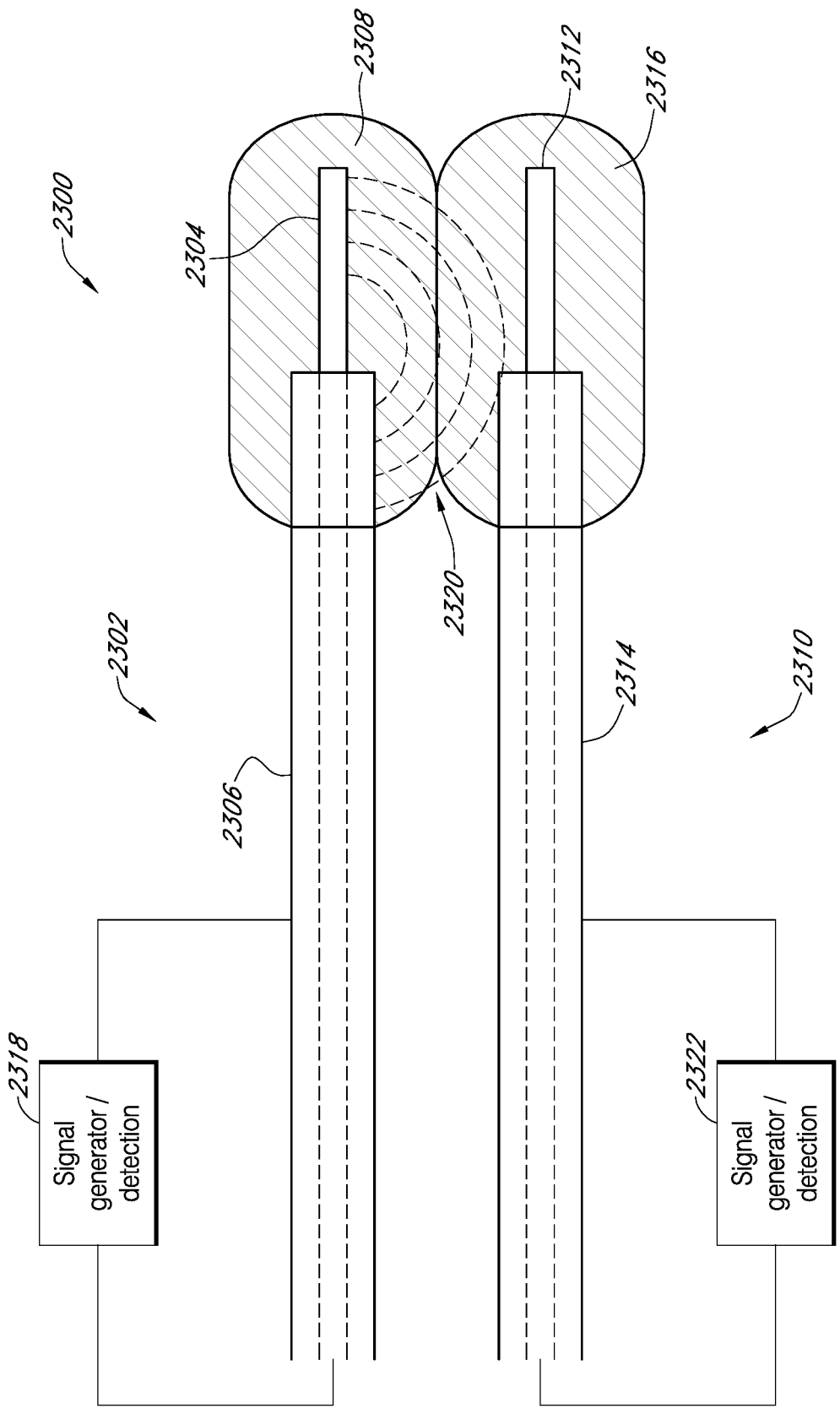
FIG. 23 is a schematic of a dual-electrode configuration used to determine sensor properties in accordance with one embodiment.

FIG. 23 is a schematic diagram of a dual-sensor configuration that can be used in a sensor system in accordance with some embodiments. The dual-sensor configuration includes a first sensor 2302, having a working electrode 2304, reference electrode 2306 and membrane 2308, and a second sensor 2310, also having a working electrode 2312, reference electrode 2314 and membrane 2316. Each sensor can be essentially the same, including having the same type of membrane, or each sensor can be different, such as having different membranes or even one of the sensors not having a membrane. In one embodiment, each sensor 2302 and 2310 is configured to measure an analyte concentration in a host. In an alternative embodiment, the second sensor 2310 does not have a discrete reference electrode. In this alternative embodiment, the reference electrode of the first sensor can also function as the reference electrode of the second sensor.

As illustrated in FIG. 23, a stimulus signal can be applied to the first sensor 2302 using signal generator/detector 2318 (the stimulus signal can be any stimulus signal described herein, such as a voltage step). The stimulus signal can elicit electric field lines 2320 to emanate from the first sensor 2302 and evoke an electrical response in the second sensor 2310. The electrical response can be measured using signal generator/detector 2322 electrically connected to the second sensor 2314. The signal generator/detectors 2318 and 2322 can include any known electrical circuitry capable of generating a desired stimulus signal discussed herein and capable of measuring a response to the stimulus signal.

Further to FIG. 23, the response measured in the second sensor 2310 can then be used to determine sensor properties, such as any sensor properties discussed herein. For example, the response can be used to calculate an impedance of the first sensor 2302 and thereafter used to determine a sensitivity of the first sensor 2302 and/or correct sensor data generated by the first sensor, using one of the processes described herein.

Alternatively or in addition, a first stimulus signal can be applied to the first sensor 2302 and measured using the second sensor 2310 and a second stimulus signal can be applied to the second sensor 2310 and measured using the first sensor 2302. The first and second stimulus signals can be essentially the same or can be different. The responses to each of the first and second stimulus signals can then be used to determine a sensor property, such as any of the sensor properties discussed herein.

The sensor to which the stimulus signal is applied can also be used to measure a response to the stimulus signal in addition to the other sensor measuring a response to the stimulus signal. For example, a first stimulus signal can be applied to the first sensor 2302 and first and second responses to the first stimulus signal can be measured by the first sensor 2302 and the second sensor 2310, respectively. The first and second responses can then be used to determine sensor properties discussed herein of either or both of the first sensor 2302 and second sensor 2310.

h. Scaling Factor

In some embodiments, a scaling factor can be used to correct differences in responses of a dual-electrode analyte sensor. In some embodiments, a dual-electrode analyte sensor that can be used is a reference sensor/system, whereby reference data can be provided for calibration (e.g., internal to the system), without the use of an external (e.g., separate from the system) analyte-measuring device. In some embodiments, the dual-electrode analyte sensor includes a first electrode that includes an enzyme reactive with a particular analyte (which can be referred to as the plus-enzyme electrode) and a second electrode that does not include the enzyme (which can be referred to as the minus-enzyme electrode).

In some embodiments, the sensor system (such as a sensor electronics module of the sensor system) is configured to determine a scaling factor (k). Briefly, a scaling factor defines a relationship between the electrodes of the dual-electrode analyte sensor. Accordingly, in some embodiments, the sensor system is configured to calibrate the analyte sensor data using the scaling factor, such that the calibrated sensor data does not include inaccuracies that can arise due to differences between the first and second working electrodes, respectively. That is, the scaling factor can be used to calculate estimated analyte values based on data generated by the sensor system U.S. Patent Publication No. US-2009-0242399-A1, the contents of which are hereby incorporated by reference in its entirety, describes in more detail dual-electrode analyte sensor systems, scaling factors and methods for using scaling factors that can be used in some embodiments.

In accordance with some embodiments, the membrane impedance of each electrode of a dual-electrode system can be used to determine or update a scaling factor. The scaling factor can then be used to calculate estimated analyte concentration values based on data generated by the sensor system.

The following illustrates an exemplary process for determining a scaling factor using impendence in accordance with one embodiment. First, membrane impedance is measured for both electrodes of a dual-electrode sensor system. Techniques described herein, such as those described with reference to FIGS. 11-14 and under the heading "Multi-electrode or multi-sensor configuration" can be used to measure the membrane impendence of each of the electrodes of the dual-electrode analyte sensor. The impendence can be measured periodically during sensor use. A scaling factor can be generated using a ratio of the measured membrane impendence of the two electrodes (e.g., a ratio of the membrane impendence of a plus-enzyme electrode and the membrane impedance of a minus-enzyme electrode). A scaling factor to generate estimated analyte values can then be determined or updated based on the generated scaling factor. The determined or updated scaling factor can then be used to generate estimated analyte values.

It has been found that acetaminophen can interfere with glucose measurements using some sensor embodiments. It has also been found that acetaminophen response can be proportional to its diffusion through a sensor membrane and sensor impedance can be indicated of membrane impedance. Thus, the above illustrative process for determining a scaling factor can be used to periodically determine an acetaminophen scaling factor by determining a ratio of the plus-enzyme and minus-enzyme electrode impedance. The acetaminophen scaling factor can be used to update a scale factor, such as one of those described above, used to calculate estimated glucose concentrations.

i. Calibration

Figure 24:
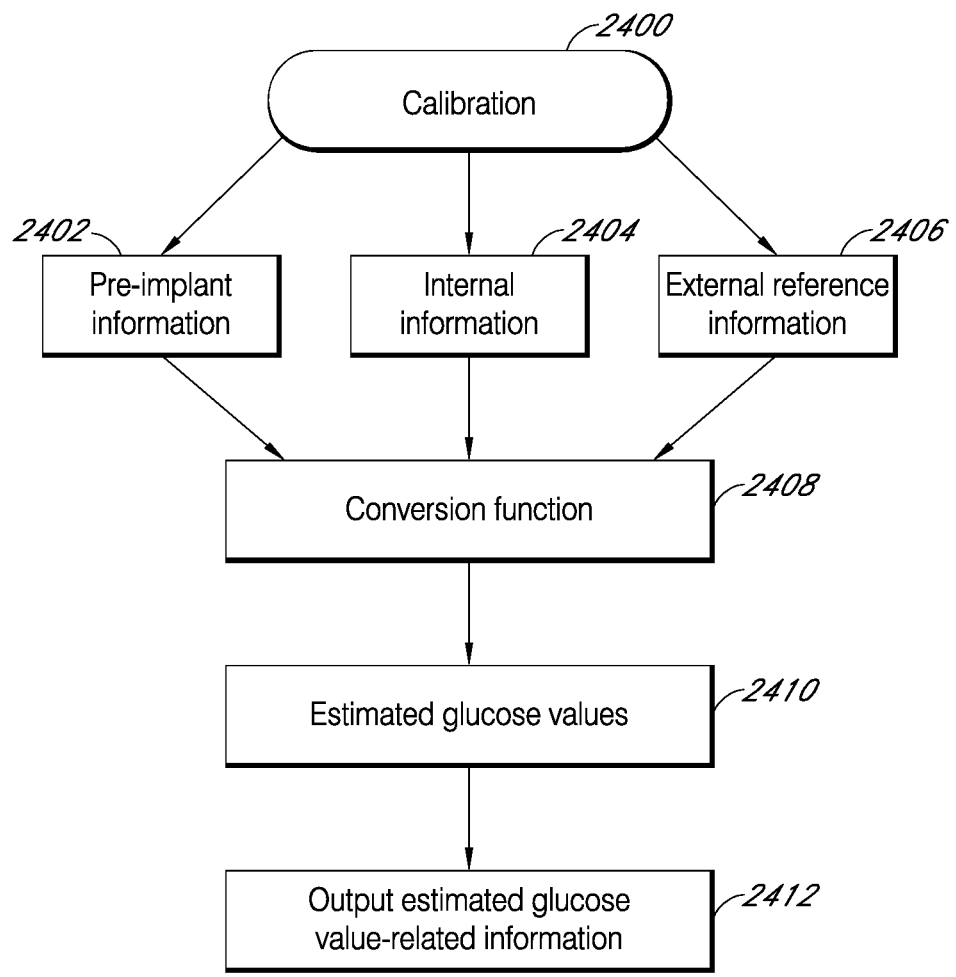
FIG. 24 is a diagram of a calibration process that uses various inputs to form a conversion function in accordance with one embodiment.

An exemplary calibration process in accordance with some embodiments will now be discussed with reference to FIG. 24. Calibration process 2400 can use one or more of pre-implant information 2402, internal diagnostic information 2404 and external reference information 2406 as inputs to form or modify a conversion function 2408. Conversion function 2408 can be used to convert sensor data (e.g., in units of current or counts) into estimated analyte values 2410 (e.g., in units of analyte concentration). Information representative of the estimated analyte values can then outputted 2412, such as displayed on a user display, transmitted to an external device (e.g., an insulin pump, PC computer, mobile computing device, etc.) and/or otherwise processed further. The analyte can be, glucose, for example.

In process 2400, pre-implant information 2402 can mean information that was generated prior to implantation of the sensor(s) presently being calibrated. Pre-implant information 2402 can include any of the following types of information:
- predetermined sensitivity profile(s) associated with the currently used (e.g., implanted) sensor, such a predicted profile of sensitivity change over time of a sensor;
- previously determined relationships between particular stimulus signal output (e.g., output indicative of an impedance, capacitance or other electrical or chemical property of the sensor) to sensor sensitivity (e.g., determined from prior in vivo and/or ex vivo studies);
- previously determined relationships between particular stimulus signal output (e.g., output indicative of an impedance, capacitance or other electrical or chemical property of the sensor) to sensor temperature (e.g., determined from prior in vivo and/or ex vivo studies);
- sensor data obtained from previously implanted analyte concentration sensors;
- calibration code(s) associated with a sensor being calibrated, as discussed herein;
- patient specific relationships between sensor and sensitivity, baseline, drift, impedance, impedance/temperature relationship (e.g., determined from prior studies of the patient or other patients having common characteristics with the patient);
- site of sensor implantation (abdomen, arm, etc.) specific relationships (different sites may have different vascular density);
- time since sensor manufacture (e.g., time sensor on shelf, date when sensor was manufactured and or shipped, time between when the sensor was manufactured an/or shipped and when the sensor is implanted); and
- exposure of sensor to temperature, humidity, external factors, on shelf.

In process 2400, internal diagnostic information 2402 can mean information generated by the sensor system in which the implanted analyte sensor (the data of which is being calibrated) is being used. Internal diagnostic information 2402 can include any of the following types of information:
- stimulus signal output (e.g., the output of which can be indicative of the sensor's impedance) of sensor using any of the stimulus signal techniques described herein (the stimulus signal output can be obtained and processed in real time);
- sensor data measured by the implanted sensor indicative of an analyte concentration (real-time data and/or previously generated sensor data using the currently implanted sensor);
- temperature measurements using the implanted sensor or an auxiliary sensor (such as a thermistor) co-located with the implanted analyte sensor or separately from the implanted analyte sensor;
- sensor data from multi-electrode sensors; for example, where one electrode of the sensor is designed to determine a baseline signal as described herein;
- sensor data generated by redundant sensors, where one or more of the redundant sensors is designed to be substantially the same as at least some (e.g., have the same sensor membrane type), if not all, of the other redundant sensors;
- sensor data generated by one or more auxiliary sensors, where the auxiliary sensor is having a different modality such (as optical, thermal, capacitive, etc.) co-located with analyte sensor or located apart from the analyte sensor;
- time since sensor was implanted and/or connected (e.g., physically or electronically) to a sensor electronics of a sensor system;
- data representative of a pressure on sensor/sensor system generated by, for example, a pressure sensor (e.g., to detect compression artifact);
- data generated by an accelerometer (e.g., indicative of exercise/movement/activity of a host);
- measure of moisture ingress (e.g., indicative of an integrity of a moisture seal of the sensor system); and
- a measure of noise in an analyte concentration signal (which can be referred to as a residual between raw and filtered signals in some embodiments).

In process 2400, external reference information 2402 can mean information generated from sources while the implanted analyte sensor (the data of which is being calibrated) is being used. External reference information 2402 can include any of the following types of information:
- real-time and/or prior analyte concentration information obtained from a reference monitor (e.g., an analyte concentration value obtained from separate sensor, such as a finger stick glucose meter);
- type/brand of reference meter (different meters can have different bias/precision);
- information indicative of carbohydrates consumed by patient;
- information from a medicament pen/pump, such as insulin on board, insulin sensitivity, glucagon on board;
- glucagon sensitivity information; and
- information gathered from population based data (e.g., based on data collected from sensors having similar characteristics, such as sensors from the same lot).

Exemplary Sensor System Configurations

Embodiments of the present invention are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

In some embodiments, a sensor system is provided for continuous measurement of an analyte (e.g., glucose) in a host that includes: a continuous analyte sensor configured to continuously measure a concentration of the analyte in the host and a sensor electronics module physically connected to the continuous analyte sensor during sensor use. In one embodiment, the sensor electronics module includes electronics configured to process a data stream associated with an analyte concentration measured by the continuous analyte sensor in order to process the sensor data and generate displayable sensor information that includes raw sensor data, transformed sensor data, and/or any other sensor data, for example. The sensor electronics module can include electronics configured to process a data stream associated with an analyte concentration measured by the continuous analyte sensor in order to process the sensor data and generate displayable sensor information that includes raw sensor data, transformed sensor data, and/or any other sensor data, for example. The sensor electronics module can include a processor and computer program instructions to implement the processes discussed herein, including the functions specified in the flowchart block or blocks presented herein.

In some embodiments, a receiver, which can also be referred to as a display device, is in communication with the sensor electronics module (e.g., via wired or wireless communication). The receiver can be an application-specific hand-held device, or a general purpose device, such as a P.C., smart phone, tablet computer, and the like. In one embodiment, a receiver can be in data communication with the sensor electronics module for receiving sensor data, such as raw and/or displayable data, and include a processing module for processing and/or display the received sensor data. The receiver can also and include an input module configured to receive input, such as calibration codes, reference analyte values, and any other information discussed herein, from a user via a keyboard or touch-sensitive display screen, for example, and can also be configured to receive information from external devices, such as insulin pumps and reference meters, via wired or wireless data communication. The input can be processed alone or in combination with information received from the sensor electronics module. The receiver's processing module can include a processor and computer program instructions to implement any of the processes discussed herein, including the functions specified in the flowchart block or blocks presented herein.

EXAMPLES

Embodiments are further detailed in the following Examples, which are offered by way of illustration and are not intended to limit the invention in any manner. As disclosed herein, studies have been conducted using a Gamry potentiostat system to analyze complex impedance of glucose sensors placed in a buffer. The Gamry potentiostat system is commercially available from Gamry under the model name Ref600. The buffer is a modified isolyte having a known concentration of glucose. In many of the examples, the glucose concentration is about 100 mg/dL. The impedance measurement error in the examples was found to be about 1 to 5% by testing the system with a known impedance.

Although some of the following examples were performed on a lab bench, the sensors under test are configured to be used in vivo to continuously or substantially continuously measure a glucose concentration of a host.

Analyte sensors used in the following examples were selected from different types of sensors. The sensors under test include sensors taken from different sensor lots, where sensors from a first lot may have been made in a different way and under different conditions, which can result in sensors for different lots exhibiting different sensitivity profiles. Further, some of the sensors studied in these examples are configured for placement in transcutaneous tissue of a host to measure the host's glucose concentration, while other sensors are configured to measure an intravenous blood glucose concentration of a host. In the following experiments, sensors intended to be used to measure an intravenous blood glucose concentration can be referred to as an "IVBG sensor type" and sensors intended to measure a blood glucose concentration in transcutaneous tissue of a host can be referred to as a "transcutaneous sensor type."

Example 1

Sensitivity and Impedance Relationship

Example 1 illustrates a relationship between sensitivity of a sensor and an impedance of the sensor. In this example, an IVBG sensor was connected to a Gamry potentiostat system and placed in a in a buffer solution of a modified isolyte having a glucose concentration of 100 mg/dL. The temperature during the experiment was 37 C. An impedance spectrum was captured at fixed intervals of time. The impedance spectrum analyzed in this experiment ranged from 1 Hz to 100 kHz and measurements of the sensor impedance and sensor sensitivity were taken at 15 minute intervals over a period of about 1200 minutes.

Figure 25:
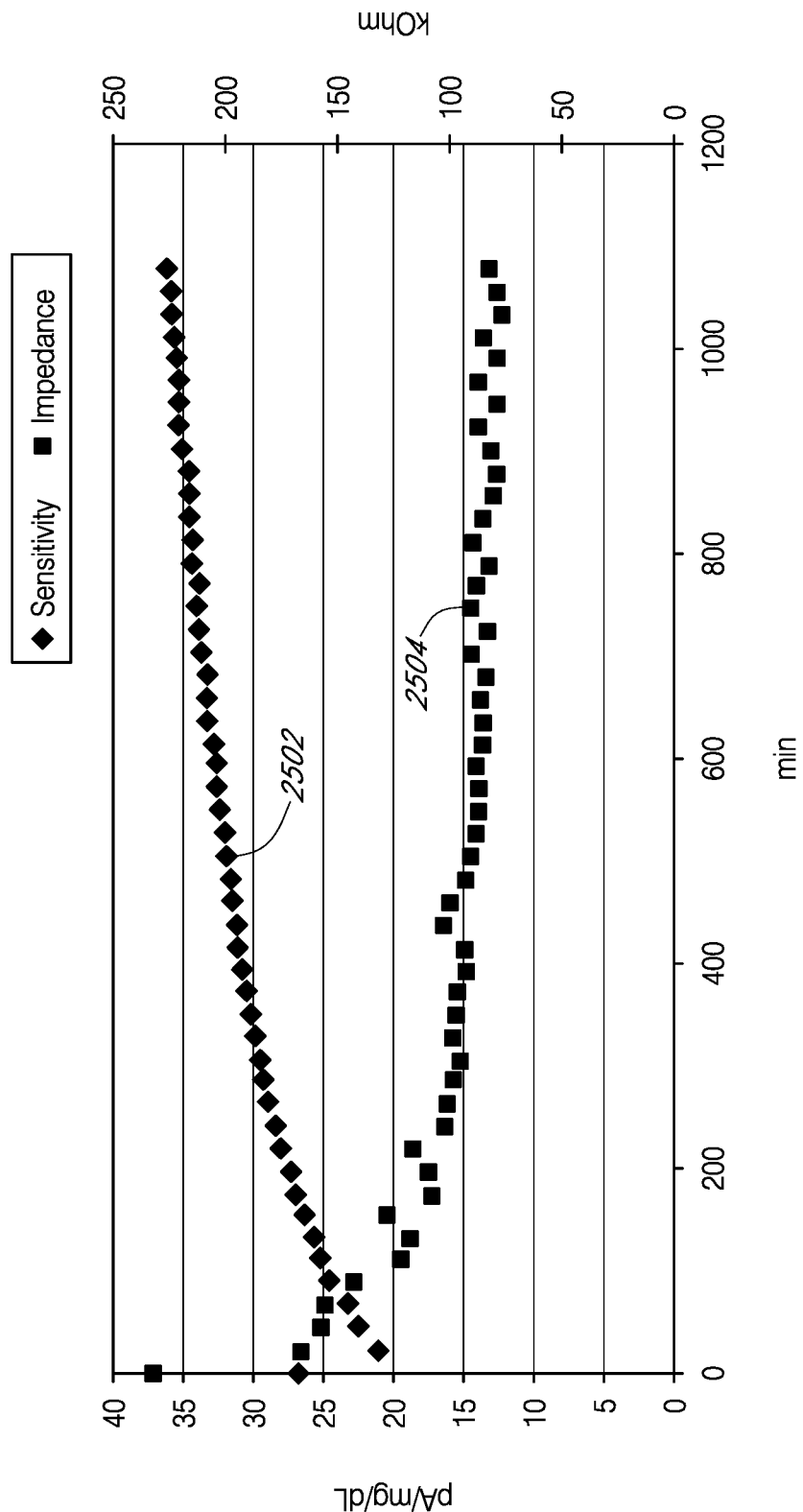
FIGS. 25-49 collectively illustrate results of studies using stimulus signals to determine sensor properties.

Reference is now made to FIG. 25, which is a graph showing absolute values of sensitivity and impedance of the sensor based on an input signal having a frequency of 1 kHz. Data points 2502 represent measured values of sensor sensitivity over a time period of 1200 minutes (20 hours), where t=0 corresponds to the time when the sensor is initially placed in the buffer. Data points 1104 represent measured values of impedance over the same time period.

The sensitivity and impedance values of FIG. 25 appear to have an inverse correlation. That is, the sensitivity initially increases quickly and then the rate of the increase gradually slows down and levels off, and the impedance initially decreases quickly and then the rate of the decrease gradually slows down and levels off. Although not wishing to be bound by theory, the initial increase in sensitivity and decrease in impedance is believed to be due to sensor run-in.

Figure 26:
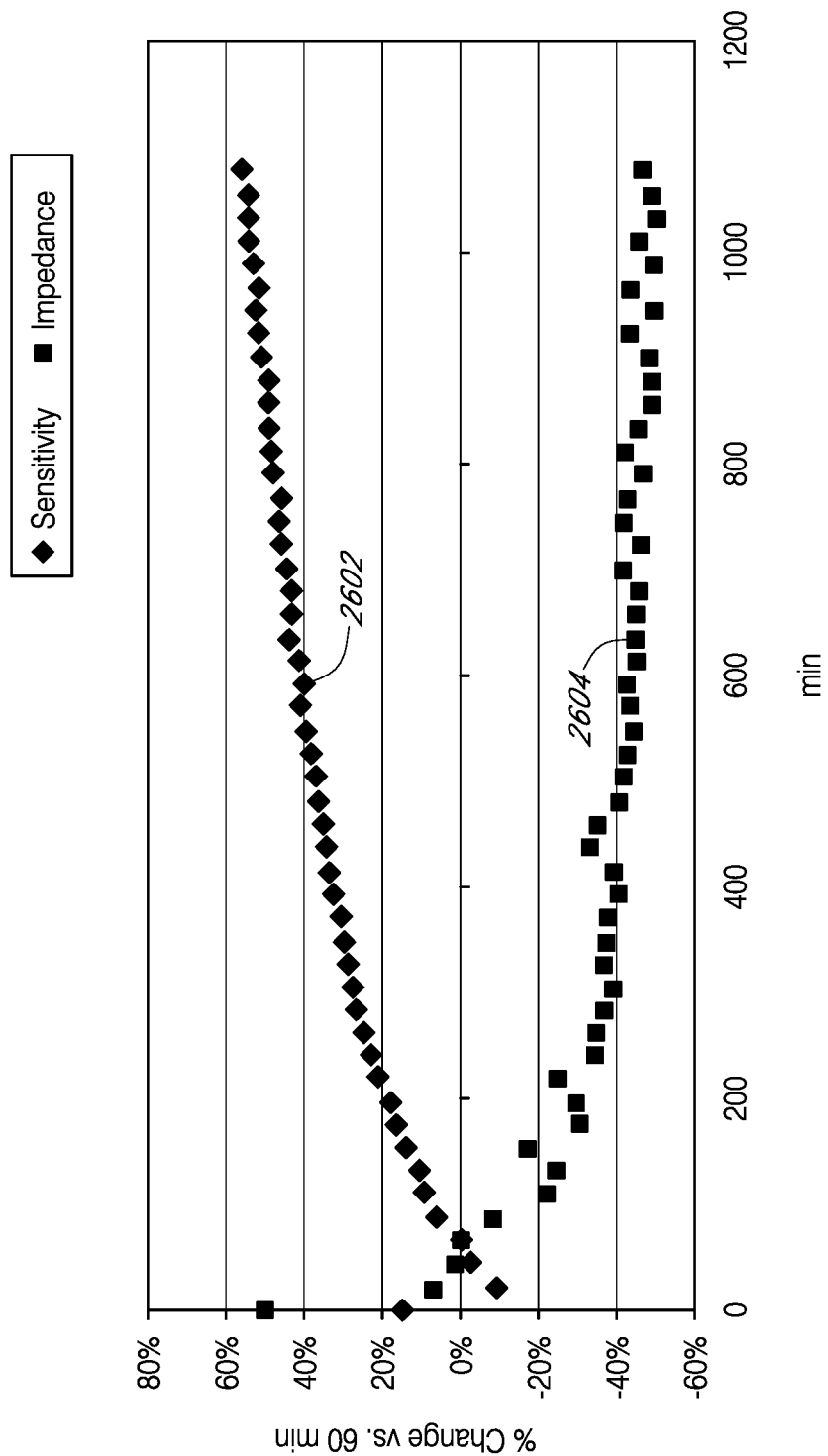

FIG. 26 is a plot of the data in FIG. 25, but the sensitivity and impedance are in terms of percent change versus one hour instead of absolute values. As can be seen, the sensitivity 2602 and impedance 2604 relative changes versus one hour also appear to have an inverse correlation.

Example 2

Retrospectively Compensating for Sensitivity Drift Using Impedance

Figure 27:
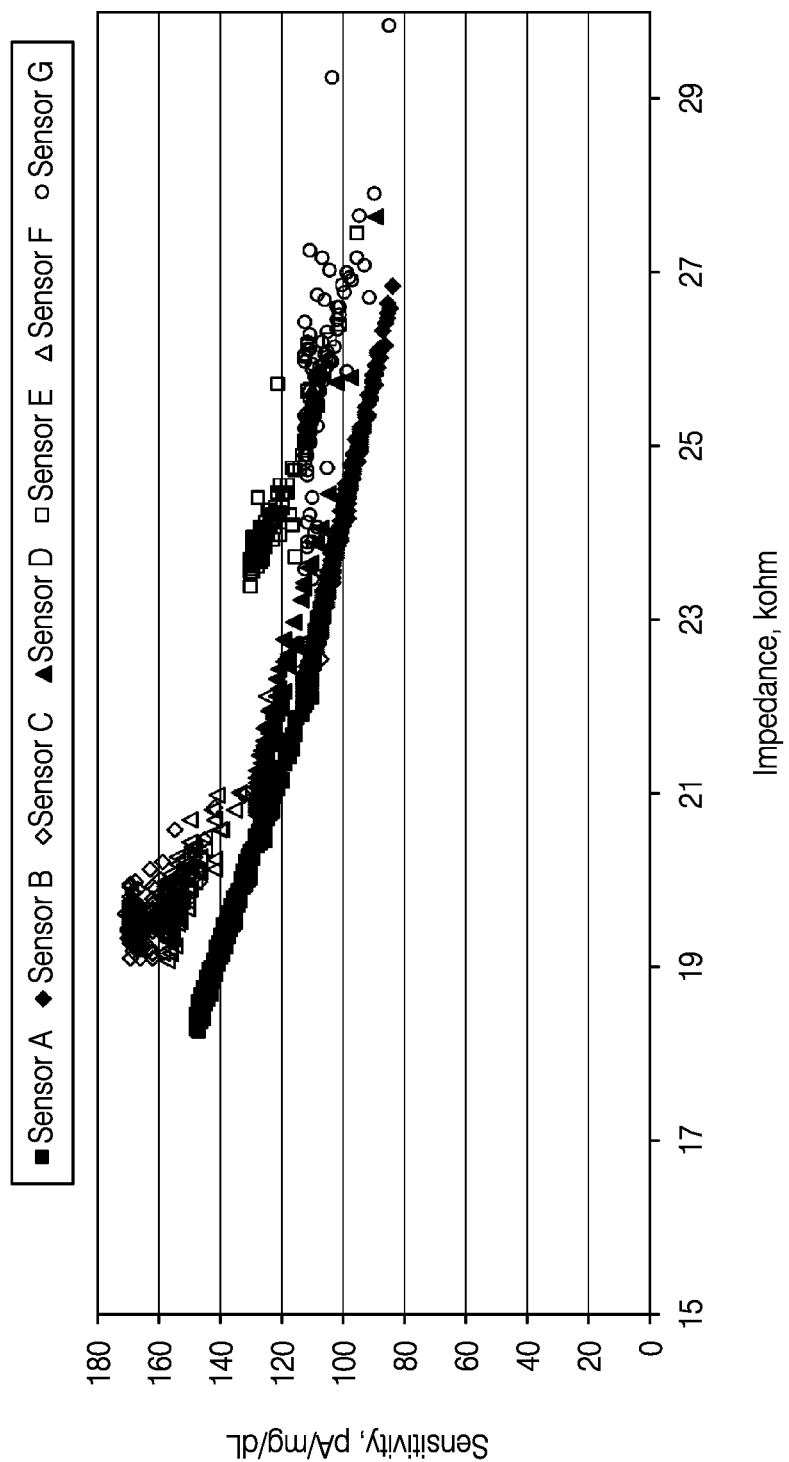

FIG. 27 is a plot of sensitivity and impedance points measured at various intervals over time using seven different sensors, Sensors A-G. Sensors A-G were transcutaneous-type sensors, but selected from several different sensor lots. Thus, even though Sensors A-G were all transcutaneous sensors, sensors from different lots may have been made in a slightly different way or under slightly different conditions, which can result in sensors from different lots exhibiting different sensitivity profiles. In this Example, Sensors A and D were selected from a first lot, Sensor B was selected from a second lot, and Sensors C, E, F and G were selected from a third lot.

Further to FIG. 27, the plotted data points are sensitivity and impedance values for each Sensor A-G. Because the sensitivity of each Sensor A-G gradually increases over time, the right most points of each Sensor's plotted data points tend to correspond to values measured around t=0 and the left most points tend to correspond to values at around t=24 hr.

As can be seen in FIG. 27, the impedance and sensitivity values of each Sensor A-G have an essentially linear relationship, where the sensitivity gradually increases and the impedance decreases correspondingly over time. The data taken from all seven Sensors A-G generally follow this linear relationship, although the data points of each sensor may be shifted as compared to the data points of the other sensors. Put another way, while the initial impedance and sensitivity values for each sensor may be different, the change in sensitivity and impedance for each sensor changes at about the same linear rate.

Figure 28:
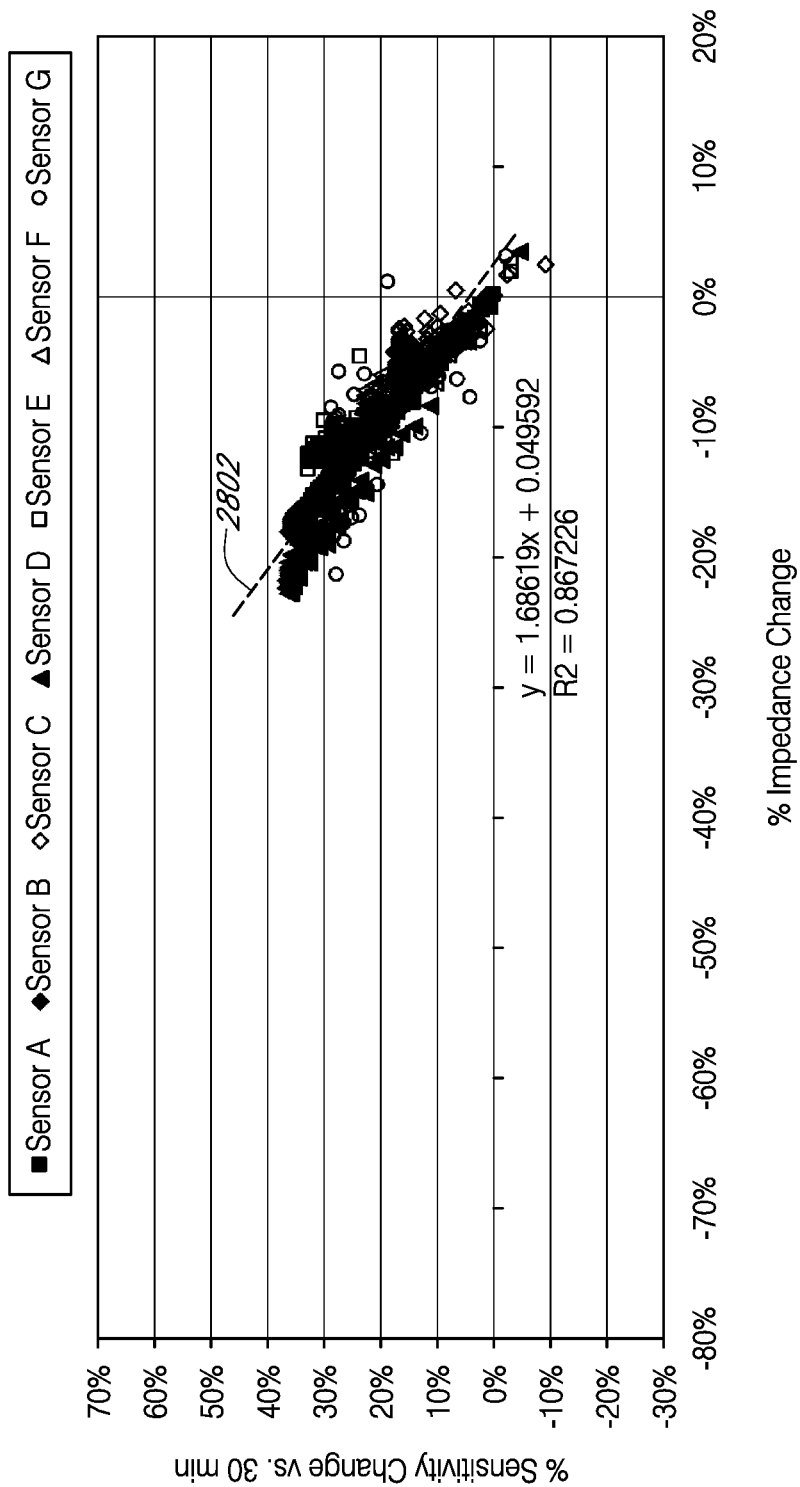

FIG. 28 is a graph further illustrating the linear relationship of impedance and sensitivity of Sensors A-G. The graph of FIG. 28 is based on the same data used in FIG. 27, but the data is graphed in terms of percent change rather than in absolute values. As can be seen in FIG. 28, Sensors A-G appear to exhibit a very similar correspondence between the change in impedance and change in sensitivity.

A computer-implemented estimative algorithm function can be used to model a relationship between the change in sensitivity and change in impedance values of the sensor data generated by Sensors A-G. The estimative algorithm function may be formed by applying curve fitting techniques that regressively fit a curve to data points by adjusting the function (e.g., by adjusting constants of the function) until an optimal fit to the available data points is obtained, as discussed above with respect to forming an estimative curve for a sensitivity profile. Additionally or alternatively, the relationship can be modeled into a look-up table stored in computer memory.

Further to FIG. 28, an estimative curve 2802 of the combined sensor data of Sensors A-G is also plotted. The curve in FIG. 28 is a straight line, but can be other types of curves depending upon the relationship between impedance and sensitivity of the sensor. As discussed herein, the curve 2802 can be used to compensate for sensitivity drift of a sensor.

Figure 29:
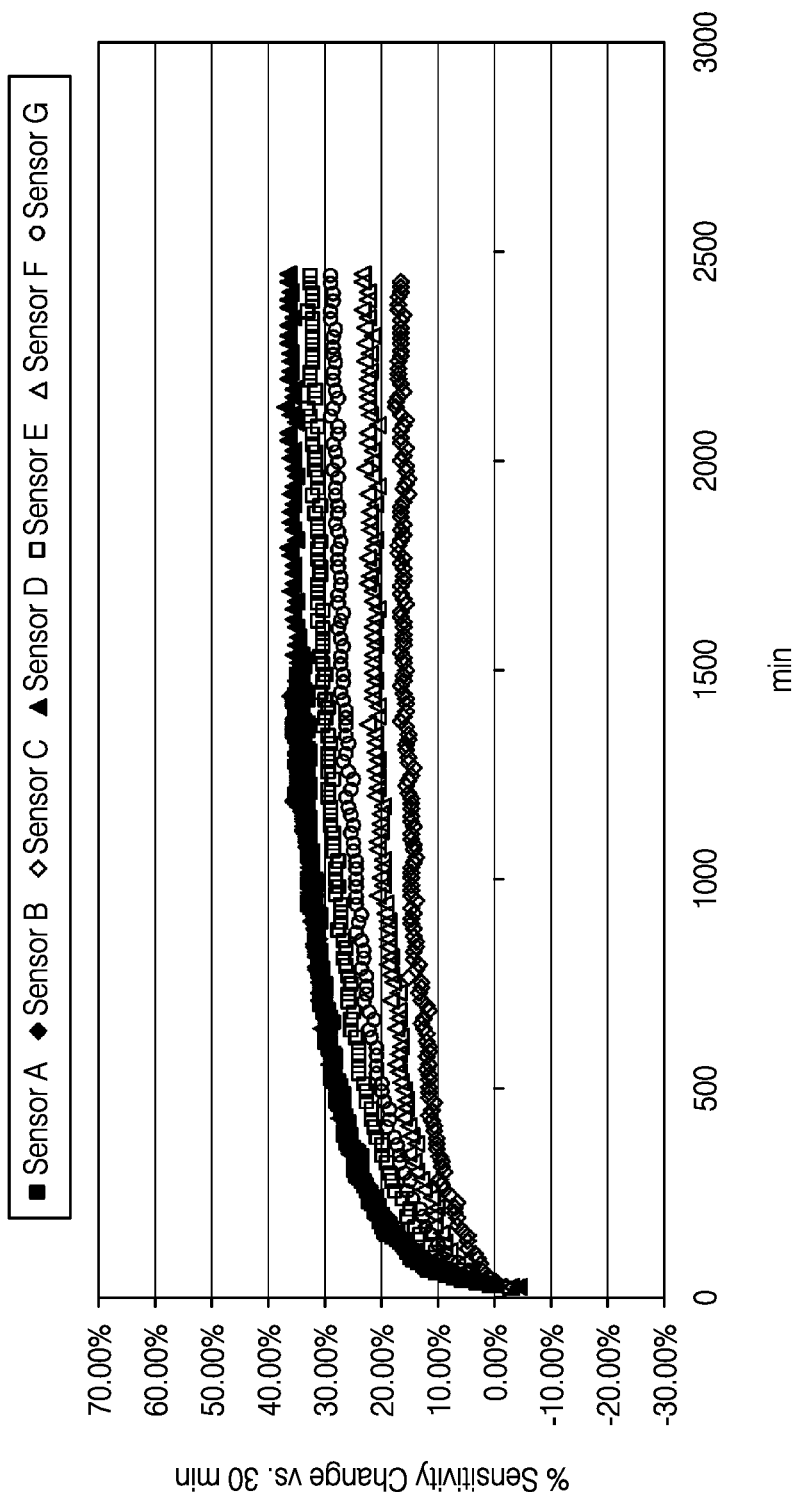
Figure 30:
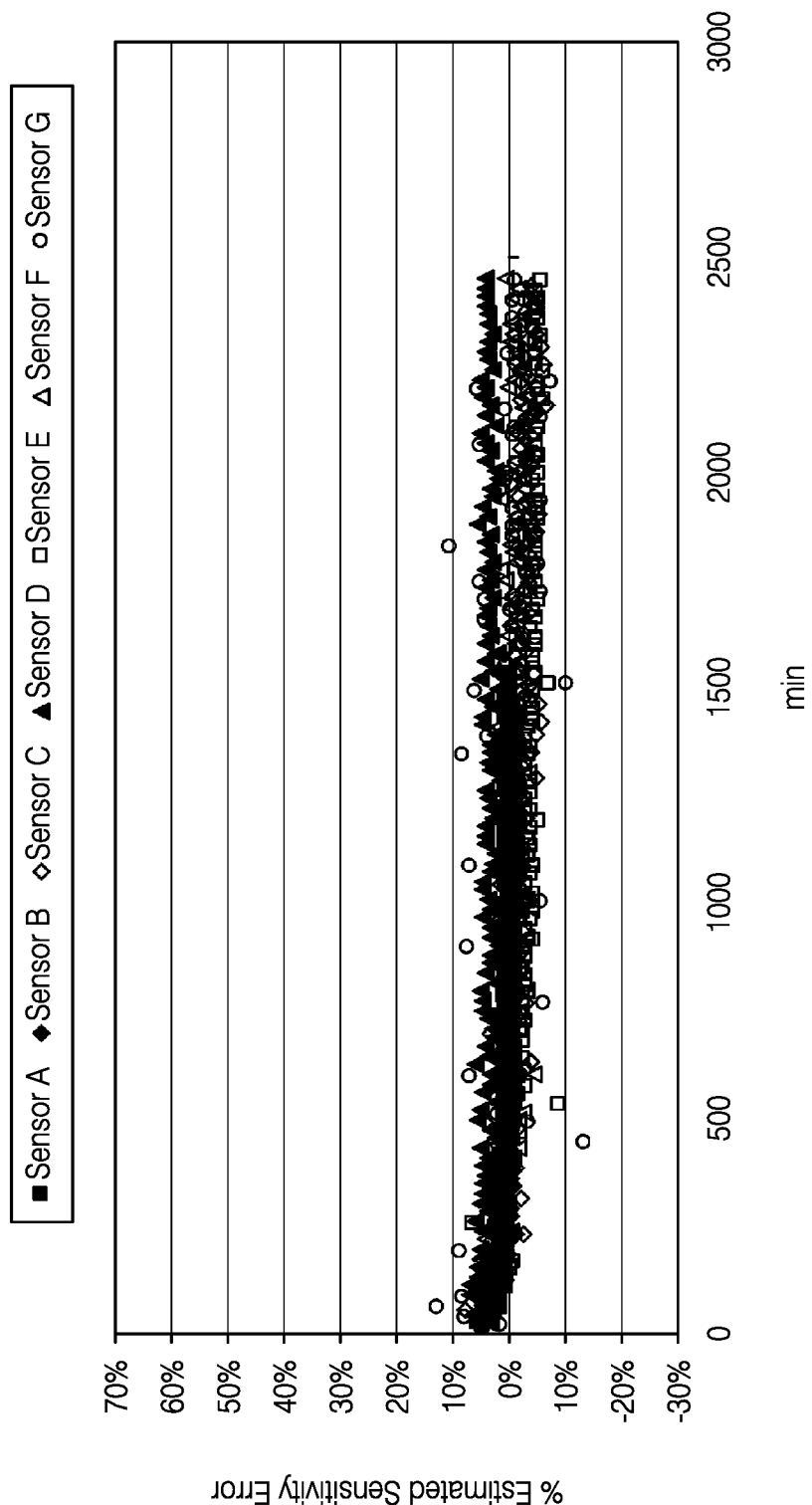

FIG. 29 and FIG. 30 illustrate compensating sensor data taken by the same sensors used to derive the estimative curve 2802. The measurements of FIGS. 29 and 30 were taken at 37 C. (Note that estimative curve 2802 was derived based on sensor measurements taken at 37 C, as discussed above with reference to FIGS. 27 and 28.) FIG. 29 is a plot of uncompensated measurements using Sensors A-G. FIG. 30 is a plot of percent estimated sensitivity error of measurements compensated using the impedance to sensitivity relationship based on the estimative curve 2802. The Mean Absolute Relative Difference (MARD) of the uncompensated sensor data is 21.8%. The MARD of the compensated data is 1.8%, which is a noticeable improvement over the uncompensated data.

Figure 31:
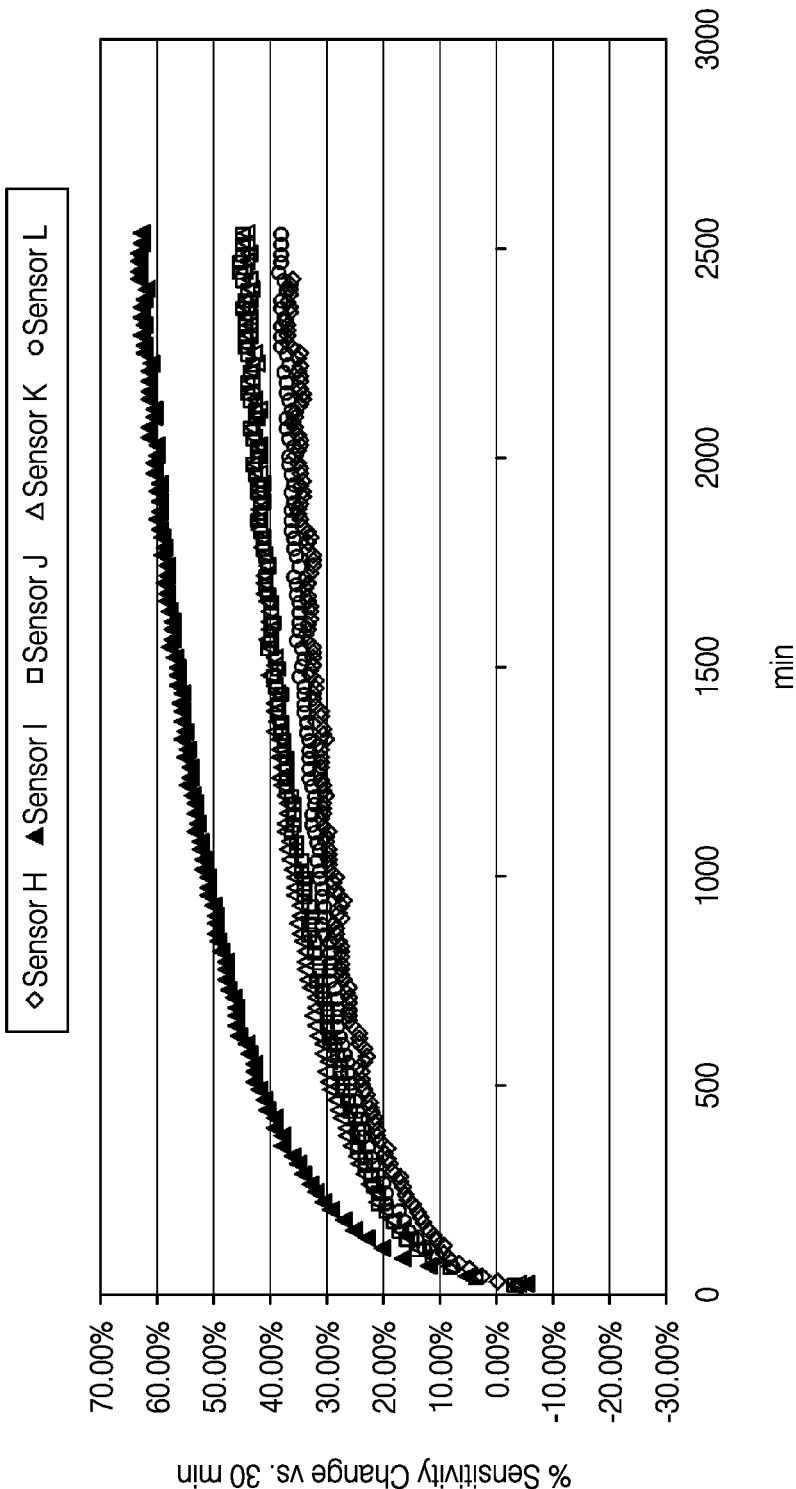
Figure 32:
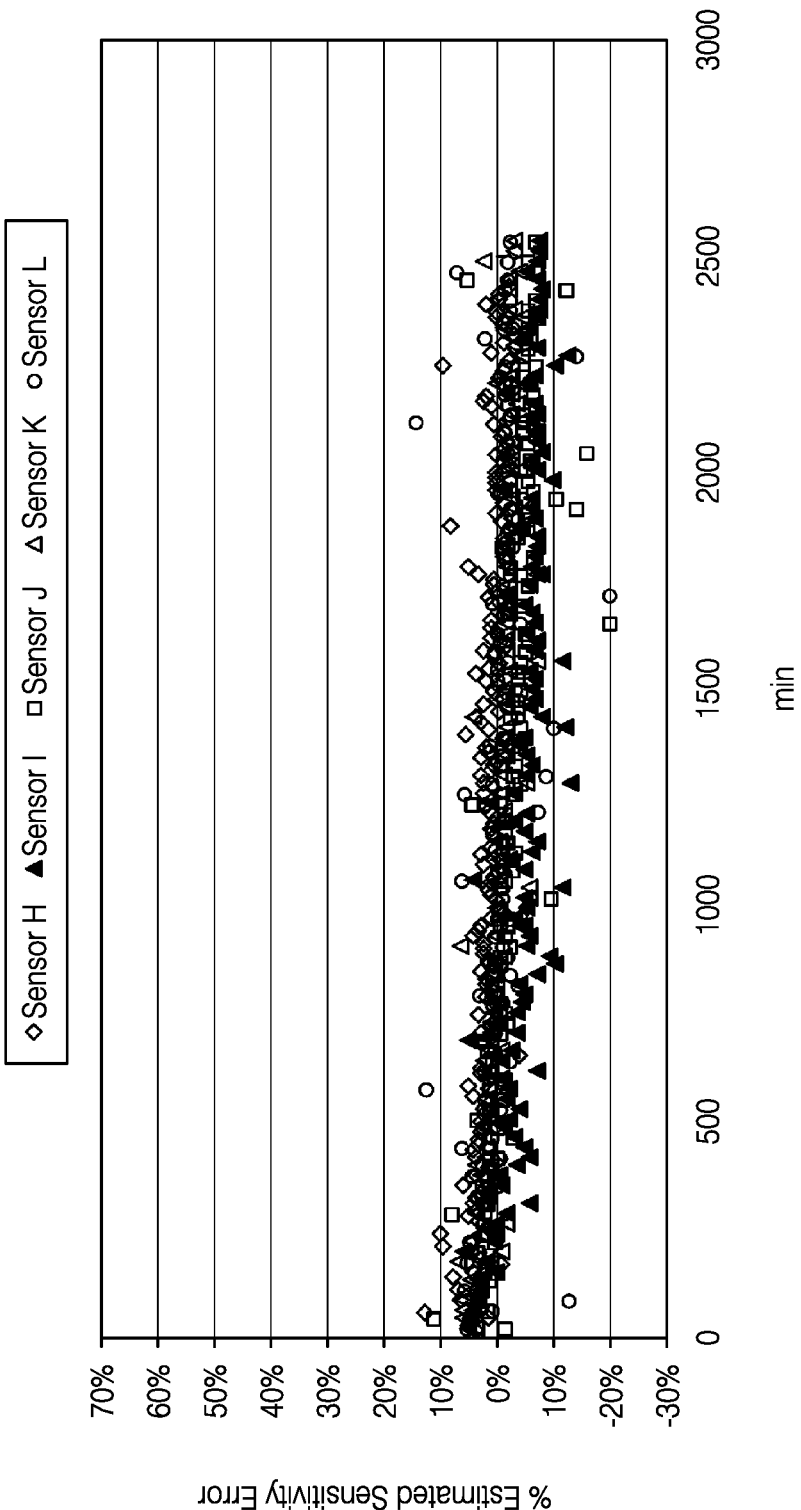

FIGS. 31 and 32 are also plots of uncompensated data and percent sensitivity error of compensated data, respectively. The data in FIGS. 31 and 32 are based on measurements using Sensors H-L. Sensors H, J, K and L were selected from the same lot of sensors as Sensors C, F and G described with reference to FIG. 27 and Sensor I was selected from the same lot as Sensors A and D described with reference to FIG. 27. Further, the measurements plotted in FIGS. 31 and 32 were taken at 25 C instead of 37C. The estimative curve 2802 derived from Sensors A-G, however, was used to compensate the data measured by Sensors H-L. (Note the estimative curve 2802 was also based on measurements taken at 37 C.) The MARD of the uncompensated data is 21.9%, nearly the same as the MARD of 21.8% calculated with respect to the sensor data in FIG. 29. The MARD of the compensated data of FIG. 18 is 4.4%, which is close to, although slightly higher than the MARD of the compensated data of FIG. 30, but still much smaller than the uncompensated MARD.

Figure 33:
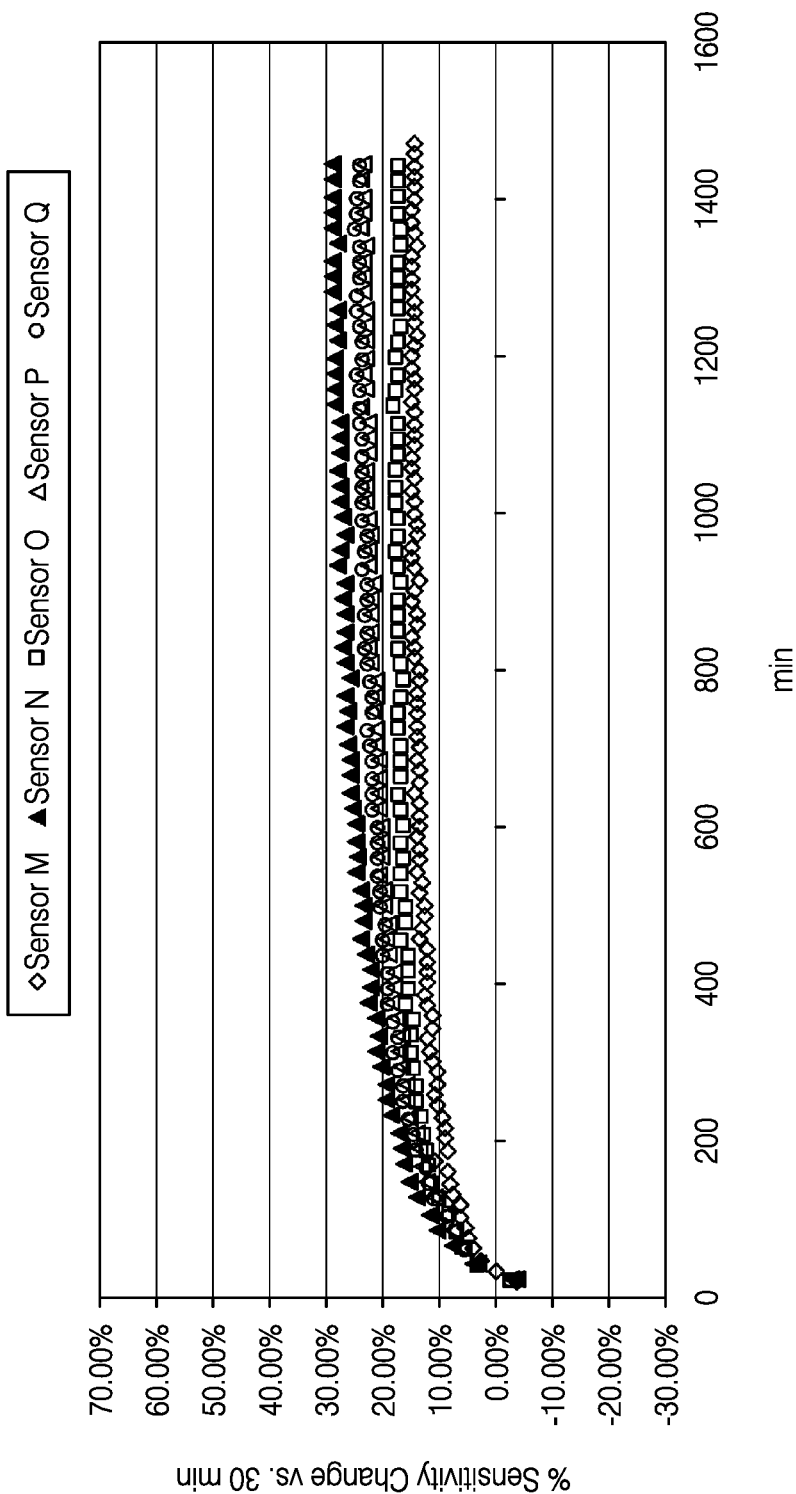
Figure 34:
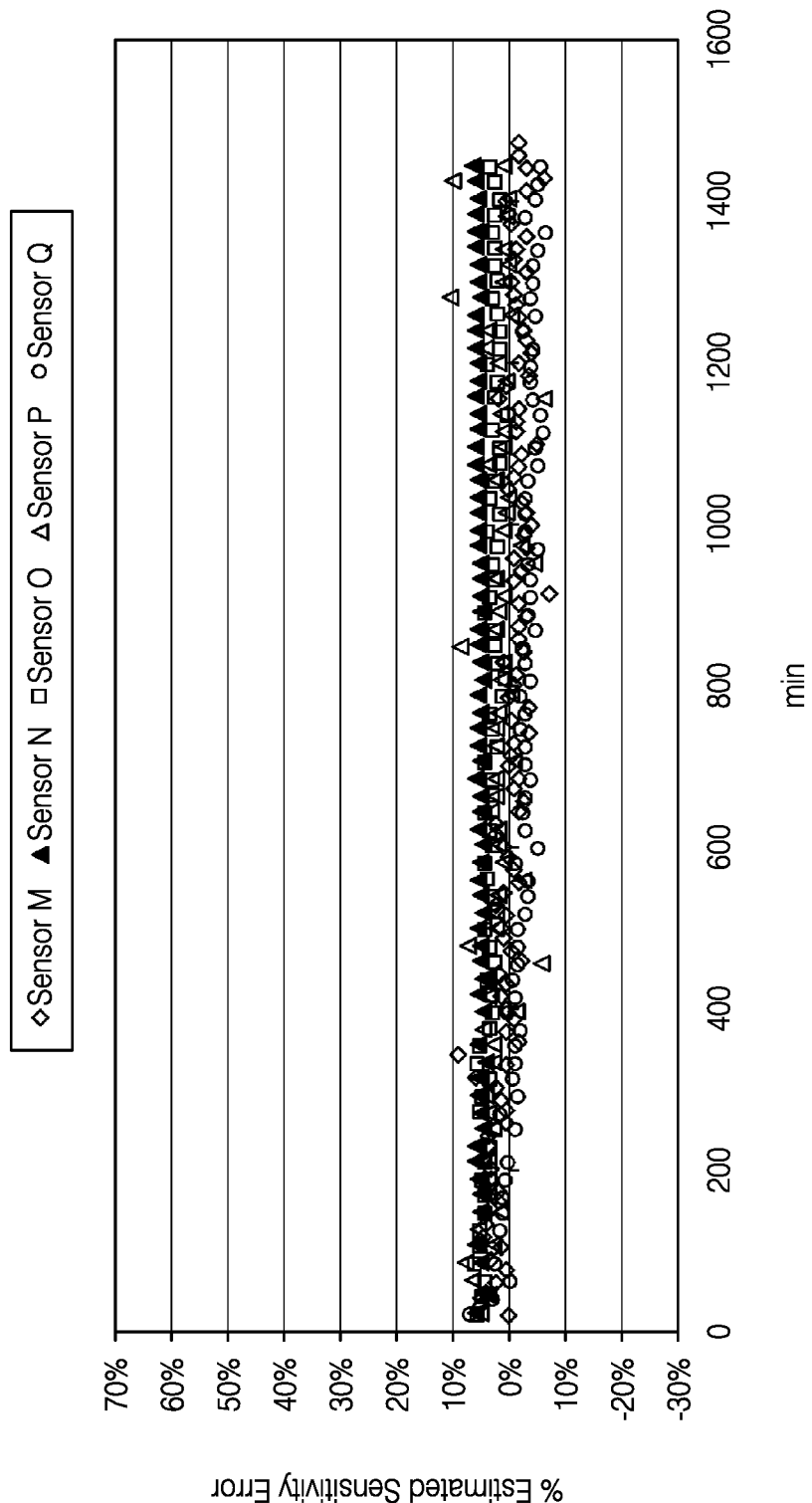

FIGS. 33 and 34 are graphs of uncompensated data and percent sensitivity error of compensated data, respectively. The data in FIGS. 33 and 34 are based on data obtained using Sensors M-Q. Sensors M, 0, P and Q were selected from the same lot as Sensors C, F and G described with reference to FIG. 27 and Sensor N was selected from the same lot as Sensors A and D described with reference to FIG. 27. The measurements of Sensors M-Q were taken at 42 C. The estimative curve 2802 derived from Sensors A-G was also used to compensate the data in FIG. 34. Here, the MARD of the uncompensated data is 13.1% and the MARD of the compensated data is 4.6%.

Accordingly, Example 2 illustrates that a change in sensitivity to change in impedance relationship determined at a first temperature can be used to compensate for sensitivity drift at temperatures different from the first temperature.

Example 3

Prospective Calibration of Sensor Data Using Impedance Measurements

Example 5 pertains to prospective calibration. Further, in this experiment, calibration of sensor data is based on a change of sensitivity to change in impedance relationship previously derived from sensors from a different sensor lot. That is, in Example 3, the estimative curve 2802 is used to compensate data obtained using Sensors R-U, each of which was selected from a fourth sensor lot, the fourth sensor lot was not included in the group of sensors used to derive the estimative curve 2802. Example 5 shows that data can be calibrated using a change in sensitivity to change in impedance relationship derived from different sensor types than the type of sensor being calibrated. This can indicate that a sensor factory calibration code need not be used to compensate for sensitivity drift.

Figure 35:
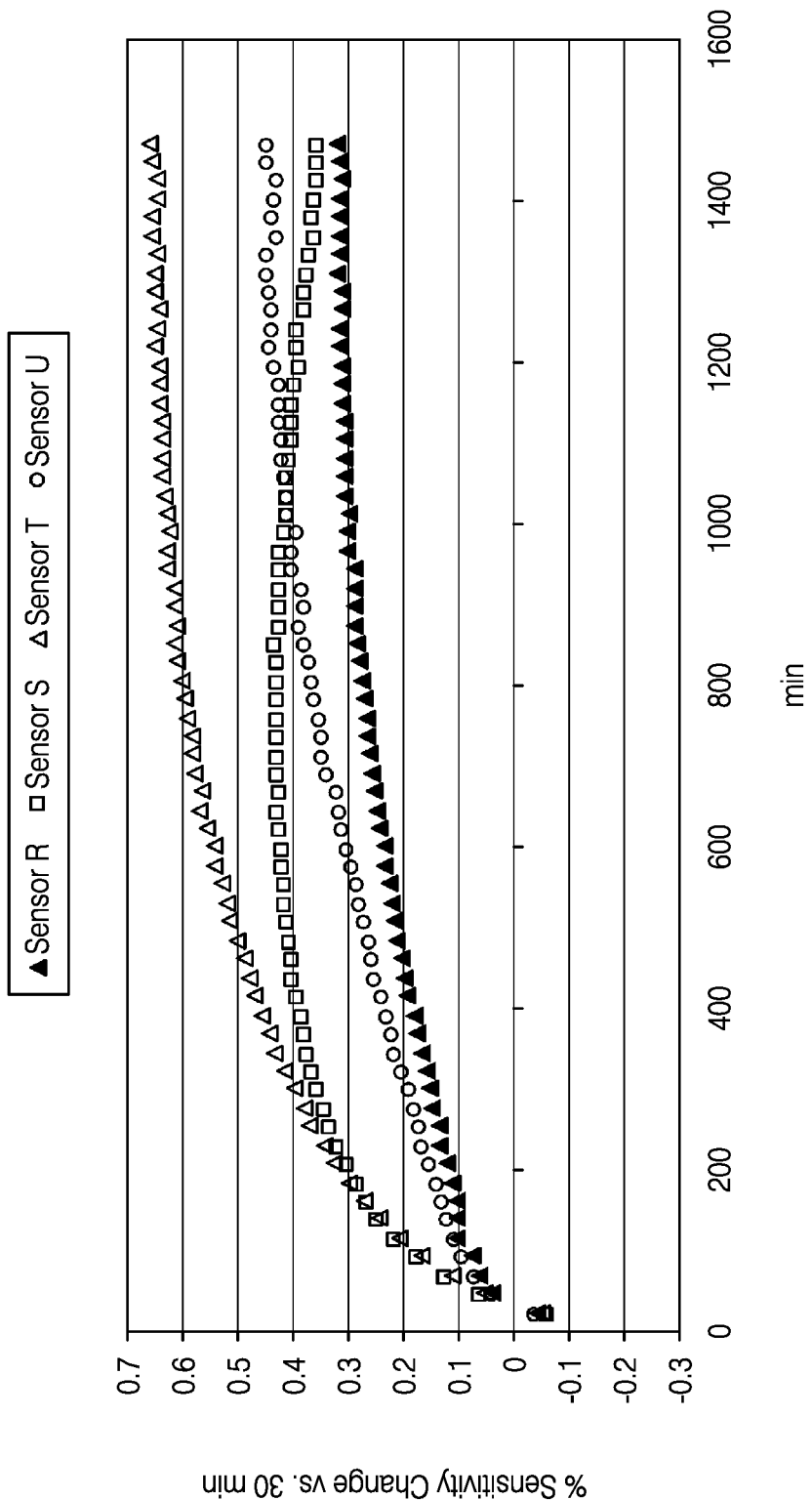
Figure 36:
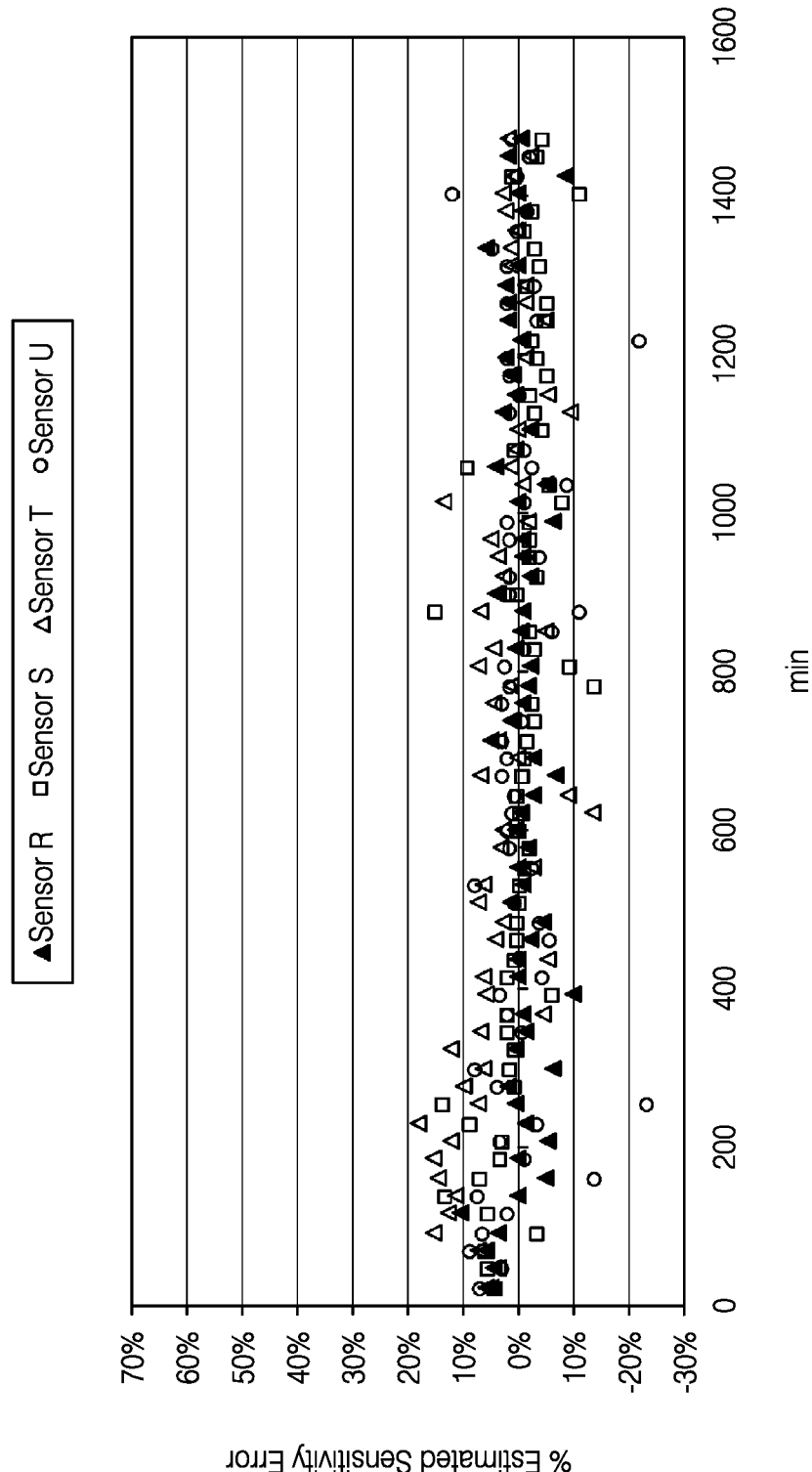

FIGS. 35 and 36 illustrate prospectively calibrating sensor data obtained from Sensors R-U. FIG. 35 is a plot of the percent sensitivity change versus 30 minutes of each of the sensors over approximately 1400 minutes. FIG. 36 illustrates the percent estimated sensitivity error of the compensated data. The MARD of the uncompensated sensor data is 24.8% (the MARD of uncompensated data in the example of FIG. 15 was 21.8%) and the MARD of the compensated sensor data is 6.6% (the MARD of compensated data in the example of FIG. 16 was 1.8%).

Figure 37:
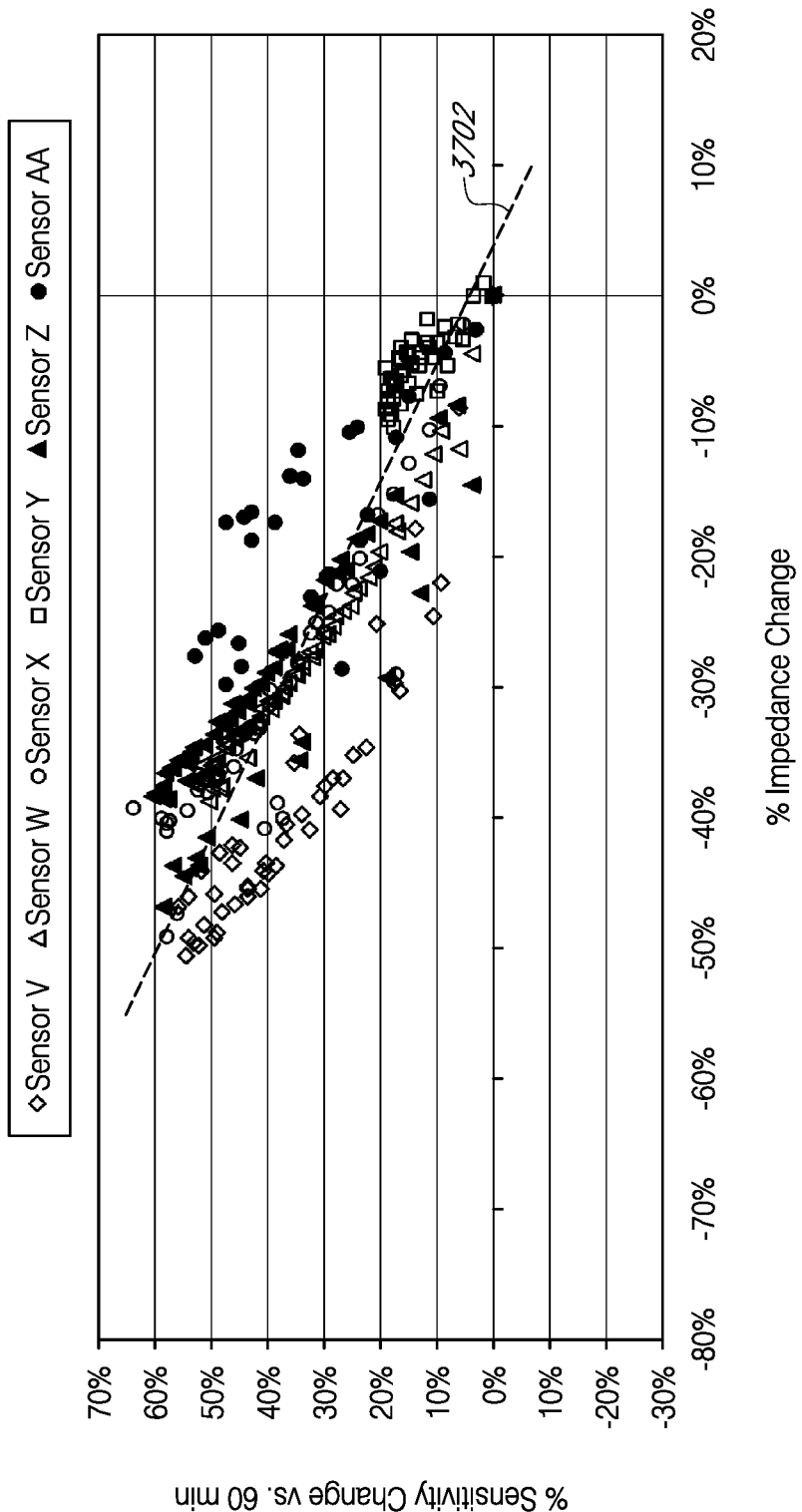
Figure 38:
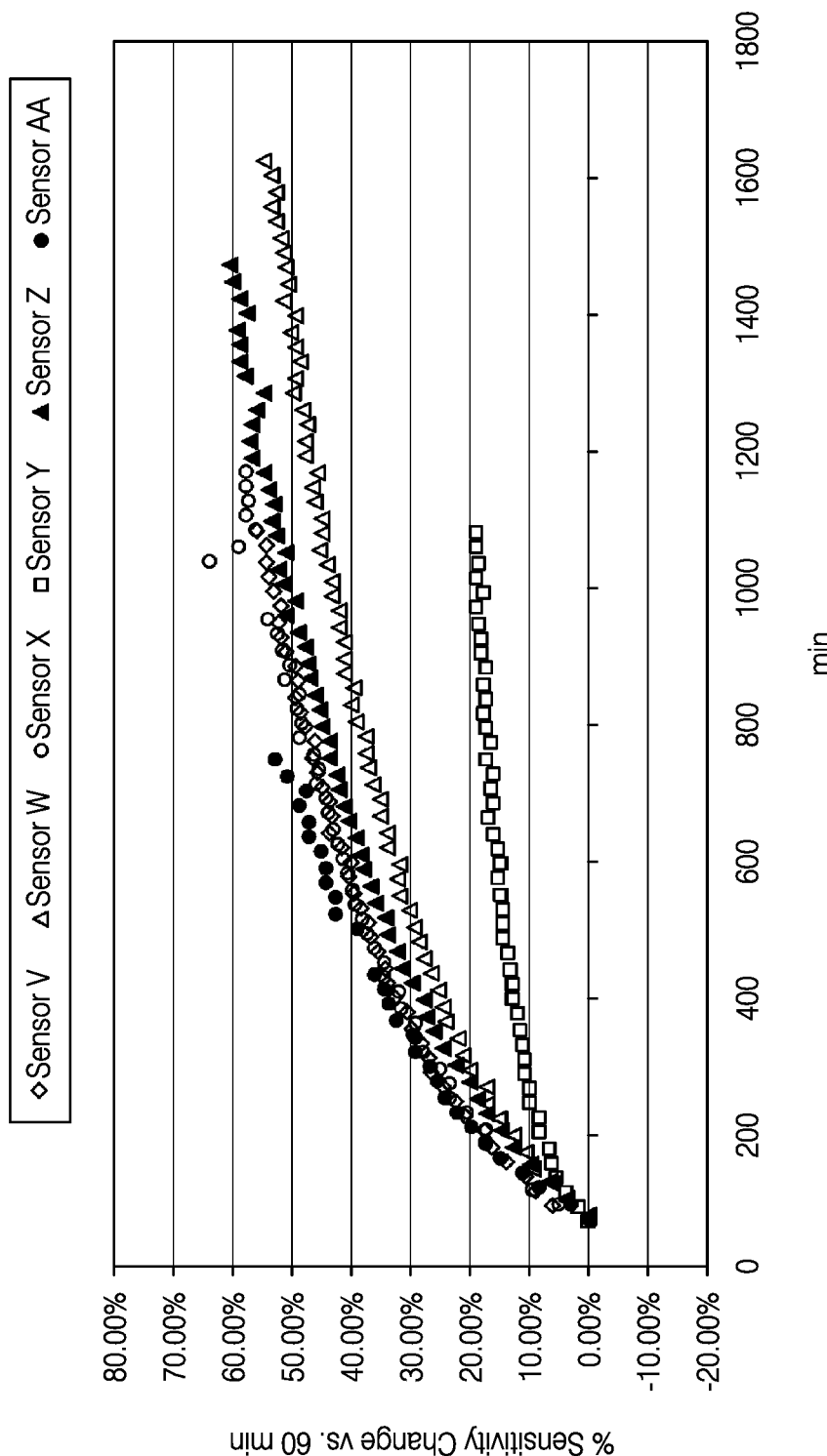
Figure 39:
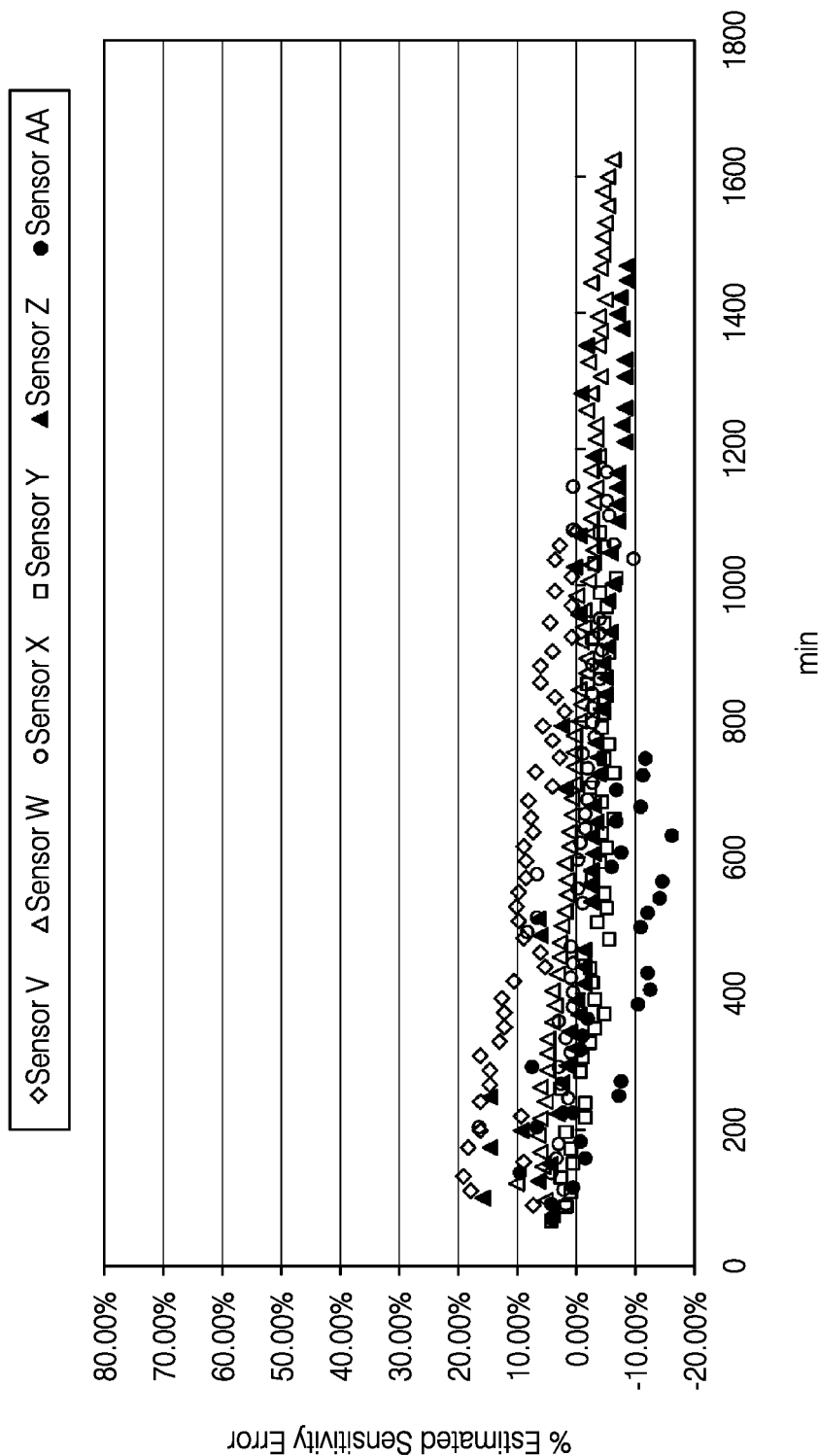

Prospective calibration of sensors will now be discussed with reference to FIGS. 37-39. Here, sensitivity and impedance data is collected from Sensors V-X, Z and AA having a membrane formed by a dipping process and Sensor Y having a membrane formed by a spray process. Referring to FIG. 37, an estimative curve 3702 is calculated based on the sensitivity and impedance data from all six Sensors V-Z and AA (i.e. using sensor data obtained from both sensors having dipped and sprayed membrane). FIG. 39 is a graph of the percent sensitivity change of versus 60 minutes of the uncompensated data of each of the six sensors. FIG. 39 is a graph of the percent estimated sensitivity error of the data of all six sensors after being compensated using estimative curve 3702 discussed above with respect to FIG. 37. The MARD of the uncompensated data is 25.3% and the MARD of the compensated data is 5.2%.

Thus, Example 5 indicates that using a change in sensitivity to change in impedance relationship derived from sensors selected from different lots than the sensor being calibrated can never-the-less significantly compensate for sensor sensitivity drift. It should be noted that curve 3702 is a straight line. It is contemplated that non-linear fits or correlations can be used instead, which may yield better results.

Example 4

Effect of Temperature

Figure 40:
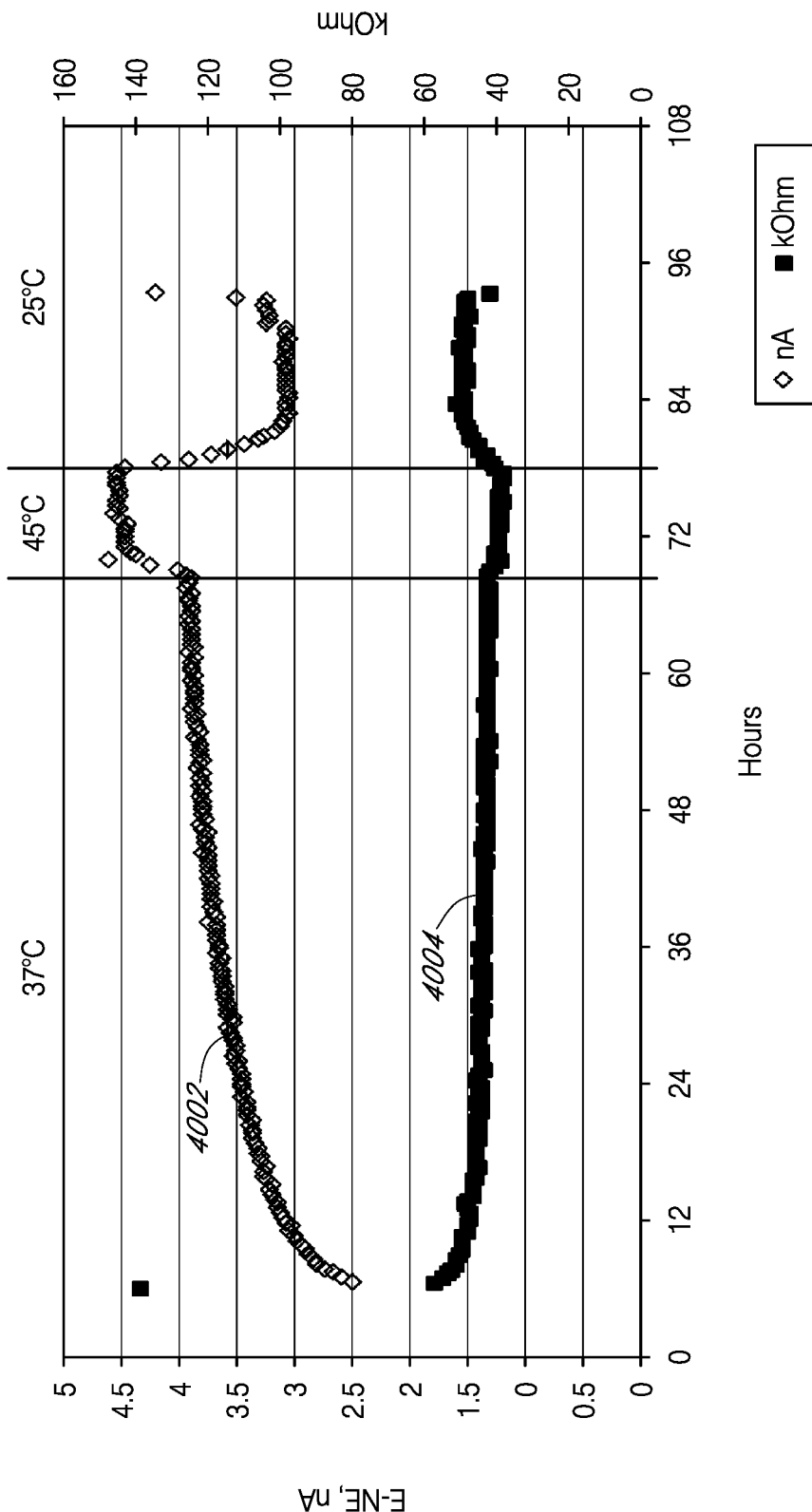

FIG. 40 illustrates a relationship of temperature on impedance and sensitivity of a sensor. Points 4002 are sensitivity values of a sensor measured over a three day time period and points 4004 are impedance values of the sensor measured over the same time period. In Example 4, the sensor is a transcutaneous-type of sensor. The temperature was initially set and maintained at 37 C, then raised to 45C, and finally lowered to 25C, as indicated in FIG. 40.

As illustrated in FIG. 40, both sensitivity and impedance of the sensor appear to have an inversely proportional relationship with changes in temperature.

Figure 41:
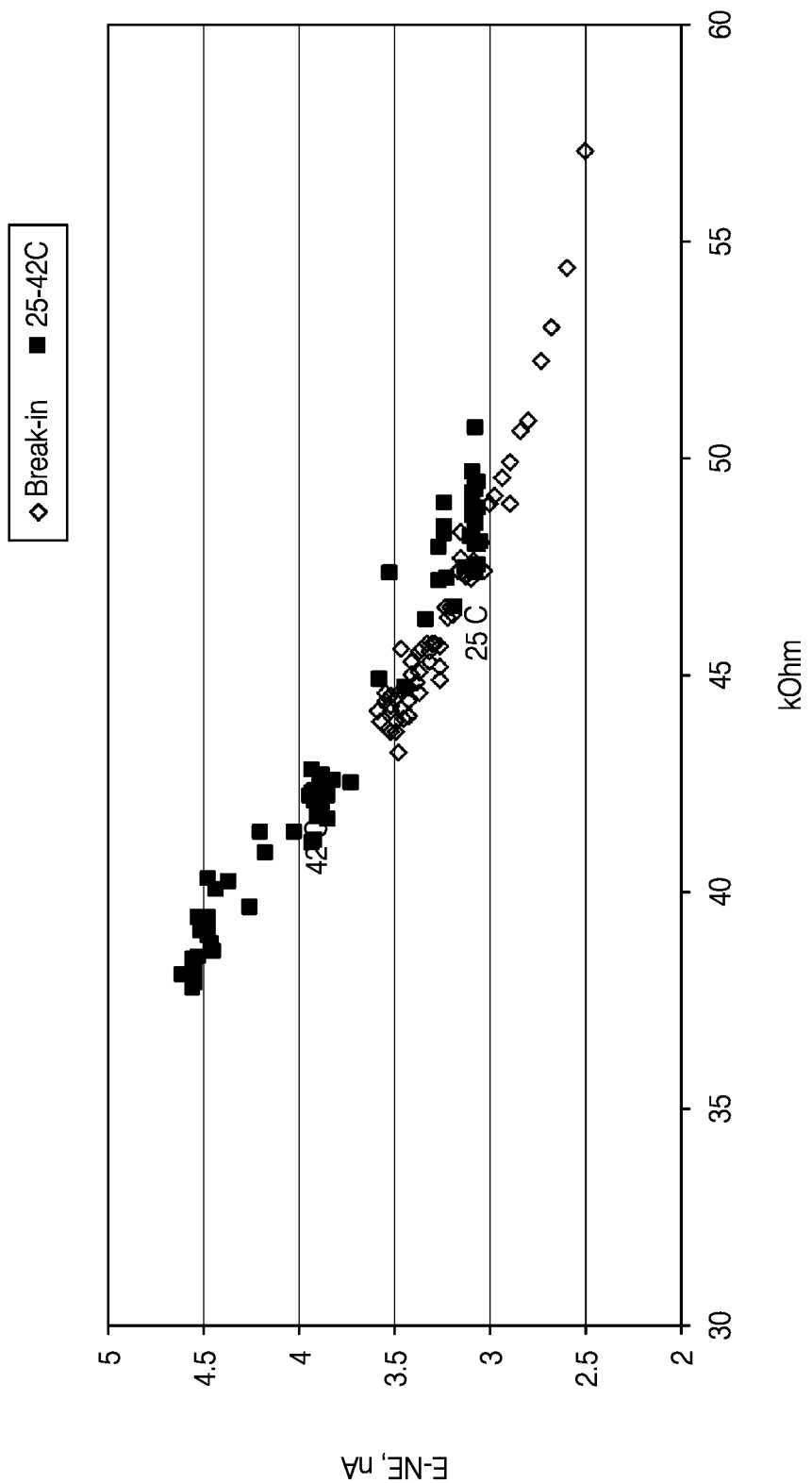

FIG. 41 is a plot of the sensitivity measurement values versus the impedance measurement values of FIG. 40. FIG. 41 illustrates points measured during sensor run-in as diamonds and points measured after run-in as squares.

Example 5

Temperature Compensation

Figure 42:
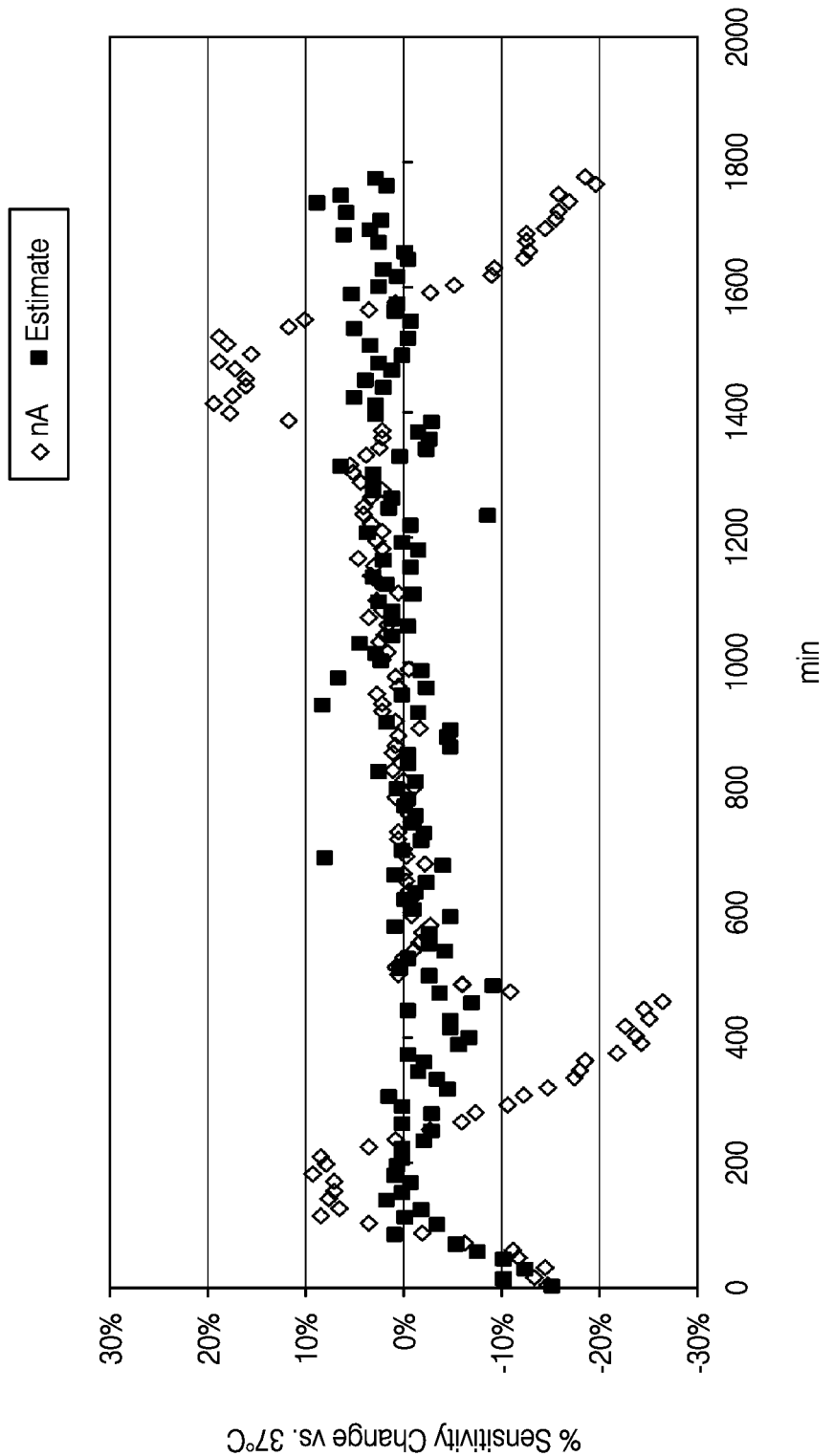

FIG. 42 illustrates compensating analyte concentration data measured by the sensor of Example 4 for effects of temperature after sensor run-in. Here, a relationship between impedance and temperature was used to compensate the sensor data. In this example, the relationship was based on an estimative curve derived from the data of FIG. 41.

The relationship between sensor sensitivity and different temperatures can then be mathematically modeled (e.g., by fitting a mathematical curve to data using one of the modeling techniques used herein), and the mathematical model can then be used to compensate for temperature effects on the sensor sensitivity. That is, a sensitivity of a sensor (which is affected by the sensor's temperature) can be determined based on a measured impedance of the sensor applied to the mathematical curve. Sensor data can then be converted to estimated glucose values based on the determined sensor sensitivity.

Further to FIG. 42, the MARD of the uncompensated data was calculated as 9.3% and the MARD of the compensated data was calculated as 2.8%.

Example 6

Moisture Ingress Detection

Example 6 involves detection of moisture ingress in components of sensor electronics used to drive a sensor. In this example, an input signal is applied to the sensor having a frequency ranging from 100 Hz to 1 kHz. A response of the signal is then measured over the range of frequencies and both impedance and phase change derived therefrom. Next, contacts typically positioned inside a sealed section of a sensor electronics module are wetted. The frequency of an input signal is varied between 100 and 1000 Hz. A response is once again measured and both impedance and phase change is derived.

In a first experiment, the contacts were wetted to the point of causing a gross failure of the sensor. The current of the sensor increased from 2.3 nA when dry to 36 nA when wetted. In a second experiment, the contacts were only slightly wetted, where the current of the sensor increased from 2.3 nA when dry to 6 nA when wetted.

Figure 43:
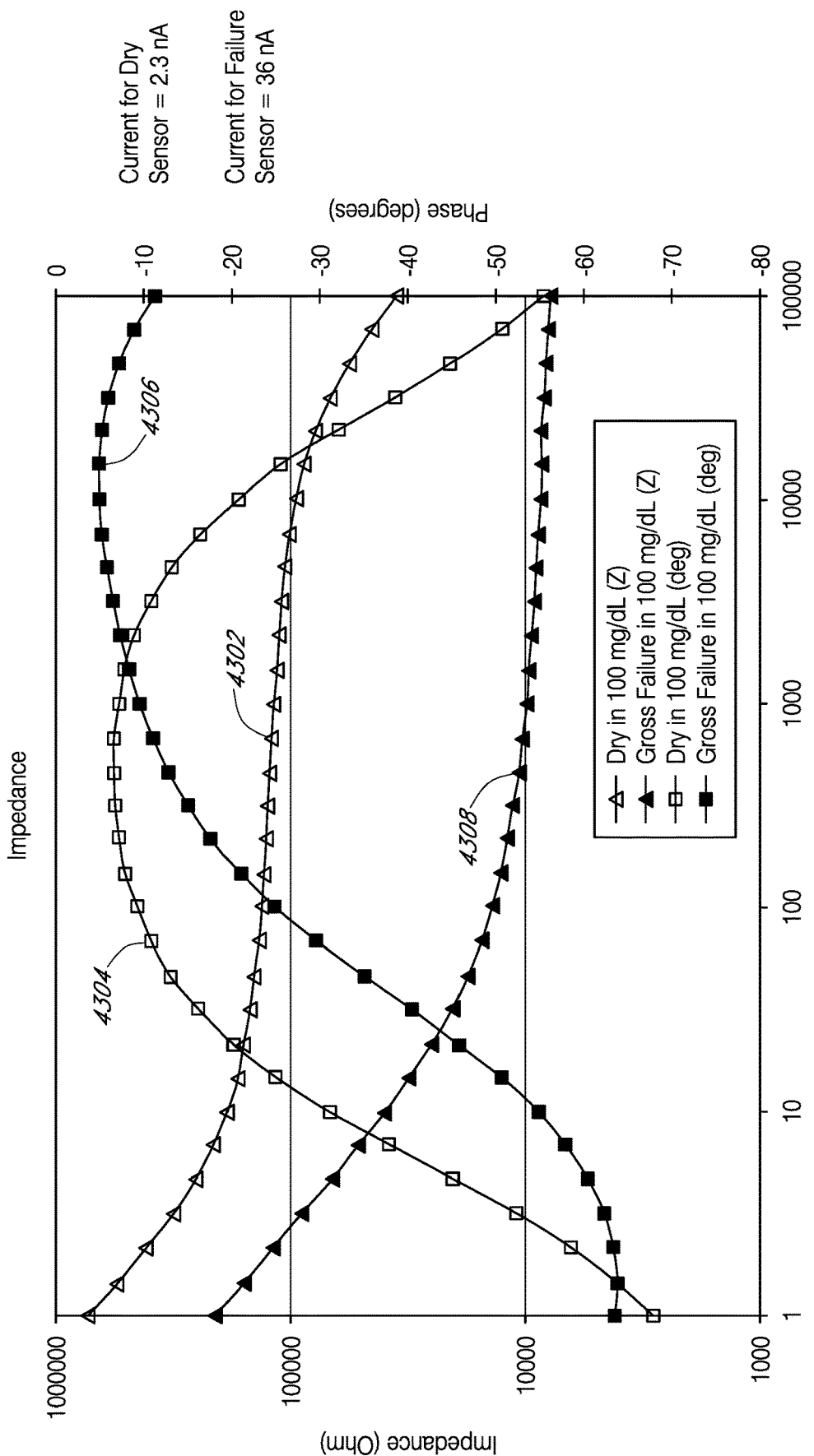

FIG. 43 is a graph of the impedance and phase changes of the first experiment, where the contacts were wetted to a point of causing a gross failure of the sensor system. Curves 4302 and 4304 are impedance and phase values, respectively, of the sensor prior to the wetting of the contacts. Curves 4306 and 4308 are impedance and phase values, respectively, of the sensor after wetting the contacts. As illustrated in FIG. 43, the impedance of the dry curve 4302 and the wet curve 4306 are noticeably different at around 1000 Hz and the phase of the dry curve 4304 and wet curve 4308 are noticeably different at about 100 Hz.

Figure 44:
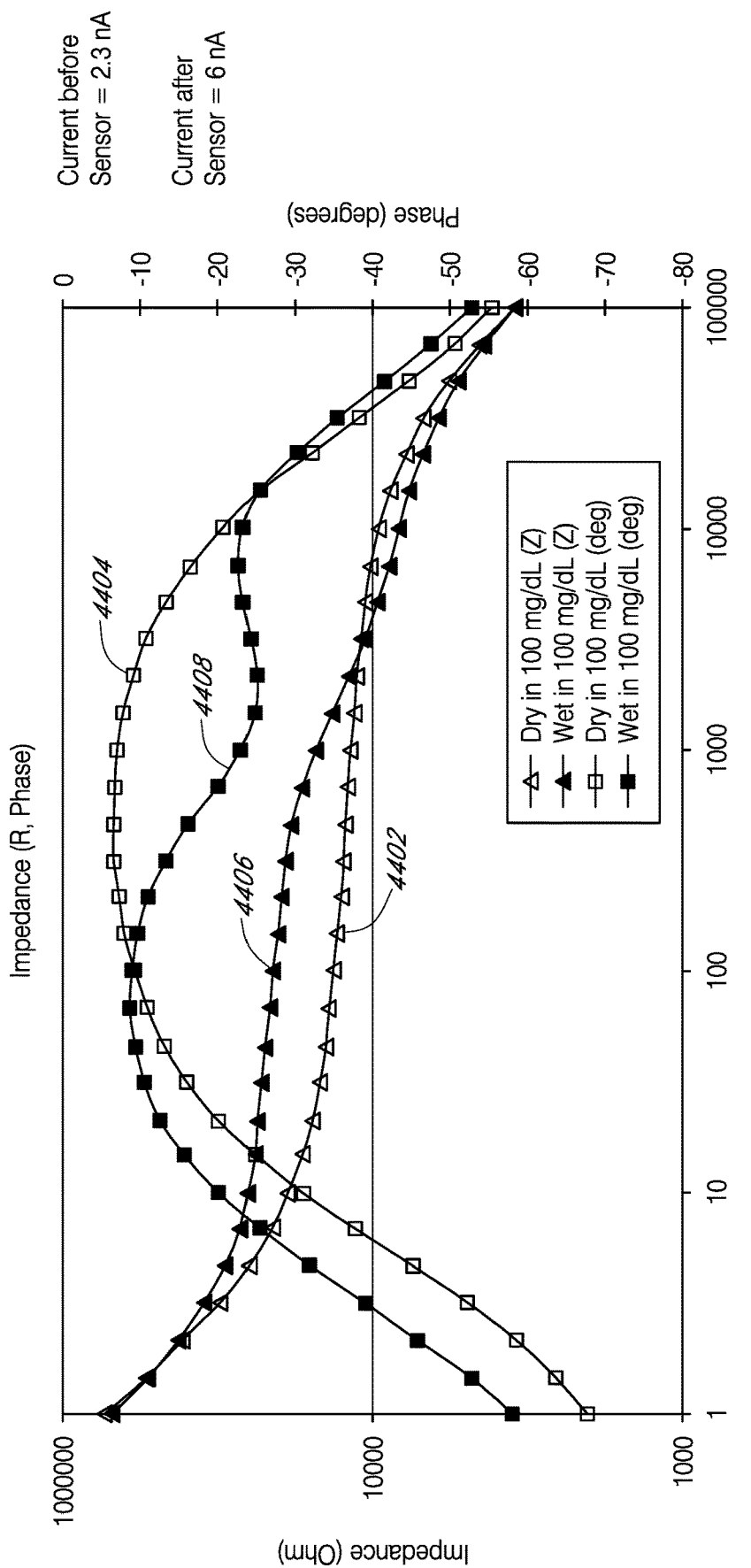

FIG. 44 is a graph of the impedance and phase changes of the second experiment, where the contacts are only slightly wetted. Curves 4402 and 4404 are impedance and phase, respectively, of the sensor prior to the wetting of the contacts. Curves 4406 and 4408 are impedance and phase, respectively, of the sensor after wetting the contacts. As illustrated in FIG. 44, the impedance of the dry curve 4402 and the wet curve 44006 are noticeably different at around 100 Hz and the phase of the dry curve 4404 and wet curve 4408 are noticeably different around 1 kHz.

Example 7

Membrane Damage Detection

Example 7 involves detection of sensor membrane damage using impedance measurements. In this example, the impedance of an analyte sensor is measured over a range of frequencies ranging from 100 to 1 kHz. A portion of the sensor's membrane is then cut using a razor blade to cause membrane damage. The impedance of the sensor is once again measured over the same range of frequencies. The impedance measurements of the sensor before the membrane is cut are then compared to the measurements of the sensor after the membrane is cut to determine whether the impedance can be used to detect membrane damage.

Figure 45:
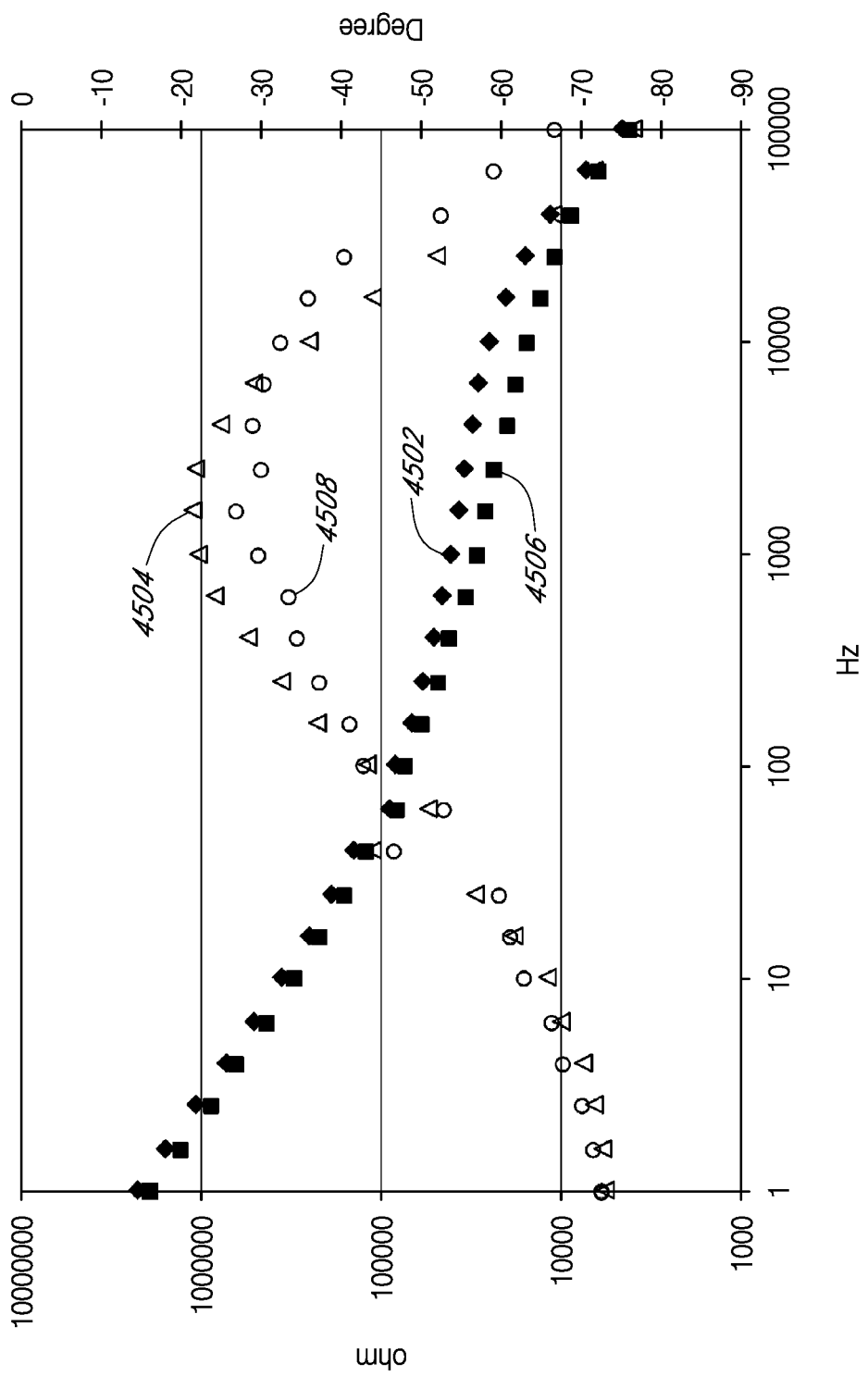

FIG. 45 is a graph of the sensor measurements before and after the membrane damage. Curves 4502 and 4504 are impedance and phase, respectively, of the sensor prior to membrane damage and curves 4506 and 4508 are impedance and phase, respectively, of the sensor after membrane damage. Both the impedance and phase relationships appear to change around the 1 kHz frequency. This relationship can then be used to detect membrane damage.

Example 8

Study Using FFT to Calculate Impedance

Figure 46:
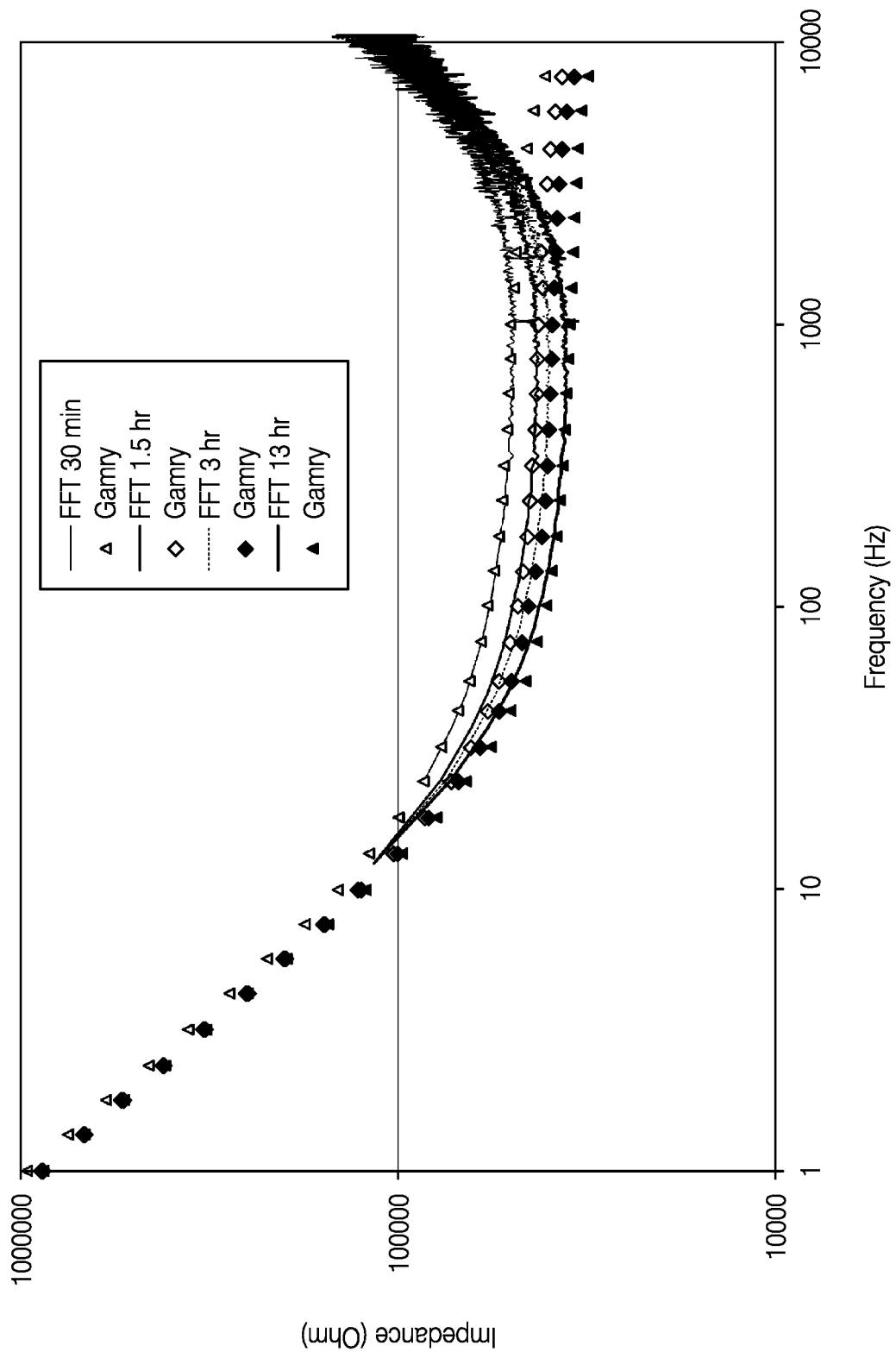

FIG. 46 is graph plotting impedance calculated using Fast Fourier Transform (FFT) and impedance measured using the Gamry for comparison. FIG. 46 illustrates FFT and corresponding Gamry measurements for 30 min., 1.5 hrs., 3 hrs. and 13 hrs. of input data. The FFT data substantially tracked the Gamry data until about the 1 kHz frequency. Note, the discrepancy after the 1 kHz frequency in FIG. 33 is believed to be due to known limitations on the system used to calculate the FFT. Thus, it is believed that using FFT can provide accurate impedance data even past the 1 kHz spectrum, thereby providing good correspondence to impedance measured using the Gamry.

Example 9

In Vivo Sensitivity Change Compensation

Figure 47:
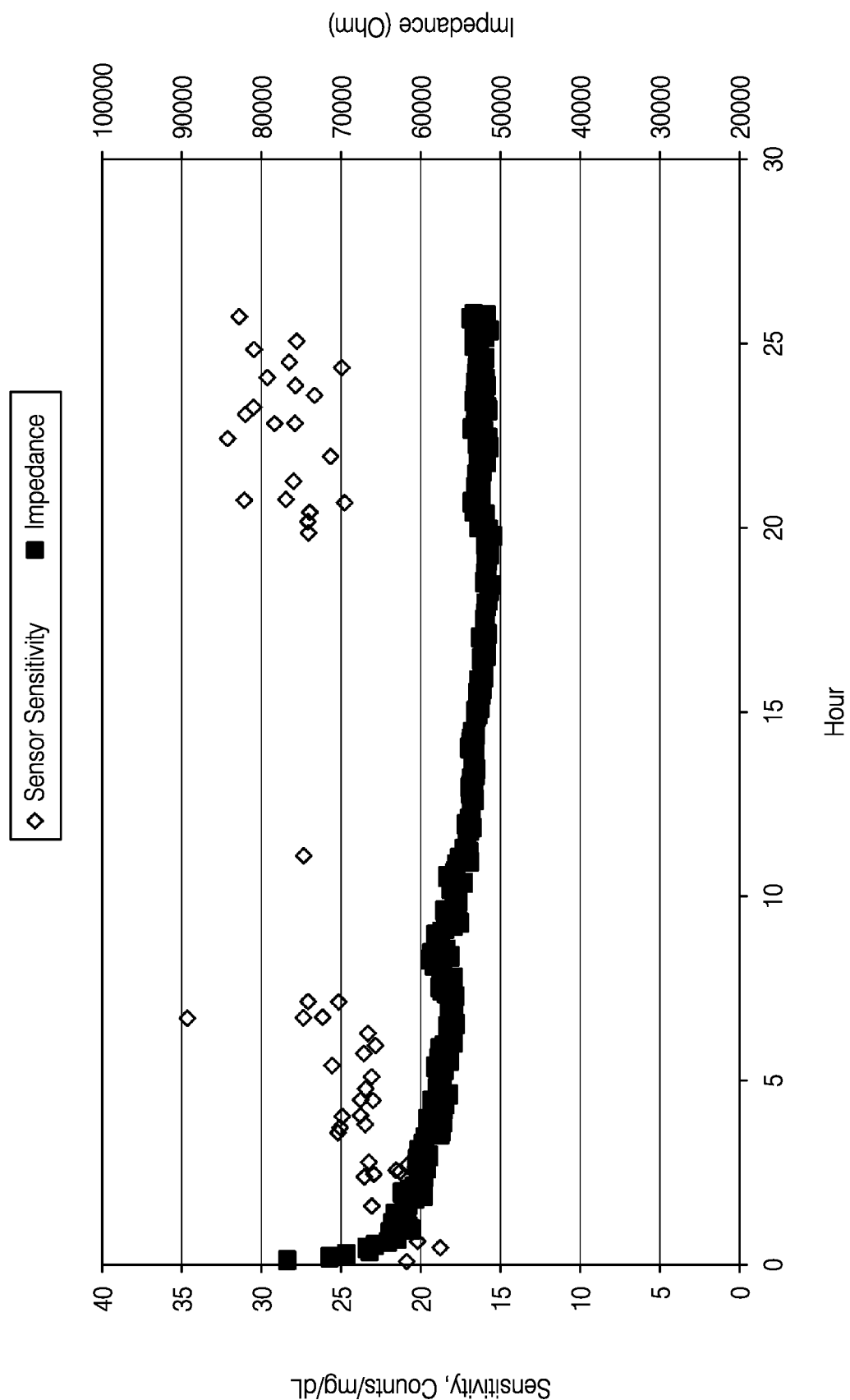
Figure 48:
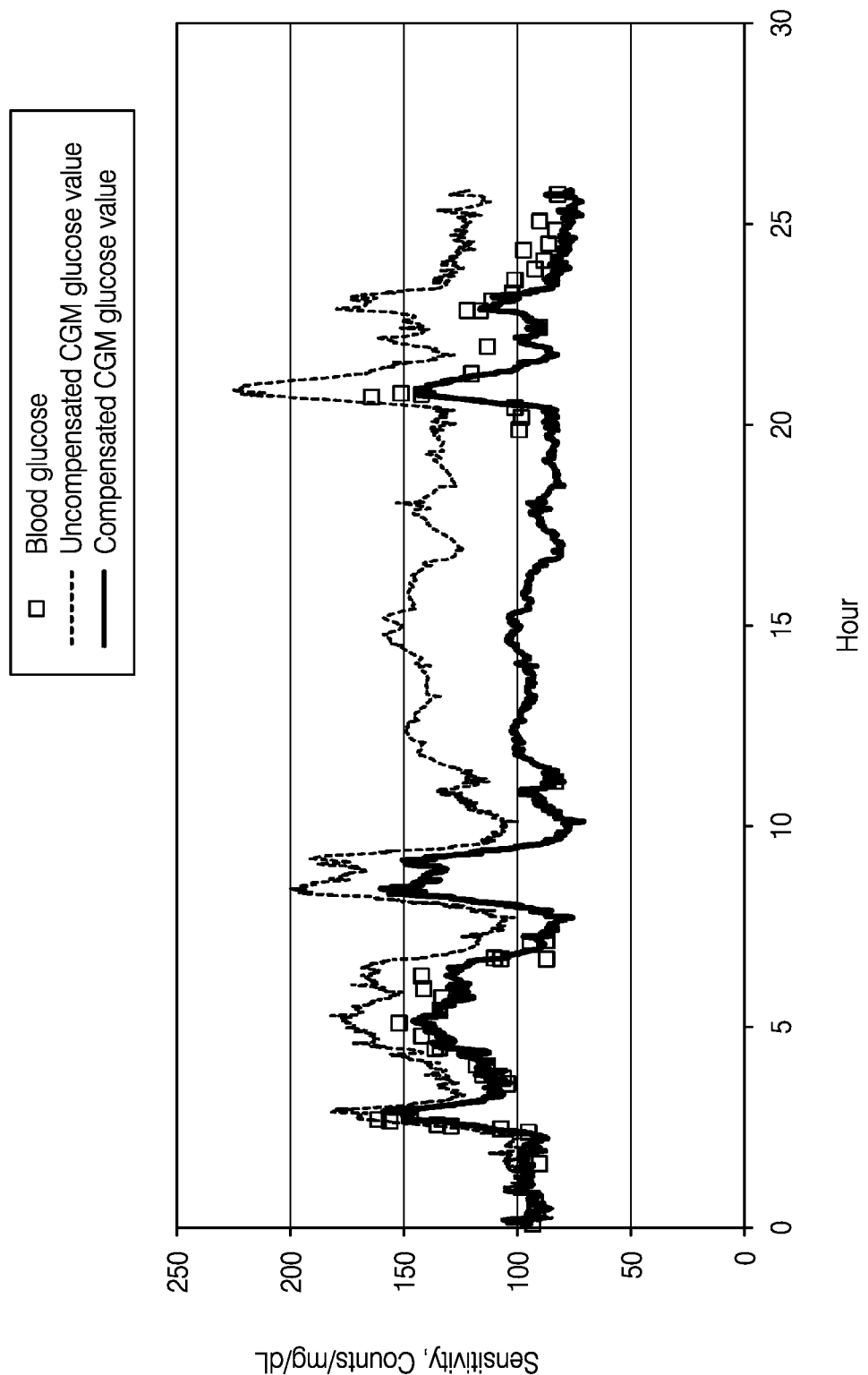
Figure 49:
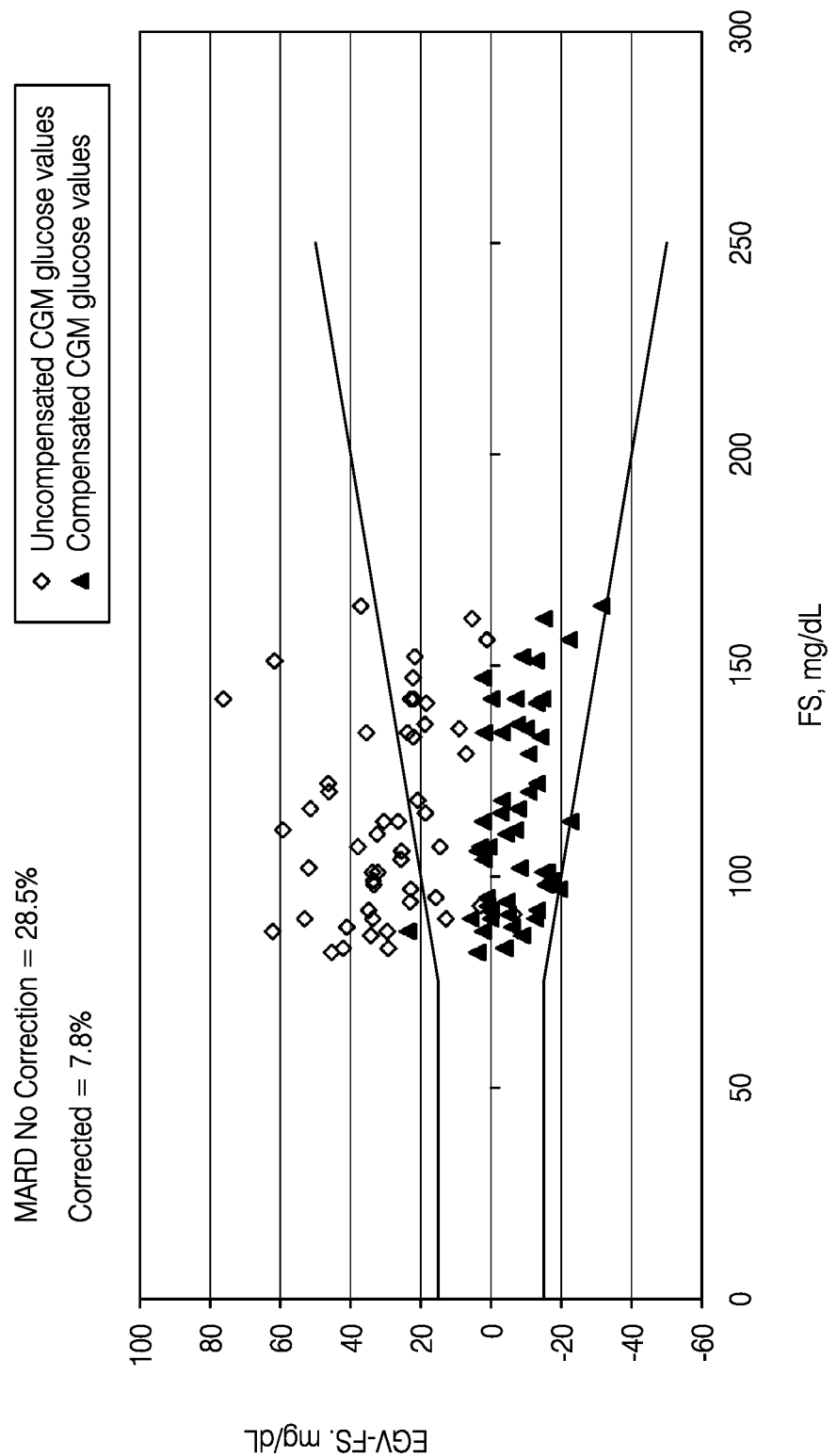

FIGS. 47-49 relate to compensating for sensitivity changes in a human using an in vivo glucose sensor.

FIG. 47 is a graph illustrating in vivo data of sensor impedance and sensitivity of a subcutaneous continuous glucose sensor (also referred to herein as a CGM sensor) over about a 25 hour time period. FIG. 47 is similar to FIG. 25, but uses in vivo data instead of in vitro data. Sensitivity data was generated using data obtained from a blood glucose finger stick monitor and raw sensor current measurements using the CGM sensor (i.e. dividing raw CGM sensor current in units of counts by time-corresponding meter glucose value in units of mg/dL to generate the sensitivity value). The impedance data was generated by applying a step voltage to the CGM sensor and calculating an impedance based on the peak current of the response, as discussed herein with reference to FIG. 13. As illustrated in FIG. 47, the impedance and sensitivity data appear to generally track a similar profile as the in vitro data of FIG. 25.

FIG. 48 is a graph of estimated glucose values using the data generated by the CGM sensor before and after sensitivity compensation using the impedance measurements of FIG. 47. The compensated and uncompensated data was calibrated once using a blood glucose reference meter measurement at the one hour mark. The compensation was performed in a manner like that described above with respect to the in vitro study of FIG. 30. FIG. 48 also illustrates blood glucose reference measurements of the host. Based on the data of FIG. 48, it appears that the compensated CGM sensor data more closely corresponds to the reference measurement data than the uncompensated CGM sensor data.

FIG. 49 is an accuracy plot showing differences between the uncompensated and compensated CGM sensor data and the finger-stick meter reference data, where the reference data corresponds to the zero line of the plot. The MARD of the uncompensated CGM sensor data is 28.5% and the MARD of the compensated CGM sensor data is 7.8%. Thus, the compensation appears to improve accuracy of the CGM sensor data.

Example 9

Comparison of a Linear Impendence-to-Sensitivity Correlation to a Non-Linear Impendence-to-Sensitivity Correlation Laboratory experiments showed that there is an inverse relationship between the changes in sensor sensitivity (drift) and the changes in impedance. Based on the measured impedance, the sensor sensitivity drift could be compensated using either linear or non-linear sensor sensitivity-impedance correlation.

The linear correlation can be expressed as the equation $\Delta S = a*\Delta I + b$, where a and b can be pre-determined coefficients determined from prior testing of similar sensors. The non-linear correlation can be expressed as $\Delta S = (a*\log(t)+b)*\Delta I$, where a and b are pre-determined constants determined from prior testing of similar sensors. The prior testing of similar sensors was performed using in vitro bench testing and the constants were derived using conventional computer plotting techniques in this experiment.

The linear and non-linear equations are derived from the relationships of change in sensitivity and change of impedance at time t since the last calibration. The percent the change of sensitivity at time t is expressed as:

$$\Delta S = \% \text{ change in sensitivity} = (\text{Sensitivity at } t - Sc)/Sc * 100\%$$

where Sc is a sensitivity determined at calibration, and t is the time since the last calibration.

The sensor impendence change from time t is expressed as:

$$\Delta I = \% \text{ impedance change} = (\text{impedance at } t - Ic)/Ic * 100\%$$

where Ic is an impedance at the time of calibration.

To calculate the linear correlation, conventional computer plotting software was used to plot change in sensitivity (y-axis) versus change in impendence (x-axis) based on in vitro test data and determine the linear best fit of the data. In this experiment, the linear best fit was $\Delta S = -4.807*\Delta I - 0.742$. The linear best fit can is used as the linear sensitivity-to-impedance correlation.

To calculate the non-linear correlation, conventional computer plotting software was used to plot change in sensitivity over change in impedance $\Delta S/\Delta I$ (y-axis) versus $\log(t)$. The linear best fit of the plotted data is then determined using the plotting software to yield $\Delta S/\Delta I = a*\log(t)+b$, from which the change is sensitivity is derived: $\Delta S = (a*\log(t)+b)*\Delta I$. In this experiment, the plotting software yielded $\Delta S/\Delta I = -1.175*\log(t) - 1.233$. From this equation, $\Delta S$ is derived: $\Delta S = (-1.175*\log(t) - 1.233)*\Delta I$.

The linear or non-linear correlation can then be applied to correct for changes in sensitivity of the sensor using impedance measurements of the sensor.

Figure 50:
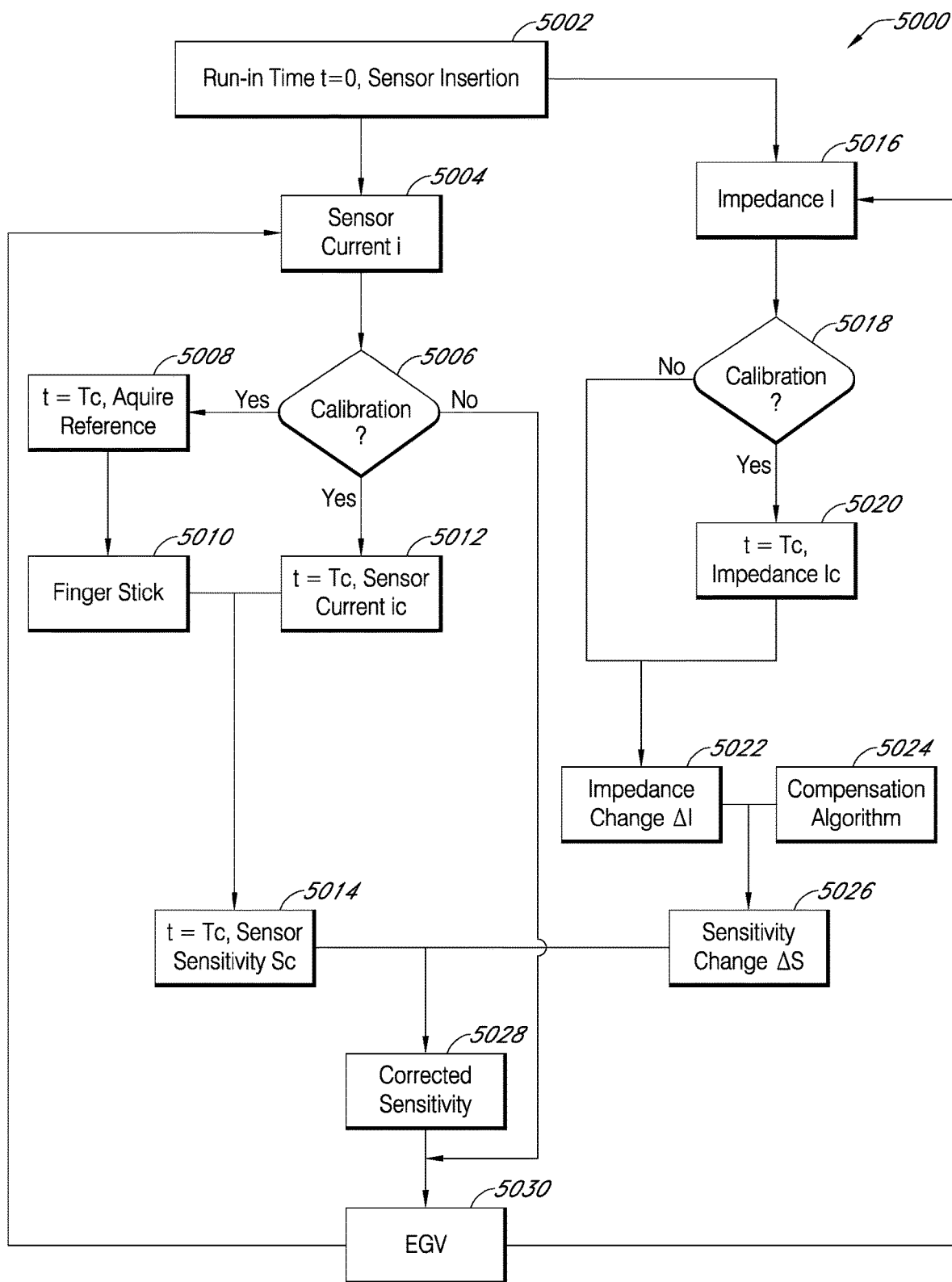
FIG. 50 is a flowchart describing a process for generating estimated analyte values using a compensation algorithm based on a measured change in impedance in accordance with one embodiment.

FIG. 50 illustrates process 5000 for correcting estimated glucose values used in this experiment. Process 5000 begins at block 5002 with sensor insertion at time t=0. Process 5000 then divides into two branches.

The first branch beings at block 5004, where sensor data is generated using the continuous glucose sensor in the form of current or counts. The first branch then proceeds to decision block 5006, where process 5000 determines whether a calibration is needed. In this experiment, a calibration is determined to be needed one hour and 24 hours after sensor insertion. If it is determined that calibration is not needed, then the first branch essentially ends. On the other hand, if it is determined that calibration is required, then process 5000 acquires a reference measurement using a finger stick meter at blocks 5008 and 5010. Sensor data corresponding in time to the reference measurement (at time Tc) is determined at block 5012 and used to calculate a sensor sensitivity, Sc, along with the reference data at block 5014.

The second branch of process 5000 begins with measuring an impendence of the sensor at block 5016. The impedance is measured using the peak current technique discussed in this application with reference to FIG. 13. Next it is determined if calibration is needed in decision block 5018. In this experiment, this is the same decision made in decision block 5006. If calibration is determined to be needed, then the impedance measured in block 5016 is flagged and stored as impedance Ic (impedance calibration) at block 5020. If calibration is not needed, then process 5000 skips block 5020 and proceeds to determine a change in impedance at block 5022 from the impedance flagged as impedance Ic, which in this experiment is the difference between the impendence measured in block 5016 and the impedance Ic. A compensation algorithm (using the linear or the non-linear compensation algorithm) is then used in block 5024 to calculate a change in sensitivity at block 5026 based on the change in impedance determined at block 5022.

The first and second branches of process 5000 then merge at block 5028 where a corrected sensitivity is determined. The corrected sensitivity is then used to convert sensor data in units of current or counts to an estimated glucose value in units of glucose concentration.

Process 5000 is repeated for each sensor data point that is converted into an estimated glucose value.

Figure 51:
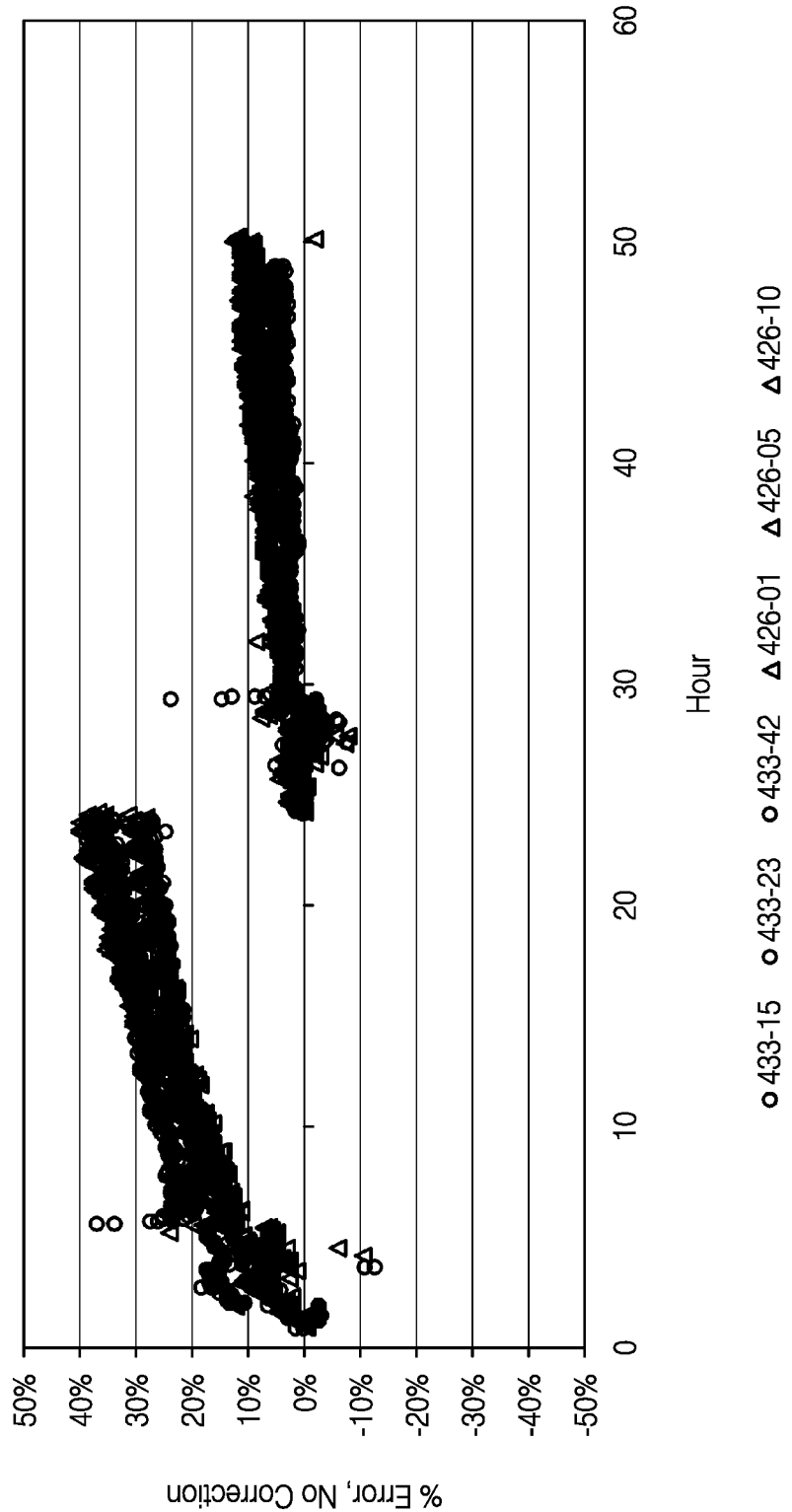
FIGS. 51-53 are graphs of studies comparing use of compensation algorithms based on measured changes in impedance.
Figure 52:
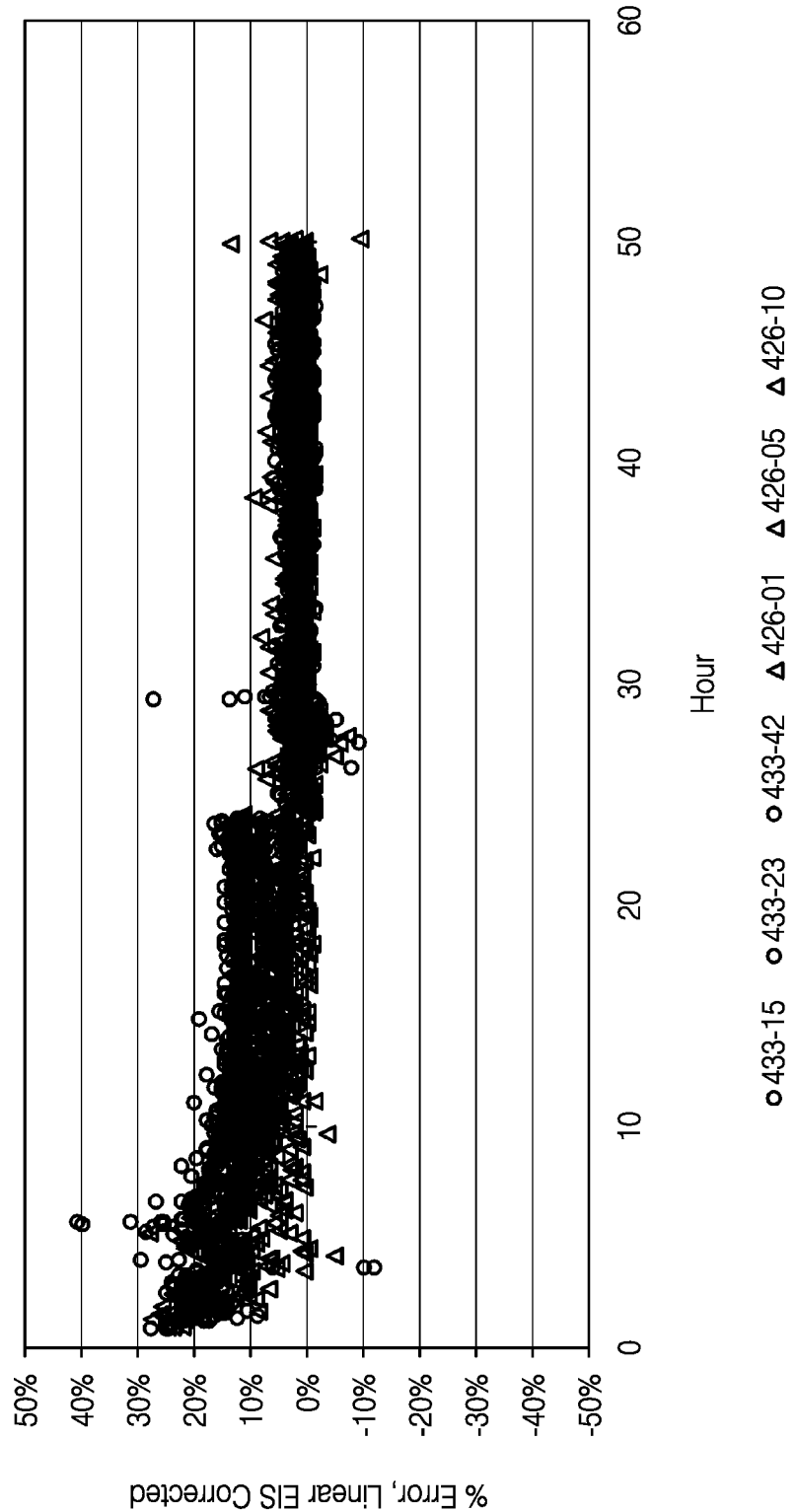
Figure 53:
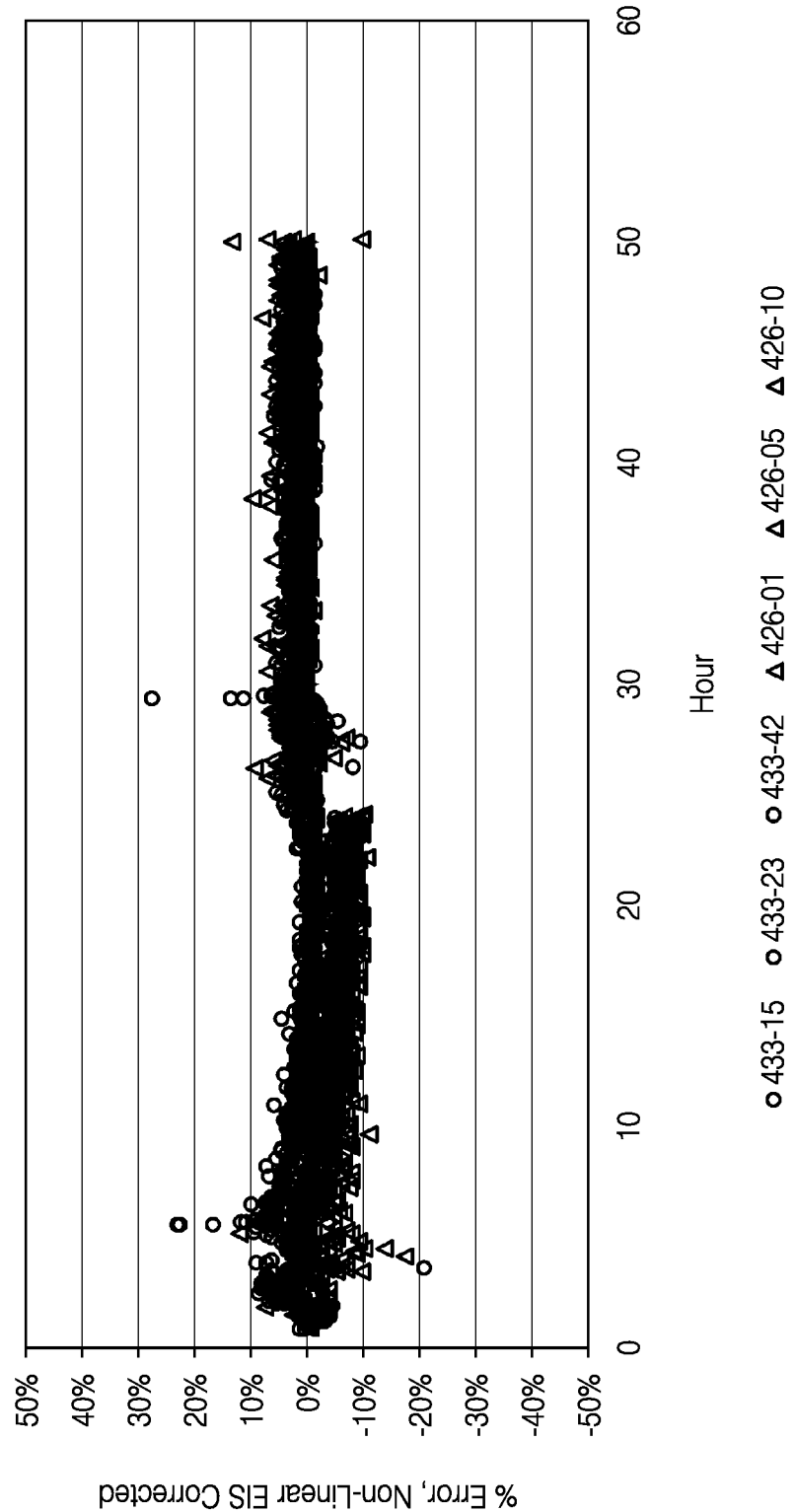

In this experiment, sensor performance improvement by impedance compensation is demonstrated below. The sensors were tested using continuous glucose sensors placed in sheep serum for 2 days. The sensor sensitivity was calculated at 1 hour and 24 hours. In FIG. 51, the sensor sensitivity obtained at calibrations (1 hour or 24 hours) was used throughout the day without any correction. In FIG. 52, sensitivity was corrected using linear impedance correction in accordance with the process illustrated in FIG. 50. In FIG. 53, sensitivity was adjusted with non-linear sensitivity-impedance correlation in accordance with the process illustrated in FIG. 50. While both linear and non-linear corrections demonstrated improved sensor performance, the non-linear correction produced better results.

Some embodiments disclosed herein continuously or iteratively apply a stimulus signal during a continuous sensor session or use and extrapolate information from the output associated with the stimulus, such as using a peak current measurement, EIS, etc. Although certain electrochemical analysis techniques were described herein, it is understood that many other techniques can be used instead to detect characteristics of sensors described herein, such as voltammetry, chronopotentiometry, current or potential step techniques, differential chrono-potentiometry, oxygen absorption rate measurements, potential/current sweep or pulse methods, etc.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method comprising:
   manufacturing a plurality of transcutaneous electrochemical glucose sensors, wherein the plurality of transcutaneous electrochemical glucose sensors comprise a first transcutaneous electrochemical glucose sensor, wherein the first transcutaneous electrochemical glucose sensor is configured to measure glucose in an interstitial fluid of the host, wherein the first transcutaneous electrochemical glucose sensor comprises an ex vivo portion and an in vivo portion, wherein the first transcutaneous electrochemical glucose sensor is configured to operably connect to sensor electronics during a sensor session;
   obtaining data associated with a first characteristic of the first transcutaneous electrochemical glucose sensor prior to the sensor session;
   determining, based at least in part on the data associated with the first characteristic, a first sensitivity associated with the first transcutaneous electrochemical glucose sensor;
   assigning a calibration code to the first transcutaneous electrochemical glucose sensor, wherein the calibration code is based at least in part on the first sensitivity;
   storing information associated with the calibration code on the sensor electronics;
   obtaining data associated with a second characteristic of the first transcutaneous electrochemical glucose sensor during the sensor session;
   determining, based at least in part on the data associated with the second characteristic, a second sensitivity associated with the first transcutaneous electrochemical glucose sensor;
   generating, based at least in part on the second sensitivity, a glucose value associated with an estimated glucose concentration; and
   displaying the glucose value on a user interface.

2. The method of claim 1, wherein the calibration code is part of a calibration encoded label.

3. The method of claim 1, wherein the first transcutaneous electrochemical glucose sensor is formed as a wire.

4. The method of claim 1, further comprising measuring a length of time the first transcutaneous electrochemical glucose sensor was dipped in a particular coating solution, and wherein the calibration code is further based at least in part on the measured dipping length of time.

5. The method of claim 1, wherein the first transcutaneous electrochemical glucose sensor comprises a membrane, wherein the first characteristic of the first transcutaneous electrochemical glucose sensor is associated with a thickness of the membrane of the first transcutaneous electrochemical glucose sensor.

6. The method of claim 5, wherein the membrane is a membrane system.

7. The method of claim 5, wherein the membrane is a membrane layer.

8. The method of claim 1, wherein the first transcutaneous electrochemical glucose sensor comprises a membrane, wherein the first characteristic of the first transcutaneous electrochemical glucose sensor is associated with a permeability of the membrane to glucose.

9. The method of claim 1, wherein the first transcutaneous electrochemical glucose sensor comprises a membrane, wherein the first characteristic of the first transcutaneous electrochemical glucose sensor is associated with a property of the membrane.

10. The method of claim 1, wherein the second characteristic of the first transcutaneous electrochemical glucose sensor is associated with a measured temperature.

11. The method of claim 1, wherein the first sensitivity is a sensitivity value.

12. The method of claim 1, wherein the first sensitivity is a sensitivity distribution.

13. The method of claim 1, wherein the second sensitivity is a sensitivity value.

14. The method of claim 1, wherein the second sensitivity is a sensitivity distribution.

15. A method comprising:
  manufacturing a plurality of transcutaneous electrochemical glucose sensors, wherein the plurality of transcutaneous electrochemical glucose sensors comprise a first transcutaneous electrochemical glucose sensor, wherein the first transcutaneous electrochemical glucose sensor is configured to measure glucose in an interstitial fluid of the host, wherein the first transcutaneous electrochemical glucose sensor comprises an ex vivo portion and an in vivo portion, wherein the first transcutaneous electrochemical glucose sensor is configured to operably connect to sensor electronics during a sensor session;
  determining a first distribution associated with a sensitivity of the first transcutaneous electrochemical glucose sensor;
  obtaining data associated with a characteristic of the first transcutaneous electrochemical glucose sensor prior to the sensor session; and
  determining, based at least in part on the first distribution and based at least in part on the data associated with the characteristic of the first transcutaneous electrochemical glucose sensor, a second distribution associated with sensor sensitivity of the first transcutaneous electrochemical glucose sensor.

16. The method of claim 15, wherein the first transcutaneous electrochemical glucose sensor comprises a membrane, wherein the characteristic of the first transcutaneous electrochemical glucose sensor is associated with a thickness of the membrane of the first transcutaneous electrochemical glucose sensor.

17. The method of claim 15, wherein the first transcutaneous electrochemical glucose sensor comprises a membrane, wherein the characteristic of the first transcutaneous electrochemical glucose sensor is associated with a permeability of the membrane to glucose.

18. The method of claim 15, wherein the first transcutaneous electrochemical glucose sensor comprises a membrane, wherein the characteristic of the first transcutaneous electrochemical glucose sensor is associated with a property of the membrane.

19. A method comprising:
  manufacturing a plurality of transcutaneous electrochemical glucose sensors, wherein the plurality of transcutaneous electrochemical glucose sensors comprise a first transcutaneous electrochemical glucose sensor, wherein the first transcutaneous electrochemical glucose sensor is configured to measure glucose in an interstitial fluid of the host, wherein the first transcutaneous electrochemical glucose sensor comprises an ex vivo portion and an in vivo portion, wherein the first transcutaneous electrochemical glucose sensor is configured to operably connect to sensor electronics during a sensor session;
  determining a distribution associated with a sensitivity of the first transcutaneous electrochemical glucose sensor;
  obtaining data associated with a characteristic of the first transcutaneous electrochemical glucose sensor prior to the sensor session; and
  determining, based at least in part on the first distribution and based at least in part on the data associated with the characteristic of the first transcutaneous electrochemical glucose sensor, a value associated with a sensitivity of the first transcutaneous electrochemical glucose sensor.

20. The method of claim 19, wherein the first transcutaneous electrochemical glucose sensor comprises a membrane, wherein the characteristic of the first transcutaneous electrochemical glucose sensor is associated with a thickness of the membrane of the first transcutaneous electrochemical glucose sensor.

21. The method of claim 19, wherein the first transcutaneous electrochemical glucose sensor comprises a membrane, wherein the characteristic of the first transcutaneous electrochemical glucose sensor is associated with a permeability of the membrane to glucose.

22. The method of claim 19, wherein the first transcutaneous electrochemical glucose sensor comprises a membrane, wherein the characteristic of the first transcutaneous electrochemical glucose sensor is associated with a property of the membrane.

23. A method comprising:
  manufacturing a plurality of transcutaneous electrochemical glucose sensors, wherein the plurality of transcutaneous electrochemical glucose sensors comprise a first transcutaneous electrochemical glucose sensor and a second transcutaneous electrochemical glucose sensor, wherein the first transcutaneous electrochemical glucose sensor and the second transcutaneous electrochemical analyte sensor are each configured to measure glucose in an interstitial fluid of a host, wherein the first transcutaneous electrochemical glucose sensor and the second transcutaneous electrochemical glucose sensor each comprises an ex vivo portion and an in vivo portion, wherein the first transcutaneous electrochemical glucose sensor and the second transcutaneous electrochemical glucose sensor are each configured to operably connect to sensor electronics during a sensor session;
  obtaining data associated with a characteristic of the first transcutaneous electrochemical glucose sensor prior to the sensor session;
  determining, based at least in part on the data associated with the first transcutaneous electrochemical glucose sensor, a first sensitivity, wherein the first sensitivity is associated with a sensitivity of the first transcutaneous electrochemical glucose sensor;
  assigning, to the first transcutaneous electrochemical glucose sensor, a first code associated with calibration, wherein the first code is associated with the first sensitivity;
  obtaining data associated with a characteristic of the second transcutaneous electrochemical glucose sensor prior to the sensor session;
  determining, based at least in part on the data associated with the second transcutaneous electrochemical glucose sensor, a second sensitivity, wherein the second sensitivity is associated with a sensitivity of the second transcutaneous electrochemical glucose sensor; and assigning, to the second transcutaneous electrochemical glucose sensor, a second code associated with calibration, wherein the second code is associated with the second sensitivity;

wherein the first code and the second code are different.

24. The method of claim 23, wherein the characteristic of the first transcutaneous electrochemical glucose sensor and the characteristic of the second transcutaneous electrochemical glucose sensor are the same.

25. The method of claim 23, wherein the first transcutaneous electrochemical glucose sensor comprises a first membrane, wherein the second transcutaneous electrochemical glucose sensor comprises a second membrane, wherein the characteristic of the first transcutaneous electrochemical glucose sensor is associated with a thickness of the first membrane of the first transcutaneous electrochemical glucose sensor, wherein the characteristic of the second transcutaneous electrochemical glucose sensor is associated with a thickness of the second membrane of the second transcutaneous electrochemical glucose sensor.

26. The method of claim 23, wherein the first transcutaneous electrochemical glucose sensor comprises a first membrane, wherein the second transcutaneous electrochemical glucose sensor comprises a second membrane, wherein the characteristic of the first transcutaneous electrochemical glucose sensor is associated with a permeability of the first membrane to glucose, wherein the characteristic of the second transcutaneous electrochemical glucose sensor is associated with a permeability of the second membrane to glucose.

27. The method of claim 23, wherein the first transcutaneous electrochemical glucose sensor and the second transcutaneous each comprises a membrane, wherein the first characteristic of the first transcutaneous electrochemical glucose sensor and the second characteristic of the second transcutaneous electrochemical sensor are each associated with a property of the membrane.

28. The method of claim 23, wherein the first sensitivity and the second sensitivity are sensitivity values.

29. The method of claim 23, wherein the first sensitivity and the second sensitivity are sensitivity distributions.

\* \* \* \* \*

UNITED STATES PATENT AND TRADEMARK OFFICE
CERTIFICATE OF CORRECTION

PATENT NO. : 10,835,162 B2
APPLICATION NO. : 16/586610
DATED : November 17, 2020
INVENTOR(S) : Sebastian Böhm It is certified that error appears in the above-identified patent and that said Letters Patent is hereby corrected as shown below:

On the Title Page

On page 3, in Column 1, item (56), U.S. PATENT DOCUMENTS, Line 5, delete "Boecker" and insert --Boecker et al.--.

On page 3, in Column 2, item (56), U.S. PATENT DOCUMENTS, Line 49, delete "Mastrototaro" and insert --Mastrototaro et al.--.

On page 5, in Column 1, item (56), U.S. PATENT DOCUMENTS, Line 16, delete "Brister et al." and insert --Dobbles et al.--.

On page 5, in Column 2, item (56), U.S. PATENT DOCUMENTS, Line 61, delete "Budiman" and insert --Budiman et al.--.

On page 12, in Column 2, item (56), Other Publications, Line 11, delete "Radiotelemetric" and insert --Radio telemetric--.

In the Drawings

In sheet 6 of 56, FIG. 4, Y-axis, Line 1, delete "DL" and insert --dL--.

In sheet 33 of 56, FIG. 30, Y-axis, Line 9, delete "10%" and insert -- -10%--.

In sheet 35 of 56, FIG. 32, Y-axis, Line 9, delete "10%" and insert -- -10%--.

In sheet 37 of 56, FIG. 34, Y-axis, Line 9, delete "10%" and insert -- -10%--.

In sheet 39 of 56, FIG. 36, Y-axis, Line 9, delete "10%" and insert -- -10%--.

In sheet 40 of 56, FIG. 37, Y-axis, Line 9, delete "10%" and insert -- -10%--.

Signed and Sealed this
Nineteenth Day of October, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,835,162 B2

In sheet 43 of 56, FIG. 40, Y-axis, Line 10, delete "0" and insert --1--.

In sheet 53 of 56, FIG. 50, reference numeral 5008, Line 1, delete "Aquire" and insert --Acquire--.

In the Specification

In Column 9, Line 53, delete "thereof" and insert --thereof.--.

In Column 14, Line 38, delete "thereof" and insert --thereof.--.

In Column 16, Line 25, delete "time" and insert --time.--.

In Column 17, Line 41, delete "is are" and insert --is--.

In Column 17, Lines 55-56, delete "andrenostenedione" and insert --androstenedione--.

In Column 17, Line 60, delete "hydroxy-cholic" and insert --hydroxycholic--.

In Column 18, Lines 3-4, delete "diptheria" and insert --diphtheria--.

In Column 18, Line 9, delete "uridyltransferase" and insert --uridylyltransferase--.

In Column 18, Line 11, delete "perioxidase" and insert --peroxidase--.

In Column 18, Lines 20-21, delete "sissomicin" and insert --sisomicin--.

In Column 18, Line 25, delete "duodenalisa" and insert --duodenalis--.

In Column 18, Line 32, delete "Trepenoma pallidium" and insert --Treponema pallidum--.

In Column 18, Line 33, delete "stomatis" and insert --stomatitis--.

In Column 18, Line 53, delete "PreState" and insert --Pre-State--.

In Column 18, Line 54, delete "barbituates" and insert --barbiturates--.

In Column 18, Line 60, delete "(analogs" and insert --(analogues--.

In Column 19, Line 2, delete "5HT" and insert --5-HT--.

In Column 19, Line 3, delete "FHIAA" and insert --5-HIAA--.

In Column 23, Line 22, delete "time" and insert --time.--.

In Column 29, Line 66, delete "the in" and insert --the--.

CERTIFICATE OF CORRECTION (continued)
U.S. Pat. No. 10,835,162 B2

In Column 30, Line 31, delete "over a over a" and insert --over a--.

In Column 39, Line 12, delete "a" and insert --an--.

In Column 42, Line 48, delete "log w" and insert --log ω--.

In Column 42, Line 49, delete "w=" and insert --ω=--.

In Column 44, Line 29, delete "where" and insert --where:--.

In Column 53, Line 35, delete "A an" and insert --An--.

In Column 56, Line 22, delete "system" and insert --system.--.

In Column 57, Line 45, delete "and or" and insert --and/or--.

In Column 57, Line 46, delete "an/or" and insert --and/or--.

In Column 60, Line 33, delete "37 C." and insert --37° C.--.

In Column 61, Line 60, delete "37 C." and insert --37° C.--.

In Column 61, Line 61, delete "37 C," and insert --37° C.,--.

In Column 62, Line 12, delete "25 C" and insert --25° C.--.

In Column 62, Line 12, delete "37C." and insert --37° C.--.

In Column 62, Line 17, delete "37 C." and insert --37° C.--.

In Column 62, Line 27, delete "0," and insert --O,--.

In Column 62, Line 31, delete "42 C." and insert --42° C.--.

In Column 63, Line 40, delete "37 C," and insert --37° C.,--.

In Column 63, Line 40, delete "45C," and insert --45° C.,--.

In Column 63, Line 41, delete "25C," and insert --25° C.,--.

In the Claims

In Column 74, Line 13, Claim 27, delete "each" and insert --electrochemical glucose sensor each--.

In Column 74, Line 16, Claim 27, delete "electrochemical sensor" and insert --electrochemical glucose sensor--.